(12) United States Patent
Blackburn et al.

(10) Patent No.: US 6,686,150 B1
(45) Date of Patent: Feb. 3, 2004

(54) AMPLIFICATION OF NUCLEIC ACIDS WITH ELECTRONIC DETECTION

(75) Inventors: Gary Blackburn, Glendora, CA (US); Bruce D. Irvine, Glendora, CA (US); Jon Faiz Kayyem, Pasadena, CA (US); Edward Lewis Sheldon, III, Arcadia, CA (US); Robert H. Terbrueggen, Manhattan Beach, CA (US)

(73) Assignee: Clinical Micro Sensors, Inc., Pasadena, CA (US)

( * ) Notice: Subject to any disclaimer, the term of this patent is extended or adjusted under 35 U.S.C. 154(b) by 183 days.

(21) Appl. No.: 09/621,275

(22) Filed: Jul. 20, 2000

Related U.S. Application Data

(63) Continuation-in-part of application No. 09/238,351, filed on Jan. 27, 1999, and a continuation of application No. 09/014,304, filed on Jan. 27, 1998, now Pat. No. 6,063,573, said application No. 09/238,351, is a continuation of application No. 09/135,183, filed on Aug. 17, 1998.
(60) Provisional application No. 60/144,698, filed on Jul. 20, 1999, provisional application No. 60/084,425, filed on May 6, 1998, provisional application No. 60/084,509, filed on May 6, 1998, provisional application No. 60/028,102, filed on Mar. 16, 1998, and provisional application No. 60/073,011, filed on Jan. 29, 1998.

(51) Int. Cl.[7] ............................ C12Q 1/68; C12P 19/34; C07H 21/00
(52) U.S. Cl. ................ 435/6; 435/91.1; 435/91.2; 536/23.1; 536/25.3
(58) Field of Search ............... 435/6, 91.1, 91.2; 436/501; 536/22.1, 25.3

(56) References Cited

U.S. PATENT DOCUMENTS

| | | | |
|---|---|---|---|
| 4,683,195 A | * | 7/1987 | Mullis et al. ............... 435/6 |
| 4,683,202 A | | 7/1987 | Mullis |
| 4,707,352 A | | 11/1987 | Stavrianopoulos |
| 4,707,440 A | | 11/1987 | Stavrianopoulos |
| 4,711,955 A | | 12/1987 | Ward et al. |
| 4,755,458 A | | 7/1988 | Rabbani et al. |
| 4,840,893 A | | 6/1989 | Hill et al. |
| 4,849,513 A | | 7/1989 | Smith et al. |
| 4,868,103 A | | 9/1989 | Stavrianopoulos et al. |
| 4,894,325 A | | 1/1990 | Englehardt et al. |
| 4,943,523 A | | 7/1990 | Stavrianopoulos |
| 4,945,045 A | * | 7/1990 | Forrest et al. ............... 435/25 |
| 4,952,685 A | | 8/1990 | Stavrianopoulos |
| 4,994,373 A | | 2/1991 | Stavrianopoulos |
| 5,002,885 A | | 3/1991 | Stavrianopoulos |
| 5,013,831 A | | 5/1991 | Stavrianopoulos |

(List continued on next page.)

FOREIGN PATENT DOCUMENTS

| | | |
|---|---|---|
| CA | 2090904 | 9/1993 |
| EP | 0 063 879 | 11/1982 |

(List continued on next page.)

OTHER PUBLICATIONS

1988 Stratagene Catalog [Published by STRATEGENE, 11011 North Torrey Pines Road, La Jolla, California 92037], 1988.*

(List continued on next page.)

*Primary Examiner*—Ardin H. Marschel
(74) *Attorney, Agent, or Firm*—Dorsey & Whitney LLP; Robin M. Silva; Renee M. Kosslak

(57) ABSTRACT

The invention relates to compositions and methods useful in the detection of nucleic acids using a variety of amplification techniques, including both signal amplification and target amplification. Detection proceeds through the use of an electron transfer moiety (ETM) that is associated with the nucleic acid, either directly or indirectly, to allow electronic detection of the ETM using an electrode.

23 Claims, 66 Drawing Sheets

U.S. PATENT DOCUMENTS

| | | | |
|---|---|---|---|
| 5,082,830 A | 1/1992 | Brakel et al. | |
| 5,089,112 A | 2/1992 | Skotheim et al. | |
| 5,130,238 A | * 7/1992 | Malek et al. | 435/91 |
| 5,156,810 A | 10/1992 | Ribi | |
| 5,175,269 A | 12/1992 | Stavrianopoulos | |
| 5,175,270 A | 12/1992 | Nilsen et al. | |
| 5,180,968 A | 1/1993 | Bruckenstein et al. | |
| 5,241,060 A | 8/1993 | Englehardt et al. | |
| 5,278,043 A | 1/1994 | Bannwarth et al. | |
| 5,312,527 A | 5/1994 | Mikkelsen et al. | |
| 5,328,824 A | 7/1994 | Ward et al. | |
| 5,356,786 A | 10/1994 | Heller et al. | |
| 5,391,272 A | 2/1995 | O'Daly et al. | |
| 5,403,451 A | 4/1995 | Riviello et al. | |
| 5,409,818 A | 4/1995 | Davey et al. | |
| 5,449,767 A | 9/1995 | Ward et al. | |
| 5,455,166 A | * 10/1995 | Walker | 435/91.2 |
| 5,472,881 A | 12/1995 | Beebe et al. | |
| 5,476,928 A | 12/1995 | Ward et al. | |
| 5,487,973 A | 1/1996 | Nilsen et al. | |
| 5,491,097 A | 2/1996 | Ribi et al. | |
| 5,494,810 A | * 2/1996 | Barany et al. | 435/91.52 |
| 5,552,270 A | 9/1996 | Khrapko et al. | |
| 5,565,552 A | 10/1996 | Magda et al. | |
| 5,571,568 A | 11/1996 | Ribi et al. | |
| 5,573,906 A | 11/1996 | Bannwarth et al. | |
| 5,591,578 A | 1/1997 | Meade et al. | |
| 5,595,908 A | 1/1997 | Fawcett et al. | |
| 5,601,982 A | 2/1997 | Sargent et al. | |
| 5,616,464 A | 4/1997 | Albagli et al. | |
| 5,620,850 A | 4/1997 | Bamdad et al. | |
| 5,681,702 A | 10/1997 | Collins et al. | |
| 5,705,346 A | 1/1998 | Okamoto et al. | |
| 5,705,348 A | 1/1998 | Meade et al. | |
| 5,741,700 A | 4/1998 | Ershov et al. | |
| 5,756,050 A | 5/1998 | Ershow et al. | |
| 5,767,259 A | 6/1998 | Albagli et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,224 A | 7/1998 | Collins et al. | |
| 5,780,234 A | 7/1998 | Meade et al. | |
| 5,824,473 A | 10/1998 | Meade et al. | |
| 5,846,717 A | 12/1998 | Brow et al. | |
| 5,851,772 A | 12/1998 | Mirzabekov et al. | |
| 5,854,033 A | 12/1998 | Lizardi | |
| 5,952,172 A | 9/1999 | Meade et al. | |
| 6,060,023 A | 5/2000 | Maracas | |
| 6,060,327 A | 5/2000 | Keen | |
| 6,071,699 A | 6/2000 | Meade et al. | |
| 6,087,100 A | 7/2000 | Meade et al. | |
| 6,096,273 A | 8/2000 | Kayyem et al. | |
| 6,107,080 A | 8/2000 | Lennox | |

FOREIGN PATENT DOCUMENTS

| | | |
|---|---|---|
| EP | 0 234 938 | 2/1987 |
| EP | 0 229 943 | 7/1987 |
| EP | 0 599 337 | 1/1994 |
| EP | 0515615 | 9/1996 |
| JP | 238166 | 10/1988 |
| JP | 6-41183 | 2/1994 |
| WO | 86/05815 | 10/1986 |
| WO | 90/05732 | 5/1990 |
| WO | 92/10757 | 6/1992 |
| WO | 93/10267 | 5/1993 |
| WO | 93/22678 | 11/1993 |
| WO | 94/22889 | 10/1994 |
| WO | 95/05480 | 2/1995 |
| WO | 95/15971 | 6/1995 |
| WO | 96/40712 | 12/1996 |
| WO | 97/01646 | 1/1997 |
| WO | 97/09337 | 3/1997 |
| WO | 97/27329 | 7/1997 |
| WO | 97/44651 | 11/1997 |
| WO | 98/04740 | 2/1998 |
| WO | 98/20162 | 5/1998 |
| WO | 98/27229 | 6/1998 |
| WO | 98/28444 | 7/1998 |
| WO | 98/35232 | 8/1998 |
| WO | 98/57159 | 12/1998 |
| WO | 99/14596 | 3/1999 |
| WO | 99/37819 | 7/1999 |
| WO | 99/67425 | 12/1999 |

OTHER PUBLICATIONS

Albers, W. M., et al., "Design of Novel Molecular Wires for Realizing Long–Distance Electron Transfer," *Bioeletrochemistry*, 42:25–33 (1997).

Allerman, K.S., et al., "Electrochemical Recitification at a Monolayer–Modified Electrode," *J. Phys. Chem*, 100:(42) 17050–17058 (1996).

Aizawa, M., et al., "Intergrated Molecular Systems for Biosensors," *Sensors and Actuators B*, B24 (Nos ⅓) part 1:1–5 (Mar. 1995).

Arkin, M., et al., "Evidence for Photoelectron Transfer Through DNA Intercalation," *J. Inorganic Biochem.* Abstracts, 6th International Conference on Bioinorganic Chemistry, 51(1) & (2):526 (1993).

Barisci, et al.,"Conducting Polymer Sensors," *TRIP*, 4(9):307–311 (1996).

Baum, R. M., "Views on Biological, Long–Range Electron Transfer Stir Debate," *C & EN*, pp 20–23 (1993).

Bechtold, R., et al., "Ruthenium–Modified Horse Heart Cytochrome c: Effect of pH and Ligation on the Rate of Intramolecular Electron Transfer between Ruthenium(II) and Heme(III)," *J. Phys. Chem.*, 90(16):3800–3804 (1986).

Bidan, "Electroconducting conjugated polymers: new sensitive matrices to build up chemical or electrochemical sensors. A Review.," *Sensors and Actuators*, B6:45–56 (1992).

Biotechnology and Genetics: Genetic Screening Integrated Circuit, *The Economist* (Feb. 25–Mar. 3, 1995).

Boguslavsky, L. et al., "Applications of redox polymers in biosensors," *Solid State Ionics*, 60:189–197 (1993).

Bowler, B. E., et al., "Long–Range Electron Transfer in Donor (Spacer) Acceptor Molecules and Proteins," *Progress in Inorganic Chemistry: Bioinorganic Chemistry*, 38:259–322 (1990).

Brun, A. M., et al., "Photochemistry of Intercalated Quaternary Diazaaromatic Salts," *J. Am. Chem. Soc.*, 113:8153–8159 (1991).

Bumm, et al., "Are Single Molecular Wires Conducting?," *Science* 271:1705–1707 (1996).

Cantor, C.R. et al., "Report on the Sequencing by Hybridization Workshop," *Genomics*, 13:1378–1383 (1992).

Carr, J.D., et al., "Novel Electrochemical Sensors for neutral Molecules," *Chem. Commun.*, 1649–1550 (1997).

Carter, et al., "Voltammetric Studies of the Interaction of Metal chelates with DNA. 2. Tris–Chelated Complexes of Cobalt (III) and Iron (II) with 10–Phenanthorile and 2,3'–Bipyridine," *J. Am. Chem. Soc.*, 11"8901–8911 (1989).

Chang, I–Jy, et al., "High–Driving–Force Electron Transfer in Metalloproteins: Intramolecular Oxidation of Ferrocytochrome c by Ru(2,2'–bpy)$_2$(im)(His–33)$^{3+}$," *J. Am. Chem. Soc.,* 113:7056–7057 (1991).

Chidsey, C.E.D., et al., "Free Energy and Temperature Dependence of Electron Transfer at the Metal Electrolyte Interface," *Science,* 251:919–923 (1991).

Davis, L. M., et al., "Electron Donor Properties of the Antitumour Drug Amsacrine as Studied by Fluorescence Quenching of DNA–Bound Ethidium," *Chem.–Biol. Interactions,* 62:45–58 (1987).

Davis, L. M., et al., "Elements of biosensor construction," *Enzyme Microb. Technol.* 17:1030–1035 (1995).

Degani et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.* 110:2615–2620 (1988).

Degani, Y., et al., "Electrical Communication between Redox Centers of Glucose Oxidase and Electrodes via Electrostatically and Covalently Bound Redox Polymers," *J. Am. Chem. Soc.,* 111:2357–2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.,* 91(6):1285–1288 (1987).

Deinhammer, R.S., et al., "Electrochemical Oxidation of Amine–containing compounds: A Route to the Surface Modification of glassy carbon electrodes," *Langmuir,* 10:1306–1313 (1994).

Dreyer, G. B., et al., "Sequence–specific cleavage of single–stranded DNA: Oligodeoxynucleotide–EDTA·Fe(II)," *Proc. Natl. Acad. Sci. USA,* 82:968–972 (1985).

Durham, B., et al., "Photoinduced Electron–Transfer Kinetics of Singly Labeled Ruthenium Bis(bipyridin) Dicarboxybipyridine Cytochrome c Derivatives," *Biochemistry,* 28:8659–8665 (1989).

Durham, B., et al., "Electron–Transfer Kinetics of Singly Labeled Ruthenium(II) Polypyridine Cytochrome c Derivatives," *American Chemical Society,* pp. 181–193 (1990).

Elias, H., et al.,"Electron–Transfer Kinetics of Zn–Substituted Cytochrome c and Its Ru(NH$_3$)$_5$(Histidine–33) Derivative," *J. Am. Chem. Soc.,* 110:429–434 (1988).

Farver, O., et al., "Long–range intramolecular electron transfer in azurins," *Proc. Natl. Acad. Sci. USA,* 86:6968–6972 (1989).

Fox, L. S., et al., "Gaussian Free–Energy Dependence of Electron–Transfer Rates in Iridium Complexes," *Science,* 247:1069–1071 (1990).

Fox, M. A., et al., "Light–Harvesting Polymer Systems," *C&EN,* pp. 38–48 (Mar. 15, 1993).

Francois, J–C., et al., "Periodic Cleavage of Poly(dA) by Oligothymidylates Covalently Linked to the 1,10–Phenanthroline–Copper Complex," *Biochemistry,* 27:2272–2276 (1988).

Friedman, A. E., et al., "Molecular 'Light Switch' for DNA: Ru(bpy)$_2$(dppz)$^{2+}$," *J. Am. Chem. Soc.,* 112:4960–4962 (1990).

Fromherz, P., et al., "Photoinduced Electron Transfer in DNA Matrix from Intercalated Ethidium to Condensed Methylviologen," *J. Am. Chem. Soc.,* 108:5361–5362 (1986).

Gardner, et al., "Application of conducting polymer technology in microsystems," *Sensors and Actuators,* A51:57–66 (1995).

Gregg, B. A., et al., "Cross–linked redox gels containing glucose oxidase for amperometric biosensor applications," *Anal. Chem.,* 62:258–263 (1990).

Gregg, B. A., et al., "Redox Polymer Films Containing Enzymes 1. A Redox–Conducting Epoxy Cement: Synthesis, Characterization, and Electrocatalytic Oxidation of Hydroquinone," *J. Phys. Chem.,* 95:5970–5975 (1991).

Hashimoto, et al., "Sequence–Specific Gene Detection with a Gold Electrode Modified with DNA Probes and an Electrochemically Active Dye," *Anal. Chem.* 66:3830–3833 (1994).

Hegner, et al., "Immobilizing DNA on gold via thiol modification for atomic force microscopy imaging in buffer solutions," *FEBS* 336(3):452–456 (1993).

Heller, A., et al., "Amperometric biosensors based on three–dimensional hydrogel–forming epoxy networks," *Sensors and Actuators,* 13–14:180–183 (1993).

Heller A., "Electrical Wiring of Redox Enzymes," *Acc. Chem. Res.,* 23:128–134 (1990).

Heller et al., "Fluorescent Energy Transfer Oligonucleotide Probes," *Fed. Proc.* 46(6):1968 (1987) Abstract No. 248.

Ho "DNA–Mediated Electron Transfer and Application to 'Biochip' Development," *Abstract. Office of Naval Research* (Report Date: Jul. 25, 1991) 1–4, RR04106.

Hobbs et al., "Polynucleotides Containing 2'–Amino–2'deoxyribose and 2'–Azido–2'–deoxyriose," *Biochemistry, 12*(25):5138–5145 (1973).

Hsung, et al., "Synthesis and Characterization of Unsymmetric Ferrocene–Terminated Phenylethynyl Oligomers," *Organometallics,* 14:4808–4815 (1995).

Hsung, et al., "Thiophenol Protecting Groups for the Palladium–Catalyzed Heck Reaction: Efficient Syntheses of Conjugated Arylthiols," *Tetrahedron Letters.* 36(26):4525–4528 (1995).

Jenkins et al., A Sequence–Specific Molecular Light Switch: Tebhering of an Oligonucleotide to a Dipyridophenazine Complex of Ruthenium (II), *J. Am. Chem. Soc.,* 114:8736–8738 (1992).

Johnston, D.H., et al., "Trans–Dioxorhenium (V)–Mediated Electrocatalytic Oxidation of DNA at Indium Tin–Oxide Electrodes: Voltammetric Detection of DNA Cleavage in Solution," *Inorg. Chem.* 33:6388–6390 (1994).

Katritzky, et al., "Pyridylethylation—A New Protection Method for Active Hydrogen Compounds," *Tetrahedron Letters,*25(12):1223–1226 (1984).

Kelley, S.O. and J.K. Barton, "Electrochemistry of Methylene Blue Bound to a DNA–Modified Electrode," *Bioconjugate Chem.,* 8:31–37 (1997).

Kojima et al., "A DNA Probe of Ruthenium Bipyridine Complex Using Photocatalytic Activity,"*Chemistry Letter,* pp 1889–1982 (1989).

Korri–Youssoufi, H., et al., "Toward Bioelectronics: Specific DNA Recognition Based on an Oligonucleotide–Functionalized Polypyrrole," *J. Am. Chem.* 119:(31) 7388–7389 (1997).

Laviron, E., "A.C. Polarography and Faradaic Impedance of Strongly Adsorbed Electroactive Species. Part I: Theoretical and Experimental Study of a Quasi–Reversible Reaction in the Case of a Langmuir Isotherm," *J. Electroanal. Chem.,* 97:135–149 (1979).

Laviron, E., "A.C. Polarography and Faradaic Impedance of Strongly Adsorbed Electoactive Species. Part III: Theoretical Complex Plane Analysis for a Surface Redox Reaction," *J. Electroanal. Chem.,* 105:35–42 (1979).

Lee, et al., "Direct Measurement of the Forces Between Complementary Strands of DNA," *Science,* 266:771–773 (1994).

Lenhard, J.R., et al., "Part VII Covalent Bonding of a Reversible–Electrode Reactanbt to Pt Electrodes Using an organosilane Reagent" *J. Electronal. Chem.,* 78:195–201 (1977).

Lincoln, P., et al., "Short–Circuiting the Molecular Wire: Cooperative Binding of Δ-[Rh(phen)$_2$dppz]$^{2+}$ and Δ-[Rh(phi)$_2$dppz]$^{3+}$ to DNA," *J. Am. Chem. Soc.,* 119:1454–1455 (1997).

Lipkin "Identifying DNA by the Speed of Electrons," *Science News,* 147(8):117 (1995).

Maskos, et al., "Oligonculeotide hybridisations on glass supports: a novel linker for oligonucleotide synthesis and hybridisation properties of oligonucleotides synthesised in situ," *Nucleic Acids Research,* 20(7):1679–1684 (1992).

McGee, et al., "2'–Amino–2'–deoxyuridine via an Intramolecular Cyclization of a Trichloroacetimidate," *J. Org. Chem.,* 61:781–785 (1996).

Meade, T. J.,"Driving–Force Effects on the Rate of Long–Range Electron Transfer in Ruthenium–Modified Cytochrome c," *J. Am. Chem. Soc.,* 111:4353–4356 (1989).

Meade, T. J., et al., "Electron Transfer through DNA: Site–Specific Modification of Duplex DNA with Ruthenium Donors and Acceptors," *Angew Chem. Int. Ed. Engl.,* 34:352 (1995).

Mestel, "'Electron Highway' Points to Identity of DNA," *New Scientist,* p. 21 (1995).

Millan, et al., "Voltammetric DNA Biosensor for Cystic Fibrosis Based on a Modified Carbon Paste Electrode," *Anal. Chem.,* 66:2943–2948 (1994).

Millan, K.M., et al., "Covalent Immobilization of DNA onto Glassy Carbon Electrodes," *Electroanalysis,* 4:929–932 (1992).

Millan, K.M. and Mikkelsen, S.R., "Sequence–Selective Biosensor for DNA Based on Electroactive Hybridization Indicators," *Anal. Chem.,* 65:2317–2323 (1993).

Miller, C., "Absorbed ω–Hydroxy Thiol Monolayers on Gold Electrodes: Evidence for Electron Tunneling to Redox Species in Solution," *J. Phys. Chem.,* 95:877–886 (1991).

Murphy, C. J., et al., "Long–Range Photoinduced Electron Transfer Through a DNA Helix," *Science,* 262:1025–1029 (1993).

Mucic, R.C., et al., "Synthesis and Characterizsation of DNA with Ferrocenyl Groups Attached to Their 5'–Termini: Electrochemical Characterization of a Redox–Active nucleotide Monolayer," *Chem. Commun.,* 555–557 (1996).

Napier, M.E., et al., "Probing Bionolecule Tecognition with Electron Transfers Electrochemical Sensors for DNA Hybridization," *Bioconjugate Chem* 8:905–913 (1997).

Orellana, G., et al., "Photoinduced Electron Transfer Quenching of Excited Ru(II) Polypyridyls Bound to DNA: The Role of the Nucleic Acid Double Helix," *Photochemistry and Photobiology,* 54(4):499–509 (1991).

Palecek, "From Polarography of DNA to Microanalysis with Nucleic Acid–Modified Electrodes," *Electroanalysis.* 8(1):7–14 (1996).

Paterson, "Electric Genes: Current Flow in DNA Could Lead to Faster Genetic Testing," *Scientific American,* 33–34 (May 1995).

Purugganan, M. D., et al., Accelerated Electron Transfer Between Metal Complexes Mediated by DNA, *Science,* 241:1645–1649 (1988).

Reimers, J.R., et al., "Towards Efficient Molecular Wires and Switches: The Brooker Ions," *BioSystems* 35:107–111 (1995).

Rhodes, D. And A. Klug, "Helical Periodicity of DNA Determined by Enzyme Digestion," *Nature,* 286:573–578 (1980).

Risser, S. M., et al., "Electron Transfer in DNA: Predictions of Exponential Growth and Decay of Coupling with Donor–Acceptor Distance," *J. Am. Chem. Soc.,* 115(6):2508–2510 (1993).

Sato, Y., et al., "Unidirectional Electron Transfer at Self–Assembled Monolayers of 11–Ferrocenyl–1– undecanethiol on Gold," *Bull. Chem. Soc. Jpn.,* 66(4):1032–1037 (1993).

Satyanarayana, S., et al., "Neither Δ– nor Λ–Tris(phenanthroline)ruthenium(II) Binds to DNA by Classical Intercalation," *Biochemistry,* 31(39):9319–9324 (1992).

Schlereth, D.D., et al., "Self–Assembled Monolayers with Biospecific Affinity for NAD (H)–Dependent Dehydrogenases: Characterization by Surface Plasmon Resonance Combined with Electrochemistry 'in situ'," *Journal of Electroanalytical Chemistry* 444:231–240 (1998).

Schreiber, et al., "Bis(purine) Complexes of trans–a$_2$Pt$^{II}$: Preparation and X–ray Structures of Bis(9–methyladenine) and Mixed 9–Methyladenine, 9–Methylguanine Complexes and Chemistry Relevant to Metal–Modified Nucelobase Triples and Quartets," *J. Am. Chem. Soc.* 118:4124–4132 (1996).

Schuhmann, W., et al., "Electron Transfer between Glucose Oxidase and Electrodes via Redox Mediators Bound with Flexible Chains to the Enzyme Surface," *J. Am. Chem. Soc.,* 113:1394–1397 (1991).

Schumm, et al., "Iterative Divergent/Convergent Approach to Linear Conjugated Oligomers by Successive Doubling of the Molecular Length: A Rapid Route to a 128 Å–Long Potential Molecular Wire," *Angew. Chem. Int. Ed. Engl.,* 33(11):1360–1363 (1994).

Sigel, G.B., et al., "A Self–Assembled Monolayer for the Binding and Study of Histidine–Tagged Proteins by Surface Plasmon Resonance," *Analytical Chemistry* 68:(3) 490–497 (1996).

Southern, E.M., et al., "Arrays of Complementary Oligonucleotides for Analysing the Hybridisation Hehavior of nucleic Acids," *Nucleic Acids Research* 22:(8) 1368–1373 (1994).

Strobel, S. A., et al., "Site–Specific Cleavage of a Yeast Chromosome by Oligonucleotide–Directed Triple–Helix Formation," *Science,* 249:73–75 (1990).

Su, et al., "Interfacial Nucleic Acid Hybridization Studied by Random Primer $^{32}$P Labelling and Liquid–Phase Acoustic Network Analysis," *Analytical Chemistry,* 66(6):769–777 (1994).

Takeda, H., et al., "Preparation of 1–Alkynyl 2–(Trimethylsilyl)ethyl Sulfides as Thiolare Anion Precursors for Self–Asdsembled Monolayers," *Tetrahedron Letters* 39:3701–3704 (1998).

Telser, J., et al., "DNA Duplexes Covalently Labeled at Two Sites: Synthesis and Characterization by Steady–State and Time–Resolved Optical Spectroscopies," *J. Am. Soc.,* 111:7226–7232 (1989).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements," *J. Am. Chem. Soc.,*111:7221–7226 (1989).

Thara, T., et al., "Gene Sensor using Ferrocenyl Oligonucleotide," *Chem. Commun.,* 1609–1610 (1997).

Tour, "Conjugated Macromolecules of Precise Length and Constitution. Organic Synthesis for the Construction of Nanoarchitectures," *Chem. Rev.,* 96:537–553 (1996).

Tour, et al., "Self–Assembled Monolayers and Multilayers of Conjugated Thiols, α–ω–Dithiols, and Thioacetyl–Containing Adsorbates. Understanding Attachments between Potential Molecular Wires and Gold Surfaces," *J. Am. Chem. Soc.,* 117:9529–9534 (1995).

Tullius, T.D. and B.A. Dombroski, "Iron(II) EDTA Used to Measure the Helical Twist Along Any DNA Molecule," *Science,* 230:679–681 (1985).

Turro, N., et al. "Photoelectron Transfer Between Molecules Adsorbed on Restricted Spaces,"*Photochem. Convers. Storage Sol. Energy, Proc. Int. Conf., 8th,* pp 121–139 (1990).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.,* 24:332–340 (1991).

Uosake, K., et al., "A Self–Assembled Monolayer of Ferrocenylalkane Thiols on Gold as an Electron Mediator for the Reduction of Fe(III)–EDTA in Solution," *Electrochemica Acta.,* 36(11/12):1799–1801 (1991).

Van Ness, J., et al., "A Versatile Solid Support System for Oligodeoxynucleotide Probe–Based Hybridization Assays," *Nucleic Acids Research,* 19(12):3345–3349 (1991).

Weber, et al., "Voltammetry of Redox–Active Groups Irreversibly Adsorbed onto Electrodes. Treatment Using the Marcus Relation between Rate and Overpotential," *Anal. Chem.* 66:3164–3172 (1994).

Williams, et al., "Studies of oligonucleotide interations by hybridisation to arrays: the influence of dangling ends on duplex yield," *Nucleic Acids Research,* 22(8):1365–1367 (1994).

Winkler, J. R., et al. "Electron Transfer in Ruthenium–Modified Proteins," *Chem. Rev.,* 92:369–379 (1992).

Xu, et al., "Immobilization of DNA on an Aluminum(III) alkaneobisphosphonate Thin Film with Electrogenerated Chemiluminescent Detection," *J. Am. Chem. Soc.,* 116:8386–8387 (1994).

Xu, et al., "Immobilization and Hybridization of DNA on an Aluminum(III) Alkanebisphosphonate Thin Film with Electrogenerated Chemiluminescent Detection," *J. Am. Chem. Soc.,* 117:2627–2631 (1995).

Yang, et al., "Growth and Characterization of Metal(II) Alkaneobisphosphonate Multilayer Thin Films on Gold Surfaces," *J. Am. Chem. Soc.,* 115:11855–11862 (1993).

Zhou, et al., "Fluorescent Chemosensors Based on Energy Migration in Conjugated Polymers: The Molecular Wire Approach to Increased Sensitivity," *J. Am. Chem. Soc.,* 117:12593–12602 (1995).

Clery, "DNA Goes Electric," *Science,* 267:1270 (1995).

*Commerce Business Daily* Issue of Sep. 26, 1996 PSA#1688.

DATABASE WPI, Derwent Publications Ltd., London, GB; AN 88–320199 & JP, A, 53 238 166 (Mitsubishi Denki KK), Oct. 4, 1988.

Chrisey, et al., "Covalent attachment of synthetic DNA to self–assembled monolayer films," *Nucleic Acids Research,* 24(15):3031–3039 (1996).

Chidsey et al., "Coadsorption of Ferrocene–Terminated and Unsubstituted Alkanethiols on Gold Electroactive Self–Assembled Monolayers," *J. Am. Chem. Soc.,* 112:4301–4306 (1990).

Walker, et al., *A Chemiluminescent DNA Probe Test Based on Strand Displacement Amplification,* Molecular Methods for Virus Detection, (1995), 329–349.

Sorscher, D. *DNA Amplification Techniques, An Overview.* Molecular Diagnostics: For the Clinical Laboratorian. Ed. W.B. Coleman and G.J. Tsongalis, Humana Press, Inc., Totowa, NJ. pp. 89–101 (1997).

Uto, et al., "Electrochemical Analysis of DNA Amplified by the Polymerase Chain Reaction with a Ferrocenylated Oligonucleotide," *Analytical Biochemistry,* 250:122–124 (1997).

Zhang et al., "Amplification of target–specific, ligation–dependent circular probe," *Gene,* 211:277–285 (1998).

Baner et al., "Signal amplification of padlock probes by rolling circle replication," Nucleic Acids Research, 26(22):5073–5078 (1998).

Daubendiek et al., "Generation of catalytic RNAs by rolling transcription of synthetic DNA nanocircles," Nature Biotechnology, 15:273–277 (1997).

Lizardi et al., Mutation detection and single–molecule counting using isothermal rollling–circle amplification, Nature Genetics, 19:225–232 (1998).

Blonder et al., "Three–dimensional Redox–Active layered Composites of Au–Au, Ag–Ag and Au–Ag Colloids," Chem. Commun. 1393–1394 (1998).

Drobyshev, A. et al., "Sequence Analysis by Hybridization with Oligonucleotide Microchip: Identification of β–thalassemia Mutations," Gene, 188:45–52 (1997).

Dubiley, S. et al., "Fractionation, phosphorylation and Ligation on Oligonucleotide Microchips to Enhance Sequencing by Hybridization," Nucleic Acids Research, 25(12):2259–2265 (1997).

Elghanian et al., "Selective Colorimetric Detection of Polynucleotides Based on the Distance–Dependent Optical Properties of Gold Nanoparticles," Science, 277:1078–1081 (1997).

Fotin, A. et al., "Parallel Thermodynamic Analysis of Duplexes on Oligodeoxyribonucleotide Microchips," Nucleic Acids Research, 26(6):1515–1521 (1998).

Guschin, D. et al., "Manual Manufacturing of Oligonucleotide, DNA, and Protein Microchips," Analytical Biochemistry, 250:203–211 (1997).

Guschin, D. et al., "Oligonucleotide Microchips as Genosensors for Determinative and Environmental Studies in Microbiology," 63(6):2397–2402 (1997).

Kamat et al., "Photochemistry on surfaces: 2. Intermolecular transfer on colloidal alumina–coated silica particles," J. Phys. Chem, 93(4):1405–1409 (1989).

Livshits, M. et al., "Theoretical Analysis of the Kinetics of DNA Hybridization with Gel–Immobilized Oligonucleotides," Biophysical Journal, 71:2795–2801 (1996).

Mirkin et al., "A DNA–based Method for Ratioally Assembling Nanoparticles into Macroscopic Materials," Nature, 382:607–609 (1996).

Mirzabekov, A. et al., "Dna Sequencing by Hybridization—a Megasequencing Method and a Diagnostic Tool," Tibtech, 12:27–32 (1994).

Mitchell et al., "Programmed Assembly of DNA Functionalized Quantum Dots," *J. Am. Chem. Soc.,* 121:8122–8123 (1999).

Mucic et al., "DNA–Directed Synthesis of Binary Nanoparticle Network Materials," *J. Am. Chem. Soc.,* 120:12674–12675 (1998).

Parinov, S., DNA Sequencing by Hybridization to Microchip octa– and Decanucleotides Extended by Stacked Pentanucleotides, Nucleic Acids Research, 24(15):2998–3004 (1996).

Proudnikov, D. "Immobilization of DNA in Polyacrylamide Gel for the manufacture of DNA and DNA–Oligonucleotide Microchips," Analytical Biochemistry, 259:34–41 (1998).

Proudnikov, D. et al., "Chemical Methods of DNA and RNA Fluorescent Labeling," Nucleic Acids Research, 24(22):4535–4542 (1996).

Storhoff et al., "One–Pot Colorimetric Differentiation of Polynucleotides with Single Base Imperfections Using Gold Nanoparticles Probes," J. Am. Chem. Soc., 120:1959–1964 (1998).

Timofeev, E. et al., "Regioselective Immobilization of Short Oligonucleotides to Acrylic Copolymer Gel," Nucleic Acids Research, 24(16):3142–3148 (1996).

Timofeev, E. et al., "Methidium Intercalator Inserted into Synthetic Oligonucleotides," Tetrahedron Letters, 37(47):8467–8470 (1996).

Velev et al., "In Situ Assembly of Colloidal Particles into Miniaturized Biosensors," The ACS Journal of Surfaces and Colloids, Langmuir, 15(11):3693–3698 (1999).

Watson et al., "Hybrid Nanoparticles with Block Copolymer Shell Structures," J. Am. Chem. Soc., 121:462–463 (1999).

Yershov, G. et al., "DNA Analysis and Diagnostics on Oligonucleotide Microchips," Proc. Natl. Acad. Sci. USA, 93:4913–4918 (1996).

Sloop et al., "Metalloorganic labels for DNA sequencing and mapping," New. J. Chem., 18: 317–326 (1994). (added Apr. 23, 2001).

Martinez–Salazar, J. of Bacteriology, 178(7): 1800–1808, 1996.*

Sambrook et al, Molecular Cloning, A Laboratory Manual, $2^{nd}$ Ed, Cold Spring Harbor pp. 17.1–17.44, 1989.*

Plotkin, S.A et al. (eds) "Vaccines", W.B. Saunders, Philadelphia Chapter 29, p. 571, Second Full Paragraph, 1988.*

* cited by examiner

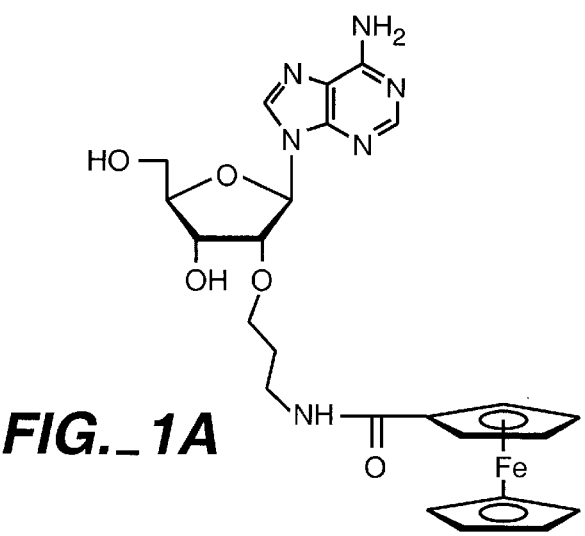
FIG._1A
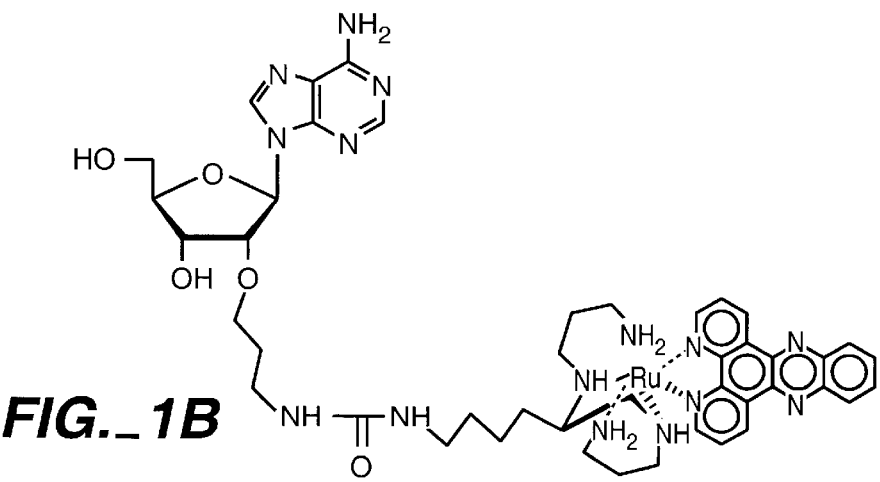
FIG._1B
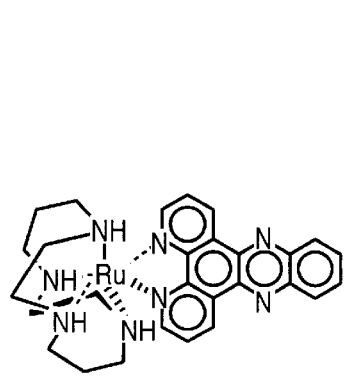
FIG._1C
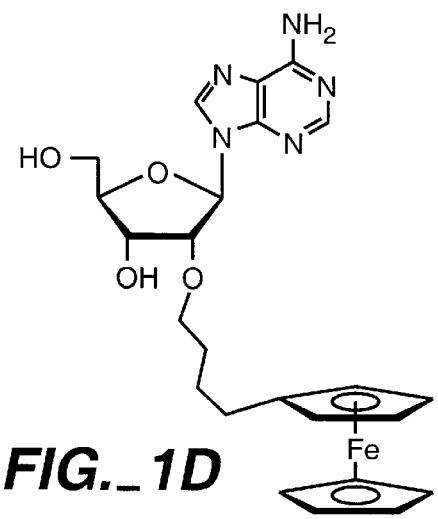
FIG._1D

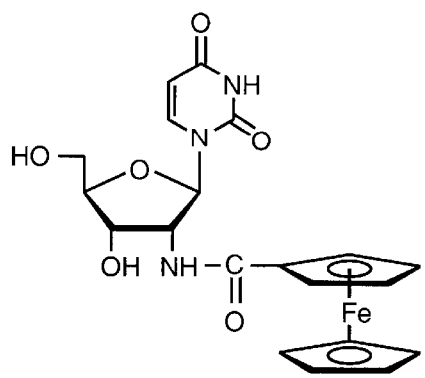
FIG._1E
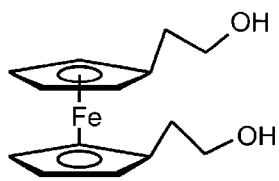
FIG._1F
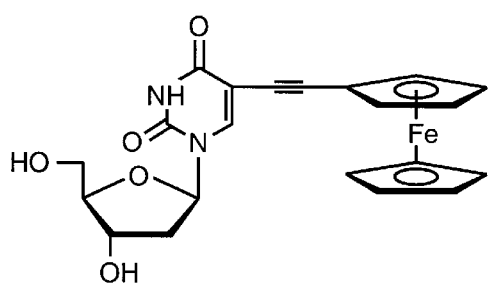
FIG._1G
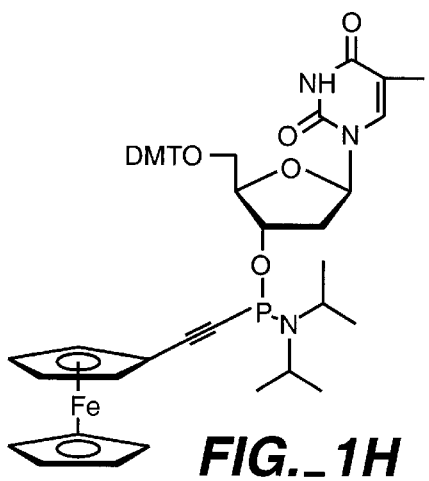
FIG._1H
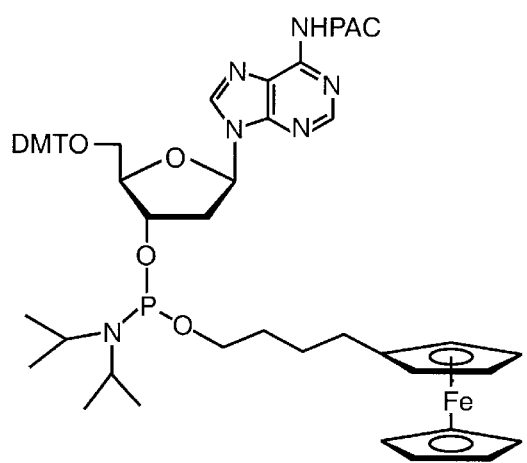
FIG._1I
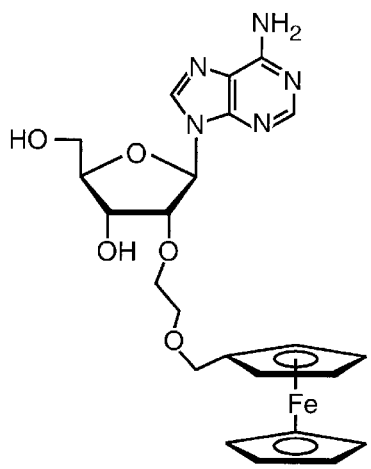
FIG._1J

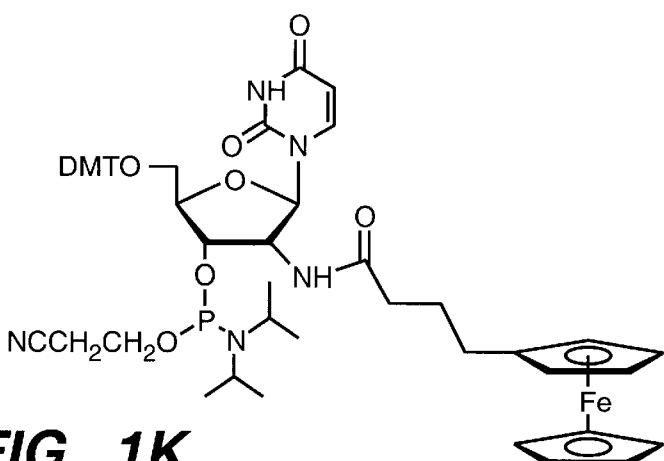
*FIG._1K*
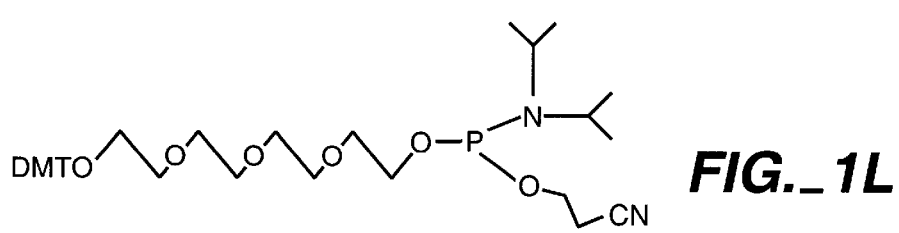
*FIG._1L*
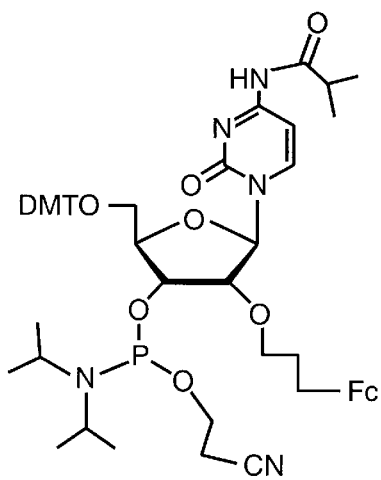
*FIG._1M*
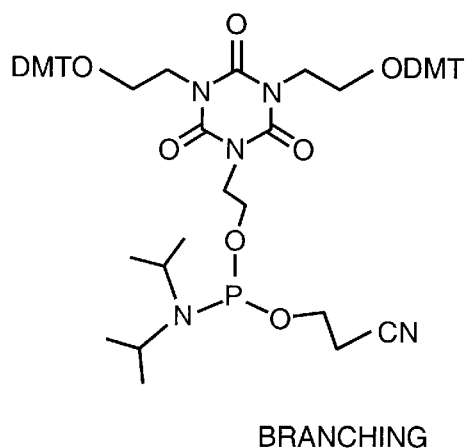
BRANCHING
*FIG._1N*
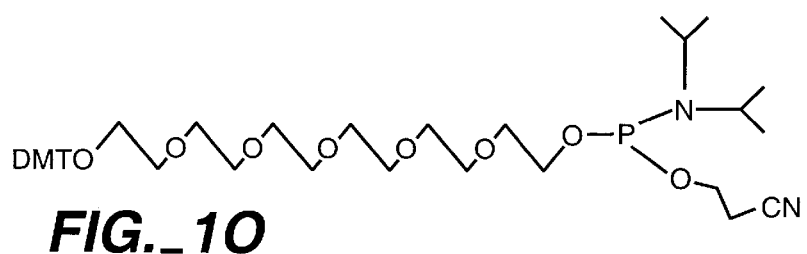
*FIG._1O*

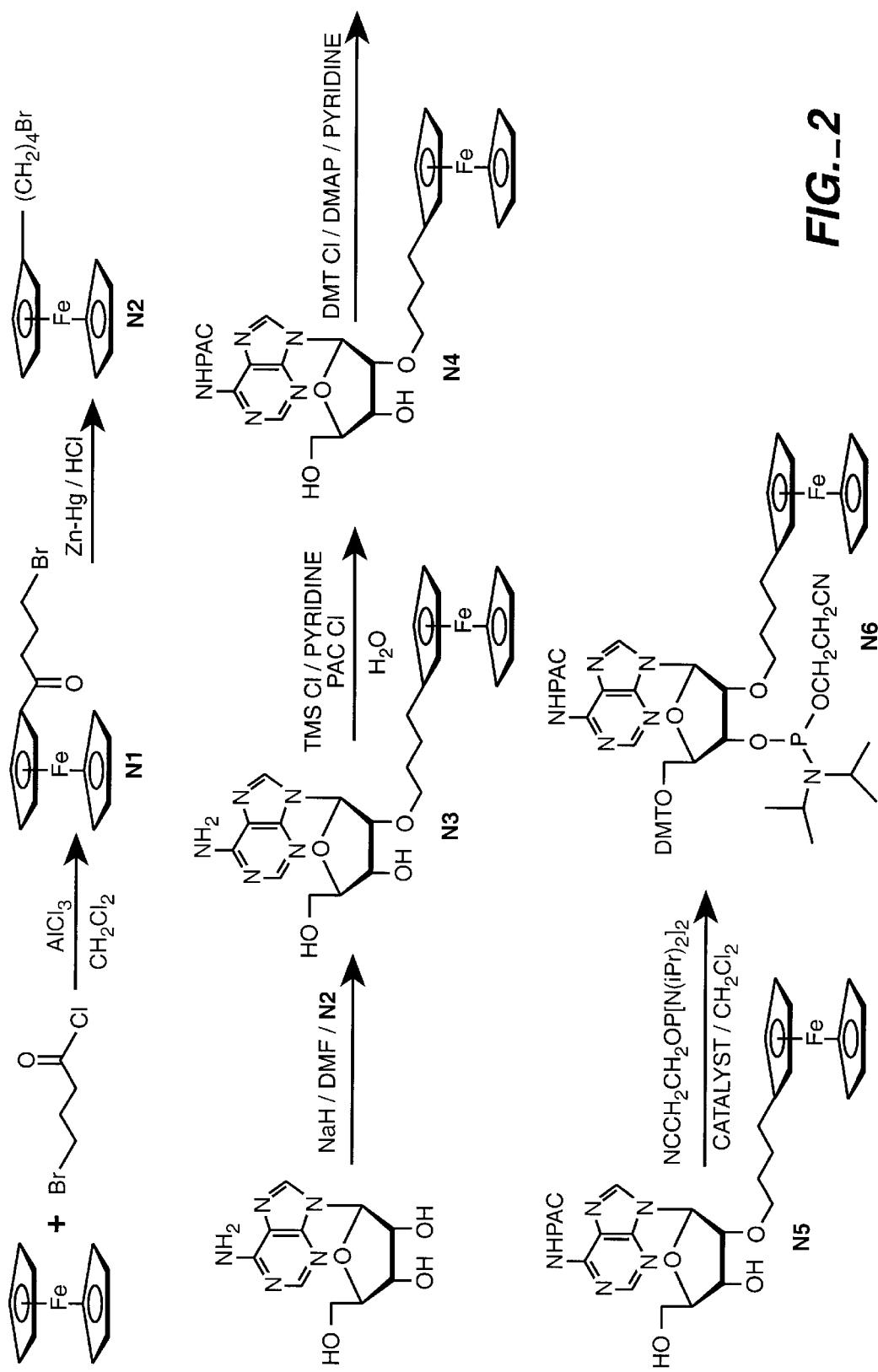
FIG. _2

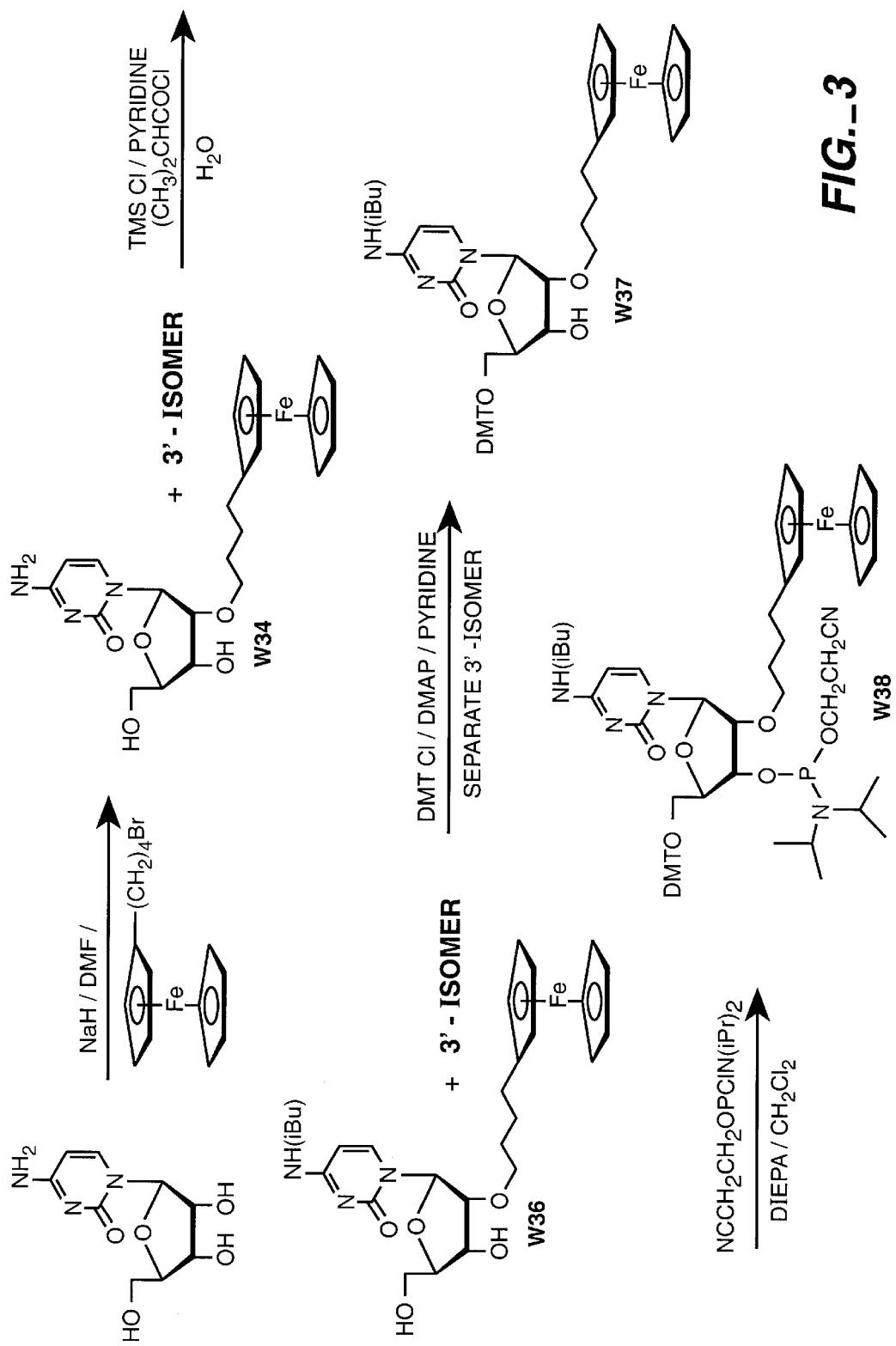
FIG._3

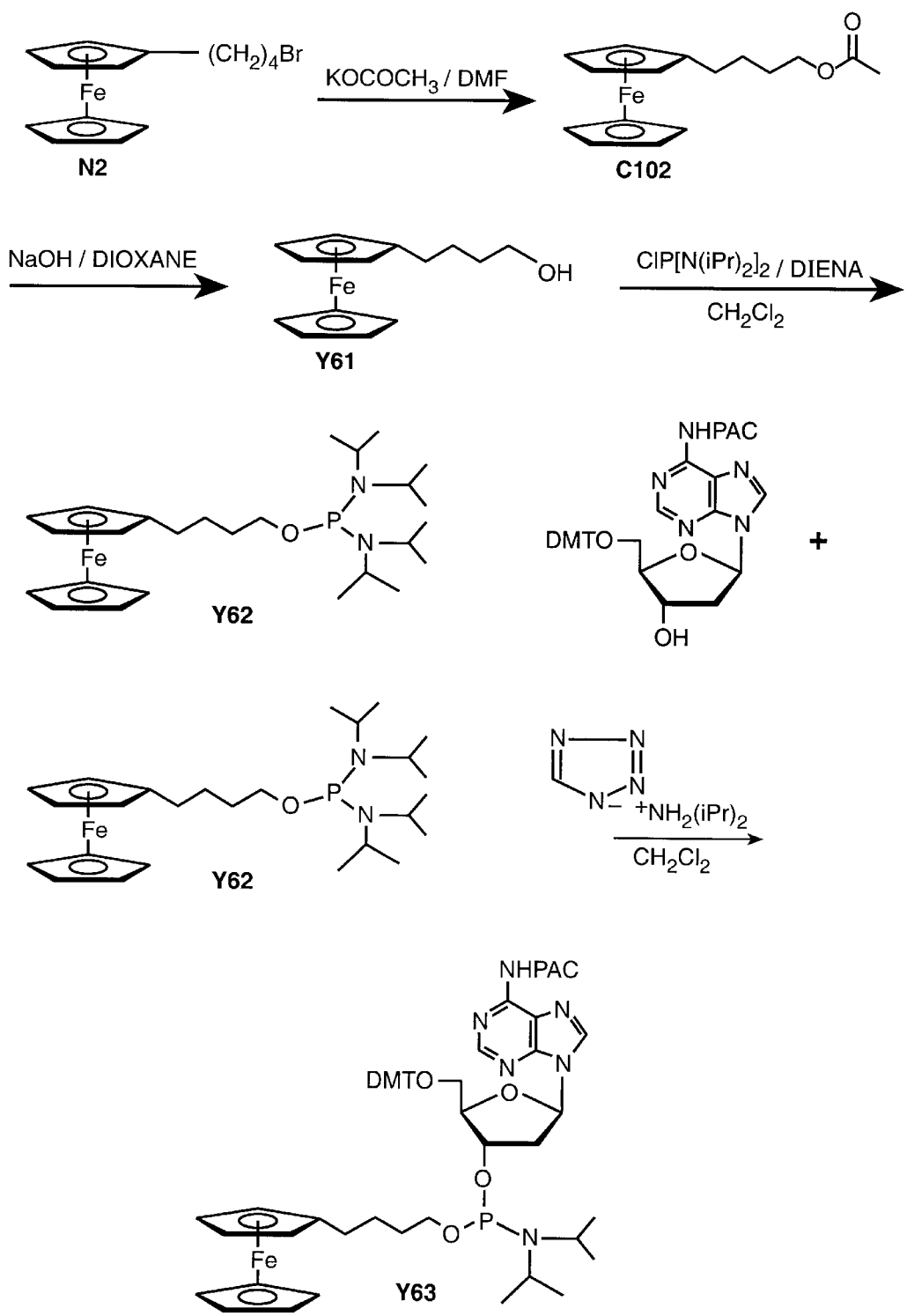
FIG._4

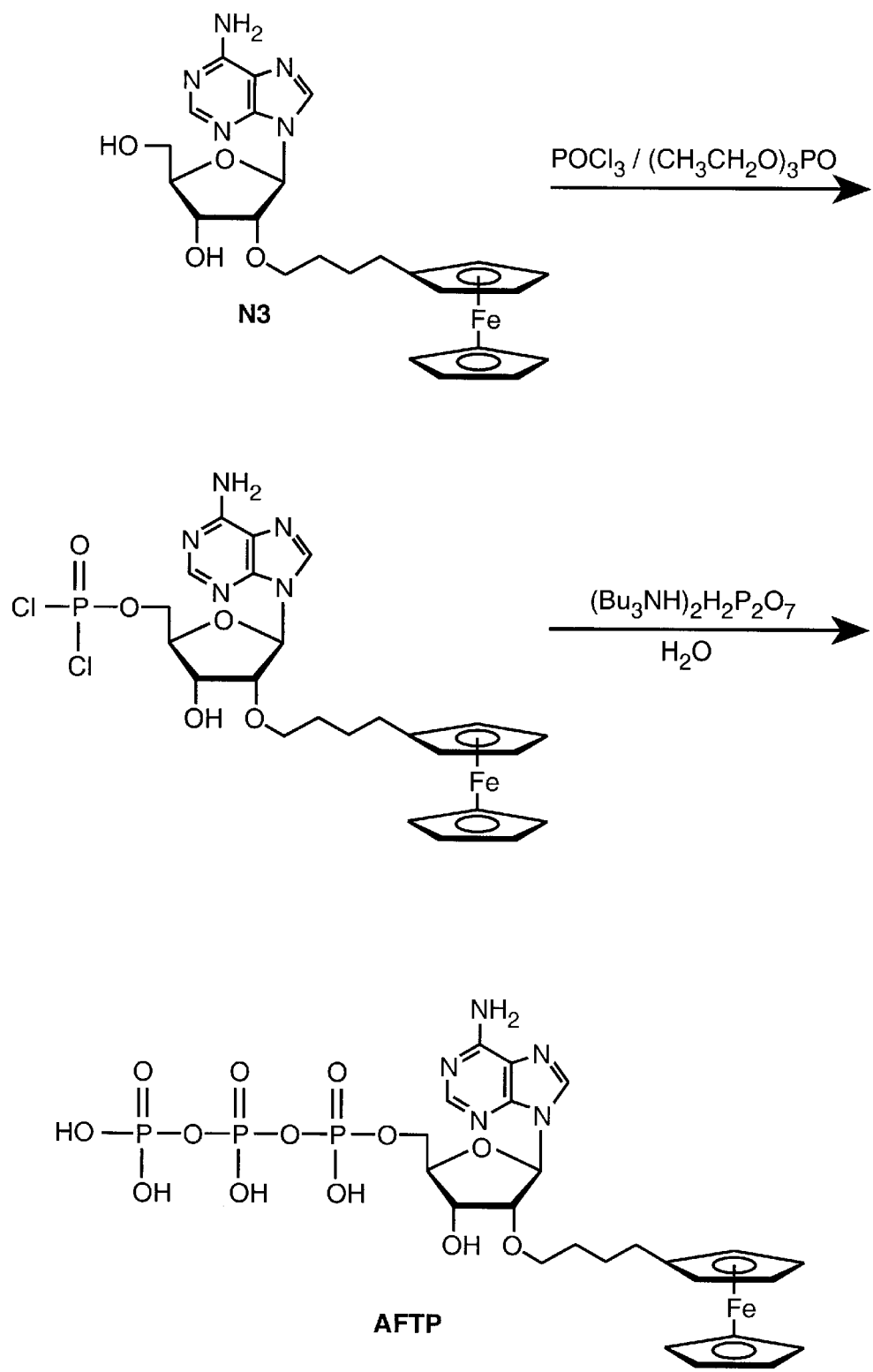
FIG._5

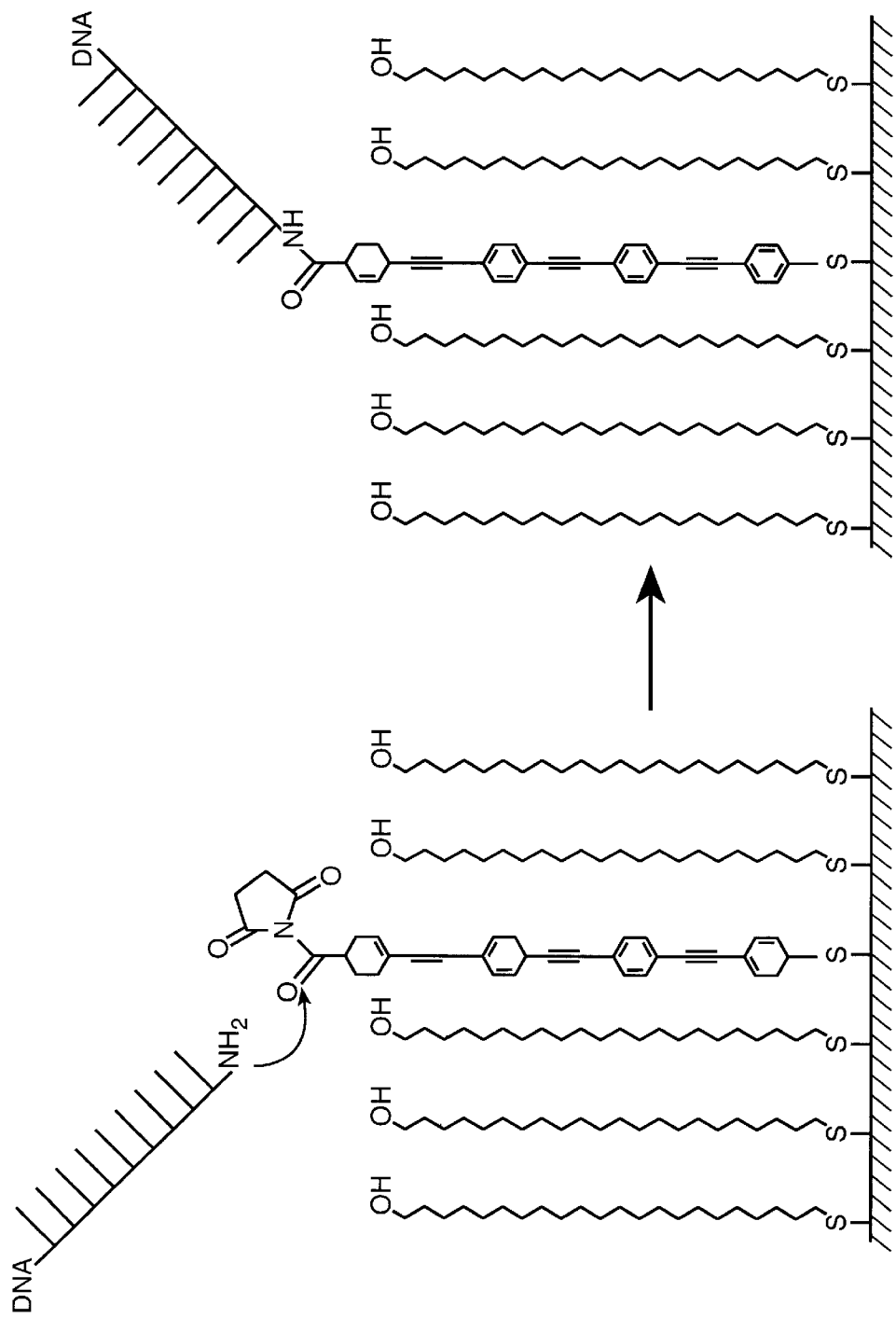
FIG._6

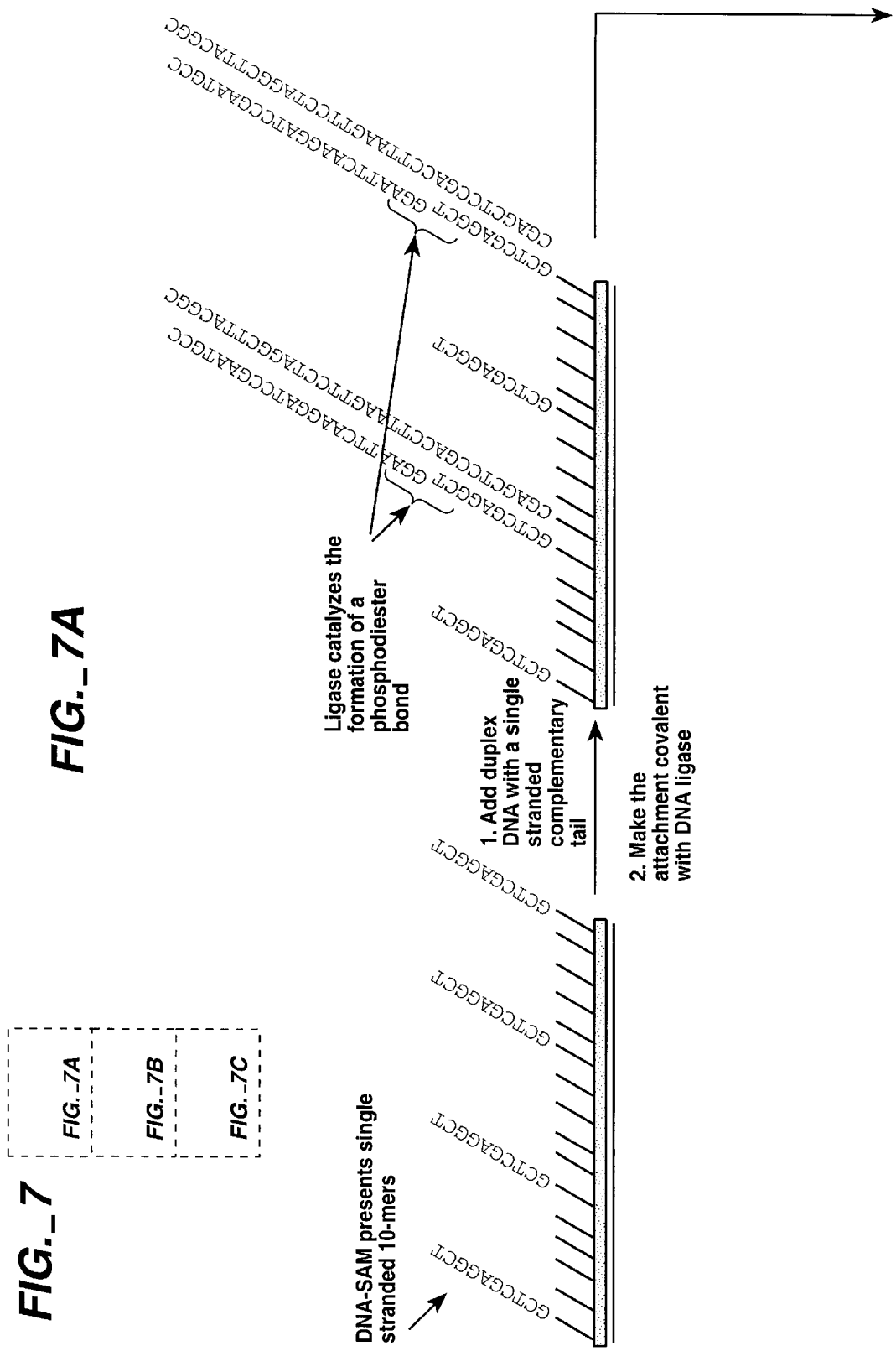

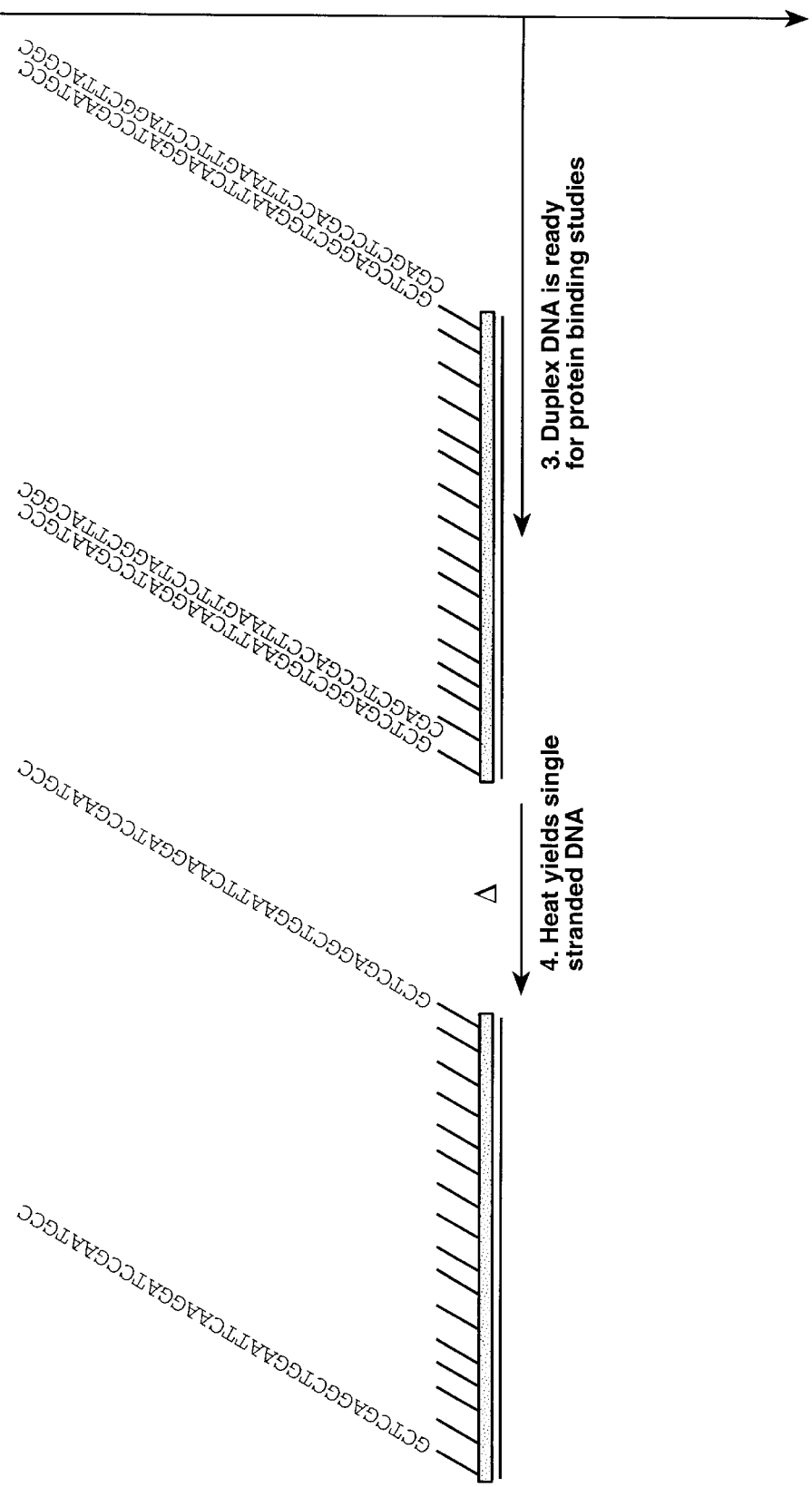
FIG._7B

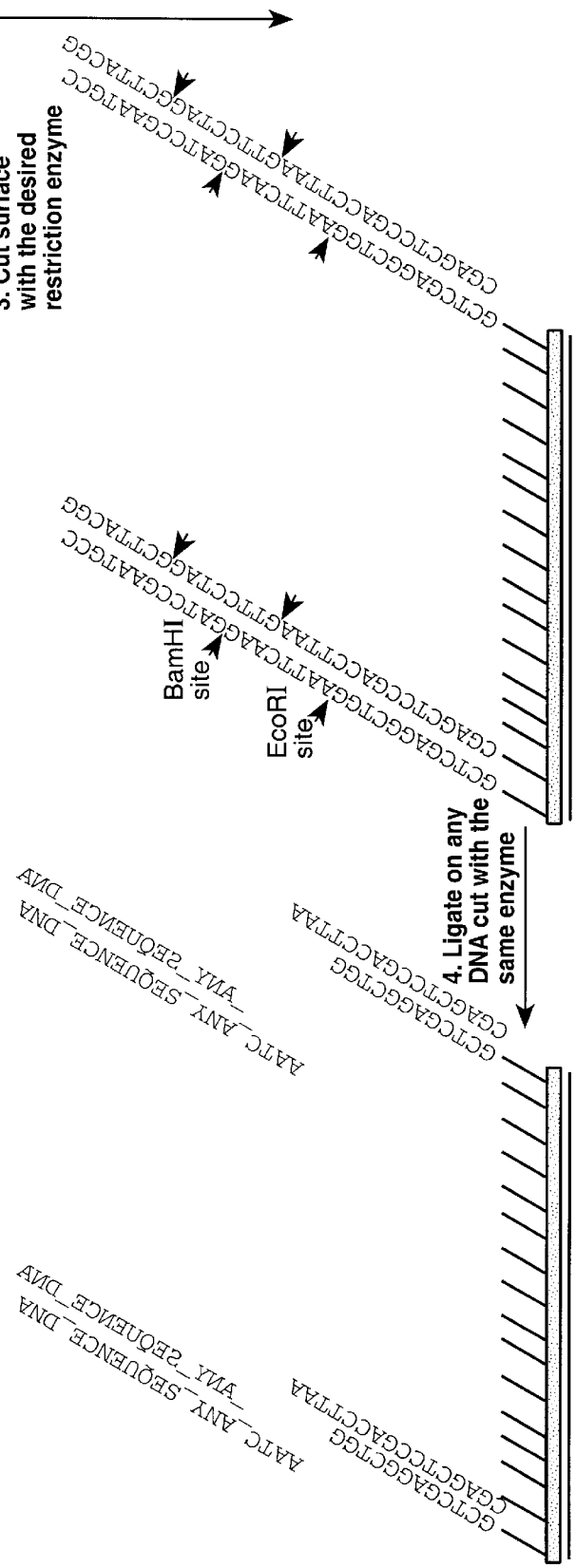
FIG._7C

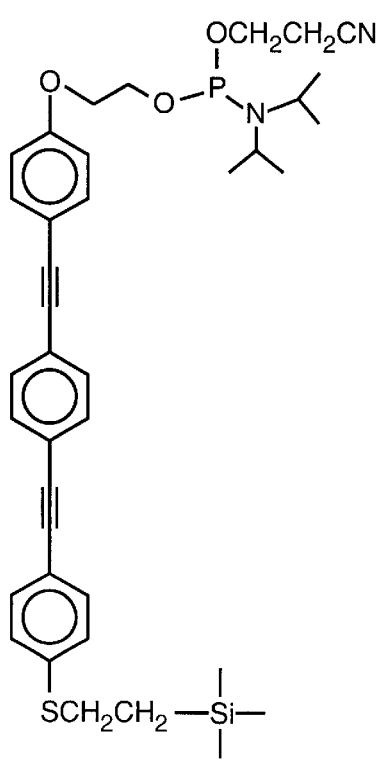
5' - ATTACHMENT
*FIG._8A*
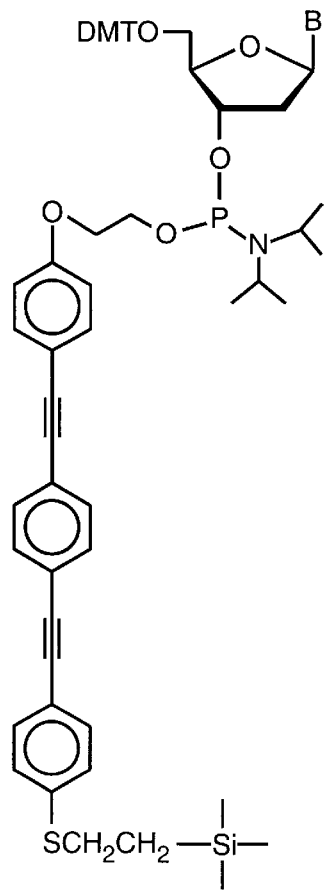
ANY POSITION ATTACHMENT
*FIG._8B*

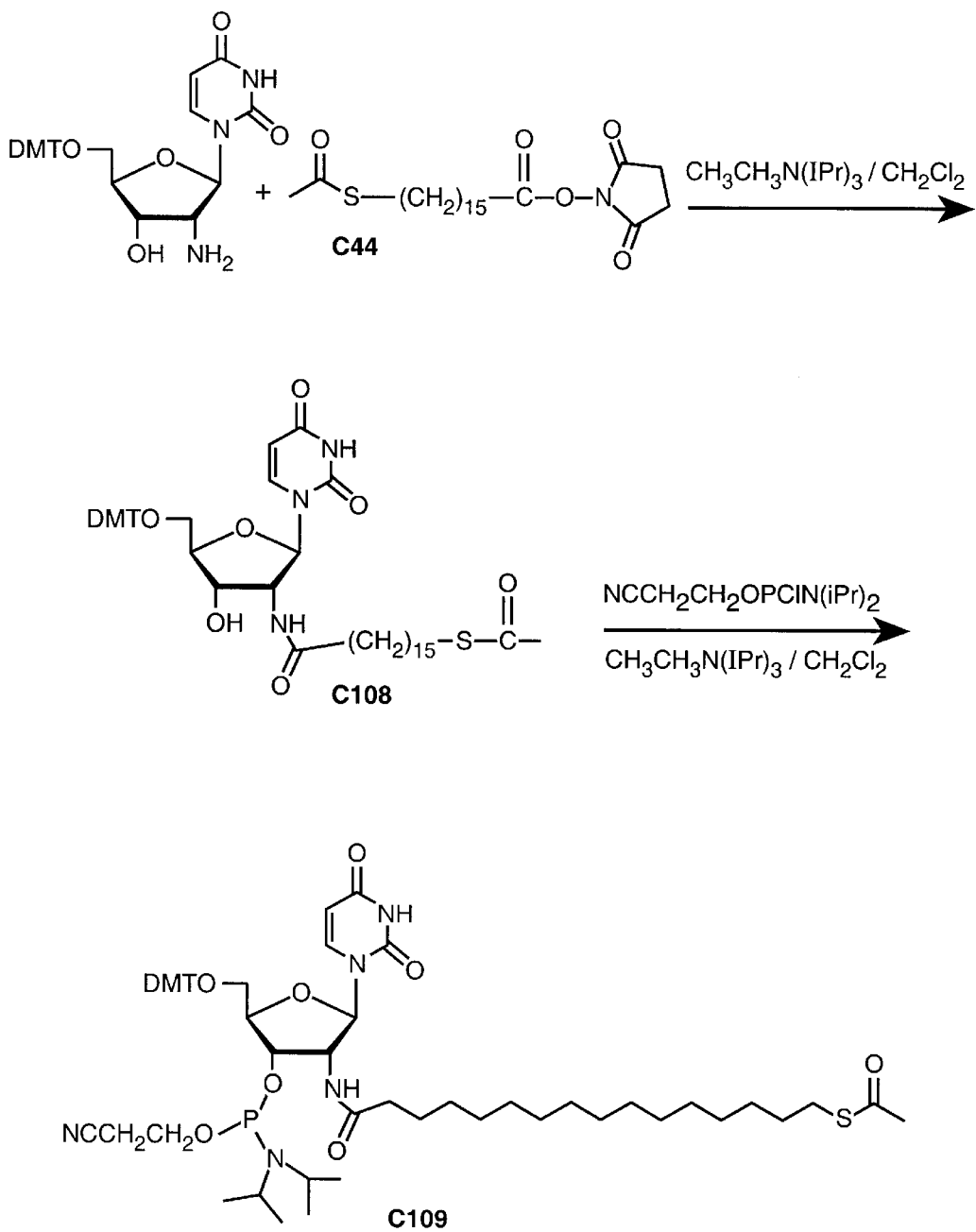
FIG._9

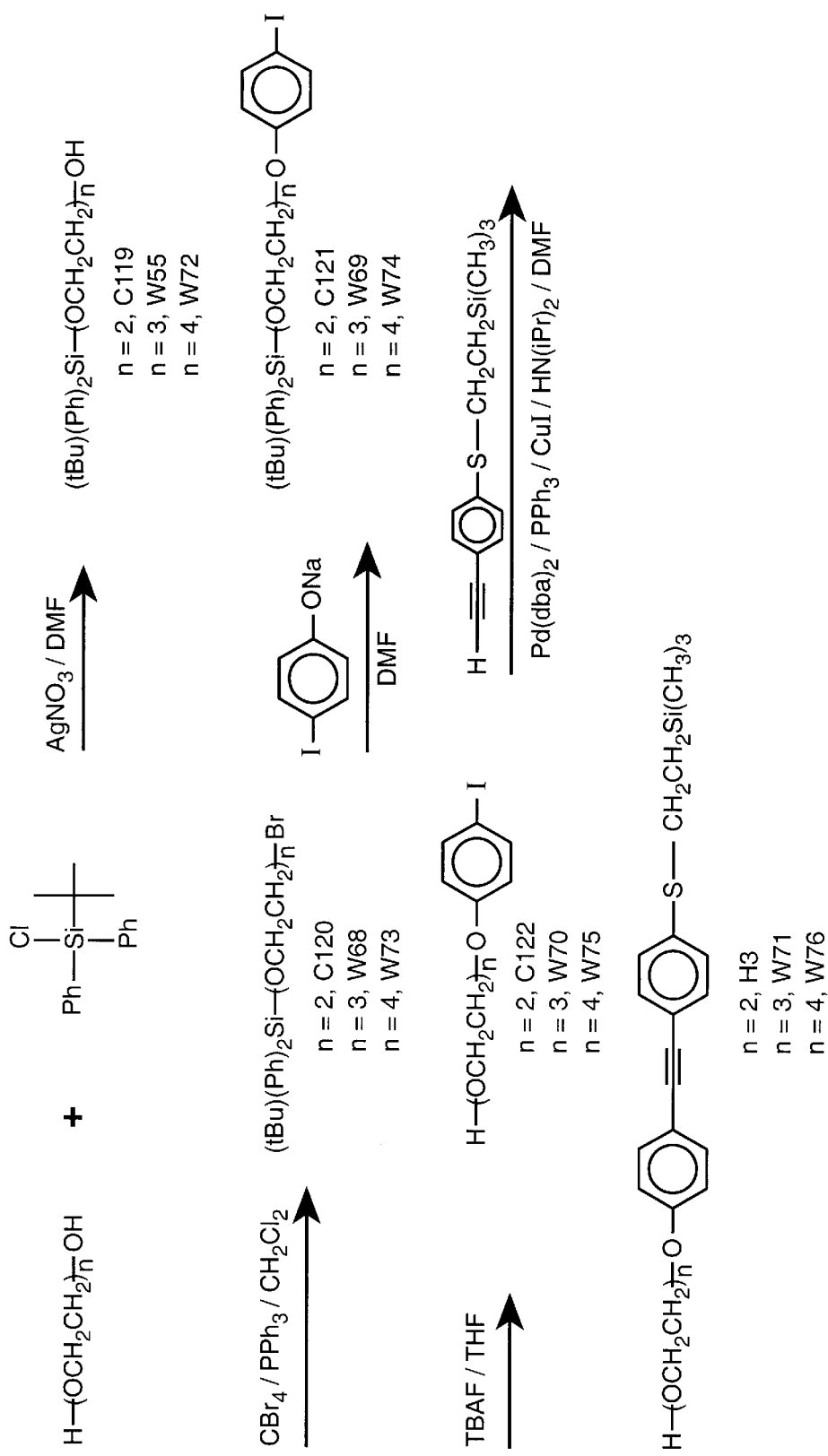
FIG._10

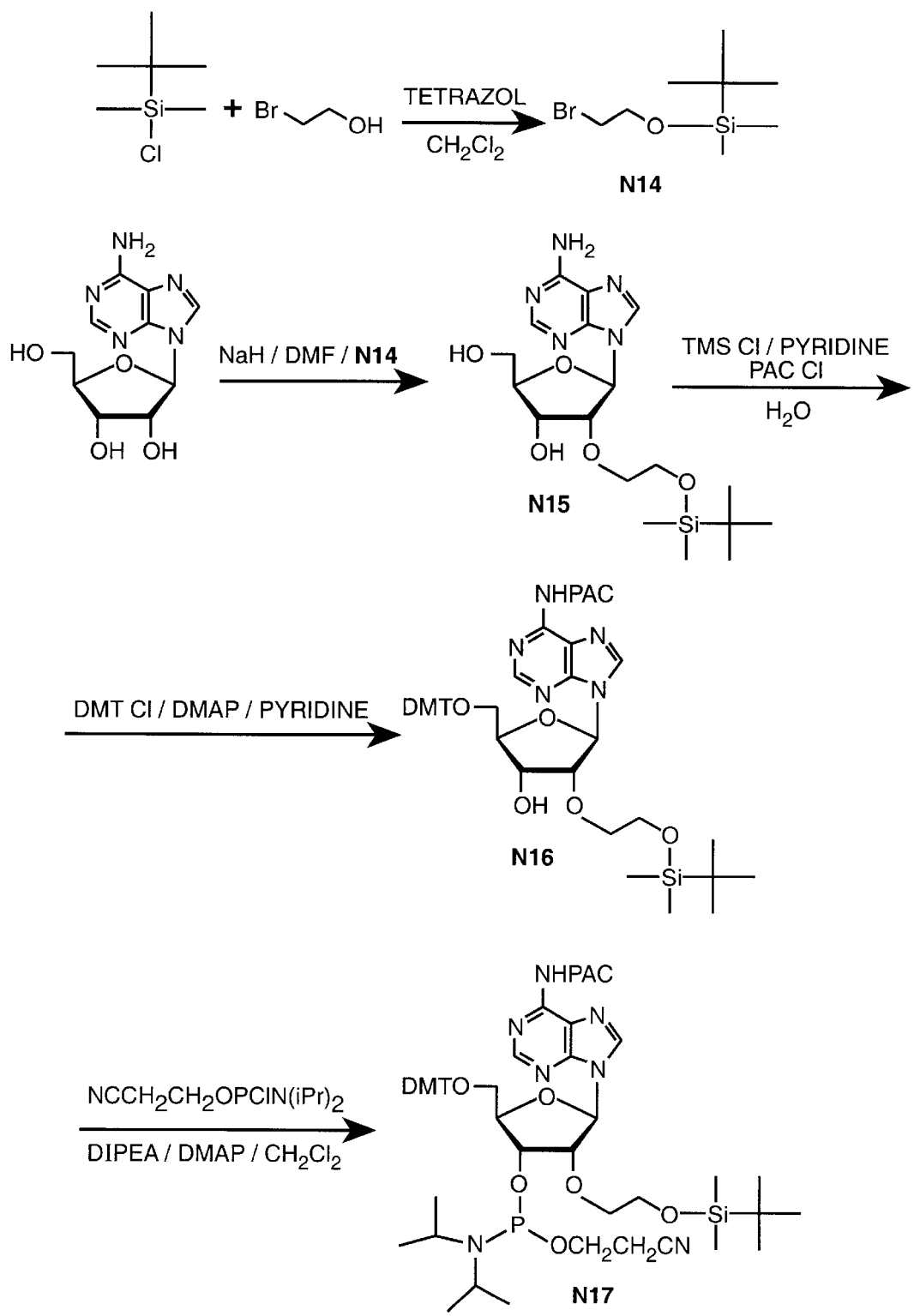
FIG._11A

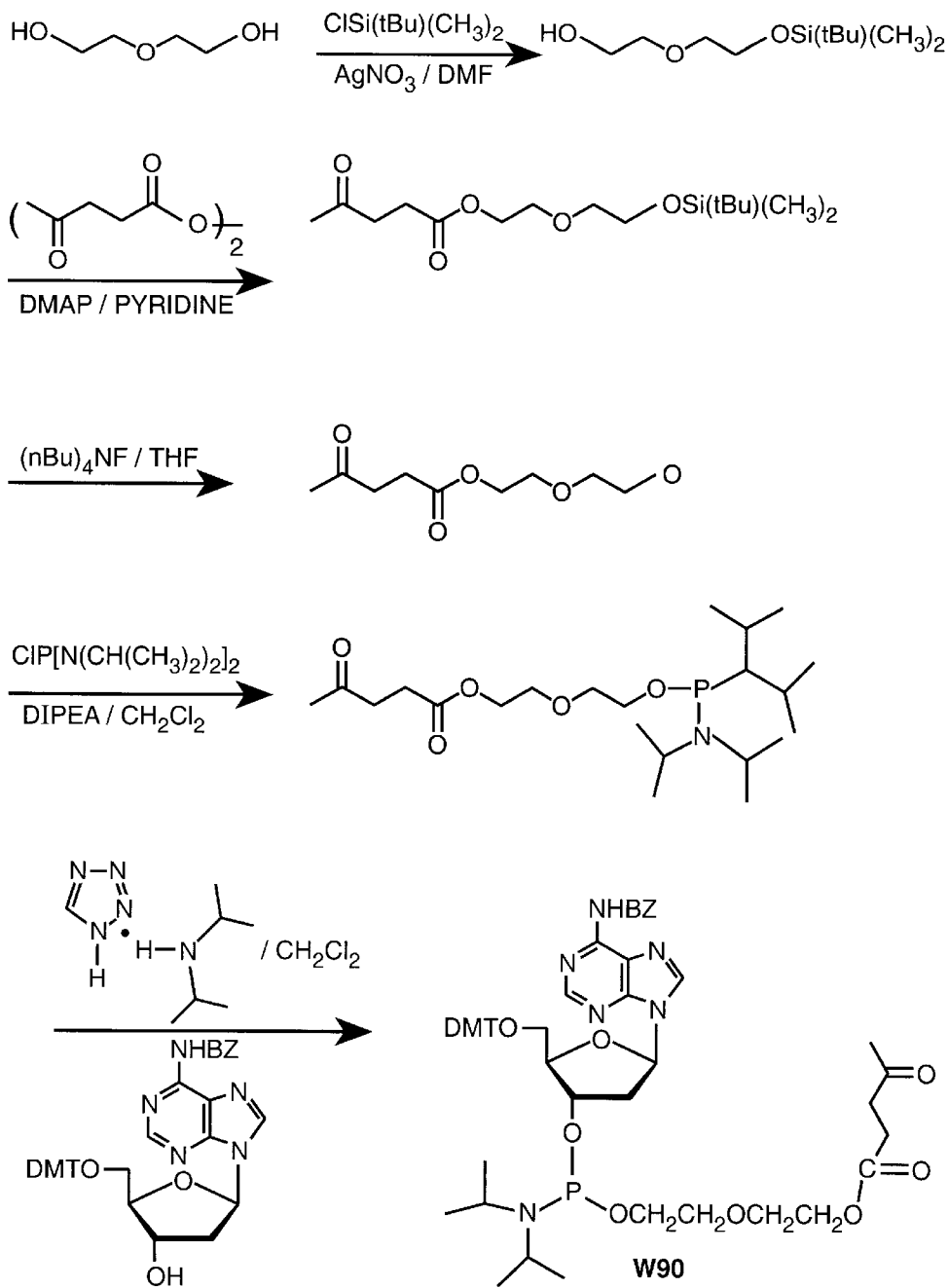
FIG._11B

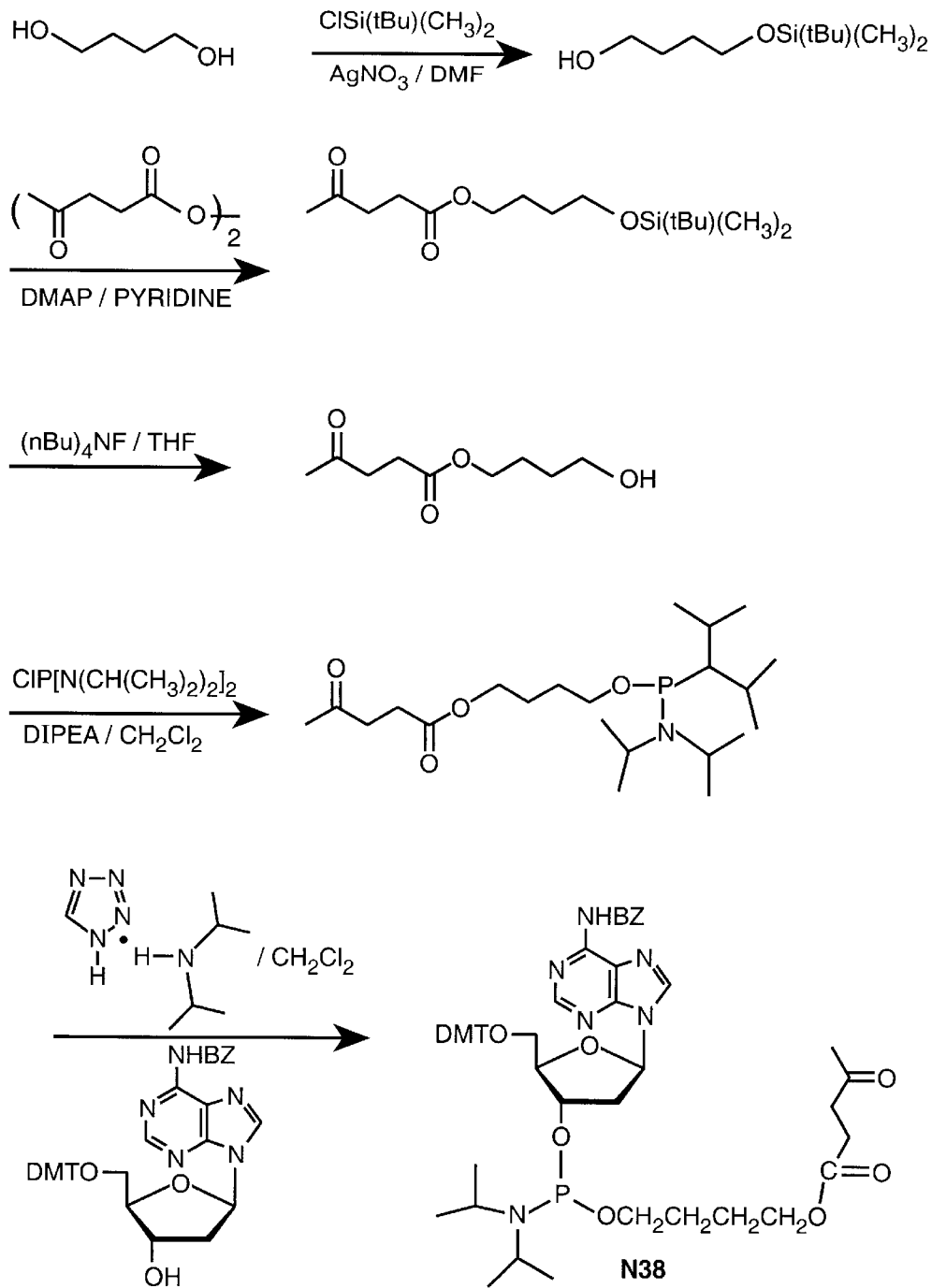
FIG._11C

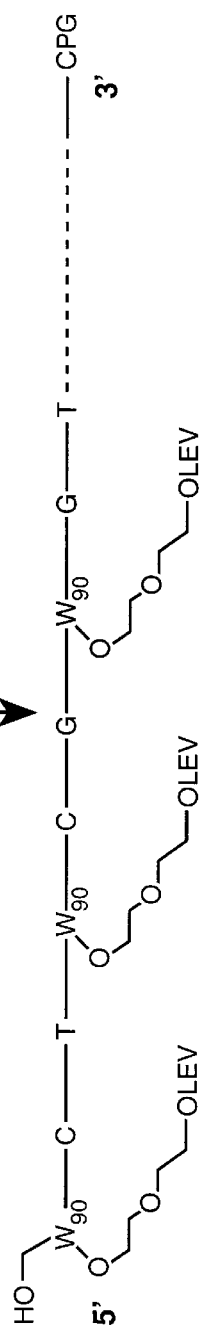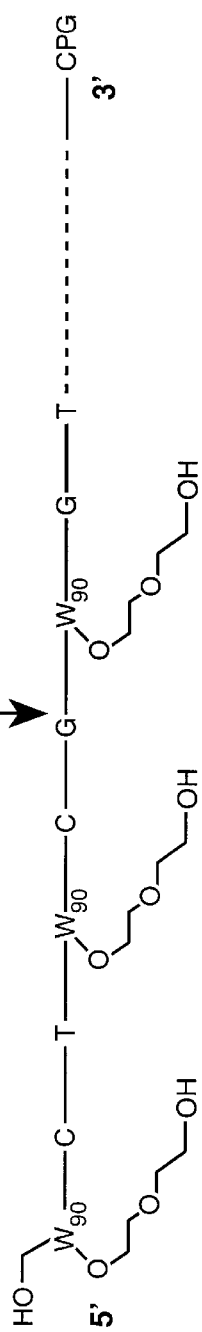
FIG._12A

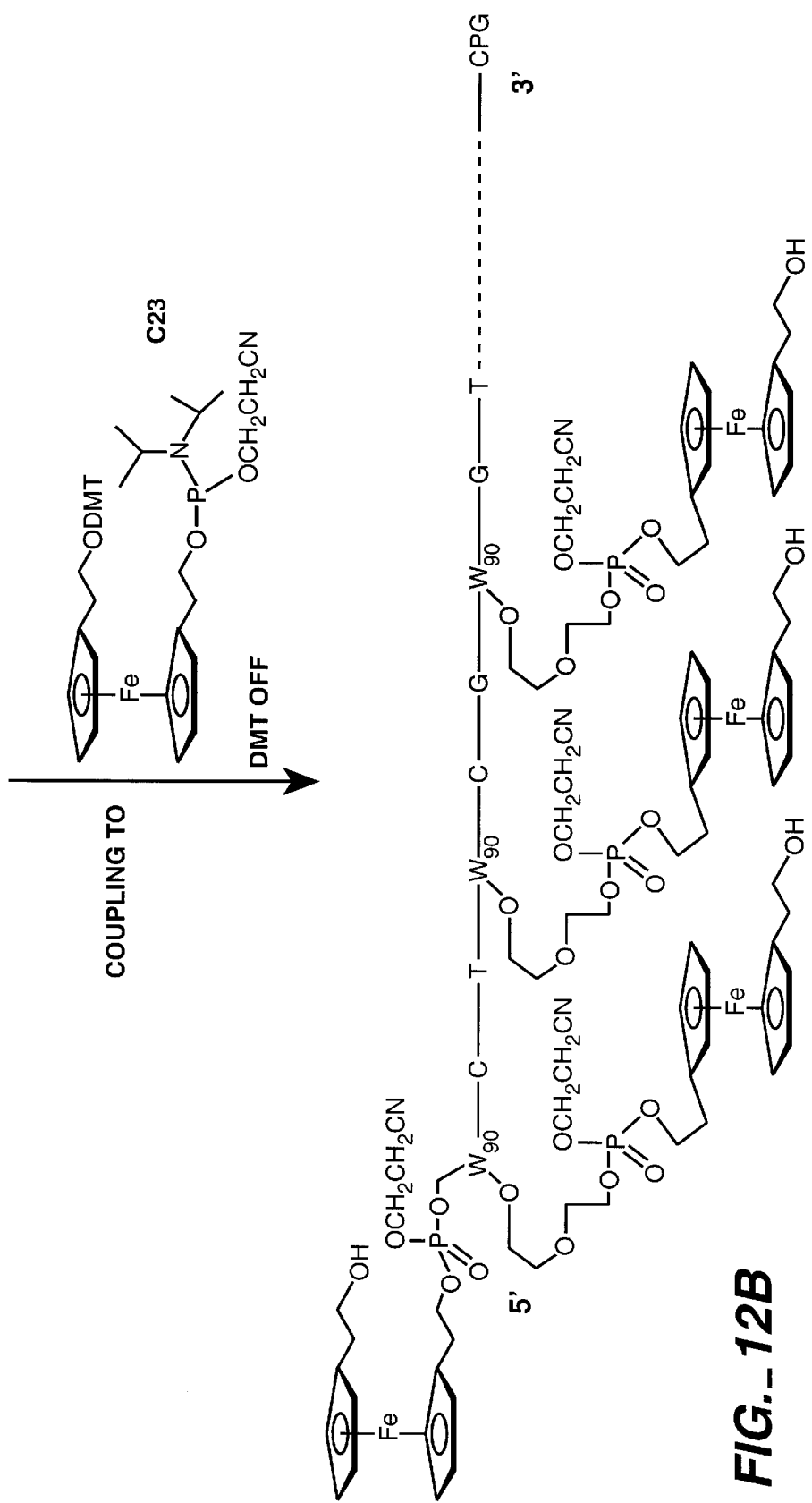
FIG._12B

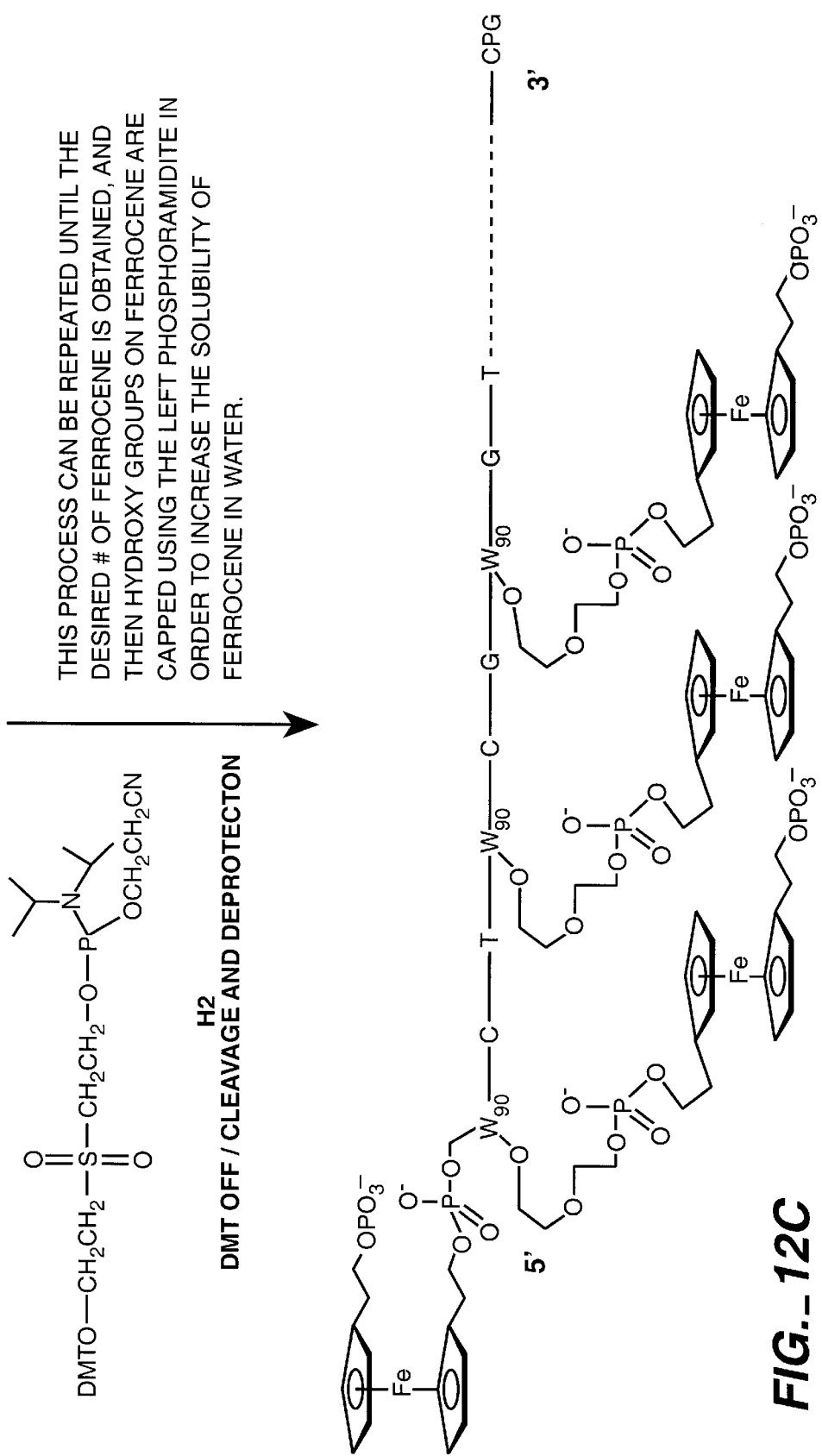
FIG._12C

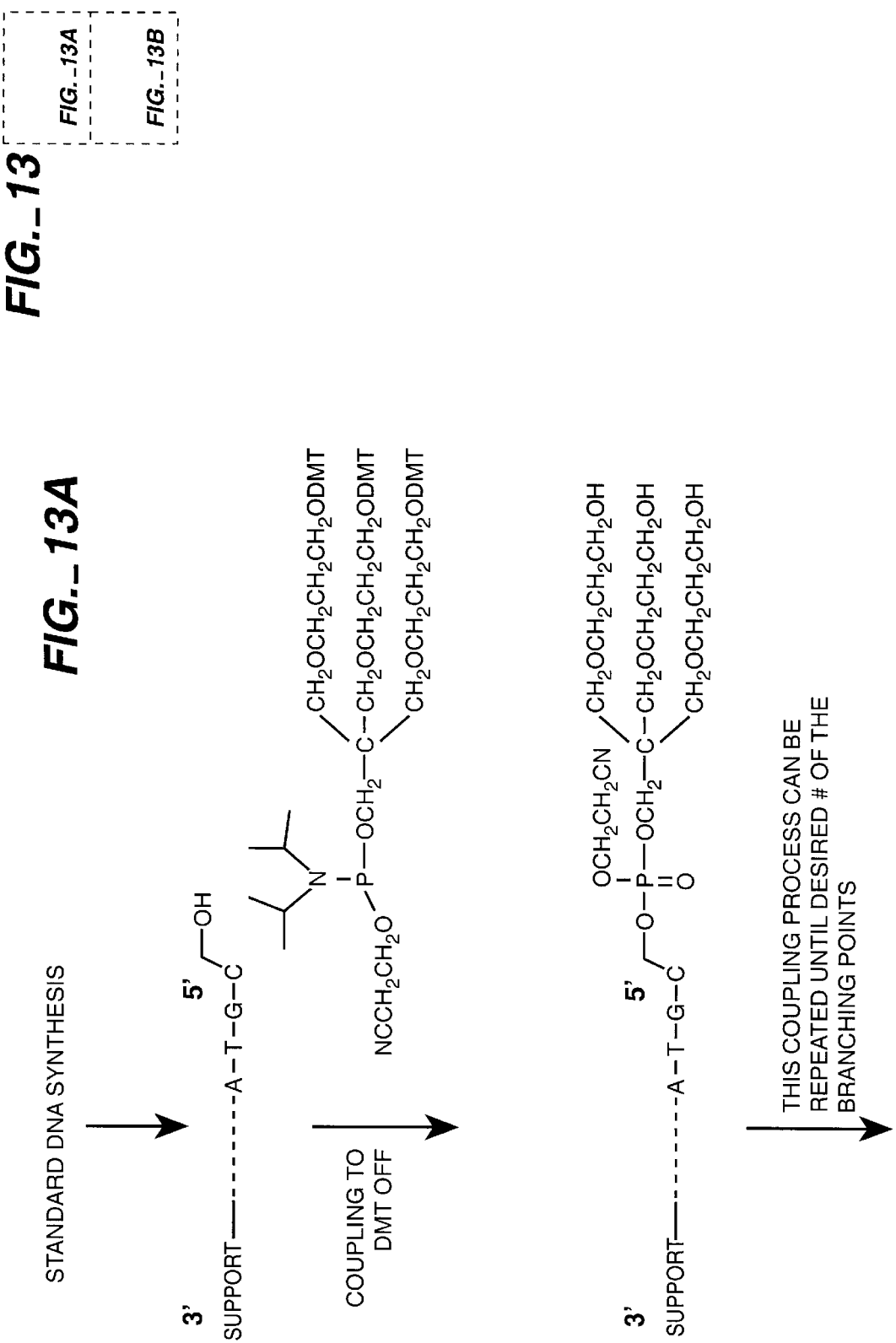

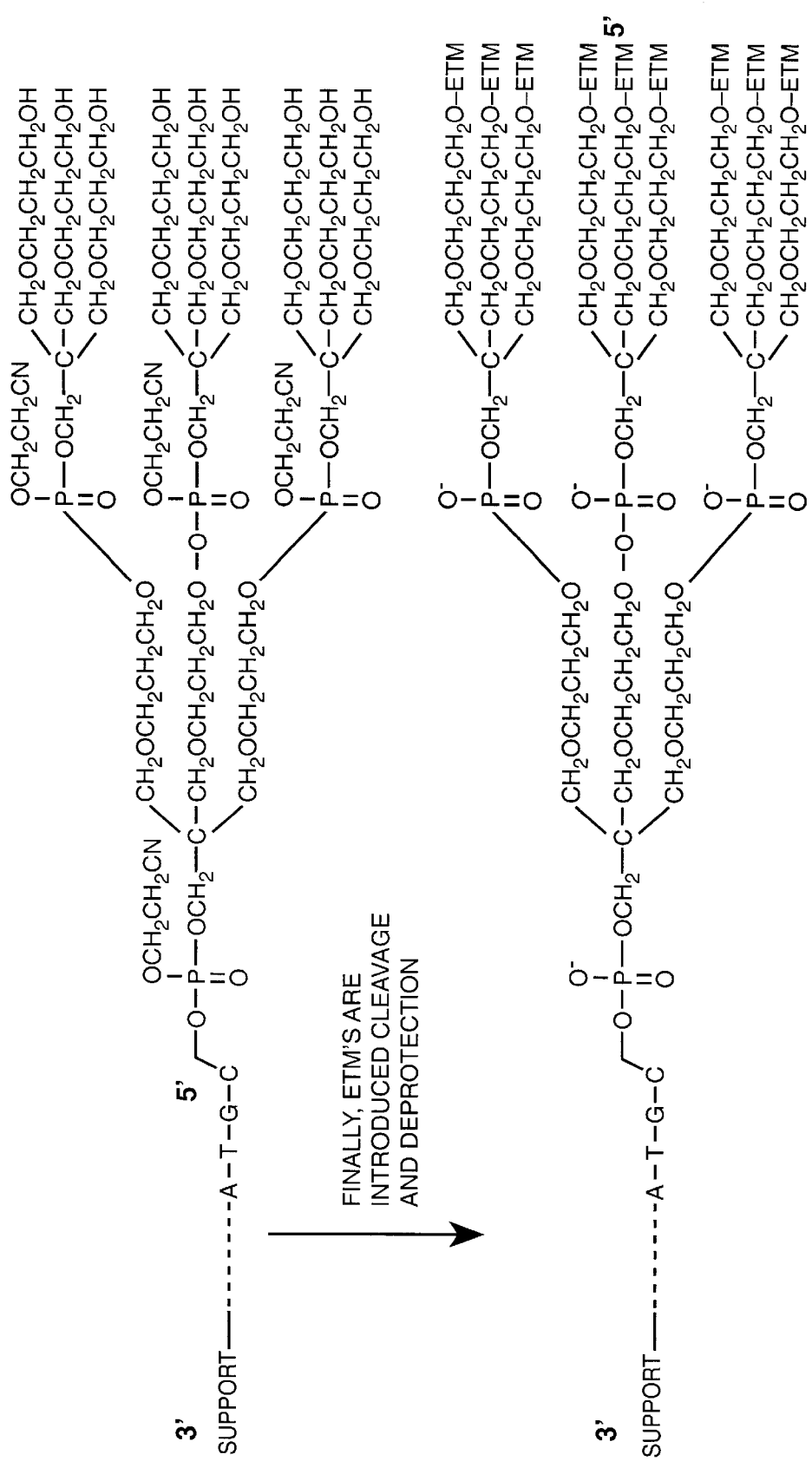
FIG._13B

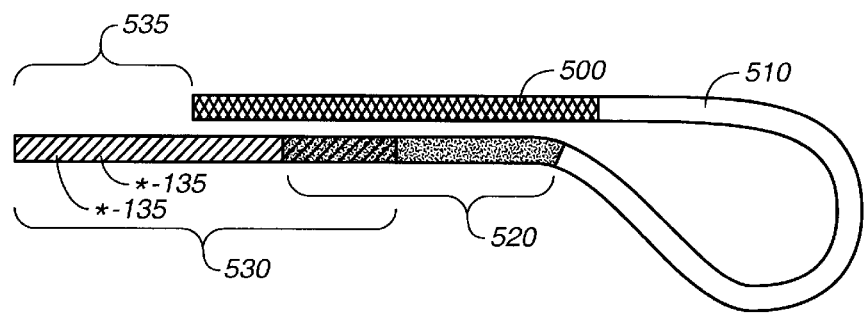
FIG._14
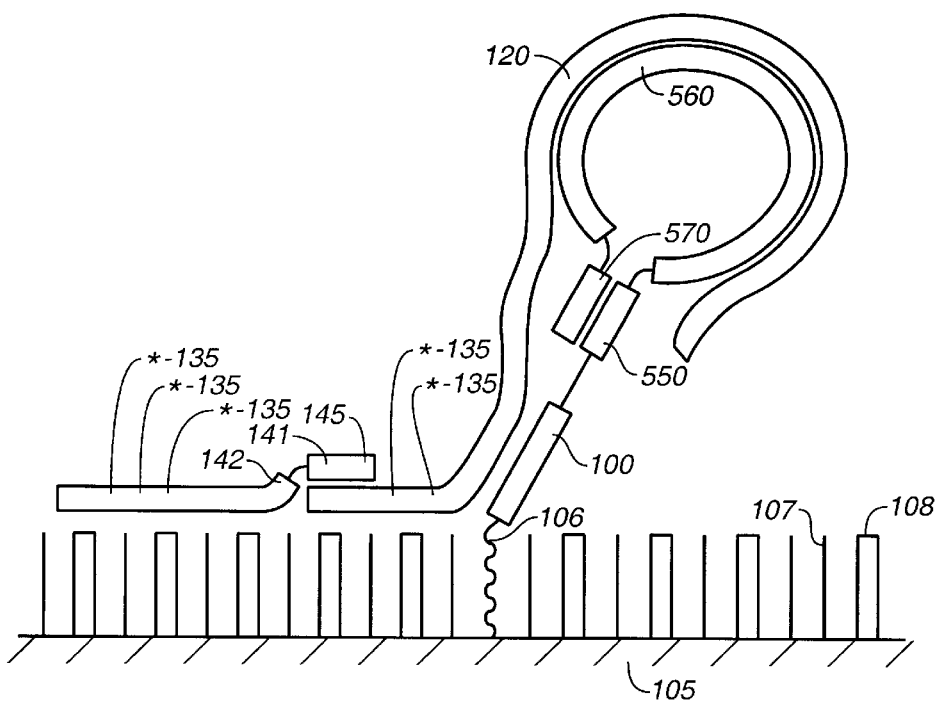
FIG._18

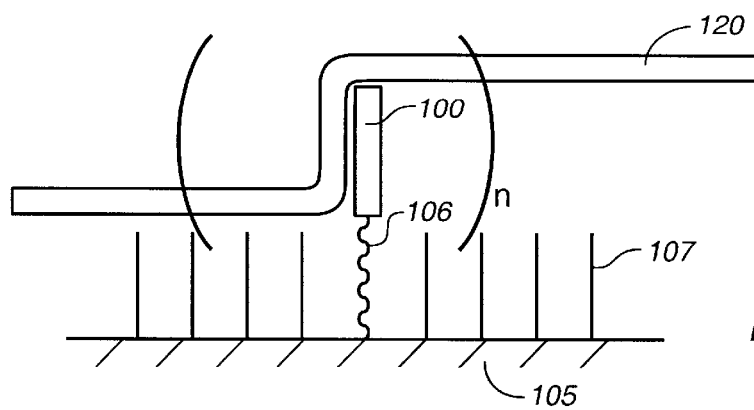
FIG._15A
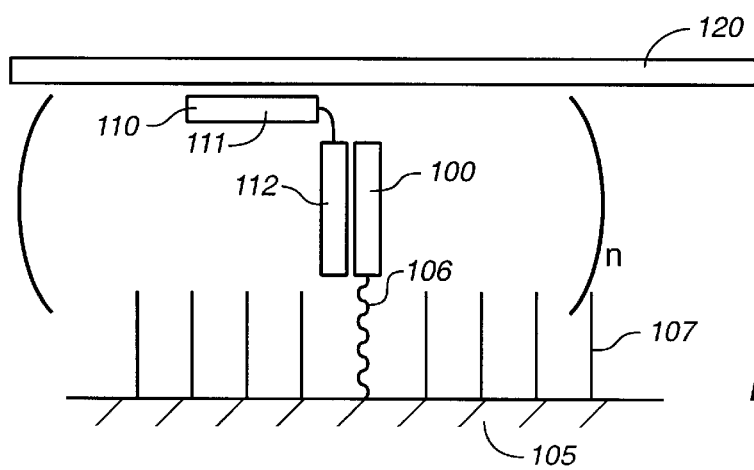
FIG._15B
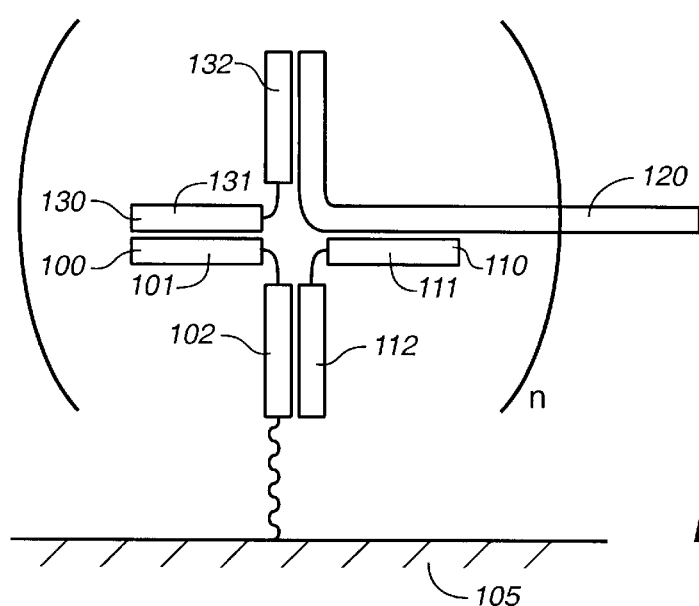
FIG._15C

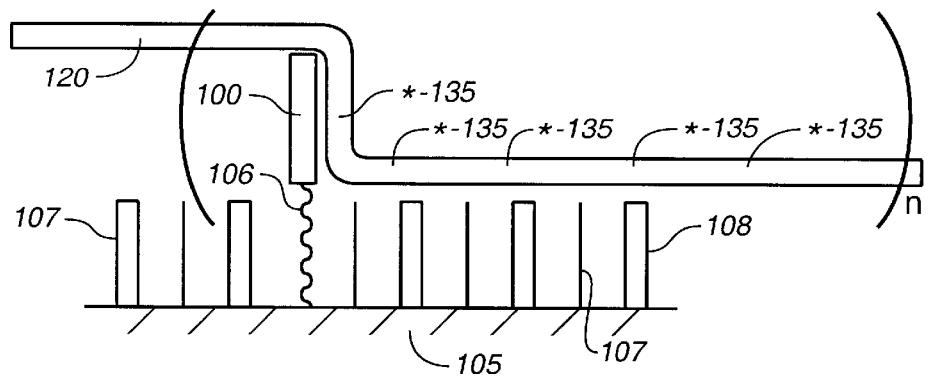
FIG._16A
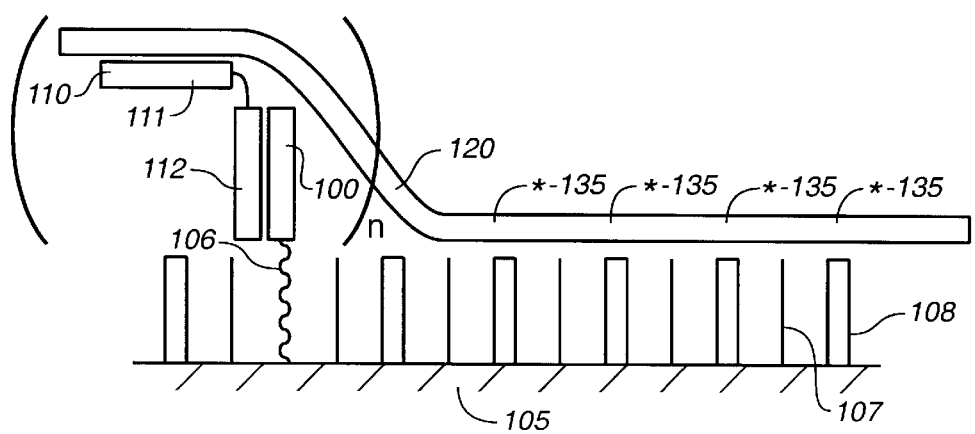
FIG._16B
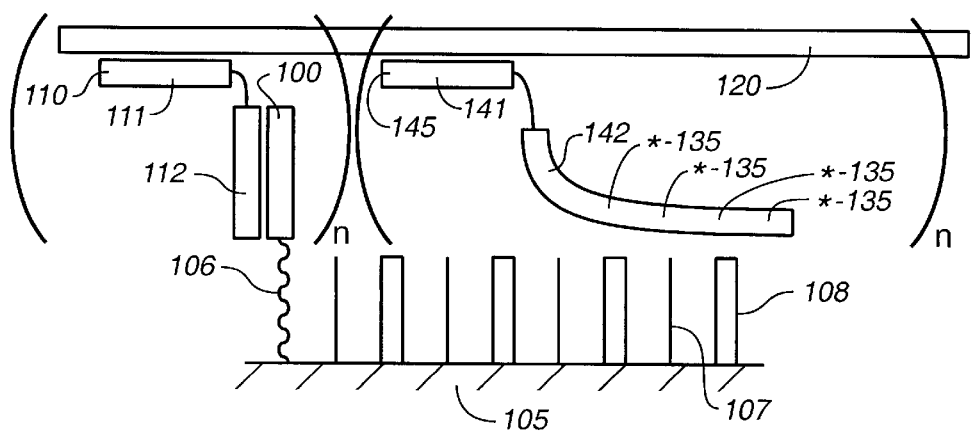
FIG._16C

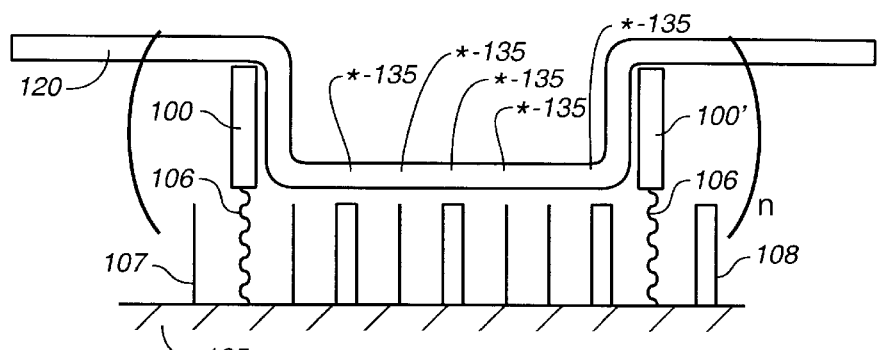
FIG._16D
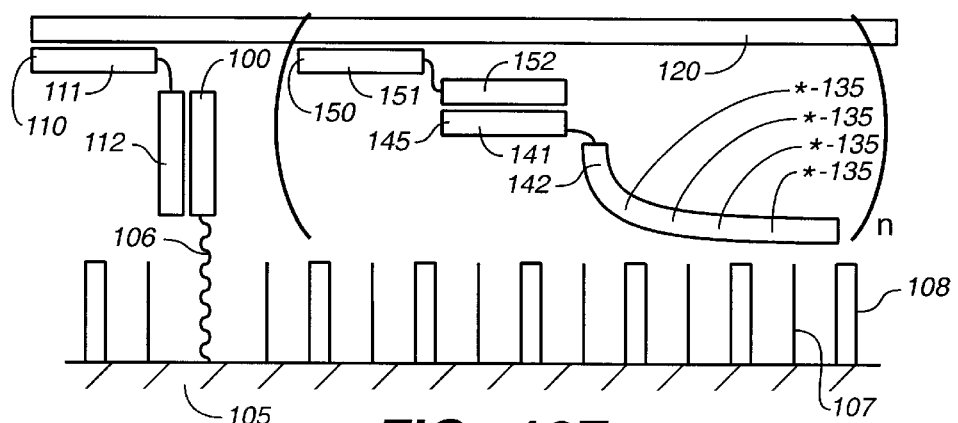
FIG._16E
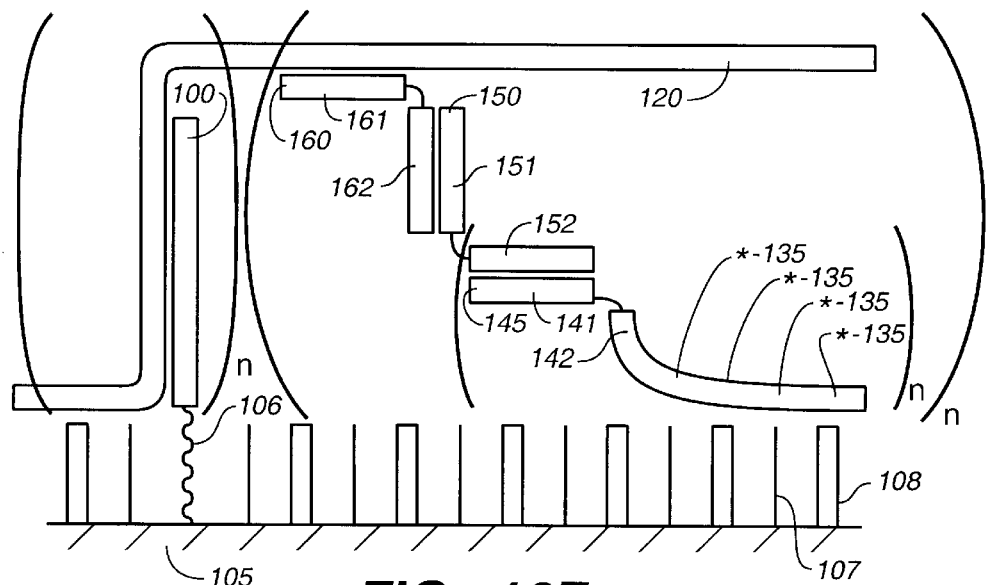
FIG._16F

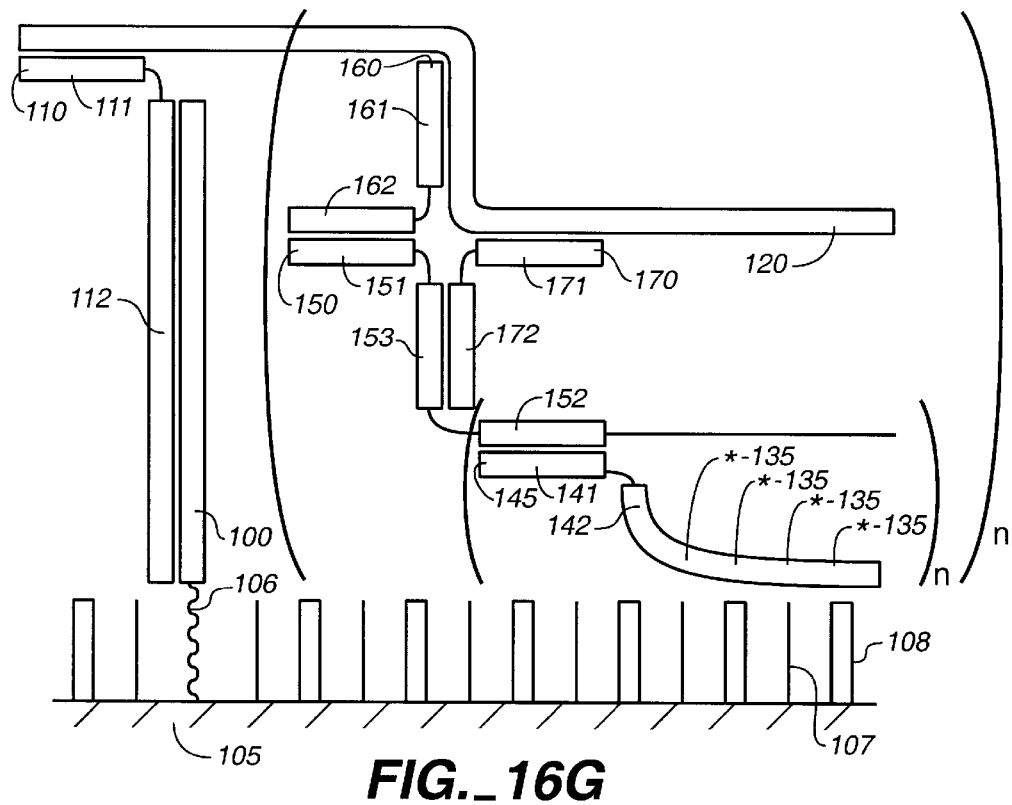
FIG._16G
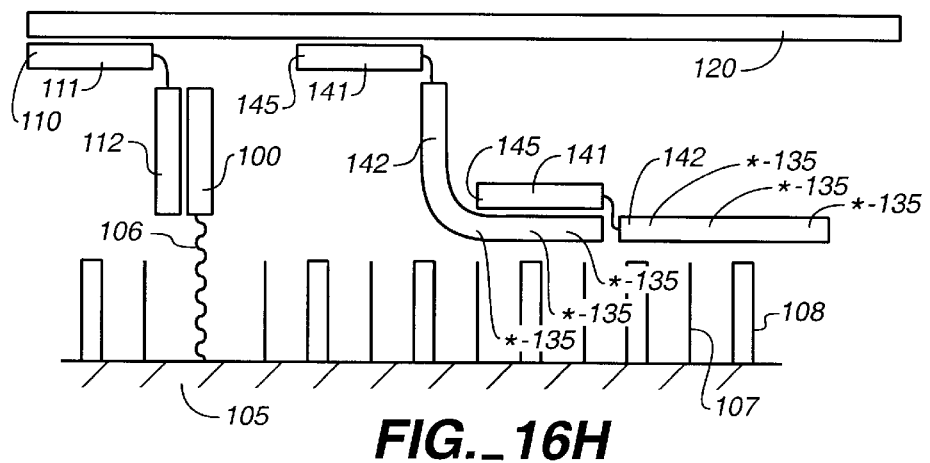
FIG._16H

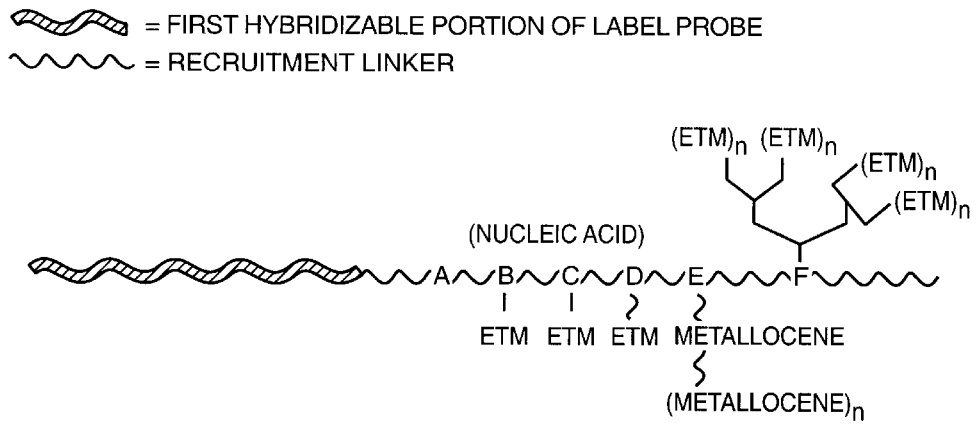
A = NUCLEOSIDE REPLACEMENT
B = ATTACHMENT TO A BASE
C = ATTACHEMENT TO A RIBOSE
D = ATTACHMENT TO A PHOSPHATE
E = METALLOCENE POLYMER, ATTACHED TO A RIBOSE, PHOSPHATE, OR BASE
F = DENDRIMER STRUCTURE, ATTACHED VIA A RIBOSE, PHOSPHATE OR BASE
FIG._17A
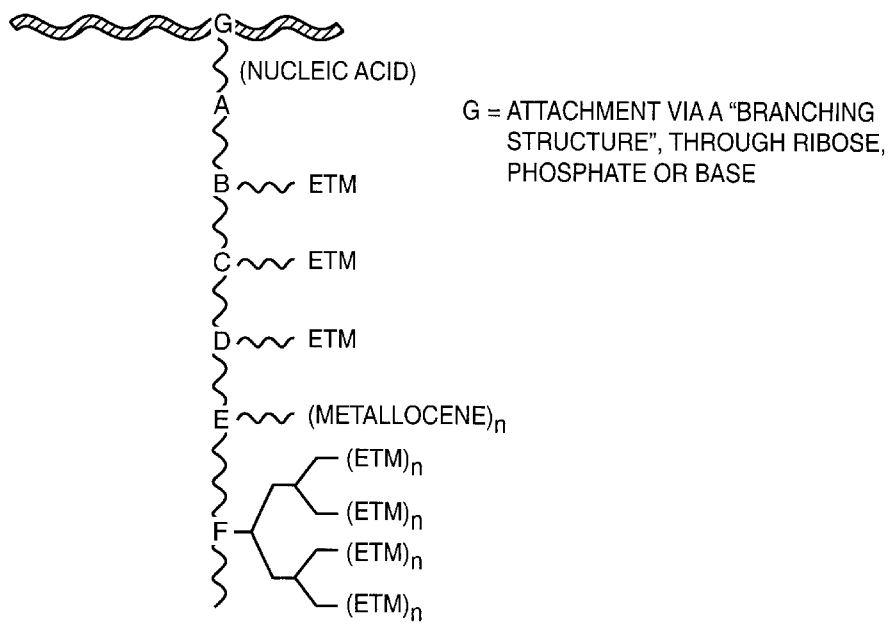
G = ATTACHMENT VIA A "BRANCHING STRUCTURE", THROUGH RIBOSE, PHOSPHATE OR BASE
FIG._17B

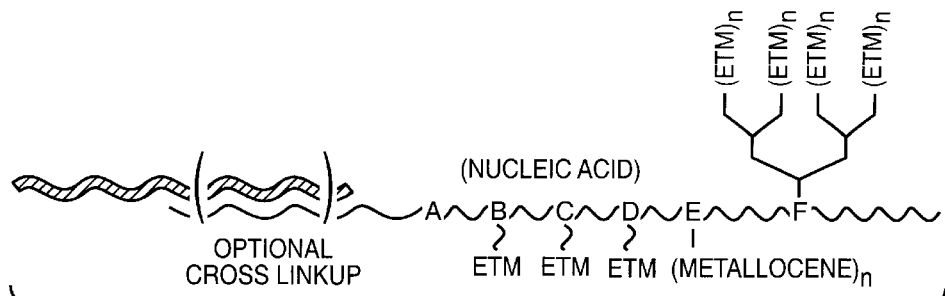
FIG._17C
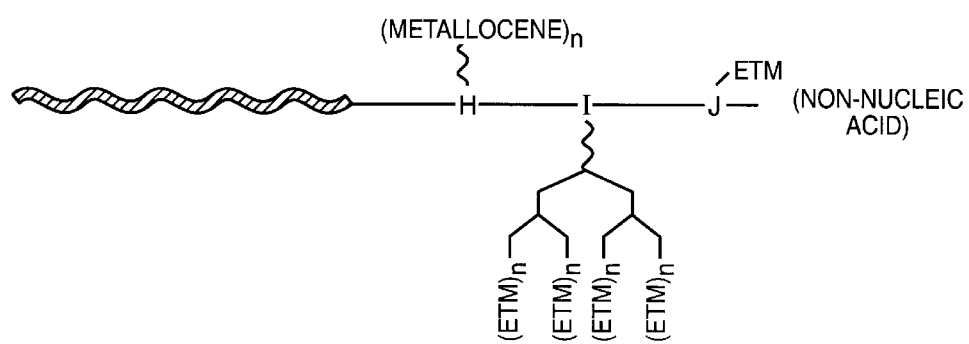
H = ATTACHMENT OF METALLOCENE POLYMERS
I = ATTACHMENT VIA DENDRIMER STRUCTURE
J = ATTACHMENT USING STANDARD LINKERS
FIG._17D
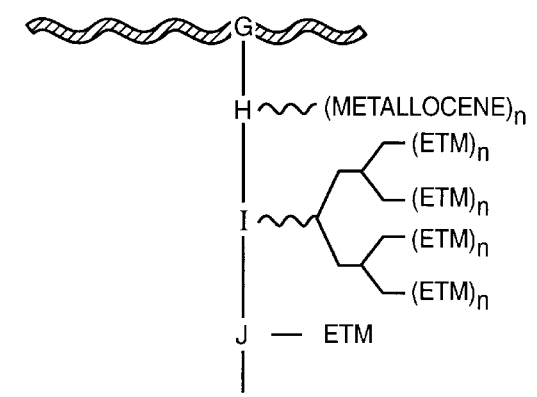
FIG._17E

D179
5' – A(C15)CCTGGTCTTGACATCCACGGAAGGCGTGGAAATACGTATTCGTGCCTA – 3'

D309 (Dendrimer)
5' – (W38)(Branching)(Branching)CATGGTTAACGTCAATTGCTGCGGTTATTAA – 3'

D295
5' – (N6)G(N6)CT(N6)C(N6)G(N6)C(N6)CCCATGGTTAGACTGAATTGCTGCGGTTATTAA – 3'

D297
5' – (N6)G(N6)CT(N6)C(N6)G(N6)C(N6)TATGCTCTTGATGGTGCTGTGGAAATCTACTGG – 3'

D298
5' – (N6)G(N6)CT(N6)C(N6)G(N6)C(N6)ATGGTGCTGTGGAAATCTACTGG – 3'

D296
5' – (N6)G(N6)CT(N6)C(N6)G(N6)C(N6)TGACTGAATTGCTGCGGTTATTAA – 3'

D112
5' – CTTCCGTGGATGTCAAGACCAGGAU – 4 unit wire (C11) – 3'

D94
5' – ACCATGGACACAGAU – 4 unit wire (C11) – 3'

D109
5' – CTGCGGTTATTAACU – 4 unit wire (C11) – 3'

2Tar
5' – TAG GCA CGA ATA CGT ATT TCC ACG ATA AAT ATA ATT AAT AAC CGC AGC AAT TGA CGT ATA AAG CTA TCC CAG TAG ATT TCC ACA GC – 3'

D349
5' – A(C15)C (C15)GT GTC CAT GGT AGT AGC TTA TCG TGG AAA TAC GTA TTC GTG CCT A – 3'

D382
5' – (Y63)G(Y63) CT(Y63) C(Y63)G (Y63)C(Y63) CCC ATG GTT AGA CTG AAT TGC TGC GGT TAT TAA – 3'

D383
5' – (Y63)G(Y63) CT(Y63) C(Y63)G (Y63)C(Y63) CCC ATG GTT AGA CTG GCT GTG GAA ATC TAC TGG – 3'

D468
5' – (N6)G(N6) CT(N6) C(N6)G (N6)C(N6) (glen)(glen)(glen) CTT TAC TCC CTT CCT CCC CGC TGA AAG TAC – 3'

D449
5' – CGG AGT TAG CCG GTG CTT CTT CTG CGG G(C131)(C131) (C131)(C131)(N6) G(N6)C T(N6)C (N6)G(N6) C(N6)T – 3'

D417
5' – CTT TAC TCC CTT CCT CCC CGC TGA AAG TAC TTT ACA ACC C – 3'

EU1
5' – ATC CTG GTC TTG ACA TCC ACG GAA GAT GTC CCT ACA GTC TCC ATC AGG CAG TTT CCC AGA CA – 3'

MT1
5' – TCT ACA TGC CGT ACA TAC GGA ACG TAC GGA GCA TCC TGG TCT TGA CAT CCA CGG AAG – 3'

D358
5' – (N6)G(N6) CT(N6) C(N6)G (N6)C(N6) CCG TAT GTA CGG CAT GTA GA – 3'

D334
5' – GCT ACT ACC ATG GAC ACA GAU – 4 unit wire (C11) – 3'

D335
5' – ACA GAC ATC AGA GTA ATC (N6)GC C(N6)G TC(N6) TGG (N6)T – 3'

LP280
5' – GAT TAC TCT GAT GTC TGT CCA TCT GTG TCC ATG GTA GTA GC – 3'

LN280
5' – GAT TAC TCT GAT GTC TGT CCT AGT ACG AGT CAG TCT CTC CA – 3'

NC112
5' – TCT ACA TGC CGT ACA TAC GGA ACG TAC GGA GCG ATT CGA CTG ACA GTC GTA ACC TCA – 3'

D336
5' – (N6)G(N6) CT(N6) C(N6)G (N6)C(N6) GCG ACA ACT GTA CCA TCT GTG TCC ATG GT – 3'

D405
5' – (C23)(C23)(C23) (C23)(C23)(C23) (C23)(C23)(C23) (C23)AT CTG TGT CCA TGG T – 3'

D429
5' – (N6)G(N6) CT(N6) C(N6)G (N6)C(N6) (C131)AT CTG TGT CCA TGG TAG TAG C – 3'

FIG._19B

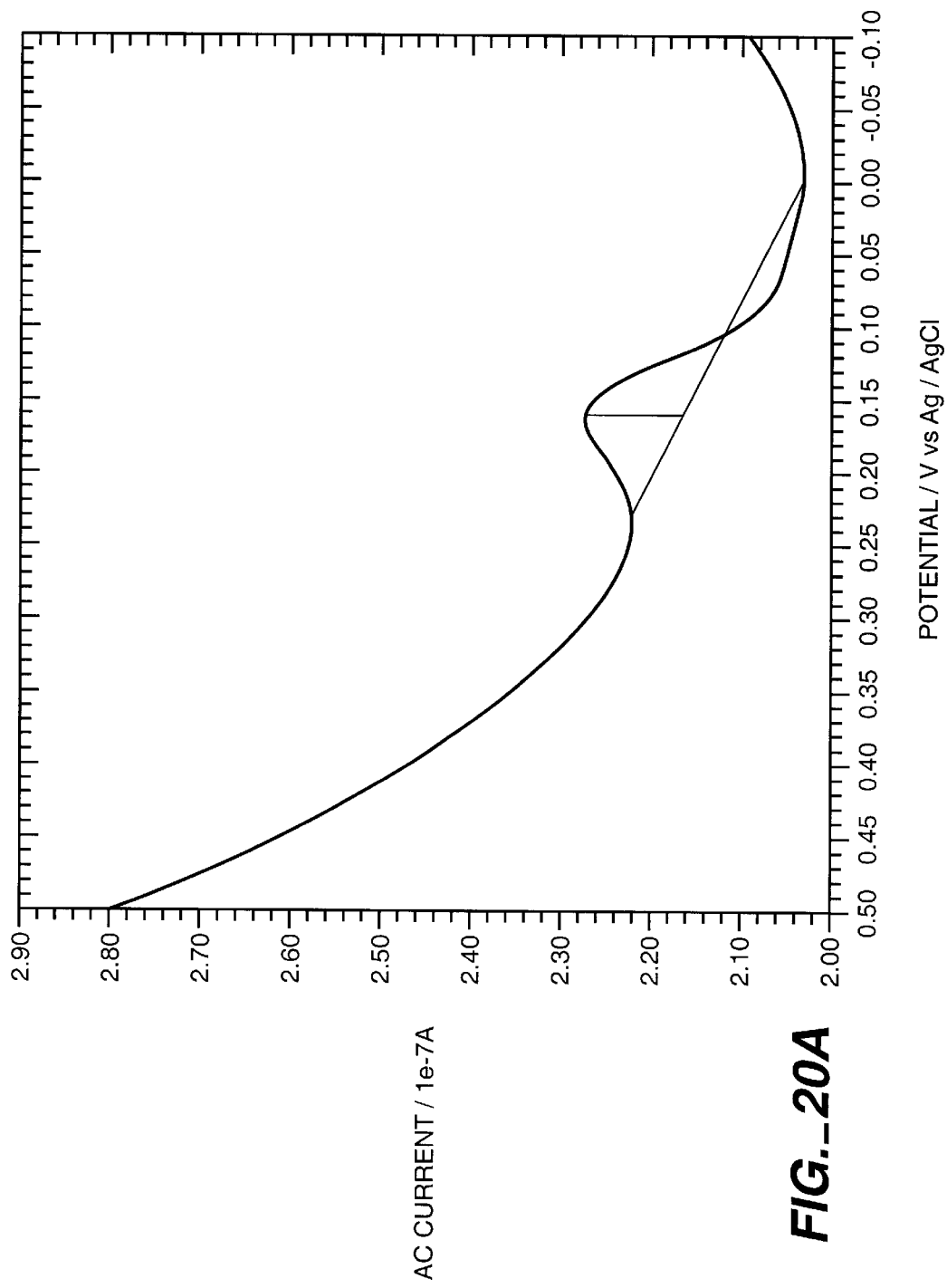
FIG._20A

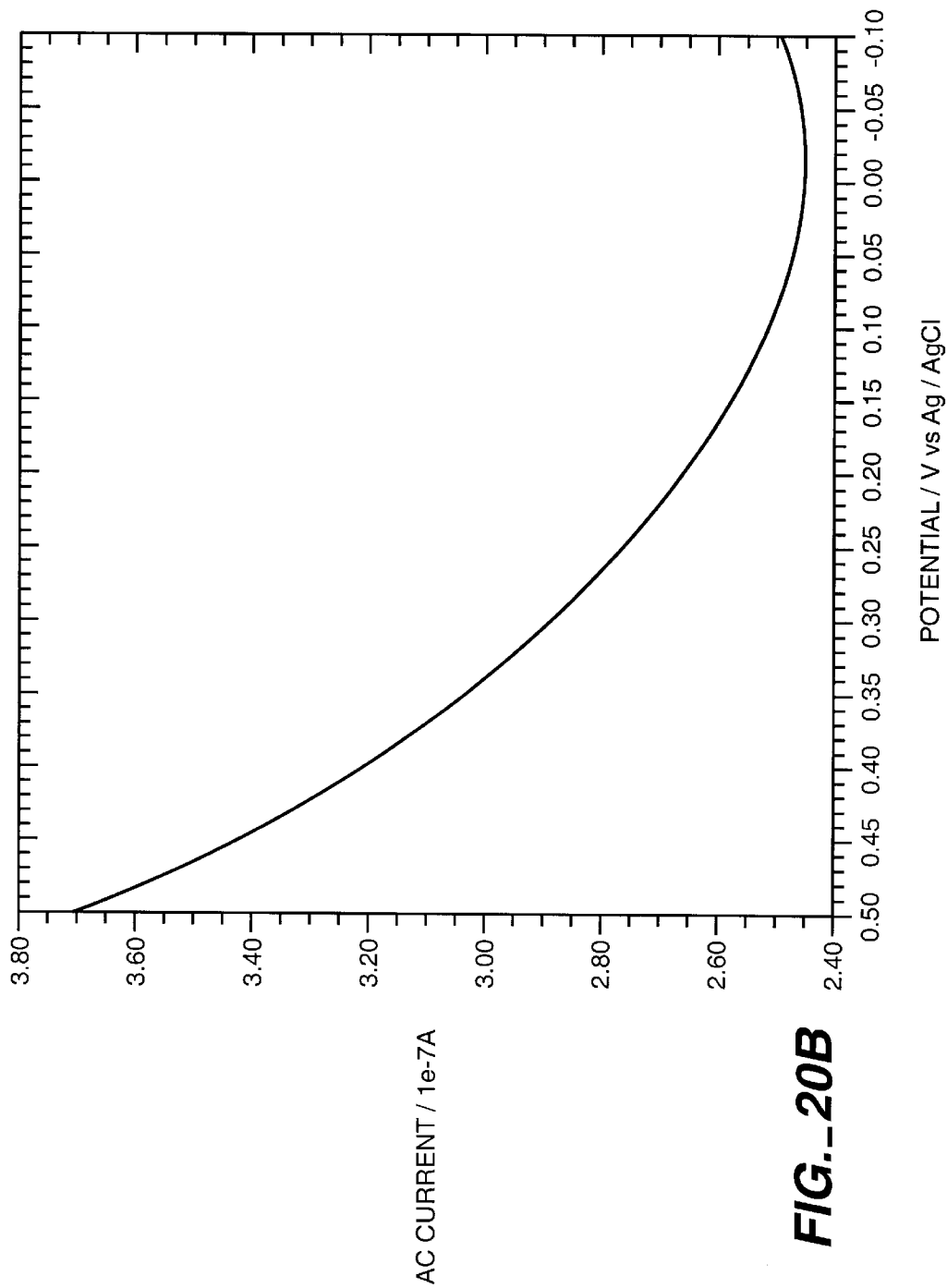
FIG._20B

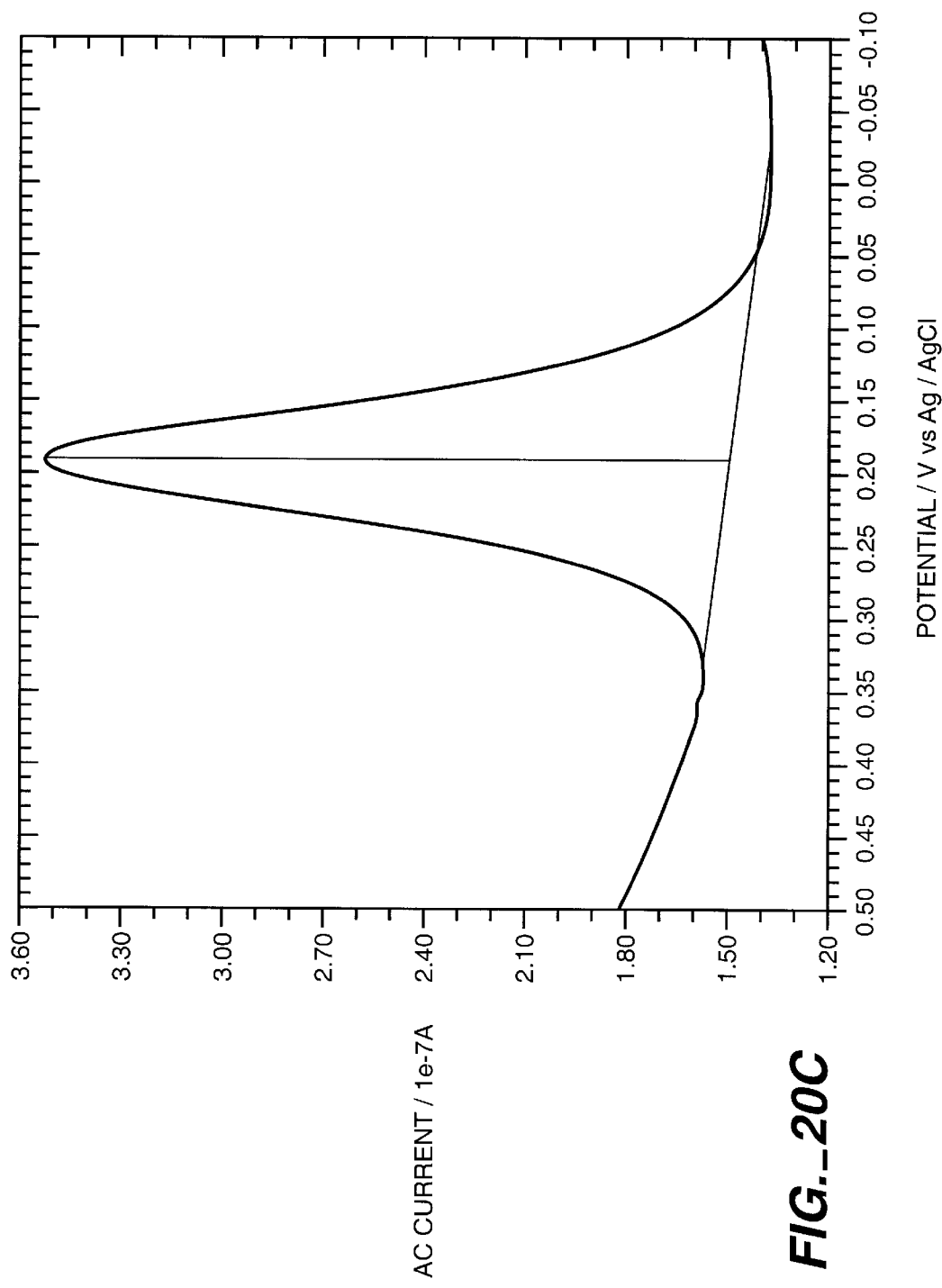
FIG._20C

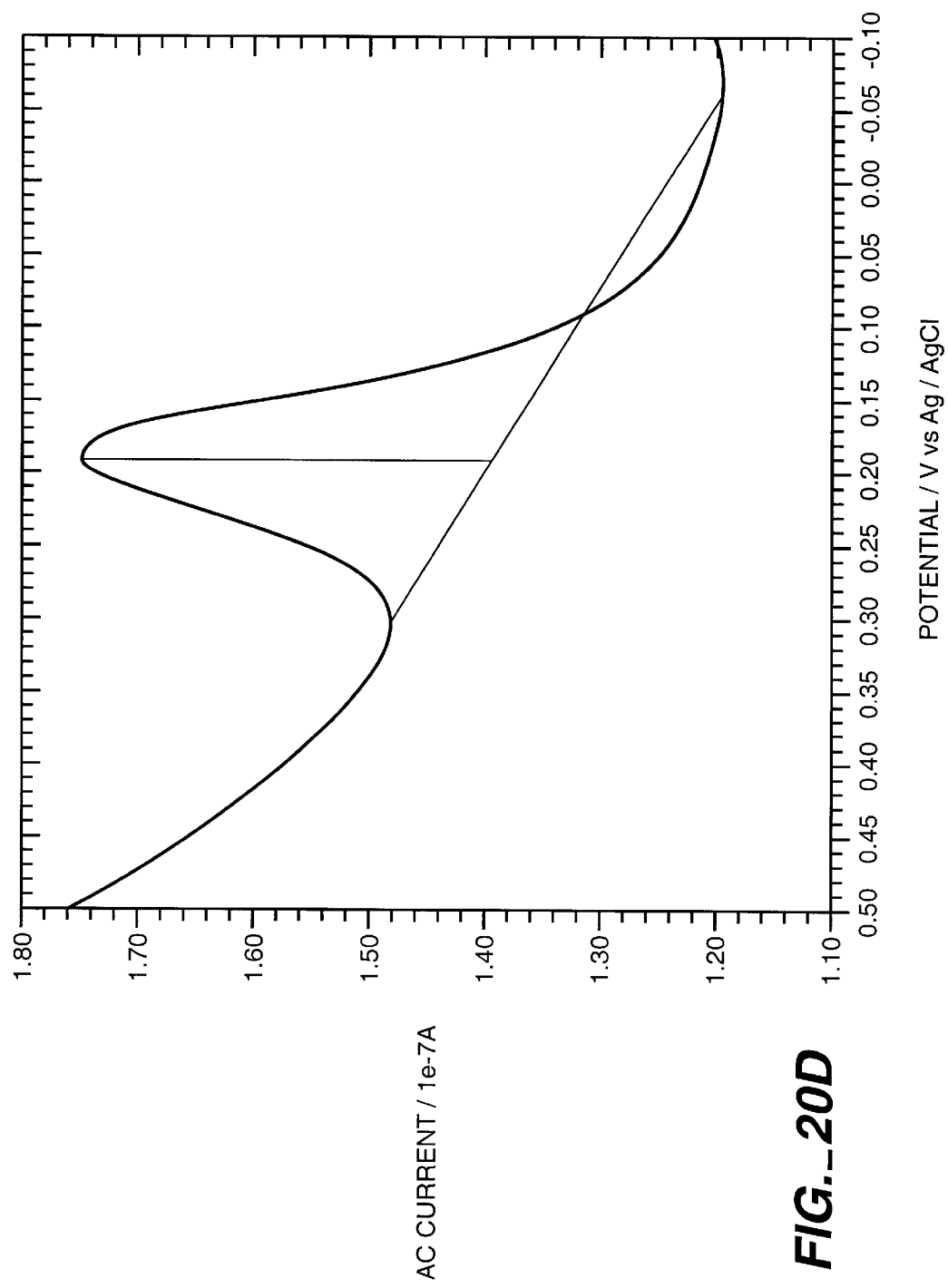

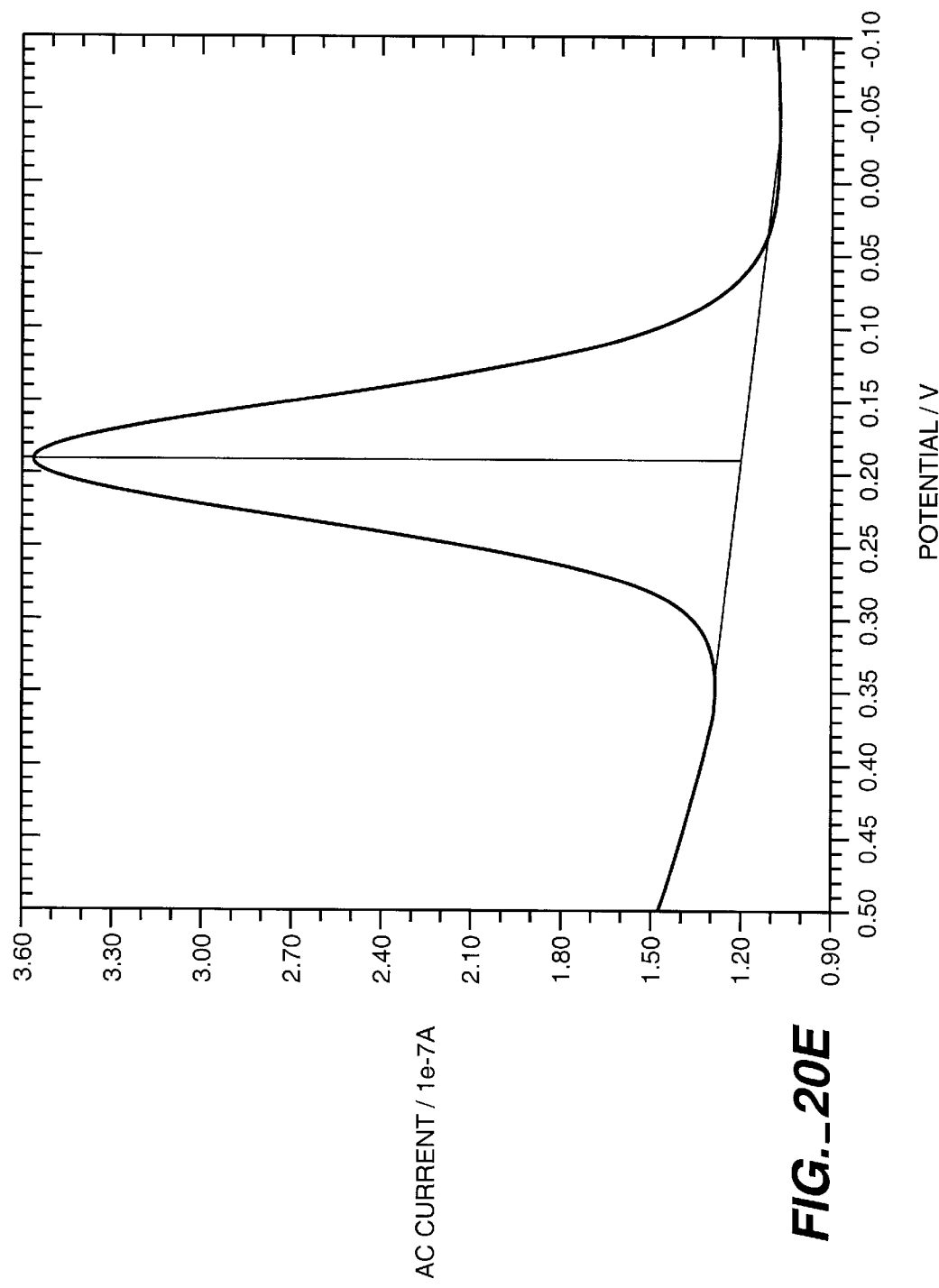
FIG._20E

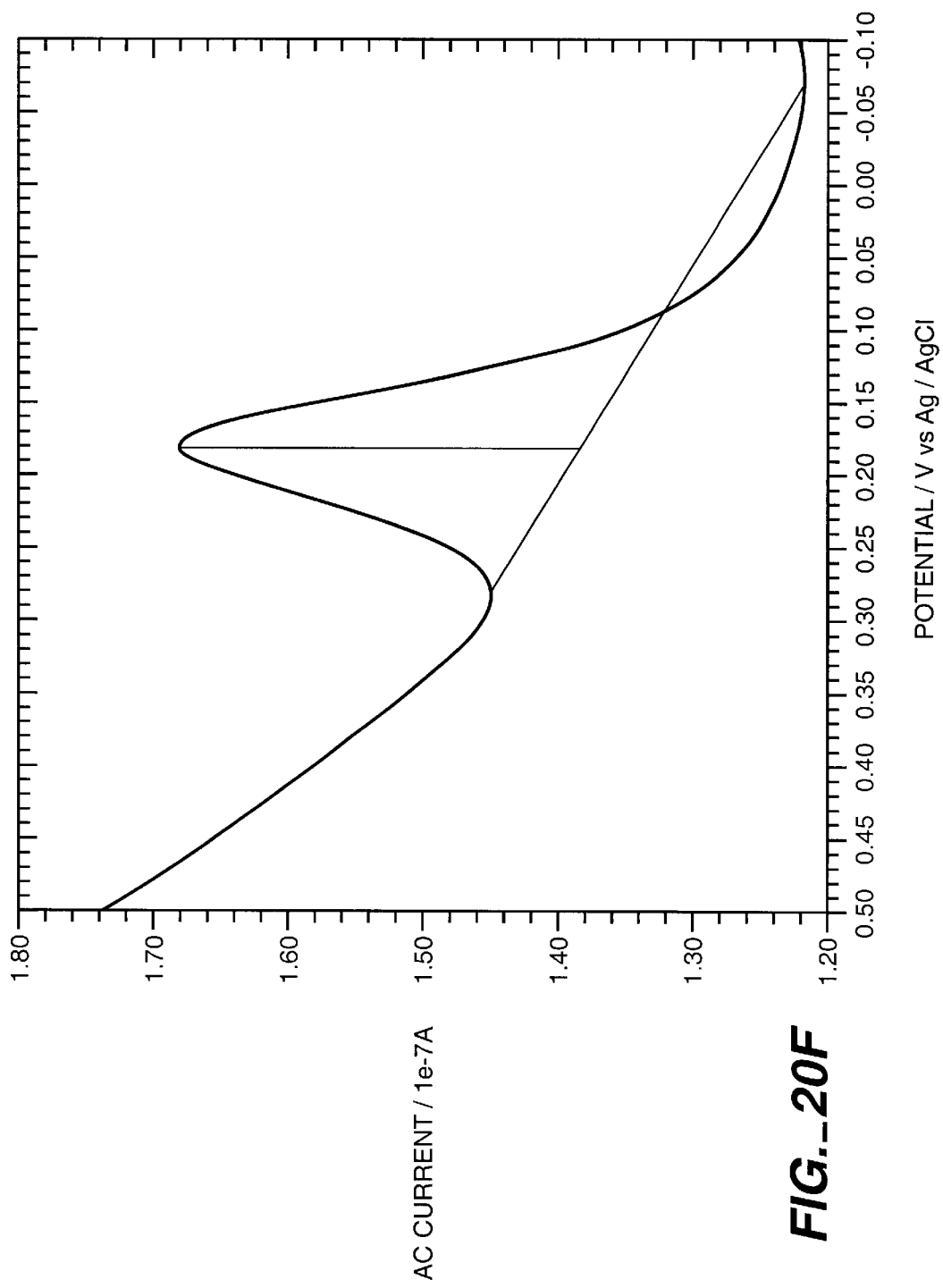
FIG._20F

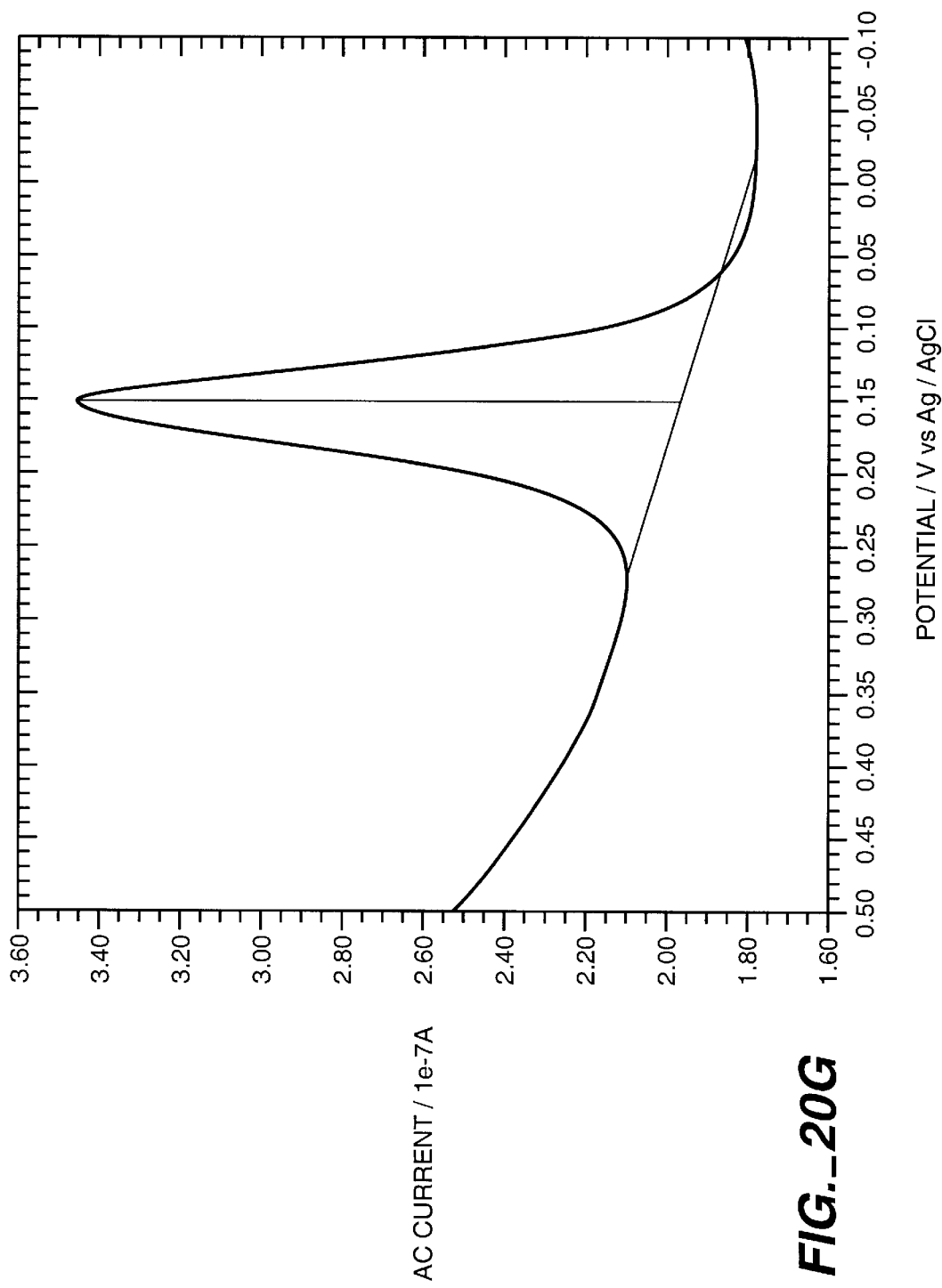
FIG._20G

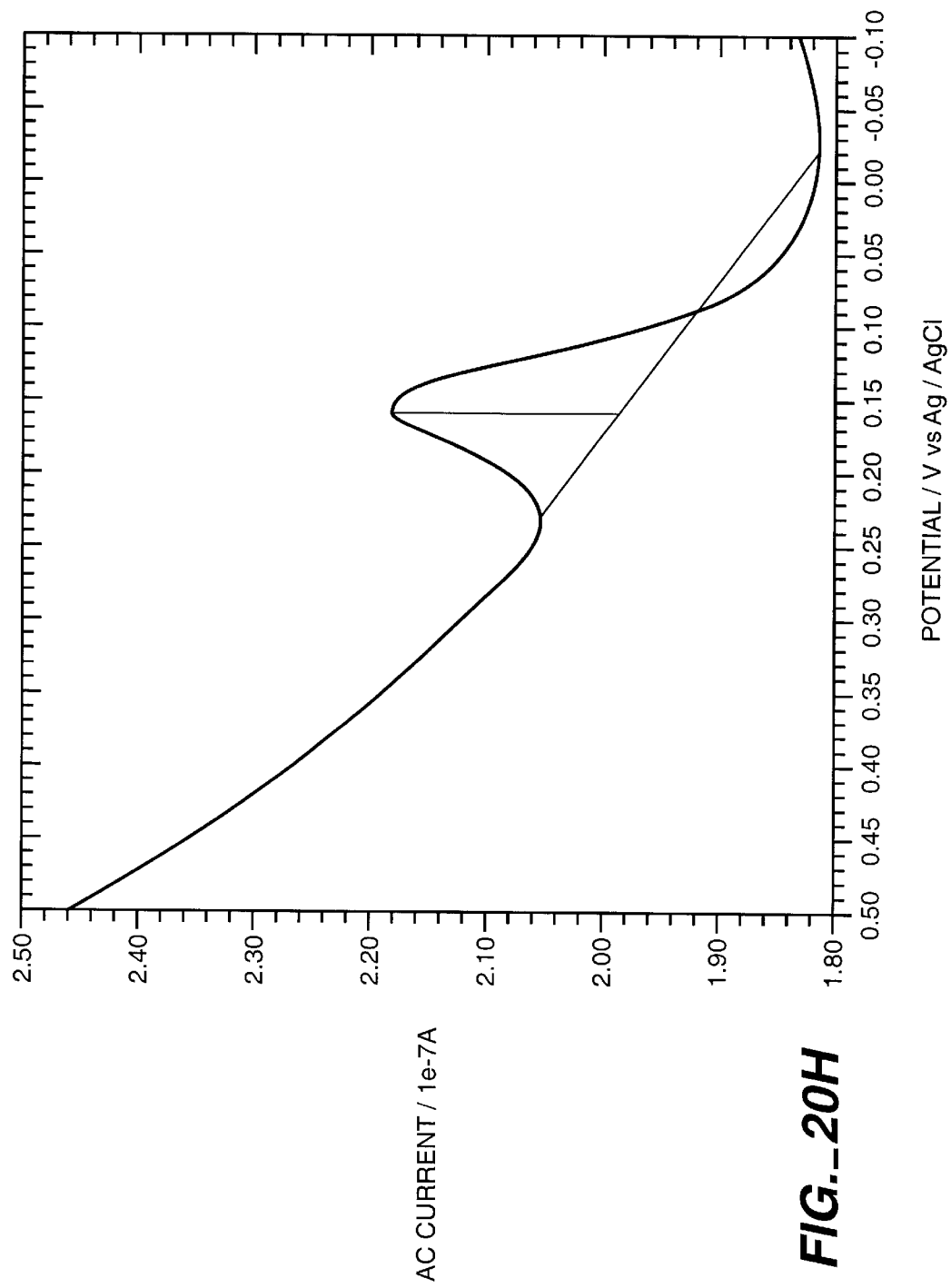
FIG._20H

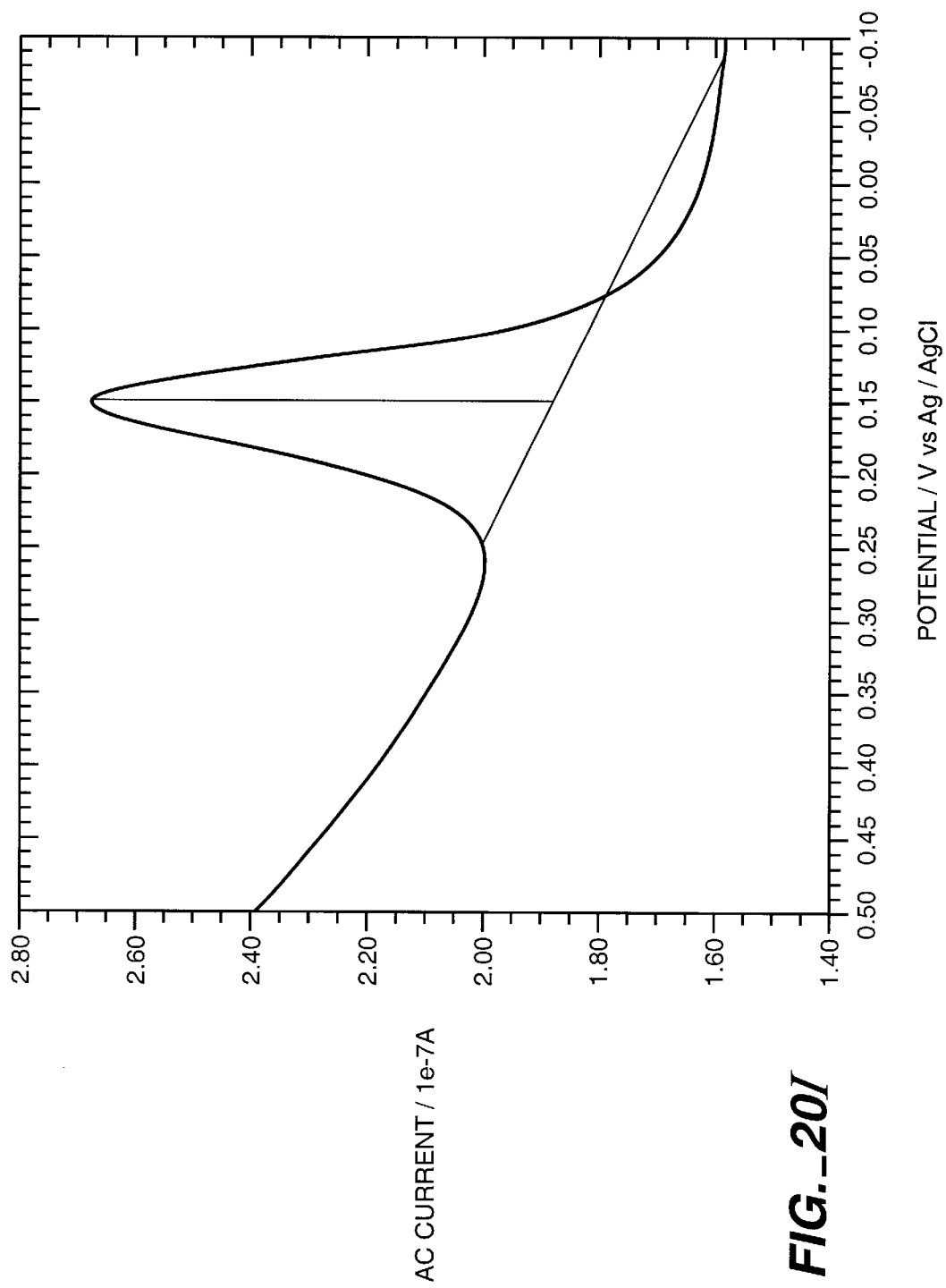
FIG._20I

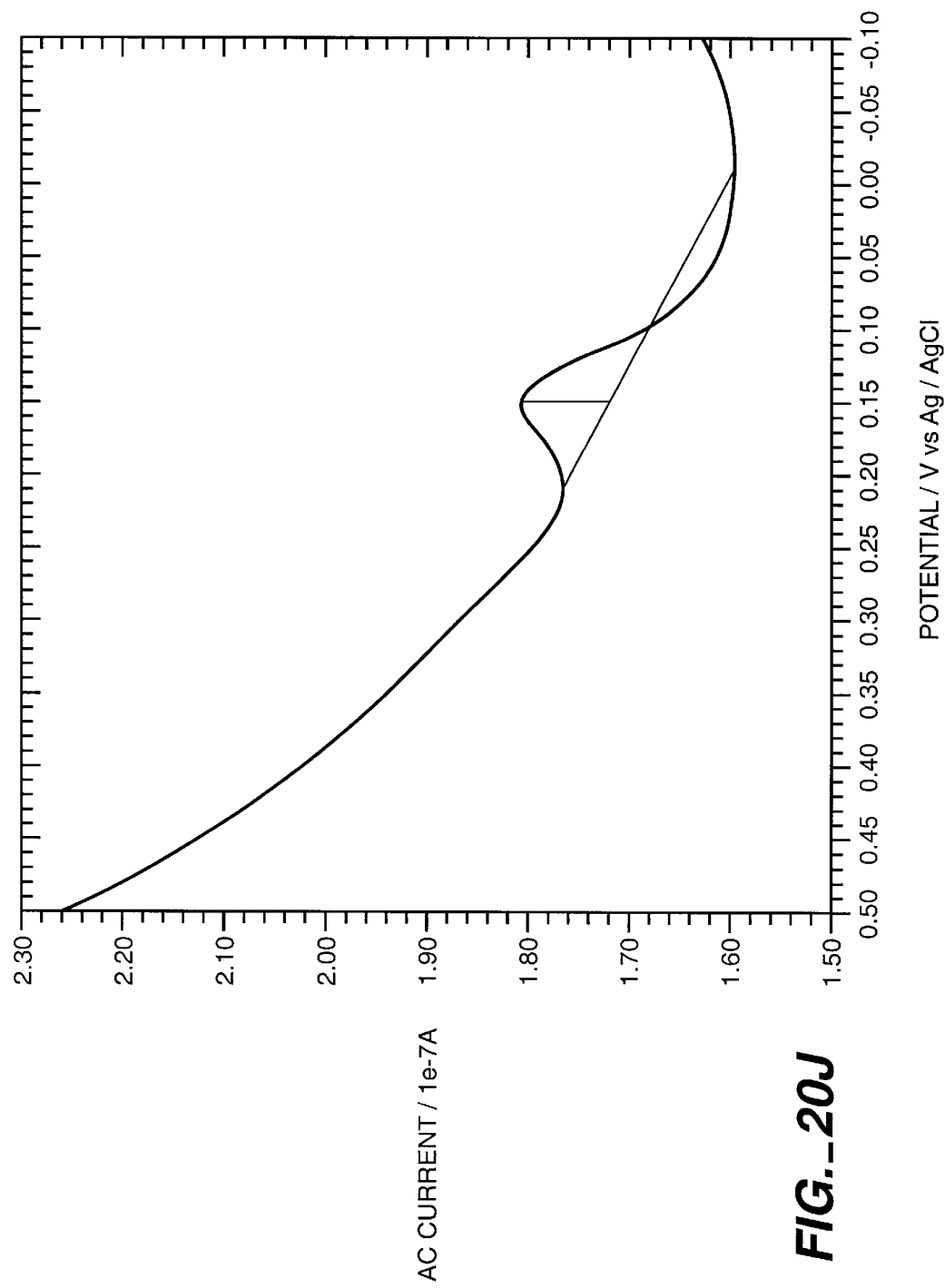
FIG._20J

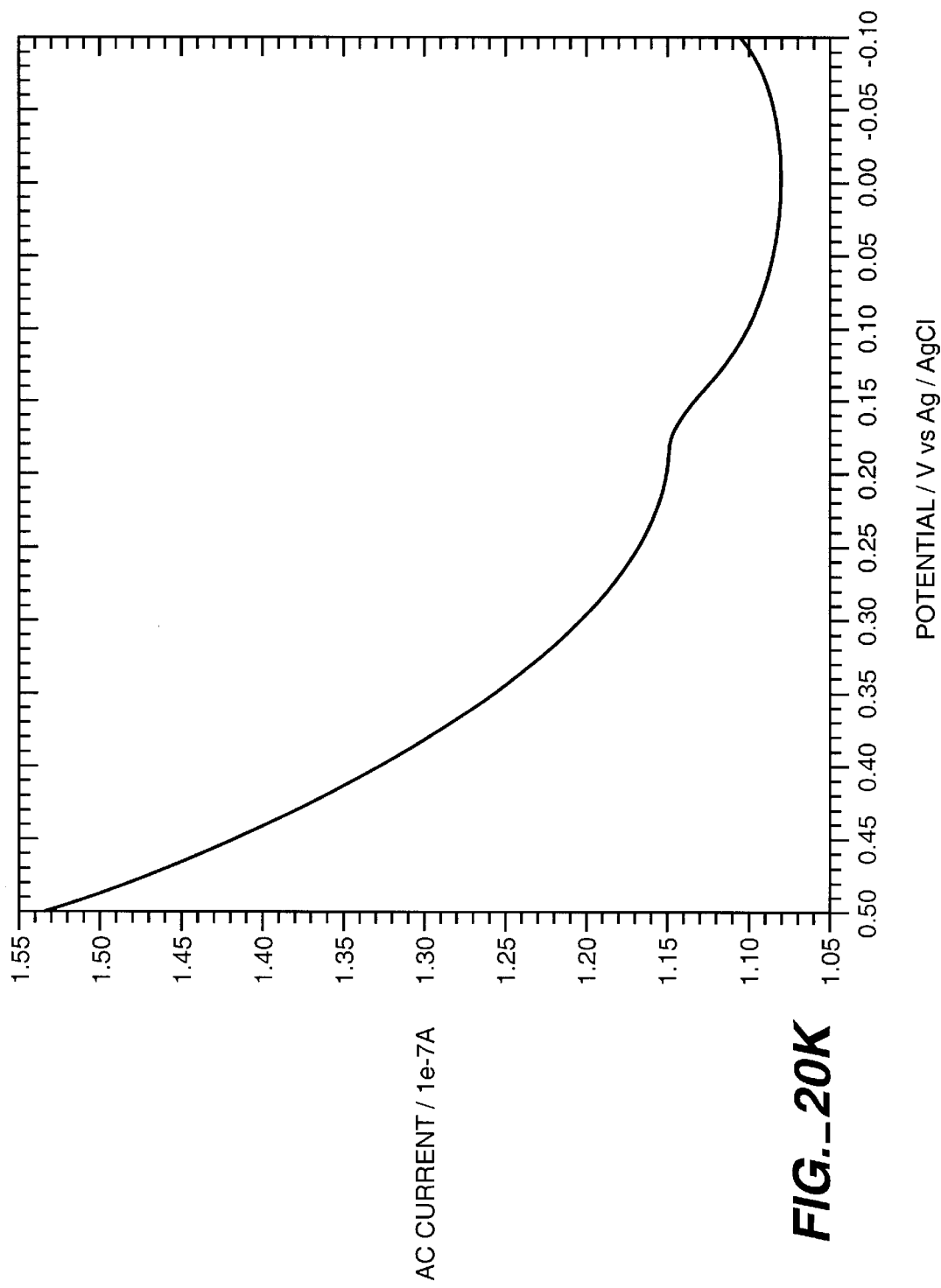
FIG._20K

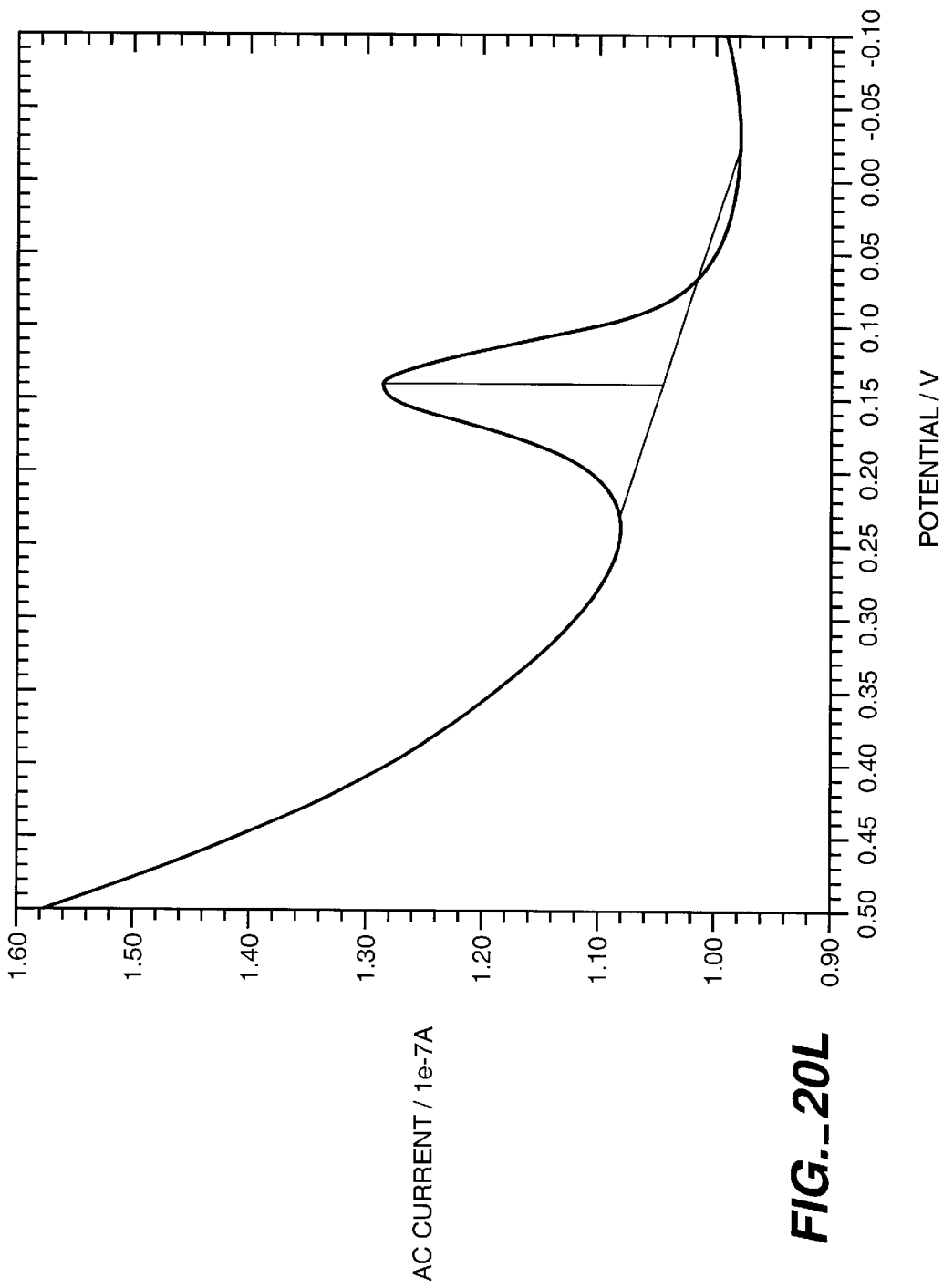
FIG._20L

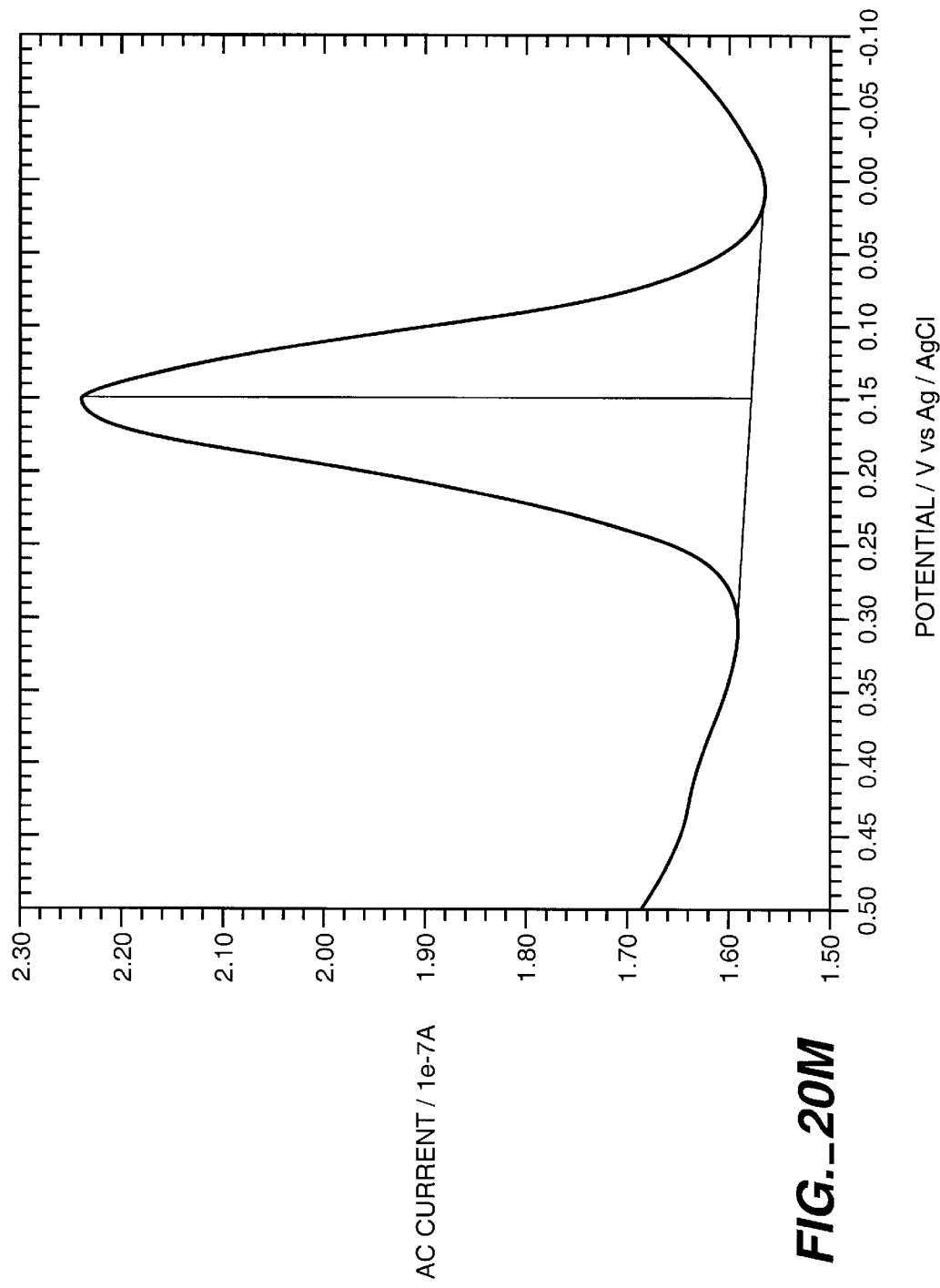
FIG._20M

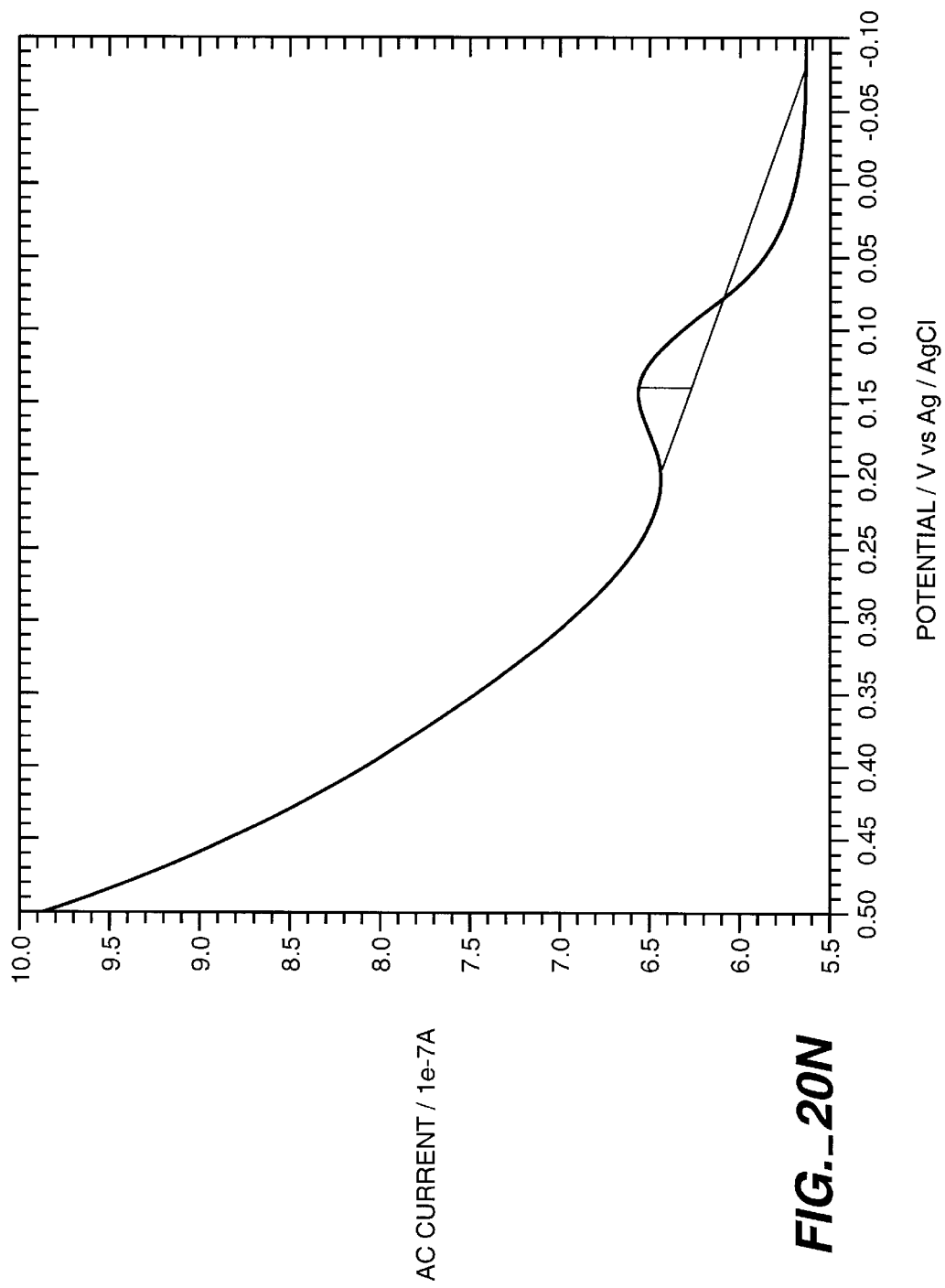
FIG._20N

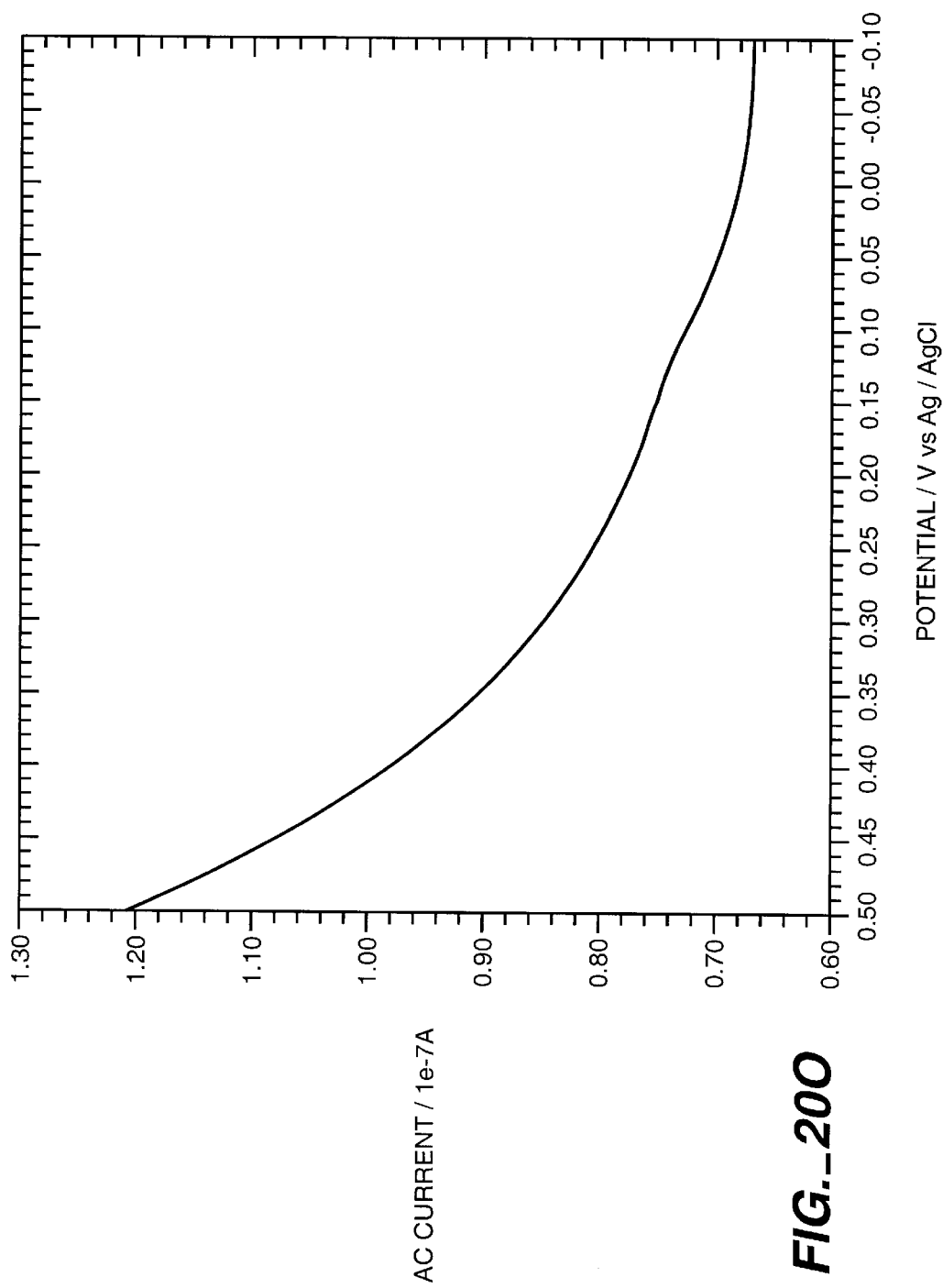
FIG._20O

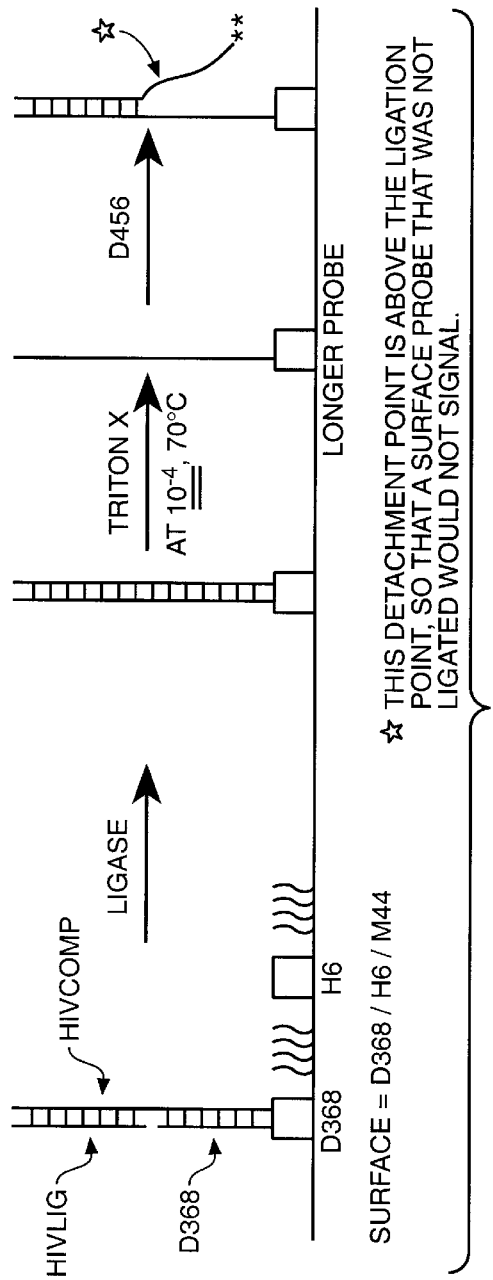
FIG._21

| MEASURER | FILE | ELECTRODE # | HYBRID CODE | ip (nA) | AVERAGE ip (nA) | STDEV ip (nA) | POTENTIAL (mV) | ip (nA) | POTENTIAL (mV) |
|---|---|---|---|---|---|---|---|---|---|
| A | 1 | 7 | 1- EU2+reg helpers+reg system | 0 | 0.36 | 0.71 | — | 1.593 | 70 |
| B | 3 | 8 | | 0 | | | — | | |
| B | 4 | 6 | | 0 | | | — | | |
| JB | 3 | 5 | | 1.42 | | | 60 | | |
| A | 2 | 3 | 1+ rRNA EU2+reg helpers+reg system | 0.7449 | 0.63 | 0.29 | 160 | | |
| B | 1 | 4 | | 0.196 | | | 140 | | |
| JB | 1 | 1 | | 0.8547 | | | 160 | | |
| JB | 2 | 2 | | 0.722 | | | 160 | | |
| A | 5 | 13 | 2- EU2+EU1, 2 reg helpers+reg system | 0.3146 | 0.19 | 0.17 | 160 | 0.2506 | 70 |
| A | 6 | 15 | | 0.3441 | | | 170 | 0.8442 | 80 |
| JB | 4 | 14 | | 0 | | | — | | |
| JB | 6 | 16 | | 0.11 | | | 160 | | |
| A | 3 | 11 | 2+ rRNA EU2+ EU1, 2 reg helpers + reg system | 0.586 | 1.06 | 0.51 | 170 | 0.05 | 70 |
| A | 4 | 12 | | 1 | | | 160 | 2.4 | 50 |
| B | 2 | 9 | | 1.6 | | | 150 | | |
| A | 8 | 22 | 3- (2) 20-Fc ETMs+reg system | 2.661 | 3.03 | 2.99 | 160 | 2.8 | 120 |
| B | 5 | 23 | | 0.9 | | | 160 | | |
| B | 8 | 24 | | 1.2 | | | 160 | | |
| JB | 7 | 21 | | 7.376 | | | 150 | | |
| A | 7 | 18 | 3+ rRNA+ (2) 20-Fc ETMs+reg system | 1.756 | 2.99 | 2.76 | 170 | 0.4778 | 350 |
| B | 6 | 19 | | 0.77 | | | 120 | | |
| B | 7 | 20 | | 7 | | | 150 | | |
| JB | 5 | 17 | | 2.448 | | | 160 | | |
| A | 11 | 29 | 4- (2) 40-Fc ETMs+reg system | 1.426 | 2.42 | 1.11 | 180 | 0.1 | 70 |
| B | 10 | 32 | | 3 | | | 150 | | |
| B | 11 | 31 | | 3.7 | | | 150 | | |
| JB | 9 | 30 | | 1.571 | | | 170 | | |
| A | 9 | 25 | 4+ rRNA+ (2) 40-Fc ETMs+reg system | 12.49 | 7.46 | 4.16 | 160 | | |
| A | 10 | 26 | | 9.278 | | | 160 | | |
| B | 9 | 28 | | 4 | | | 130 | | |
| JB | 8 | 27 | | 4.088 | | | 150 | | |

FIG._22A

| MEASURER | FILE | ELECTRODE | HYBRID CODE | RAW DATA | AVERAGE | STDEV | E₀ (mV) | 2/π*ip (nA) | E₀ (mV) |
|---|---|---|---|---|---|---|---|---|---|
| JZ | 2 | 46 | 5- | 1.041 | 1.93 | 1.25 | 170 | 4.465 | 60 |
| A | 3 | 47 | | 2.811 | | | 170 | | |
| A | 1 | 41 | 5+ | 5.7 | 3.39 | 2.03 | 170 | 0.96 | 60 |
| JZ | 1 | 43 | | 1.862 | | | 170 | | |
| A | 2 | 44 | | 2.613 | | | 180 | | |
| A | 5 | 53 | 6- | 0.6566 | 2.23 | 2.55 | 170 | 2.1 | 60 |
| JZ | 5 | 55 | | 0.8548 | | | 170 | | |
| A | 6 | 56 | | 5.167 | | | 180 | | |
| JZ | 3 | 49 | 6+ | 5.799 | 5.82 | 2.64 | 170 | 1.64 | 60 |
| A | 4 | 50 | | 8.468 | | | 180 | | |
| JZ | 4 | 52 | | 3.187 | | | 180 | | |
| JZ | 7 | 61 | 7- | 0.1988 | 0.73 | 0.60 | 160 | 1.147 | 60 |
| A | 8 | 62 | | 1.382 | | | 170 | 1.04 | 50 |
| JZ | 8 | 64 | | 0.6104 | | | 160 | 0.1958 | 60 |
| JZ | 6 | 58 | 7+ | 1.459 | 1.25 | 0.29 | 160 | 2.38 | 60 |
| A | 7 | 59 | | 1.042 | | | 160 | | |
| JZ | 10 | 70 | 8- | 0.3208 | 0.56 | 0.34 | 160 | 0.504 | 60 |
| A | 11 | 71 | | 0.7994 | | | 190 | 2.22 | 60 |
| JZ | 9 | 65 | 8+ | 3.297 | 2.54 | 0.94 | 170 | 0.71 | 60 |
| A | 9 | 67 | | 1.492 | | | 160 | | |
| A | 10 | 68 | | 2.841 | | | 170 | | |
| JZ | 12 | 76 | 9- | 1.215 | 1.22 | #DIV/0! | 170 | 4.414 | 50 |
| JZ | 11 | 73 | 9+ | 3.768 | 4.68 | 1.29 | 170 | 0.7741 | 50 |
| A | 12 | 74 | | 5.592 | | | 170 | 0.53 | 60 |
| A | 14 | 78 | 10- | 2.842 | 5.12 | 3.22 | 170 | 2.319 | 50 |
| A | 14 | 80 | | 7.4 | | | 170 | | |
| A | 13 | 77 | 10+ | 5.582 | 4.96 | 0.88 | 170 | 3.173 | 50 |
| JZ | 13 | 79 | | 4.337 | | | 160 | | |

FIG._22B

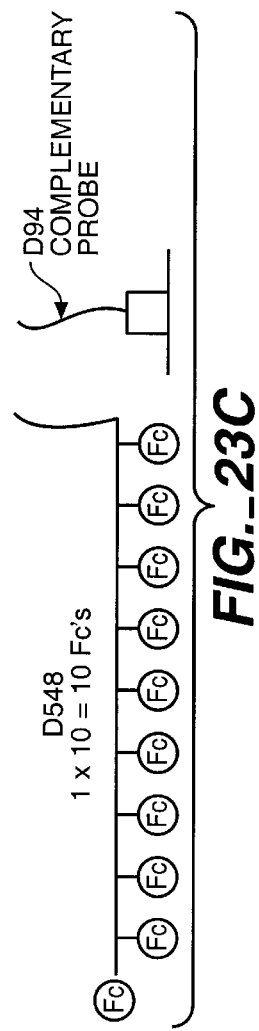
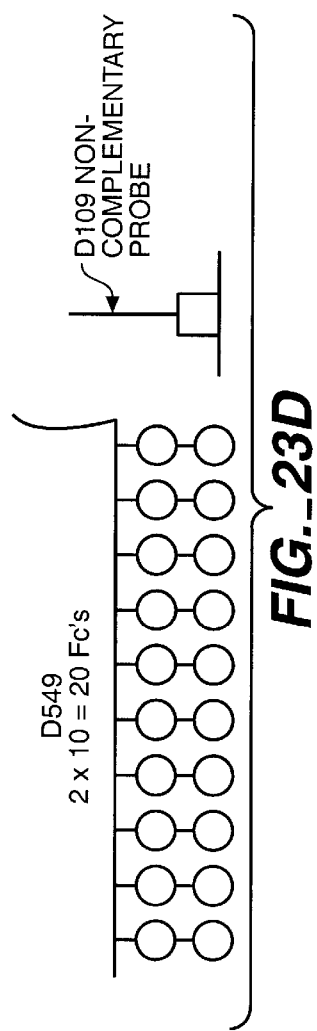
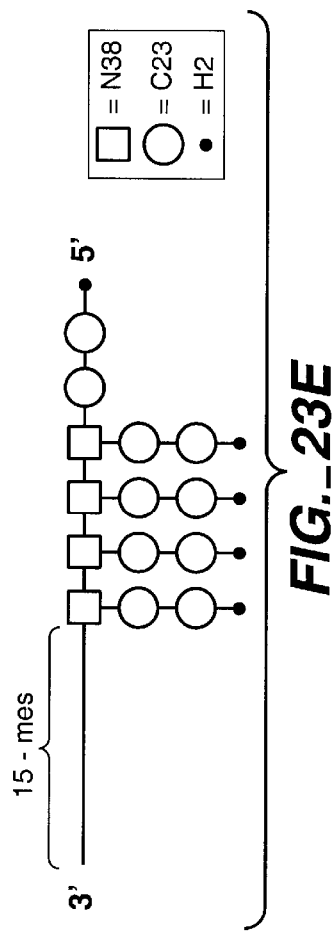
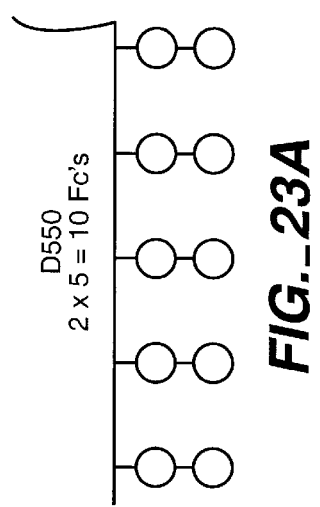
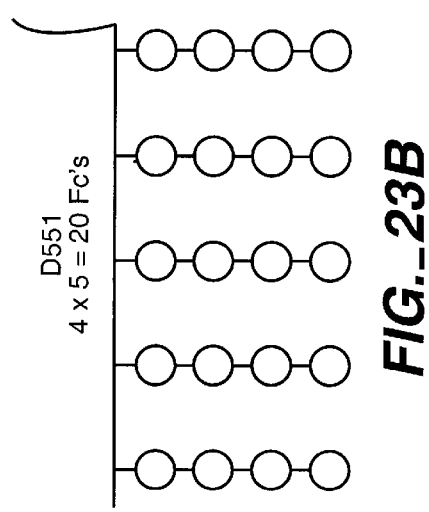

| MEASURER | EXPT | FILE | ELECTRODE | SURFACE | HYBRID | 2/π*ip (nA) | E₀ (mV) | AVERAGE 2/π*ip (nA) | STDEV 2/π*ip (nA) |
|---|---|---|---|---|---|---|---|---|---|
| A<br>A<br>N<br>N | 409<br>409<br>73<br>73 | 1<br>17<br>8<br>22 | 1<br>17<br>8<br>24 | "+" Surface<br>2:2:1<br>D94 / H6 / M44*,<br>total<br>thiol = 833 uM | D548<br>(1x10)** | 22.6<br>9.622<br>14.51<br>11.15 | 150<br>200<br>100<br>110 | 14.5 | 5.8 |
| A<br>A<br>N<br>N | 409<br>409<br>73<br>73 | 8<br>22<br>1<br>17 | 7<br>23<br>2<br>18 | | D549<br>(2x10) | 53.52<br>71.13<br>71.66<br>45.9 | 200<br>220<br>110<br>120 | 60.6 | 12.9 |
| A<br>A<br>N<br>N | 409<br>409<br>73<br>73 | 4<br>18<br>7<br>19 | 3<br>19<br>6<br>22 | | D550<br>(2x5) | 72.4<br>30.67<br>44.49<br>34.43 | 190<br>210<br>120<br>120 | 45.5 | 18.9 |
| A<br>A<br>N<br>N | 409<br>409<br>73<br>73 | 7<br>19<br>4<br>18 | 5<br>21<br>4<br>20 | | D551<br>(4x5) | 105.8<br>48.66<br>70.42<br>74.77 | 210<br>230<br>130<br>130 | 74.9 | 23.5 |
| A<br>A<br>N<br>N | 409<br>409<br>73<br>73 | 9<br>25<br>16<br>30 | 9<br>25<br>16<br>32 | "-" Surface<br>2:2:1<br>D109 / H6 M44*,<br>total<br>thiol = 833 uM | D548<br>(1x10) | 5.665<br>0.6443<br>0.0864<br>0 | 200<br>250<br>120<br>— | 1.6 | 2.7 |
| A<br>A<br>N<br>N | 409<br>409<br>73<br>73 | 16<br>30<br>9<br>25 | 15<br>31<br>10<br>26 | | D549<br>(2x10) | 10.24<br>14.57<br>7.881<br>0.5476 | 230<br>260<br>130<br>140 | 8.3 | 5.9 |
| A<br>A<br>N<br>N | 409<br>409<br>73<br>73 | 12<br>26<br>15<br>27 | 11<br>27<br>14<br>30 | | D550<br>(2x5) | 4.513<br>4.264<br>4.553<br>1.314 | 230<br>260<br>150<br>140 | 3.7 | 1.6 |
| A<br>A<br>N<br>N | 409<br>409<br>73<br>73 | 15<br>27<br>12<br>26 | 13<br>29<br>12<br>28 | | D551<br>(4x5) | 10.31<br>17.46<br>7.445<br>0.8812 | 240<br>280<br>160<br>90 | 9.0 | 6.9 |

\* Note: M44 = M43.  \*\* Also note: (n x m) means there are m bristles, each with n Fc's.

FIG._23F

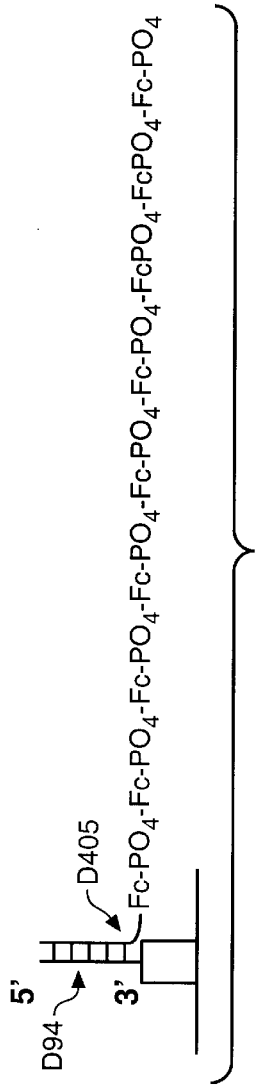
FIG._24A
| MEASURER | EXPT | FILE | ELECTRODE | SURFACE | HYBRID | $2/\pi * i_p$ (nA) | $E_o$ (mV) | AVERAGE $2/\pi * i_p$ (nA) | STDEV $2/\pi * i_p$ (nA) |
|---|---|---|---|---|---|---|---|---|---|
| A | 52 | 1 | 1 | "+" Surface 2:2:1 D94 / H6 / M44*, total thiol = 833 uM | 10 uM D405 in 6x SSC w/50% FCS | 4.81 | 170 | 18.04 | 14.53 |
| A | 52 | 4 | 3 | | | 20.63 | 180 | | |
| N | 384 | 1 | 2 | | | 37.42 | 170 | | |
| N | 384 | 4 | 4 | | | 9.31 | 160 | | |
| A | 52 | 7 | 5 | "−" Surface 2:2:1 D109 / H6 / M44*, total thiol = 833 uM | 10 uM D405 in 6x SSC w/50% FCS | 0.1 | 160 | 3.12 | 4.70 |
| A | 52 | 10 | 7 | | | 9.97 | 160 | | |
| N | 384 | 5 | 6 | | | 0 | — | | |
| N | 384 | 8 | 8 | | | 2.425 | 180 | | |
*NOTE: M44 = M43
FIG._24B

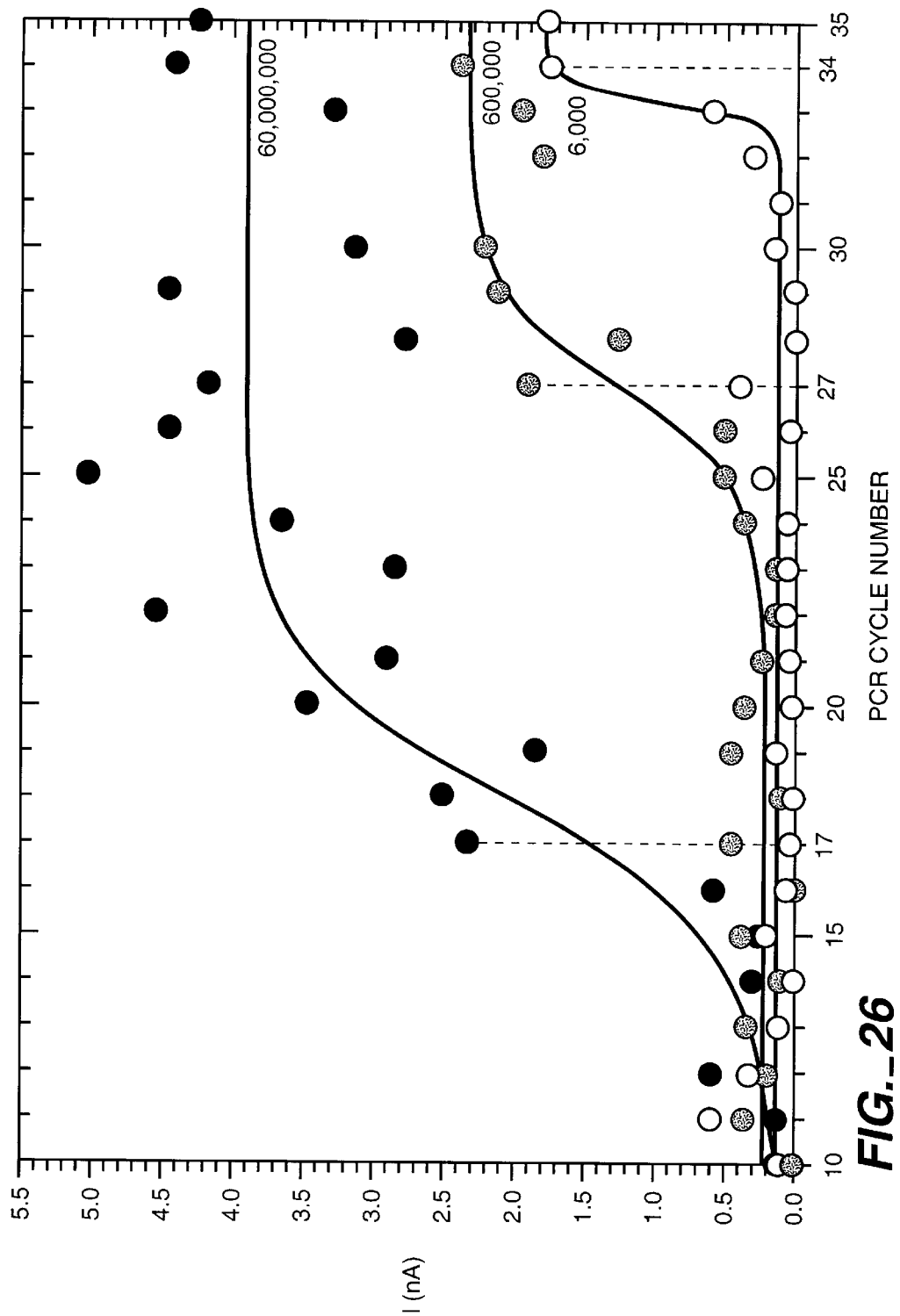
FIG._26

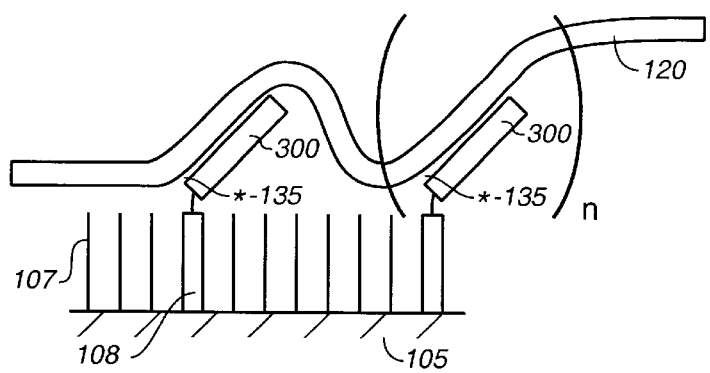
FIG._27A
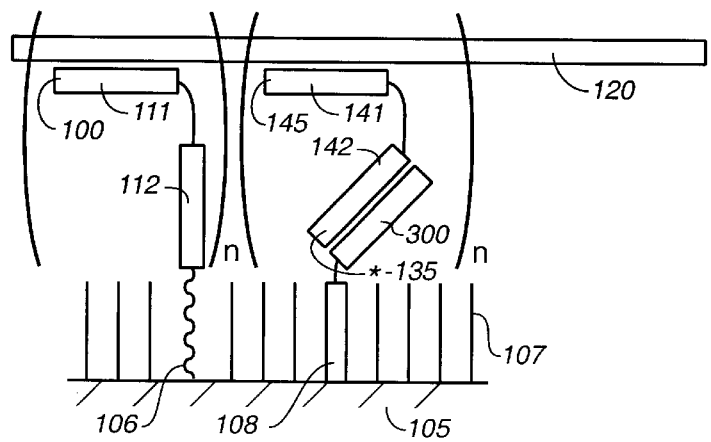
FIG._27B
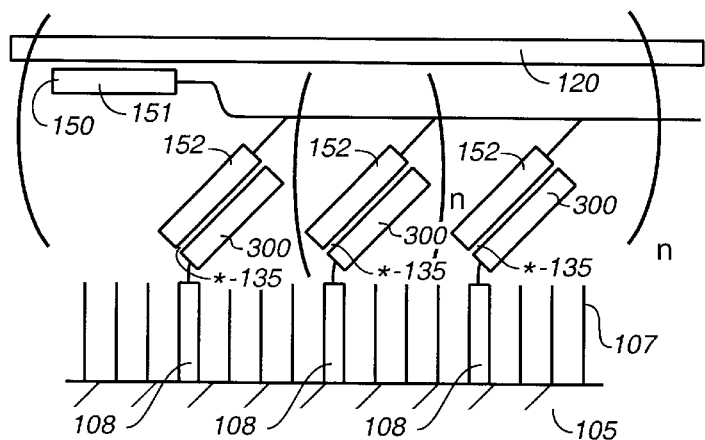
FIG._27C

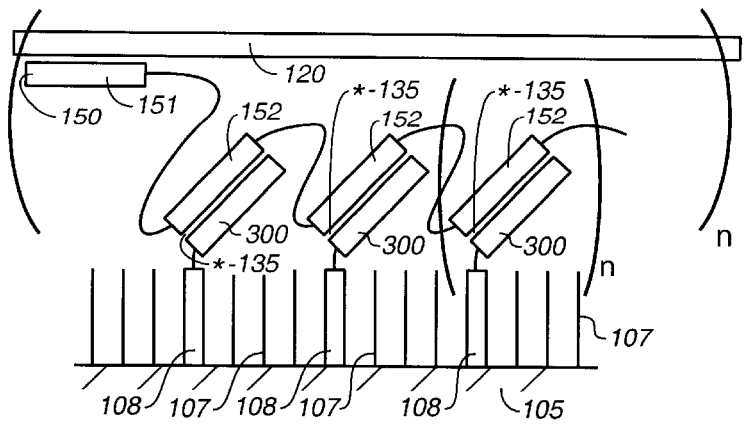
FIG._27D
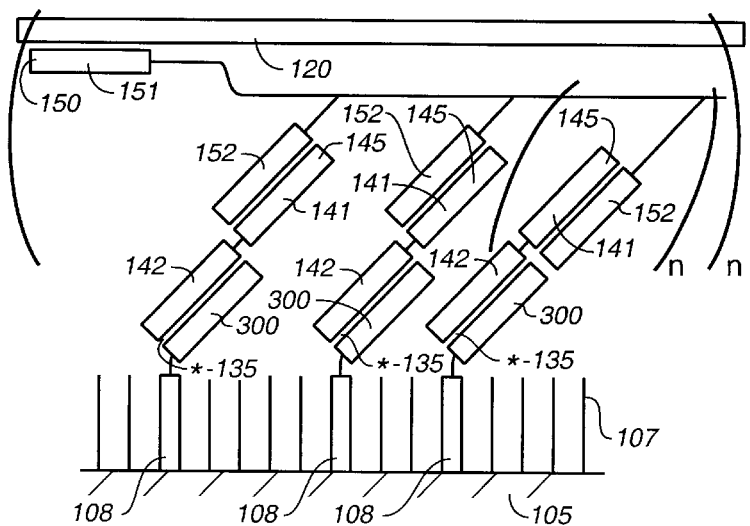
FIG._27E
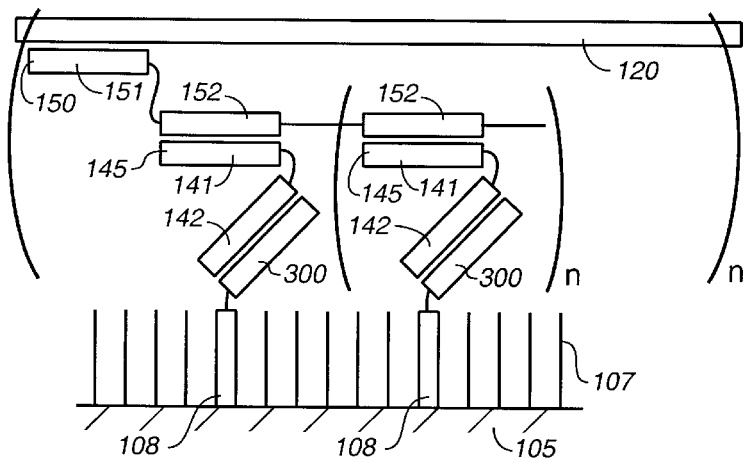
FIG._27F

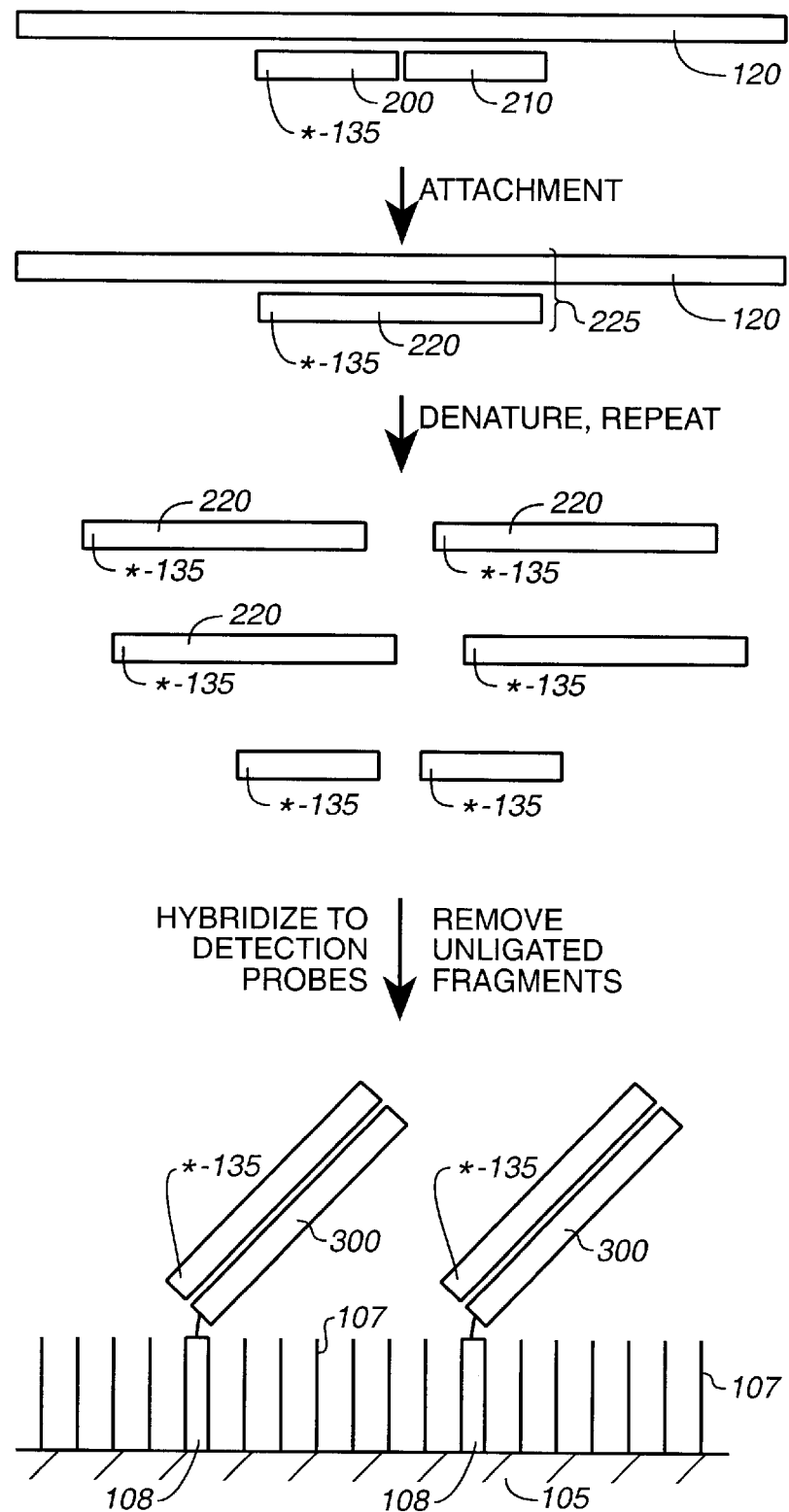
FIG._28

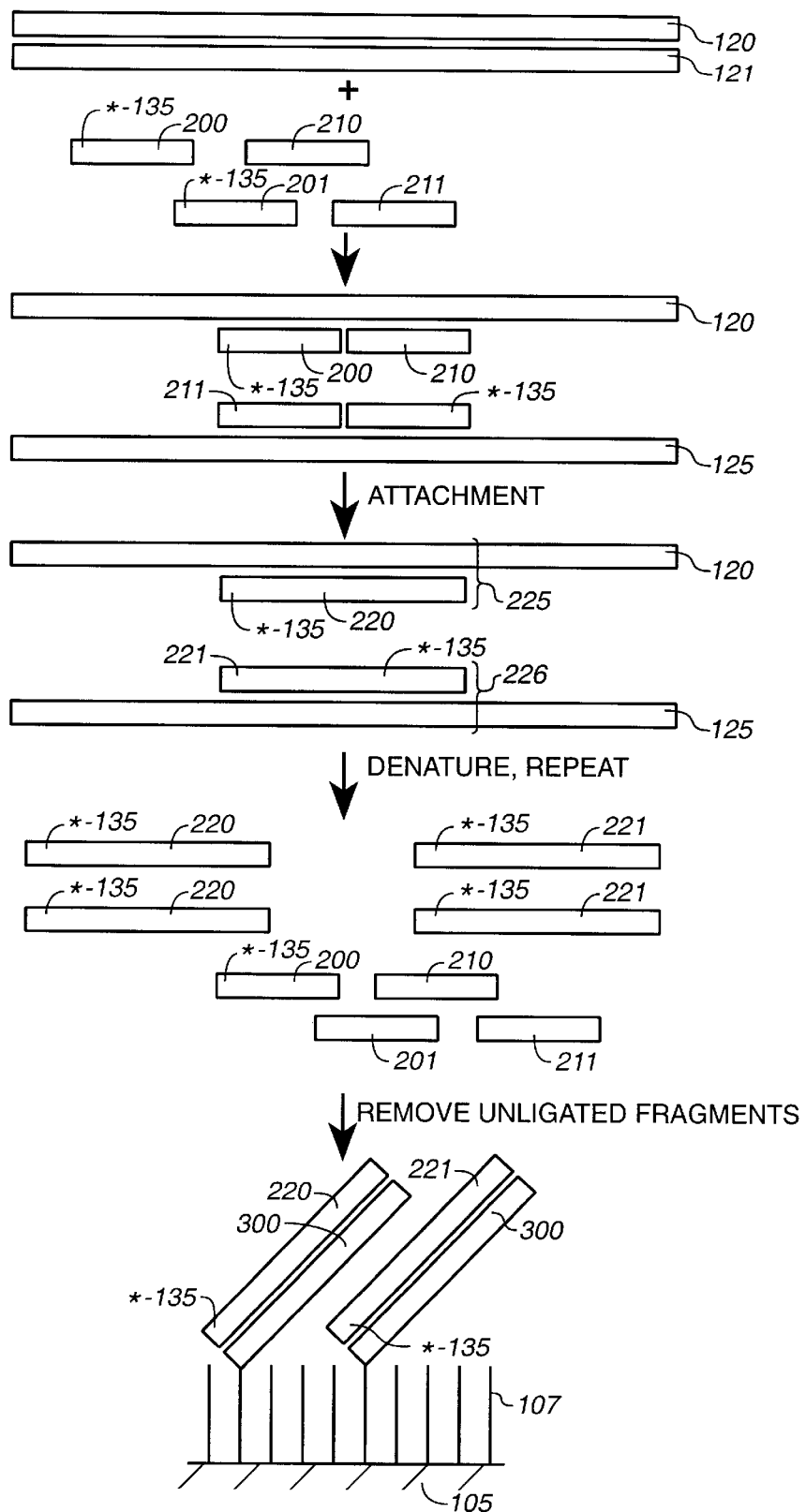
FIG._29

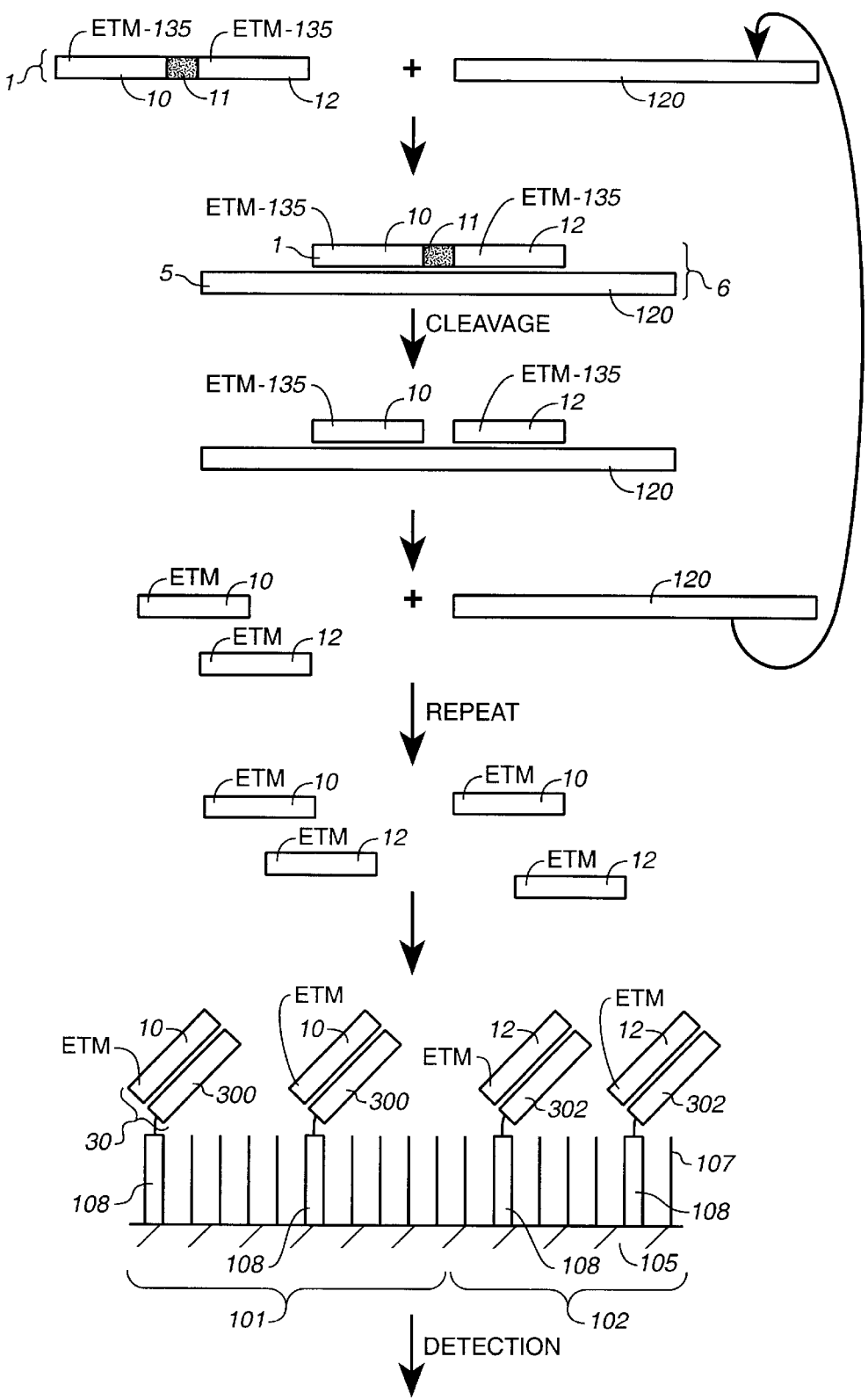
FIG._30

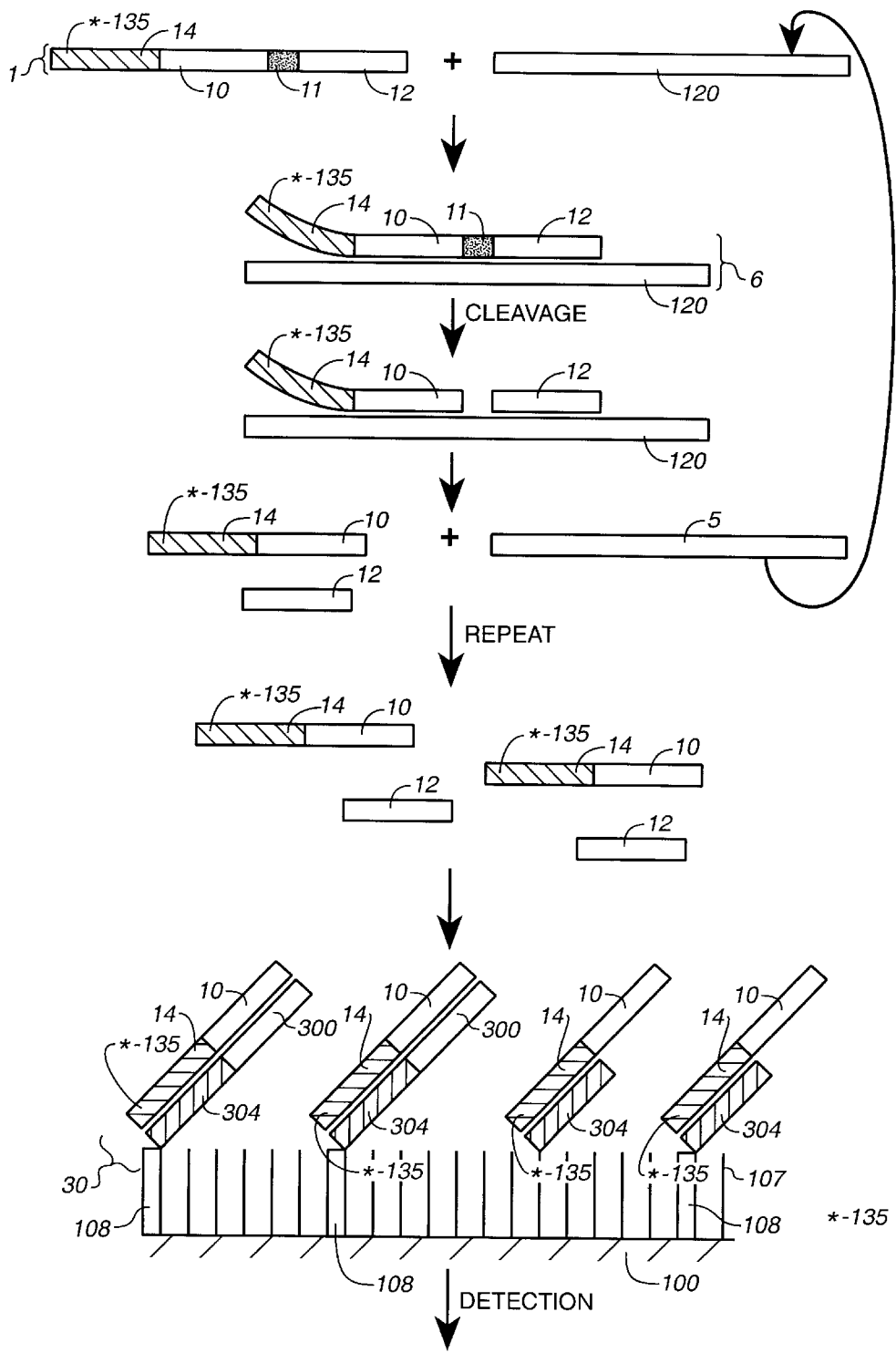
FIG._31

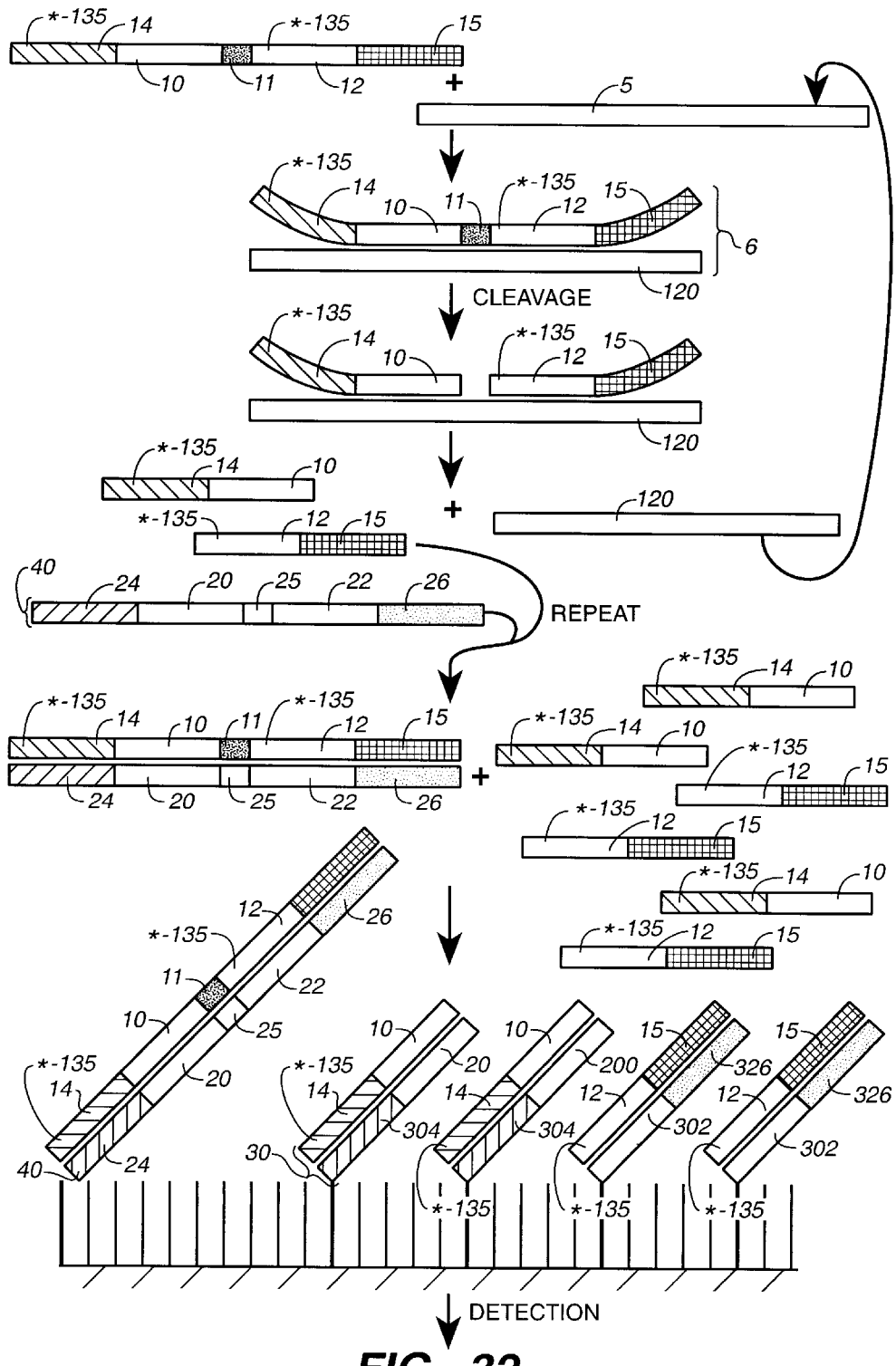
FIG._32

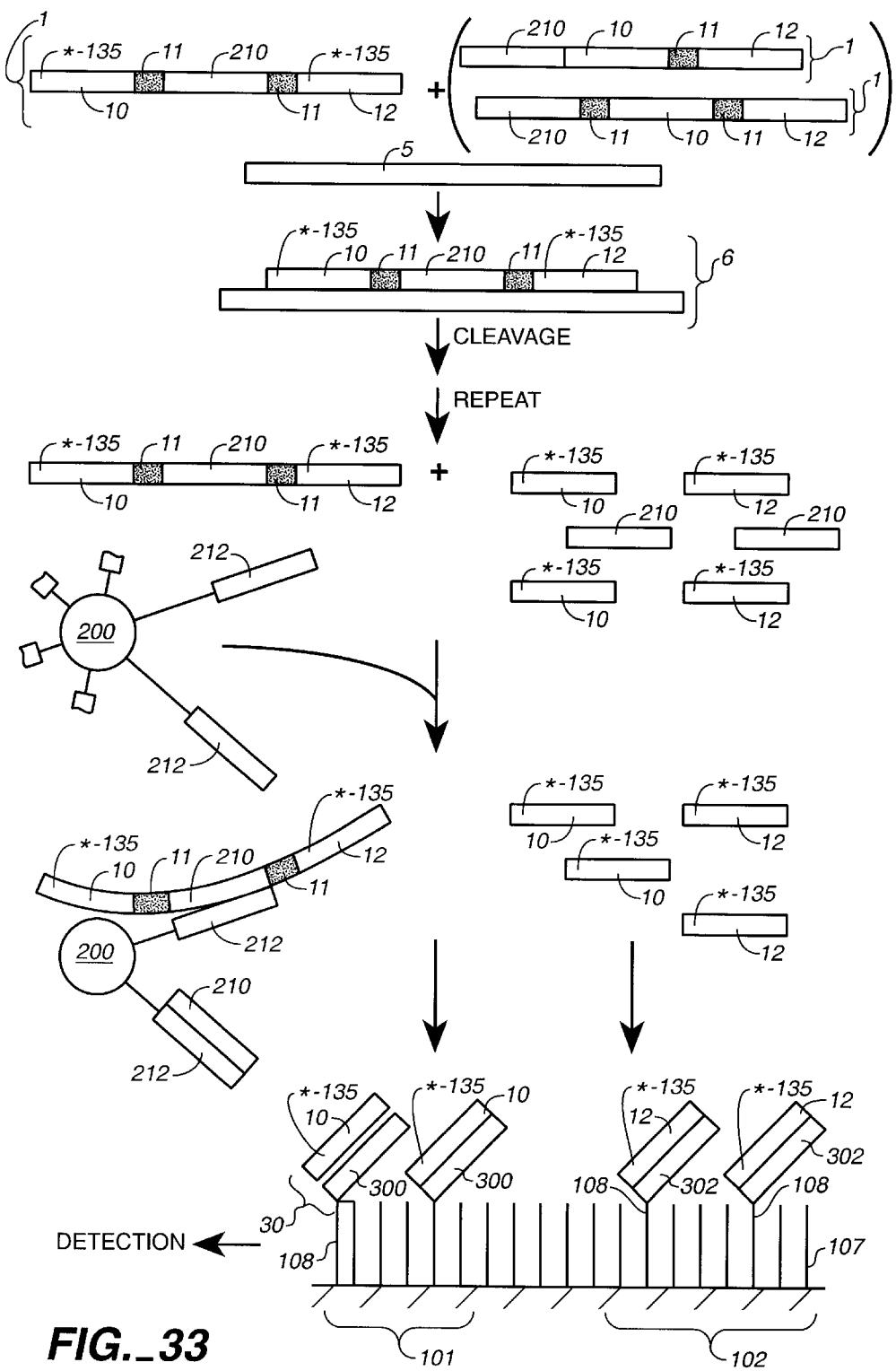
FIG._33

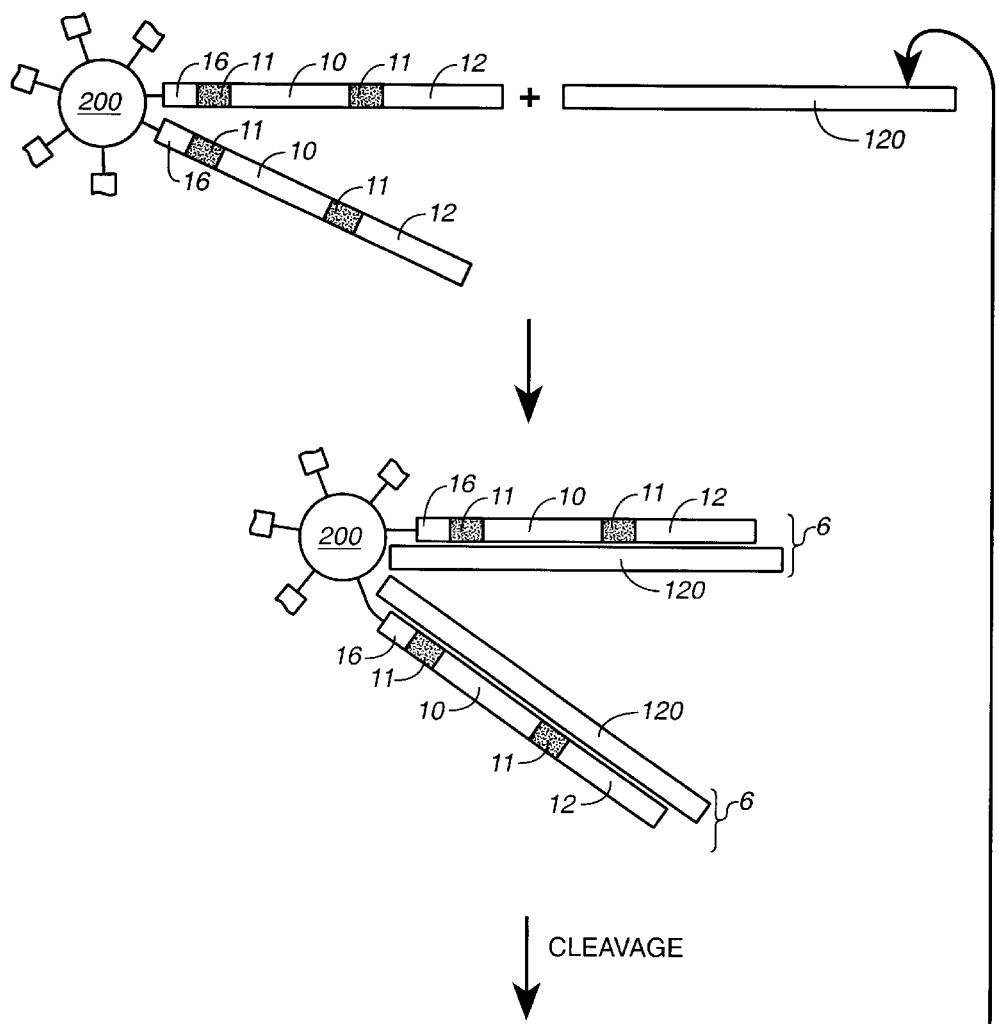
FIG._34A

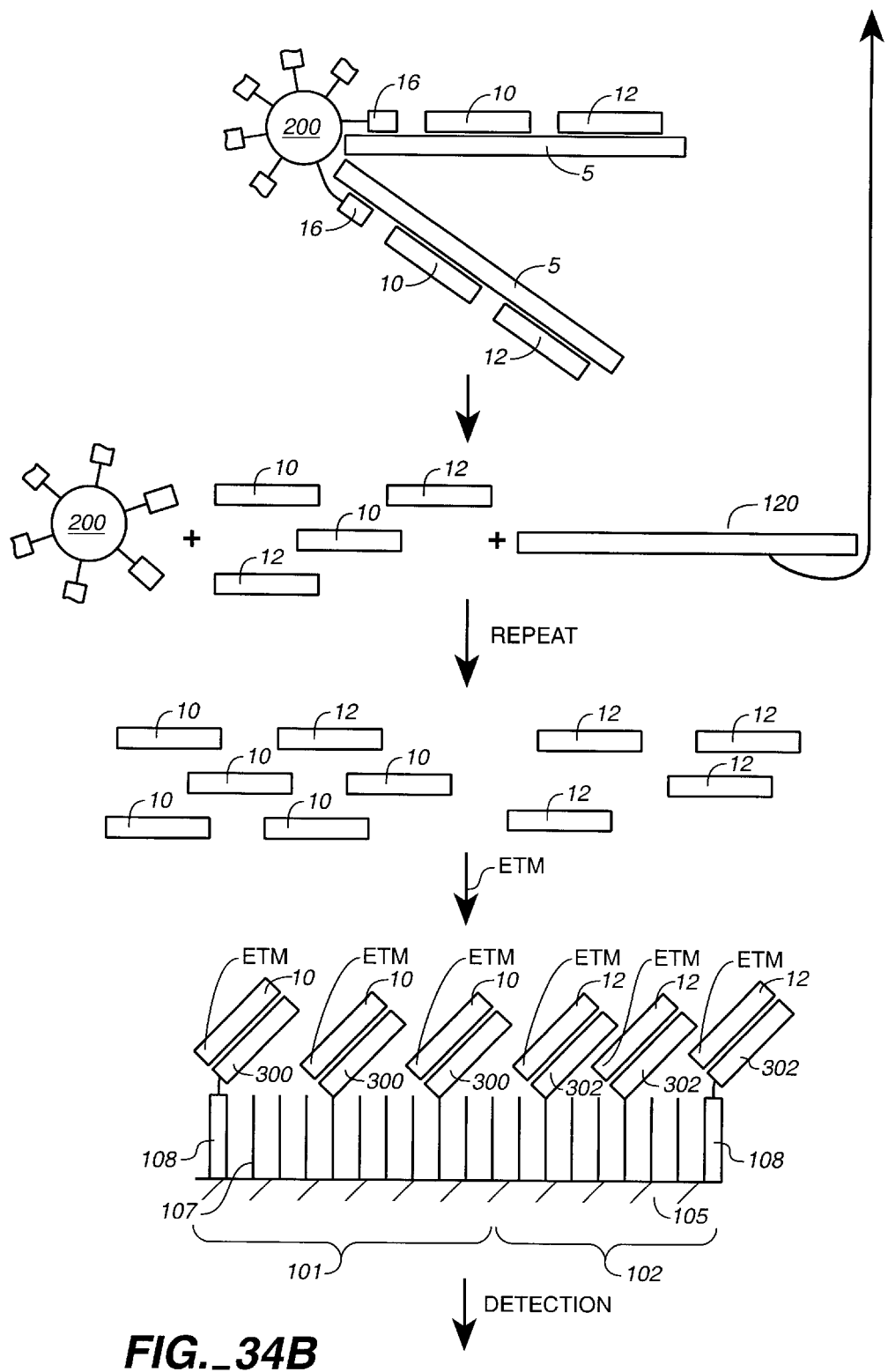
FIG._34B

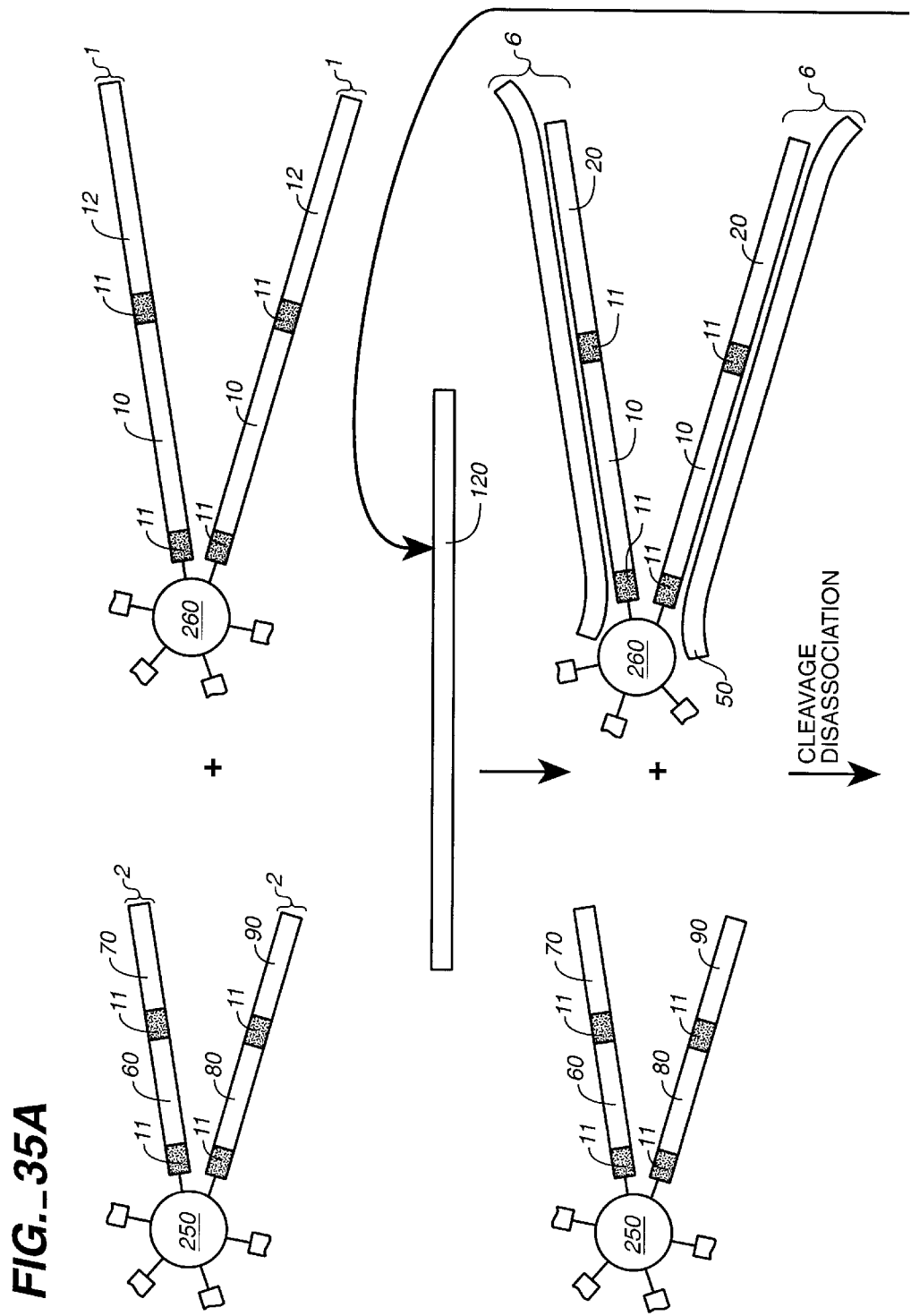
FIG._35A

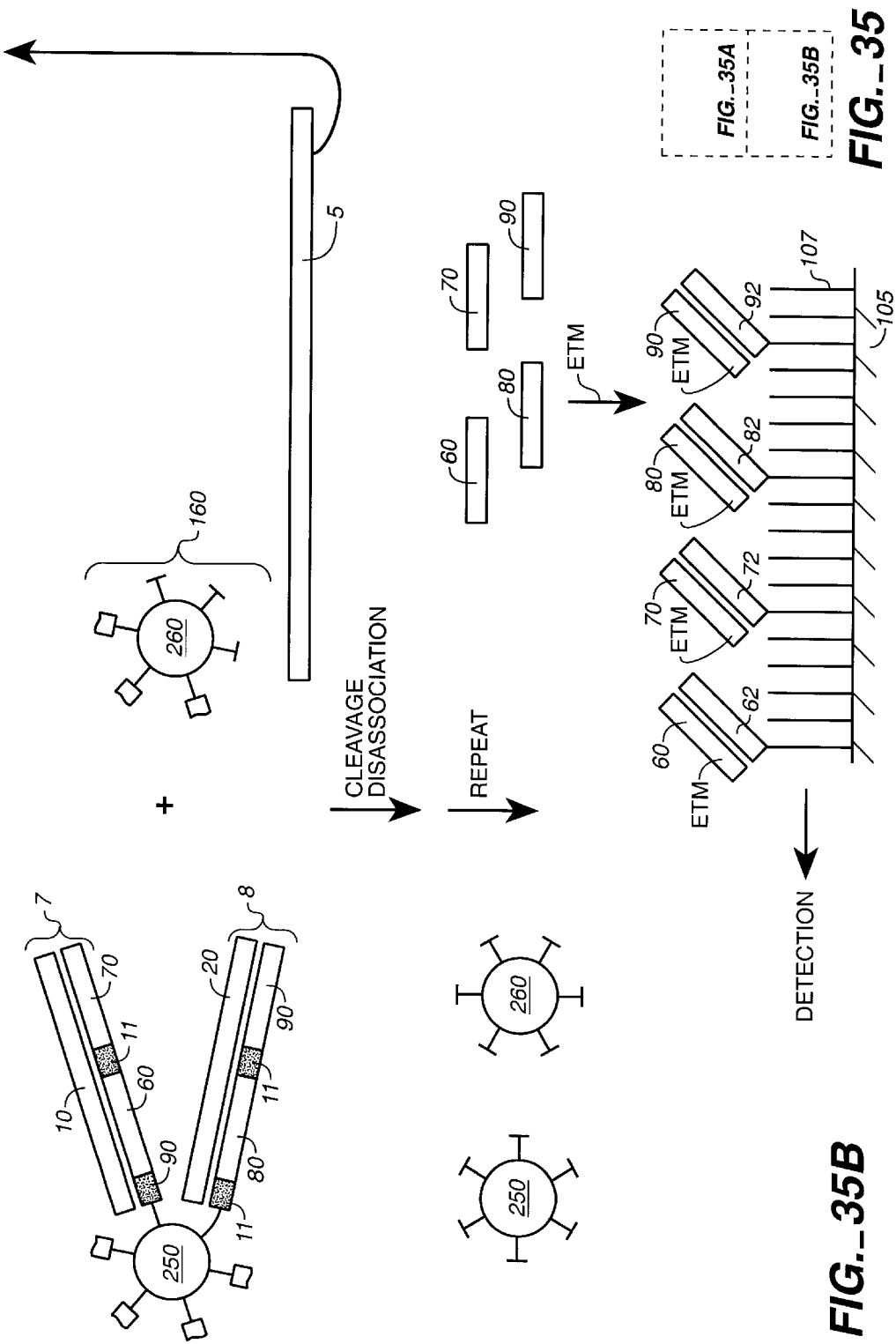

AMPLIFICATION OF NUCLEIC ACIDS WITH ELECTRONIC DETECTION

The present invention is a continuing application of U.S. Ser. Nos. 60/144,698, filed Jul. 20, 1999; and a CIP of Ser. No. 09/238,351, filed Jan. 27, 1999; and a con of Ser. No. 09/014,304, filed Jan. 27, 1998 now U.S. Pat. No. 6,063,573; No. 60/073,011, filed Jan. 29, 1998; No. 60/028,102, filed Mar. 16, 1998; No. 60/084,425, filed May 6, 1998; No. 60/084,509, filed May 6, 1998; and a con of Ser. No. 09/135,183, filed Aug. 17, 1998, all of which are expressly incorporated herein in their entirety.

FIELD OF THE INVENTION

The invention relates to compositions and methods useful in the detection of nucleic acids using a variety of amplification techniques, including both signal amplification and target amplification. Detection proceeds through the use of an electron transfer moiety (ETM) that is associated with the nucleic acid, either directly or indirectly, to allow electronic detection of the ETM using an electrode.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis as outlined below (for a review, see Abramson et al., Current Opinion in Biotechnology, 4:41–47 (1993)).

Sensitivity, i.e. detection limits, remain a significant obstacle in nucleic acid detection systems, and a variety of techniques have been developed to address this issue. Briefly, these techniques can be classified as either target amplification or signal amplification. Target amplification involves the amplification (i.e. replication) of the target sequence to be detected, resulting in a significant increase in the number of target molecules. Target amplification strategies include the polymerase chain reaction (PCR), strand displacement amplification (SDA), nucleic acid sequence based amplification (NASBA), and transcription mediated amplification (TMA).

Alternatively, rather than amplify the target, alternate techniques use the target as a template to replicate a signalling probe, allowing a small number of target molecules to result in a large number of signalling probes, that then can be detected. Signal amplification strategies include the ligase chain reaction (LCR), cycling probe technology (CPT), Invader™, Q-beta replicase (QBR), and the use of "amplification probes" such as "branched DNA"that result in multiple label probes binding to a single target sequence.

The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which may also find use in the invention, including "quantitative competitive PCR"or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtration", among others.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818; Sooknanan et al., Nucleic Acid Sequence-Based Amplification, Ch. 12 (pp. 261–285) of Molecular Methods for Virus Detection, Academic Press, 1995; and "Profiting from Gene-based Diagnostics", CTB International Publishing Inc., N.J., 1996, both of which are incorporated by reference.

Transcription mediated amplification (TMA) is generally described in U.S. Pat. Nos. 5,399,491, 5,888,779, 5,705,365, 5,710,029, all of which are incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

The ligation chain reaction (LCR) involve the ligation of two smaller probes into a single long probe, using the target sequence as the template for the ligase. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, all of which are incorporated by reference.

Q-beta replicase (QBR) is a mRNA amplification technique, similar to NASBA and TMA, that relies on an RNA-dependent RNA polymerase derived from the bacteriophage Q-beta that can synthesize up to a billion stands of product from a template.

Invader™ technology is based on structure-specific polymerases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614, 402; 5,719,028; 5,541,311; and 5,843,669, all of which are hereby incorporated by reference.

"Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) Nuc. Acids Res. 26:5073–5078; Barany, F. (1991) Proc. Natl. Acad. Sci. USA 88:189–193; Lizardi et al. (1998) Nat. Genet. 19:225–232; Zhang et al., Gene 211:277 (1998); and Daubendiek et al., Nature Biotech. 15:273 (1997); all of which are incorporated by reference in their entirety.

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Similarily, dendrimers of nucleic acids serve to vastly increase the amount of label that can be added to a single molecule, using a similar idea but different compositions. This technology is as described in U.S. Pat. No. 5,175,270 and Nilsen et al., J. Theor. Biol. 187:273 (1997), both of which are incorporated herein by reference.

Finally, U.S. Pat. Nos. 5,591,578, 5,824,473, 5,770,369, 5,705,348, and 5,780,234, and PCT application WO098/20162 describe novel compositions comprising nucleic acids containing electron transfer moieties, including electrodes, which allow for novel detection methods of nucleic acid hybridization.

SUMMARY OF THE INVENTION

In accordance with the objects outlined above, the present invention provides methods for detecting a target nucleic acid sequence. The methods comprise hybridizing at least a first primer nucleic acid to the target sequence to form a first hybridization complex, and contacting the first hybridization complex with a first enzyme to form a modified first primer nucleic acid. The first hybridization complex is then disassociated. These steps may be repeated a plurality of times. A first assay complex is then formed comprising at least one ETM and the modified first primer nucleic acid. The assay complex is covalently attached to an electrode. Electron transfer is then detected between the ETM and the electrode as an indication of the presence of the target sequence. The method can include the same method on a second target sequence substantially complementary to the the first target sequence.

In an additional aspect, the method utilizes a DNA polymerase and the modification to the primer is an extension of the primer such that the polymerase chain reaction (PCR) occurs.

In a further aspect, the method utilizes a ligase and the modification to the primer comprises a ligation of the first primer which hybridizes to a first domain of the first target sequence to a third primer which hybridizes to a second adjacent domain of the first target sequence, such that the ligase chain reaction (LCR) occurs.

In an additional aspect, the method utilizes a first primer comprising a first probe sequence, a first scissile linkage and a second probe sequence. The enzyme will cleave the first scissile linkage resulting in the separation of the first and the second probe sequences and the disassociation of the hybridization complex while leaving the first target sequence intact, such that the cycling probe technology (CPT) reaction occurs.

In a further aspect, the method utilizes a first enzyme that is a polymerase that extends the first primer to form a modified first primer comprising a first newly synthesized strand, and said method further comprises the addition of a second enzyme comprising a nicking enzyme that nicks the extended first primer leaving the first target sequence intact. The method additionally comprises extending from the nick using the polymerase, thereby displacing the first newly synthesized strand and generating a second newly synthesized strand, such that strand displacement amplification (SDA) occurs.

In an additional aspect, the method utilizes a first target sequence that is a RNA target sequence, a first primer nucleic acid that is a DNA primer comprising an RNA polymerase promoter, and the first enzyme is a reverse-transcriptase that extends the first primer to form a first newly synthesized DNA strand. The method further comprises the addition of a second enzyme comprising an RNA degrading enzyme that degrades the first target sequence. A third primer is then added that hybridizes to the first newly synthesized DNA strand. A third enzyme is added comprising a DNA polymerase that extends the third primer to form a second newly synthesized DNA strand, to form a newly synthesized DNA hybrid. A fourth enzyme is then added comprising an RNA polymerase that recognizes the RNA polymerase promoter and generates at least one newly synthesized RNA strand from the DNA hybrid, such that nucleic acid sequence-based amplification (NASBA) occurs.

In a further aspect, the invention provides methods for detecting a target nucleic acid sequence comprising forming a first hybridization complex comprising an amplifier probe and a target sequence, wherein the amplifier probe comprises at least two amplification sequences and hybridizing a first portion of at least one label probe to all or part of at least one amplification sequence. A second portion of the label probe is then hybridized to a detection probe covalently attached to an electrode via a conductive oligomer to form a second hybridization complex that contains at least a first electron transfer moiety (ETM). The label probe is then detected by measuring electron transfer between said first ETM and said electrode.

In an additional aspect, the invention provides methods for detecting a target nucleic acid sequence comprising forming a first hybridization complex comprising an amplifier probe and a target sequence, wherein the amplifier probe comprises at least two amplification sequences and wherein the first hybridization complex is covalently attached to an electrode comprising a monolayer comprising conductive oligomers. At least one label probe comprising at least one electron transfer moiety (ETM) is hybridized to all or part of at least one amplification sequence, and the label probe is detected by measuring electron transfer between said first ETM and said electrode.

In a further aspect, the invention provides kits for the detection of a first target nucleic acid sequence comprising at least a first nucleic acid primer substantially complementary to at least a first domain of the target sequence and at least a first enzyme that will modify the first nucleic acid primer. The kits additionally comprise an electrode comprising at least one detection probe covalently attached to the electrode via a conductive oligomer.

In an additional aspect, the invention provides methods of detecting target sequences comprising providing a rolling circle probe (RCP) comprising a first ligation sequence substantially complementary to a first domain of said target sequence, a second ligation sequence substantially complementary to a second domain of said target sequence; and a priming sequence. The methods further comprise hybridizing the first ligation sequence to said first domain and the second ligation sequence to the second domain to form a first hybridization complex and ligating the first and second ligation sequences together. A primer substantially complementary to said priming sequence, a polymerase, dNTPs and an ETM are added to the first hybridization complex under conditions whereby a rolling circle concatamer is formed, and the ETM is detected as an indicator of the presence of the target sequence. The RCP may further optionally comprise a cleavage site and a capture sequence.

In a further aspect, the invention provides methods for detecting a first target nucleic acid sequence comprising hybridizing an invader primer and a signaling primer to form a first hybridization complex. The signaling primer comprises a first portion comprising a sequence that will hybridize to a first portion of the target sequence; a cleavage site and a detection sequence that does not hybridize with the target sequence. The first hybridization complex is contacted with a structure specific cleavage enzyme such that the signaling primer is cleaved and the detection sequence is released. The released detection sequence is contacted with an electrode comprising a capture probe to form a second hybridization complex, wherein the second hybridization complex comprises at least one ETM. The ETM is detected as an indication of the presence of said target sequence.

BRIEF DESCRIPTION OF THE DRAWINGS

FIGS. 1A–1O depict depict a number of different compositions of the invention; the results are shown in Example 1 and 2. FIG. 1A depicts I, also referred to as P290. FIG. 1B depicts II, also referred to as P291. FIG. 1C depicts III, also referred to as W31. FIG. 1D depicts IV, also referred to as N6. FIG. 1E depicts V, also referred to as P292. FIG. 1F depicts II, also referred to as C23. FIG. 1G depicts VII, also referred to as C15. FIG. 1H depicts VII, also referred to as C95. FIG. 1I depicts Y63. FIG. 1J depicts another compound of the invention. FIG. 1K depicts N11. FIG. 1L depicts C131, with a phosphoramidite group and a DMT protecting group. FIG. 1M depicts W38, also with a phosphoramidite group and a DMT protecting group. FIG. 1N depicts the commercially available moiety that enables "branching" to occur, as its incorporation into a growing oligonucleotide chain results in addition at both the DMT protected oxygens. FIG. 1O depicts glen, also with a phosphoramidite group and a DMT protecting group, that serves as a non-nucleic acid linker. FIGS. 1A to 1G and 1J are shown without the phosphoramidite and protecting groups (i.e. DMT) that are readily added.

FIG. 2 depicts the synthetic scheme of a preferred attachment of an ETM, in this case ferrocene, to a nucleoside (in this case adenosine) via an oxo linkage to the ribose, forming the N6 compound of the invention.

FIG. 3 is similar to FIG. 2 except that the nucleoside is cytidine, forming the W38 compound of the invention.

FIG. 4 depicts the synthetic scheme of a preferred attachment of an ETM, in this case ferrocene, to a nucleoside via the phosphate, forming the Y63 compound of the invention.

FIG. 5 depicts the synthetic scheme of a triphosphate nucleotide, in this case adenosine, with an attached ETM, in this case ferrocene, via an oxo linkage to the ribose.

FIG. 6 depicts the use of an activated carboxylate for the addition of a nucleic acid functionalized with a primary amine to a pre-formed SAM.

FIG. 7 (SEQ ID NOS: 1–7) depicts a schematic of the use of "universal" type gene chips, utilizing restriction endonuclease sites.

FIGS. 8A and 8B depicts two phosphate attachments of conductive oligomers that can be used to add the conductive oligomers at the 5' position, or any position.

FIG. 9 depicts the synthesis of an insulator (C109) to the ribose of a nucleoside for attachment to an electrode.

FIG. 10 depicts the synthetic scheme of ethylene glycol terminated conductive oligomers.

FIGS. 11A, 11B and 11C depict the synthesis of three different "branch" points (in this case each using adenosine as the base), to allow the addition of ETM polymers. FIG. 11A depicts the synthesis of the N17 compound of the invention. FIG. 11B depicts the synthesis of the W90 compound, and FIG. 11C depicts the synthesis of the N38 compound.

FIG. 12 depicts a schematic of the synthesis of simultaneous incorporation of multiple ETMs into a nucleic acid, using the N17 "branch" point nucleoside.

FIG. 13 depicts a schematic of an alternate method of adding large numbers of ETMs simultaneously to a nucleic acid using a "branch" point phosphoramidite, in this case utilizing three branch points (although two branch points are also possible; see for example FIG. 1N) as is known in the art. As will be appreciated by those in the art, each end point can contain any number of ETMs.

FIG. 14 shows a representative hairpin structure. 500 is a target binding sequence, 510 is a loop sequence, 520 is a self-complementary region, 530 is substantially complementary to a detection probe, and 530 is the "sticky end", that is, a portion that does not hybridize to any other portion of the probe, that contains the ETMs.

FIGS. 15A, 15B and 15C depict three preferred embodiments for attaching a target sequence to the electrode. FIG. 15A depicts a target sequence 120 hybridized to a capture probe 100 linked via a attachment linker 106, which as outlined herein may be either a conductive oligomer or an insulator. The electrode 105 comprises a monolayer of passivation agent 107, which can comprise conductive oligomers (herein depicted as 108) and/or insulators (herein depicted as 109). As for all the embodiments depicted in the figures, n is an integer of at least 1, although as will be appreciated by those in the art, the system may not utilize a capture probe at all (i.e. n is zero), although this is generally not preferred. The upper limit of n will depend on the length of the target sequence and the required sensitivity. FIG. 15B depicts the use of a single capture extender probe 110 with a first portion 111 that will hybridize to a first portion of the target sequence 120 and a second portion that will hybridize to the capture probe 100. FIG. 15C depicts the use of two capture extender probes 110 and 130. The first capture extender probe 110 has a first portion 111 that will hybridize to a first portion of the target sequence 120 and a second portion 112 that will hybridize to a first portion 102 of the capture probe 100. The second capture extender probe 130 has a first portion 132 that will hybridize to a second portion of the target sequence 120 and a second portion 131 that will hybridize to a second portion 101 of the capture probe 100. As will be appreciated by those in the art, any of these attachment configurations may be used with any of the other systems, including the embodiments of FIG. 16.

FIGS. 16A, 16B, 16C, 16D, 16E, 16F and 16G depict some of the embodiments of the invention. All of the monolayers depicted herein show the presence of both conductive oligomers 108 and insulators 107 in roughly a 1:1 ratio, although as discussed herein, a variety of different ratios may be used, or the insulator may be completely absent. In addition, as will be appreciated by those in the art, any one of these structures may be repeated for a particular target sequence; that is, for long target sequences, there may be multiple assay complexes formed. Additionally, any of the electrode-attachment embodiments of FIG. 15 may be used in any of these systems.

FIGS. 16A, 16B and 16D have the target sequence 120 containing the ETMs 135; as discussed herein, these may be added enzymatically, for example during a PCR reaction using nucleotides modified with ETMs, resulting in essentially random incorporation throughout the target sequence, or added to the terminus of the target sequence. FIG. 16C depicts the use of two different capture probes 100 and 100', that hybridize to different portions of the target sequence 120. As will be appreciated by those in the art, the 5'-3' orientation of the two capture probes in this embodiment is different.

FIG. 16C depicts the use of label probes 145 that hybridize directly to the target sequence 120. FIG. 16C shows the use of a label probe 145, comprising a first portion 141 that hybridizes to a portion of the target sequence 120, a second portion 142 comprising ETMs 135.

FIGS. 16E, 16F and 16G depict systems utilizing label probes 145 that do not hybridize directly to the target, but rather to amplifier probes that are directly (FIG. 16E) or indirectly (FIGS. 16F and 16G) hybridized to the target sequence. FIG. 16E utilizes an amplifier probe 150 has a first portion 151 that hybridizes to the target sequence 120 and at least one second portion 152, i.e. the amplifier sequence, that hybridizes to the first portion 141 of the label probe. FIG. 16F is similar, except that a first label extender probe 160 is used, comprising a first portion 161 that hybridizes to the target sequence 120 and a second portion 162 that hybridizes to a first portion 151 of amplifier probe 150. A second portion 152 of the amplifier probe 150 hybridizes to a first portion 141 of the label probe 140, which also comprises a recruitment linker 142 comprising ETMs 135. FIG. 16G adds a second label extender probe 170, with a first portion 171 that hybridizes to a portion of the target sequence 120 and a second portion that hybridizes to a portion of the amplifier probe.

FIG. 16H depicts a system that utilizes multiple label probes. The first portion 141 of the label probe 140 can hybridize to all or part of the recruitment linker 142.

FIGS. 17A, 17B, 17C, 17D and 17E depict different possible configurations of label probes and attachments of ETMs. In FIGS. 17A–C, the recruitment linker is nucleic acid; in FIGS. 17D and E, is is not. A=nucleoside replacement; B=attachment to a base; C=attachment to a ribose; D=attachment to a phosphate; E=metallocene polymer (although as described herein, this can be a polymer of other ETMs as well), attached to a base, ribose or phosphate (or other backbone analogs); F=dendrimer structure, attached via a base, ribose or phosphate (or other backbone analogs); G=attachment via a "branching" structure, through base, ribose or phosphate (or other backbone analogs); H=attachment of metallocene (or other ETM) polymers; I=attachment via a dendrimer structure; J=attachment using standard linkers.

FIG. 18 depicts an improvement utilizing a stem-loop probe. This can be desirable as it creates torsional strain on the surface-bound probe, which has been shown to increase binding efficiency and in some cases thermodynamic stability. In this case, the surface bound probe comprises a capture probe 100, a first stem-loop sequence 550, a target binding sequence 560, and a second stem-loop sequence 570 that is substantially complementary to the first stem-loop sequence. Upon addition of the target sequence 120, which can contain the ETMs 135 either directly or indirectly using a label probe 145, the effective concentration of the target at the surface increases.

FIGS. 19A–B (SEQ ID NOS: 8–34) depicts some of the sequences used in Example 1.

FIGS. 20A–20O depict representative scans from the experiments outlined in Example 1. Unless otherwise noted, all scans were run at initial voltage −0.11 V, final voltage 0.5 V, with points taken every 10 mV, amplitude of 0.025, frequency of 10 Hz, a sample period of 1 sec, a quiet time of 2 sec. FIG. 20A has a peak potential of 0.160 V, a peak current of $1.092 \times 10^{-8}$ A, and a peak A of $7.563 \times 10^{-10}$ VA. FIG. 20C has a peak potential of 0.190 V, a peak current of $2.046 \times 10^{-7}$ A, and a peak area of $2.046 \times 10^{-8}$ VA. FIG. 20d has a peak potential of 0.190 V, a peak current of $3.552 \times 10^{-8}$ A, and a peak A of $3.568 \times 10^{-9}$ VA. FIG. 20E has a peak potential of 0.190 V, a peak current of $2.3762 \times 10^{-7}$ A, and a peak area of $2.594 \times 10^{-8}$ VA. FIG. 20F has a peak potential of 0.180 V, a peak current of $2.992 \times 10^{-8}$ A, and a peak area of $2.709 \times 10^{-9}$ VA. FIG. 20G has a peak potential of 0.150 V, a peak current of $1.494 \times 10^{-7}$ A, and a peak area of $1.1 \times 10^{-8}$ VA. FIG. 20H has a peak potential of 0.160 V, a peak current of $1.967 \times 10^{-8}$ A, and a peak area of $1.443 \times 10^{-9}$ VA. FIG. 20I has a peak potential of 0.150 V, a peak current of $8.031 \times 10^{-8}$ A, and a peak area of $6.033 \times 10^{-9}$ VA. FIG. 20J has a peak potential of 0.150 V, a peak current of $8.871 \times 10^{-9}$ A, and a peak area of $5.51 \times 10^{-10}$ VA. FIG. 20L has a peak potential of 0.140 V, a peak current of $2.449 \times 10^{-8}$ A, and a peak area of $1.706 \times 10^{-9}$ VA. FIG. 20M has a peak potential of 0.150 V, a peak current of $6.637 \times 10^{-8}$ A, and a peak area of $7.335 \times 10^{-9}$ VA. FIG. 20N has a peak potential of 0.140 V, a peak current of $2.877 \times 10^{-9}$ A, and a peak area of $2.056 \times 10^{-10}$ VA.

FIG. 21 (SEQ ID NOS: 35–38) depicts the ligation chain reaction (LCR) experiment of Example 13.

FIGS. 22A and 22B depicts the results of Example 12. The "hybrid code" refers to the system number; + and − refer to the presence or absence of the rRNA target.

FIGS. 23A, 23B, 23C, 23D, 23E and 23F depict the compositions and results of Example 13.

FIGS. 24A and 24B depict the compositions and results from Example 13.

FIG. 26 shows the results of a PCR experiment as outlined in Example 9.

FIGS. 27A, 27B, 27C, 27D, 27E and 27F depict some "mechanism-1" detection systems. FIG. 27A shows portions of target sequence 120 hybridized to detection probes 300 linked via conductive oligomers 108 to electrode 105. The hybridization complex comprises an ETM 135 that can be covalently linked either to the target sequence or the detection probe 300, or non-covalently (i.e. a hybridization indicator). The monolayer is depicted with insulators 107, although as outlined herein, any type of passivation agent may be used. FIG. 27B depicts the use of capture probe 100 linked via attachment linker 106 to electrode 105, although as will be appreciated, since the label probe 145 hybridizes to the detection probe 300 this can serve as a type of capture probe. A label probe 145 comprising a first portion 141 that hybridizes to a portion of the target sequence 120 and a second portion 142 that hybridizes to the detection probe 300. FIG. 27C depicts the use of branched amplifier probe 150 comprising a first portion 151 that hybridizes to the target sequence 120 (although label extender probes can be used as well) and amplification sequences 152 that hybridize directly to the detection probes 300. The target sequence may be additionally attached to the electrode using capture probes as outlined in FIG. 15. FIG. 27D depicts the same thing utilizing a linear amplification probe 150. FIG. 27E depicts a similar system, but uses label probes 145 comprising a first portion 141 that hybridizes to the amplification sequence 152 and a second portion 142 that hybridizes to a detection probe 300. FIG. 27F depicts the same thing but using a linear amplification probe 150.

FIG. 28 depicts an LCR embodiment of the invention. A first probe nucleic acid 200 and a second probe nucleic acid 210 are hybridized to a a first and second target domains of a single-stranded target sequence 120. The probes are attached, generally through ligation, to form a ligated probe 220. The first hybridization complex 225 is denatured, and the process is repeated, to generate a pool of ligated probes 220. The unligated probes 200 and 210 are removed as is known in the art, and then the ligated probes 220 are hybridized to detection probes 300 and detected as outlined herein. As will be appreciated by those in the art, the target domains depicted are directly adjacent, i.e. contiguous, but gaps that are then filled using nucleotides and polymerase can also be used. In addition, the probes are depicted with attached ETMs 135, although as will be appreciated, non-covalently attached ETMs may also be used.

FIG. 29 depicts an alternate LCR embodiment of the invention. A first probe nucleic acid 200 and a second probe nucleic acid 210 are hybridized to a a first and second target domains of a single-stranded target sequence 120. A third probe nucleic acid 200 and a fourth probe nucleic acid 210 are hybridized to a third and fourth target domains of the complementary single-stranded target sequence 125. The probes are attached, generally through ligation, to form ligated probes 220 and 221. The hybridization complexes 225 and 226 are denatured, and the process is repeated to generate a pool of ligated probes 220 and 221. The unligated probes 200, 201, 210 and 211 are removed as is known in the art, and then the ligated probes 220 and 221 are hybridized to detection probes 300 and detected as outlined herein. As will be appreciated by those in the art, the target domains depicted are directly adjacent, i.e. contiguous, but gaps that are then filled using nucleotides and polymerase can also be used. In addition, the probes are depicted with attached ETMs, although as will be appreciated, non-covalently attached ETMs may also be used.

FIG. 30 depicts a preferred CPT embodiment of the invention; FIG. 30 depicts a "mechanism-1" system, but as will be appreciated by those in the art, "mechanism-2" systems may be used as well. A primary probe 1, comprising a first probe sequence 10, a scissile linkage 11, and a second probe sequence 12, with two covalently attached ETMs 13, is added to a target sequence 120, to form a hybridization complex, 6. While FIG. 30 depicts two ETMs, only one of the probe sequences may be covalently labeled with an ETM. Furthermore, additional probe sequences, and additional scissile linkages, may also be used. Upon subjection to cleavage conditions, the scissile linkage 11 is cleaved, leaving the two probe sequences 10 and 12 hybridized to the target sequence 120. These probe sequences then disassociate, leaving the probe sequences 10 and 12, and the target sequence 120. The target sequence is then free to hybridize with additional primary probes 1, and the reaction is repeated, generating a pool of probe sequences. The uncleaved primary probes are removed as outlined herein, and the pool of probe sequences is added to an electrode 105, with an optional layer of passivation agent 107, and detection probes 300 and 302 covalently attached via conductive oligomers 108. The detection probes and the probe sequences form a hybridization complex, 30. The detection probes may be mixed on the electrode, or may be at separate addresses 101 and 102. Additional ETMs in the form of hybridization indicators may optionally be added. Electron transfer is then initiated as is outlined herein. In addition, while this figure depicts a soluble reaction, the primary probes may be bound to a solid support as is described herein.

FIG. 31 depicts an additional CPT embodiment utilizing a single capture sequence. A primary probe 1, comprising a first capture sequence 14, first probe sequence 10, a scissile linkage 11, and a second probe sequence 12, with a covalently attached ETM 135, is added to a target sequence 124, to form a hybridization complex, 6. Preferably, the capture sequence 14 does not hybridize to the target, although it can. While FIG. 31 depicts only one covalently attached ETM, the other probe sequence 12 may be covalently labeled with an ETM. Furthermore, additional probe sequences, and additional scissile linkages, may also be used. Upon subjection to cleavage conditions, the scissile linkage 11 is cleaved, leaving the two probe sequences 10 and 12 hybridized to the target sequence 120. These probe sequences then disassociate, leaving the probe sequences 14–10 and 12, and the target sequence 5. The target sequence is then free to hybridize with additional primary probes 1, and the reaction is repeated, generating a pool of probe sequences. The uncleaved primary probes are removed as outlined herein, and the pool of probe sequences is added to an electrode 105, with an optional layer of passivation agent 107, and a detection probe, comprising the substantial complement of the capture sequence 24 and the substantial complement of the first probe sequence 20, covalently attached via conductive oligomers 108. Also depicted are detection probes 304 that only comprise probes for the capture sequence. The detection probes and the probe sequences form a hybridization complex, 30. Additional ETMs in the form of hybridization indicators may optionally be added. Electron transfer is then initiated as is outlined herein. In addition, while this figure depicts a soluble reaction, the primary probes may be bound to a solid support as is described herein.

FIG. 32 depicts the use of two capture sequences in a CPT aplication. A primary probe 1, comprising a first capture sequence 14, a first probe sequence 10, a scissile linkage 11, a second probe sequence 12, and a second capture sequence 15, with two covalently attached ETMs 135, is added to a target sequence 120, to form a hybridization complex, 6. Preferably, the capture sequence 14 does not hybridize to the target, although it can. While FIG. 32 depicts two covalently attached ETMs, there may be only one or none. Furthermore, additional probe sequences, and additional scissile linkages, may also be used. Upon subjection to cleavage conditions, the scissile linkage 11 is cleaved, leaving the two probe sequences with associated capture sequences, 14–10 and 12–15 hybridized to the target sequence 120. These probe sequences then disassociate, leaving the probe/capture sequences 14–10 and 12–15, and the target sequence 120. The target sequence is then free to hybridize with additional primary probes 1, and the reaction is repeated, generating a pool of probe sequences. The uncleaved primary probes is neutralized by the addition of a substantially complementary neutralization probe 40, comprising sequences that are the substantial complement of the first capture sequence 24, the first probe sequence 20, the scissile linkage 25, the second probe sequence 22, and the second capture sequence 26. As will be appreciated by those in the art, the complementary scissile linkage 25 is only required in those embodiments that utilize nucleic acid scissile linkages. As is depicted, the neutralization probe 40 may also be bound to the electrode. The pool of probe sequences is added to an electrode 105, with an optional layer of passivation agent 107, and detection probes, comprising the substantial complement of the capture sequence 24 and the substantial complement of the first probe sequence 20, and the substantial complement of the capture sequence 22 and the substantial complement of the first probe sequence 26, covalently attached via conductive oligomers 108. The detection probes and the probe sequences form a hybridization complex, 30. Additional ETMs in the form of hybridization indicators may optionally be added. Electron transfer is then initiated as is outlined herein. In addition, while this figure depicts a soluble reaction, the primary probes may be bound to a solid support as is described herein.

FIG. 33 depicts a similar reaction, where a separation sequence 210 is used to remove the uncleaved scissile probe, in this case a primary probe 1. A primary probe 1, comprising a first probe sequence 10, a first scissile linkage 11, a separation sequence 210, a second scissile linkage 11, and a second probe sequence 12, with two covalently attached ETMs 13, is added to a target sequence 120, to form a hybridization complex, 6. Other configurations include those depicted. While FIG. 33 depicts two ETMs, only one of the probe sequences may be covalently labeled with an ETM. Furthermore, additional probe sequences, and additional scissile linkages, may also be used. Upon subjection to cleavage conditions, the scissile linkage 11 is cleaved, leaving the two probe sequences 10 and 12 and the separation sequence 210 hybridized to the target sequence 120. In alternate embodiments, the separation sequence does not hybridize to the target, for example when it is at a terminus of the probe; this may be preferred as it allows generic "separation beads" to be used with any target. These probe sequences then disassociate, leaving the probe sequences 10 and 12, and separation sequence 210, and the target sequence 120. The target sequence is then free to hybridize with additional primary probes 1, and the reaction is repeated, generating a pool of probe sequences. The uncleaved primary probes are removed by the addition of a solid support bead 200, with the substantial complement of the separation sequence 212 attached, generally via a linker. This bead then binds up the uncleaved probe 1 and the cleaved separation sequences 210, leaving only cleaved probe sequences in solution. The pool of probe sequences is added to an electrode 105, with an optional layer of passivation agent 107, and detection probes 300 and 302 covalently attached via conductive oligomers 108. The detection probes and the probe sequences form a hybridization complex, 30. The detection probes may be mixed on the electrode, or may be at separate addresses 101 and 102. Additional ETMs in the form of hybridization indicators may optionally be added. Electron transfer is then initiated as is outlined herein.

FIG. 34 depicts the use of solid-support bound primary scissile probes. A solid support bead 200 with attached primary probes 1 is added to the target sequence 120, to form a hybridization complex, 6. The primary probes may comprise an optional additional sequence 16 (which may be used to stabilize the first scissile linkage hybrid, if necessary), a first scissile linkage 11, a first probe sequence 10, a second scissile linkage 11, and a second probe sequence 12. While FIG. 34 does not utilize covalently attached ETMs, one or more of the probe sequences may be so labelled. Furthermore, additional probe sequences, and additional scissile linkages, may also be used. Upon subjection to cleavage conditions, the scissile linkage 11 is cleaved, leaving the two probe sequences 10 and 12 hybridized to the target sequence 120. These probe sequences then disassociate, leaving the probe sequences 10 and 12, and the target sequence 120. The target sequence is then free to hybridize with additional primary probes 1, and the reaction is repeated, generating a pool of probe sequences. The uncleaved primary probes are removed by removing the beads, and the pool of probe sequences is added to an electrode 105, with an optional layer of passivation agent 107, and detection probes 300 and 302 covalently attached via conductive oligomers 108. The detection probes and the probe sequences form a hybridization complex, 30. The detection probes may be mixed on the electrode, or may be at separate addresses 101 and 102. ETMs in the form of hybridization indicators are then added, and electron transfer is then initiated as is outlined herein.

FIG. 35 depicts the use of bead-bound primary and secondary probes. Two (or more) types of beads are used. The first type is a solid support bead 250 with attached secondary scissile probes 2 comprising a first scissile linkage 11, a first secondary probe sequence 60, a second scissile linkage 11, and a second secondary probe sequence 70. In addition, as depicted, a second secondary scissile probe may be preferably used, comprising a first scissile linkage 11, a first secondary probe sequence 80, a second scissile linkage 11, and a second secondary probe sequence 90. These are depicted in FIG. 35 as being on the same bead, although two sets of beads may be preferably used. The primary probe beads 260 have attached primary probes 1 comprising a first scissile linkage 11, a first probe sequence 10, a second scissile linkage 11, and a second probe sequence 12. As outlined above, the probes may contain optional additional sequences (depicted herein as 16), or additional probe sequences or scissile linkages. The beads 250 and 260 are added to the target sequence 120. The primary probes form a hybridization complex, 6, with the target 120. While FIG. 35 does not utilize covalently attached ETMs, any or all of the probe sequences may be so labelled. Upon subjection to cleavage conditions, the scissile linkages 11 are cleaved, leaving the two primary probe sequences 10 and 12 hybridized to the target sequence 120. These probe sequences then disassociate, leaving the probe sequences 10 and 12, and the target sequence 120. The target sequence is then free to hybridize with additional primary probes 1, and the reaction is repeated, generating a pool of probe sequences. The primary probe sequences are then free to diffuse to the secondary beads 250, where they may serve as the next "target", hybridizing to the secondary probes to form additional hybridization complexes, 7 and 8. Cleavage, followed by secondary probe sequence disassociation from the primary probe sequence "targets", generates a pool of secondary probe sequences which can be detected. The uncleaved probes are removed by removing the beads, and the pool of probe sequences is added to an electrode 105, with an optional layer of passivation agent 107, and detection probes 62, 72, 82, and 92 covalently attached via conductive oligomers 108. While FIG. 35 does not show this, there may be detection probes for the primary probe sequences as well. The detection probes and the probe sequences form hybridization complexes. The detection probes may be mixed on the electrode, or may be at separate addresses. ETMs in the form of hybridization indicators are then added, and electron transfer is then initiated as is outlined herein.

DETAILED DESCRIPTION OF THE INVENTION

Figure 25A:
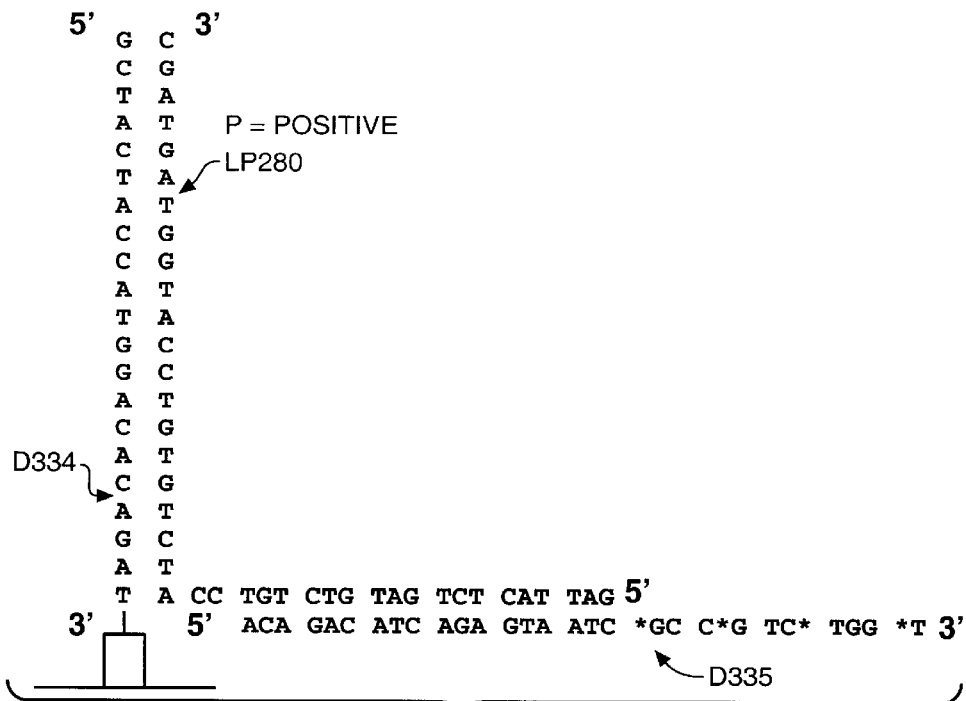
FIGS. 25A (SEQ ID NOS: 27–29) and 25B (SEQ ID NOS: 14, 25, 26) depict the set up of two of the experiments of Example 8.
Figure 25B:
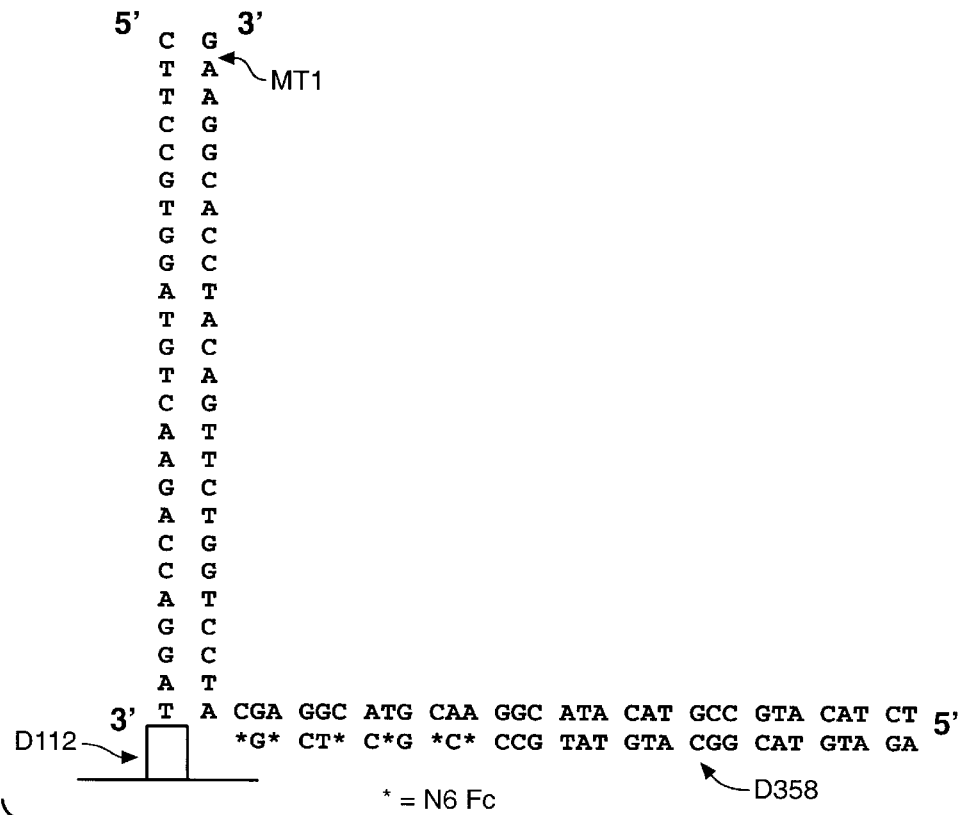

The present invention is directed to compositions and methods useful in the detection of nucleic acids using a variety of amplification techniques, including both signal amplification and target amplification. Once amplification has occurred, detection proceeds based on electron transfer, as is described below and generally outlined in U.S. Pat. Nos. 5,591,578, 5,824,473, 5,770,369, 5,705,348, and 5,780,234, and PCT application WO098/20162, all of which are expressly incorporated herein by reference in their entirety.

Accordingly, in a preferred embodiment, the present invention provides methods of detecting target nucleic acids utilizing amplification. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 100 to 10,000 basepairs, with fragments of roughly 500 basepairs being preferred in some embodiments. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. The sample comprising the target sequence may be virtually any tissue from any organism, including blood, bone marrow, lymph, hard tissues (e.g. organs such as liver, spleen, kidney, heart, lung, etc.) saliva, vaginal and anal secretions, urine, feces, perspiration, tears, and other bodily fluids, as well as cell lysates of bacteria and pathogens, including viruses.

In a preferred embodiment, particularly when detection of pathogens such as bacteria is desired, the target nucleic acid comprises all or a portion of rRNA. rRNA is a particularly preferred target sequence because of the high levels of rRNA in bacteria; accordingly, in many embodiments, no amplification reaction needs to be done. Suitable rRNA targets include, but are not limited to, those outlined in U.S. Pat. Nos. 4,851,330; 5,288,611; 5,723,597; 6,641,632; 5,738,987; 5,830,654; 5,763,163; 5,738,989; 5,738,988; 5,723,597; 5,714,324; 5,582,975; 5,747,252; 5,567,587; 5,558,990; 5,622,827; 5,514,551; 5,501,951; 5,656,427; 5,352,579; 5,683,870; 5,374,718; 5,292,874; 5,780,219; 5,030,557; and 5,541,308, all of which are expressly incorporated by reference.

When rRNA is used as the target sequence, preferred embodiments utilize "helper" sequences as outlined in WO 89/04876, hereby incorporated by reference. As is known in the art, rRNA takes on specific secondary and tertiary structures that can hinder the formation of hybridization complexes with the probes of the invention. Accordingly, helper sequences bind to rRNA sequences and impose different secondary or tertiary structures and thus facilitate the binding of the probes to the target rRNA.

In some embodiments, for example when rRNA is used as the target sequence, it may be desirable to utilize a plurality of capture probes or capture probe extenders, to "tack down" large targets periodically. The use of a single type of capture probe with multiple capture probe extenders, each with a first portion that will hybridize to the capture probe and a second portion that will hybridize to a unique portion of the target sequence.

A particularly preferred embodiment of the invention is the formation of assay complexes comprising rRNA target sequences, capture probes and label probes.

As is outlined more fully below, probes (including primers) are made to hybridize to target sequences to determine the presence or absence of the target sequence in a sample. Generally speaking, this term will be understood by those skilled in the art.

The target sequence may also be comprised of different target domains; for example, in "sandwich" type assays as outlined below, a first target domain of the sample target sequence may hybridize to a capture probe or a portion of capture extender probe, a second target domain may hybridize to a portion of an amplifier probe, a label probe, or a different capture or capture extender probe, etc. In addition, the target domains may be adjacent (i.e. contiguous) or separated. For example, when LCR techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below.

Unless otherwise noted, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

If required, the target sequence is prepared using known techniques. For example, the sample may be treated to lyse the cells, using known lysis buffers, sonication, electroporation, etc., with purification occuring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

A primer nucleic acid is then contacted to the target sequence to form a hybridization complex. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The probes (including primers) comprise nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments. In addition, it should be noted that the use of the terms "DNA" and "RNA" include nucleic acid analogs.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique.

In addition, the different amplification techniques may have further requirements of the primers, as is more fully described below.

Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identification of the enzyme will depend on the amplification technique used, as is more fully outlined below. Similarly, the modification will depend on the amplification technique, as outlined below, although generally the first step of all the reactions herein is an extension of the primer, that is, nucleotides are added to the primer to extend its length.

Once the enzyme has modified the primer to form a modified primer, the hybridization complex is disassociated. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

After a suitable time or amplification, the modified primer is incorporated into an assay complex, as is more fully outlined below. The assay complex is covalently attached to an electrode, and comprises at least one electron transfer moiety (ETM), described below. Electron transfer between the ETM and the electrode is then detected to indicate the presence or absence of the original target sequence, as described below.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), nucleic acid sequence based amplification (NASBA), and transcription mediated amplification (TMA).

In a preferred embodiment, the target amplification technique is PCR. The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtration", among others. In one embodiment, the amplification technique is not PCR.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostabile polymerase such as Taq I polymerase and thermal cycling.

Accordingly, the PCR reaction requires at least one PCR primer and a polymerase.

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25–100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'-O-(1-thiotriphosphate), 5-methyldeoxycytidine 5'-triphosphate, 2'-deoxyuridine 5'-triphosphate, adn 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'-3' exonuclease activity. However, if less than all the nucleotides are substituted, the polymerase preferably lacks 5'-3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindII, AvaI, Fnu4HI, TthlIII, NcII, BstXI, BamI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'→3', thereby creating another newly synthesized strand. The polymerase chosen should be able to intiate 5'→3' polymerization at a nick site, should also displace the polymerized strand downstream from the nick, and should lack 5'→3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

In this way, a number of target molecules are made. As is more fully outlined below, these reactions (that is, the products of these reactions) can be detected in a number of ways. In general, either direct or indirect detection of the target products can be done. "Direct" detection as used in this context, as for the other amplification strategies outlined herein, requires the incorporation of a label, in this case an electron transfer moiety (ETM), into the target sequence, with detection proceeding according to either "mechanism-1" or "mechanism-2", outlined below. In this embodiment, the ETM(s) may be incorporated in three ways: (1) the primers comprise the ETM(s), for example attached to the base, a ribose, a phosphate, or to analogous structures in a nucleic acid analog; (2) modified nucleosides are used that are modified at either the base or the ribose (or to analogous structures in a nucleic acid analog) with the ETM(s); these ETM modified nucleosides are then converted to the triphosphate form and are incorporated into the newly synthesized strand by a polymerase; or (3) a "tail" of ETMs can be added, as outlined below. Either of these methods result in a newly synthesized strand that comprises ETMs, that can be directly detected as outlined below.

Alternatively, indirect detection proceeds as a sandwich assay, with the newly synthesized strands containing few or no ETMs. Detection then proceeds via the use of label probes that comprise the ETM(s); these label probes will hybridize either directly to the newly synthesized strand or to intermediate probes such as amplification probes, as is more fully outlined below. In this case, it is the ETMs on the label probes that are used for detection as outlined below.

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261–285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template"), is contacted with a first primer, generally referred to herein as a "NASBA primer" (although "TMA primer" is also suitable). Starting with a DNA target sequence is described below. These primers generally have a length of 25–100 nucleotides, with NASBA primers of approximately 50–75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf thymus.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage φII, Salmonella phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

As outlined herein, the detection of the newly synthesized strands can proceed in several ways. Direct detection can be done when the newly synthesized strands comprise ETM labels, either by incorporation into the primers or by incorporation of modified labelled nucleotides into the growing strand. Alternatively, as is more fully outlined below, indirect detection of unlabelled strands (which now serve as "targets" in the detection mode) can occur using a variety of sandwich assay configurations. As will be appreciated by those in the art, any of the newly synthesized strands can serve as the "target" for form an assay complex on a surface with a capture probe. In NASBA and TMA, it is preferable to utilize the newly formed RNA strands as the target, as this is where significant amplification occurs.

In a preferred embodiment, the amplification technique is signal amplification. Signal amplification involves the use of limited number of target molecules as templates to either generate multiple signalling probes or allow the use of multiple signalling probes. Signal amplification strategies include LCR, CPT, Invader™, and the use of amplification probes in sandwich assays.

In a preferred embodiment, the signal amplification technique is LCR, as is generally depicted in FIGS. 21, 28 and 29. The method can be run in two different ways; in a first embodiment, only one strand of a target sequence is used as a template for ligation (FIG. 28); alternatively, both strands may be used (FIG. 29). See generally U.S. Pat. Nos. 5,185, 243 and 5,573,907; EP 0 320 308 B1; EP 0 336 731 B1; EP 0 439 182 B1; WO 90/01069; WO 89/12696; and WO 89/09835, and U.S. S. Nos. 60/078,102 and 60/073,011, all of which are incorporated by reference.

In a preferred embodiment, the single-stranded target sequence comprises a first target domain and a second target domain, and a first LCR primer and a second LCR primer nucleic acids are added, that are substantially complementary to its respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two LCR primers are then covalently attached, for example using a ligase enzyme such as is known in the art. This forms a first hybridization complex comprising the ligated probe and the target sequence. This hybridization complex is then denatured (disassociated), and the process is repeated to generate a pool of ligated probes. In addition, it may be desirable to have the detection probes, described below, comprise a mismatch at the probe junction site, such that the detection probe cannot be used as a template for ligation.

In a preferred embodiment, LCR is done for two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Again, as outlined above, the detection of the LCR reaction can occur directly, in the case where one or both of the primers comprises at least one ETM, or indirectly, using sandwich assays, through the use of additional probes; that is, the ligated probes can serve as target sequences, and detection may utilize amplification probes, capture probes, capture extender probes, label probes, and label extender probes, etc.

A variation of LCR utilizes a "chemical ligation" of sorts, as is generally outlined in U.S. Pat. Nos. 5,616,464 and 5,767,259, both of which are hereby expressly incorporated by reference in their entirety. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes.

At least one of the side chains of the primers comprises an activatable cross-linking agent, generally covalently attached to the side chain, that upon activation, results in a chemical cross-link or chemical ligation. The activitible group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the disassocation of the hybridization complex, thus freeing up the target to serve as a template for the next ligation or cross-linking. In this way, signal amplification occurs, and can be detected as outlined herein.

In a preferred embodiment the signal amplification technique is RCA. Rolling-circle amplification is generally described in Baner et al. (1998) Nuc. Acids Res. 26:5073–5078; Barany, F. (1991) Proc. Natl. Acad. Sci. USA 88:189–193; Lizardi et al. (1998) Nat. Genet. 19:225–232; Zhang et al., Gene 211:277 (1998); and Daubendiek et al., Nature Biotech. 15:273 (1997); all of which are incorporated by reference in their entirety.

In general, RCA may be described as follows. First, as is outlined in more detail below, a single RCA probe is hybridized with a target nucleic acid. Each terminus of the probe hybridizes adjacently on the target nucleic acid (or alternatively, there are intervening nucleotides that can be "filled in" using a polymerase and dNTPs, as outlined below) and the OLA assay as described above occurs. When ligated, the probe is circularized while hybridized to the target nucleic acid. Addition of a primer, a polymerase and dNTPs results in extension of the circular probe. However, since the probe has no terminus, the polymerase continues to extend the probe repeatedly. Thus results in amplification of the circular probe. This very large concatemer can be detected intact, as described below, or can be cleaved in a variety of ways to form smaller amplicons for detection as outlined herein.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent (either directly or indirectly, as outlined herein) to the first domain. Hybridization of the probe to the target nucleic acid results in the formation of a hybridization complex. Ligation of the "primers" (which are the discrete ends of a single oligonucleotide, the RCA probe) results in the formation of a modified hybridization complex containing a circular probe i.e. an RCA template complex. That is, the oligonucleotide is circularized while still hybridized with the target nucleic acid. This serves as a circular template for RCA. Addition of a primer, a polymerase and the required dNTPs to the RCA template complex results in the formation of an amplified product nucleic acid. Following RCA, the amplified product nucleic acid is detected as outlined herein. This can be accomplished in a variety of ways; for example, the polymerase may incorporate labelled nucleotides; a labeled primer may be used, or alternatively, a label probe is used that is substantially complementary to a portion of the RCA probe and comprises at least one label is used.

Accordingly, the present invention provides RCA probes (sometimes referred to herein as "rolling circle probes (RCPs) or "padlock probes" (PPs)). The RCPs may comprise any number of elements, including a first and second ligation sequence, a cleavage site, a priming site, a capture sequence, nucleotide analogs, and a label sequence.

In a preferred embodiment, the RCP comprises first and second ligation sequences. As outlined above for OLA, the ligation sequences are substantially complementary to adjacent domains of the target sequence. The domains may be directly adjacent (i.e. with no intervening bases between the 3' end of the first and the 5' of the second) or indirectly adjacent, with from 1 to 100 or more bases in between.

In a preferred embodiment, the RCPs comprise a cleavage site, such that either after or during the rolling circle amplification, the RCP concatamer may be cleaved into amplicons. In some embodiments, this facilitates the detection, since the amplicons are generally smaller and exhibit favorable hybridization kinetics on the surface. As will be appreciated by those in the art, the cleavage site can take on a number of forms, including, but not limited to, the use of restriction sites in the probe, the use of ribozyme sequences, or through the use or incorporation of nucleic acid cleavage moieties.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA (or in some cases, during the reaction), the product nucleic acid is contacted with the appropriate restriction endonuclease. This results in cleavage of the product nucleic acid into smaller fragments. The fragments are then hybridized with the capture probe that is immobilized resulting in a concentration of product fragments onto the detection electrode. Again, as outlined herein, these fragments can be detected in one of two ways: either labelled nucleotides are incorporated during the replication step, for example either as labeled individual dNTPs or through the use of a labeled primer, or an additional label probe is added.

In a preferred embodiment, the restriction site is a single-stranded restriction site chosen such that its complement occurs only once in the RCP.

In a preferred embodiment, the cleavage site is a ribozyme cleavage site as is generally described in Daubendiek et al., Nature Biotech. 15:273 (1997), hereby expressly incorporated by reference. In this embodiment, by using RCPs that encode catalytic RNAs, NTPs and an RNA polymerase, the resulting concatamer can self cleave, ultimately forming monomeric amplicons.

In a preferred embodiment, the cleavage site comprises one or more labile bases such as UTP or dUTP, and cleavage is effected either chemically (e.g. using basic conditions) or enzymatically. For example, uracil-N-glycosylase cleaves at uracil groups; similarly, RNAse H cleaves ribose-containing bases in RNA/DNA hybrids.

In a preferred embodiment, cleavage is accomplished using DNA cleavage reagents. For example, as is known in the art, there are a number of intercalating moieties that can effect cleavage, for example using light.

In a preferred embodiment, the RCPs do not comprise a cleavage site. Instead, the size of the RCP is designed such that it may hybridize "smoothly" to many capture probes on a surface. Alternatively, the reaction may be cycled such that very long concatamers are not formed.

In a preferred embodiment, the RCPs comprise a priming site, to allow the binding of a DNA polymerase primer. As is known in the art, many DNA polymerases require double stranded nucleic acid and a free terminus to allow nucleic acid synthesis. However, in some cases, for example when RNA polymerases are used, a primer may not be required (see Daubendiek, supra). Similarly, depending on the size and orientation of the target strand, it is possible that a free end of the target sequence can serve as the primer; see Baner et al., supra.

Thus, in a preferred embodiment, the padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

In a preferred embodiment, a primer is used that hybridizes both to a portion of the target sequence and to a priming site on the RCP. This may be done to increase the specificity of the system, and allows the use of higher hybridization temperatures.

In a preferred embodiment, the primer may comprise the covalently attached ETMs.

In a preferred embodiment, the RCPs comprise a capture sequence. A capture sequence, as is outlined herein, is substantially complementary to a capture probe, as outlined herein.

In a preferred embodiment, the RCPs comprise a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

In a preferred embodiment, the RCPs comprise nucleotide analogs. For example, since it may be desirable to incorporate ETMs at specific locations within the amplicon (for example, at a cluster of 8–10 ETMs in a 20–30 basepair stretch, to allow optimal signaling and configuration of the detection hybridization complex), unique bases may be incorporated into the RCP. As is known in the art, isocytosine is a nucleoside analog that will only basepair with isoguanine, as is generally described in U.S. Pat. No. 5,681, 702, hereby incorporated by reference in its entirety. By utilizing either isoC or isoG in the RCP, deoxy-isoC or deoxy-isoG labeled with an ETM can be added to the pool of nucleotides, resulting in the incorporation of ETMs at predetermined, specific locations.

In a preferred embodiment, the RCP/primer sets are designed to allow an additional level of amplification, sometimes referred to as "hyperbranching" or "cascade amplification". As described in Zhang et al., supra, by using several priming sequences and primers, a first concatamer can serve as the template for additional concatamers. In this embodiment, a polymerase that has high displacement activity is preferably used. In this embodiment, a first antisense primer is used, followed by the use of sense primers, to generate large numbers of concatamers and amplicons, when cleavage is used.

Thus, the invention provides for methods of detecting using RCPs as described herein. Once the ligation sequences of the RCP have hybridized to the target, forming a first hybridization complex, the ends of the RCP are ligated together as outlined above for OLA. The RCP primer is added, if necessary, along with a polymerase and dNTPs (or NTPs, if necessary).

The polymerase can be any polymerase as outlined herein, but is preferably one lacking 3' exonuclease activity (3' exo⁻). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

Thus, in a preferred embodiment the OLA/RCA is performed in solution followed by restriction endonuclease cleavage of the RCA product. The cleaved product is then applied to an array as described herein. The incorporation of an endonuclease site allows the generation of short, easily hybridizable sequences. Furthermore, the unique capture sequence in each rolling circle padlock probe sequence allows diverse sets of nucleic acid sequences to be analyzed in parallel on an array, since each sequence is resolved on the basis of hybridization specificity.

Again, these copies are subsequently detected by one of two methods; either hybridizing a label probe comprising ETMs which is complementary to the circular target or via the incorporation of ETM-labeled nucleotides in the amplification reaction. The label is detected a described herein.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template.

The amplified circular DNA sequence is then detected by methods known in the art and as described herein. Detection is accomplished by hybridizing with a labeled probe. The probe is labeled directly or indirectly. Alternatively, labeled nucleotides are incorporated into the amplified circular DNA product. The nucleotides can be labeled directly, or indirectly as is further described herein.

The RCA as described herein finds use in allowing highly specific and highly sensitive detection of nucleic acid target sequences. In particular, the method finds use in improving the multiplexing ability of DNA arrays and eliminating costly sample or target preparation. As an example, a substantial savings in cost can be realized by directly analyzing genomic DNA on an array, rather than employing an intermediate PCR amplification step. The method finds use in examining genomic DNA and other samples including mRNA.

In addition the RCA finds use in allowing rolling circle amplification products to be easily detected by hybridization to probes in a solid-phase format. An additional advantage of the RCA is that it provides the capability of multiplex analysis so that large numbers of sequences can be analyzed in parallel. By combining the sensitivity of RCA and parallel detection on arrays, many sequences can be analyzed directly from genomic DNA.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected as outlined herein.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

In one embodiment, the entire scissile probe is made of RNA, the nicking is facilitated especially when carried out with a double-stranded ribonuclease, such as RNAseH or Exo III. RNA probes made entirely of RNA sequences are particularly useful because first, they can be more easily produced enzymatically, and second, they have more cleavage sites which are accessible to nicking or cleaving by a nicking agent, such as the ribonucleases. Thus, scissile probes made entirely of RNA do not rely on a scissile linkage since the scissile linkage is inherent in the probe.

In a preferred embodiment, when the scissile linkage is a nucleic acid such as RNA, the methods of the invention may be used to detect mismatches, as is generally described in U.S. Pat. Nos. 5,660,988, and WO 95/14106, hereby expressly incorporated by reference. These mismatch detection methods are based on the fact that RNAseH may not bind to and/or cleave an RNA:DNA duplex if there are mismatches present in the sequence. Thus, in the $NA_1$-R-$NA_2$ embodiments, $NA_1$ and $NA_2$ are non-RNA nucleic acids, preferably DNA. Preferably, the mismatch is within the RNA:DNA duplex, but in some embodiments the mismatch is present in an adjacent sequence very close to the desired sequence, close enough to affect the RNAseH (generally within one or two bases). Thus, in this embodiment, the nucleic acid scissile linkage is designed such that the sequence of the scissile linkage reflects the particular sequence to be detected, i.e. the area of the putative mismatch.

In some embodiments of mismatch detection, the rate of generation of the released fragments is such that the methods provide, essentially, a yes/no result, whereby the detection of the virtually any released fragment indicates the presence of the desired target sequence. Typically, however, when there is only a minimal mismatch (for example, a 1-, 2- or 3-base mismatch, or a 3-base delection), there is some generation of cleaved sequences even though the target sequence is not present. Thus, the rate of generation of cleaved fragments, and/or the final amount of cleaved fragments, is quantified to indicate the presence or absence of the target. In addition, the use of secondary and tertiary scissile probes may be particularly useful in this embodiment, as this can amplify the differences between a perfect match and a mismatch. These methods may be particularly useful in the determination of homozygotic or heterozygotic states of a patient.

In this embodiment, it is an important feature of the scissile linkage that its length is determined by the suspected difference between the target and the probe. In particular, this means that the scissile linkage must be of sufficient length to encompass the suspected difference, yet short enough the scissile linkage cannot inappropriately "specifically hybridize" to the selected nucleic acid molecule when the suspected difference is present; such inappropriate hybridization would permit excision and thus cleavage of scissile linkages even though the selected nucleic acid molecule was not fully complementary to the nucleic acid probe. Thus in a preferred embodiment, the scissile linkage is between 3 to 5 nucleotides in length, such that a suspected nucleotide difference from 1 nucleotide to 3 nucleotides is encompassed by the scissile linkage, and 0, 1 or 2 nucleotides are on either side of the difference.

Thus, when the scissile linkage is nucleic acid, preferred embodiments utilize from 1 to about 100 nucleotides, with from about 2 to about 20 being preferred and from about 5 to about 10 being particularly preferred.

CPT may be done enzymatically or chemically. That is, in addition to RNAseH, there are several other cleaving agents which may be useful in cleaving RNA (or other nucleic acid) scissile bonds. For example, several chemical nucleases have been reported; see for example Sigman et al., Annu. Rev. Biochem. 1990, 59, 207–236; Sigman et al., Chem. Rev. 1993, 93, 2295–2316; Bashkin et al., J. Org. Chem. 1990, 55, 5125–5132; and Sigman et al., Nucleic Acids and Molecular Biology, vol. 3, F. Eckstein and D. M. J. Lilley (Eds), Springer-Verlag, Heidelberg 1989, pp. 13–27; all of which are hereby expressly incorporated by reference.

Specific RNA hydrolysis is also an active area; see for example Chin, Acc. Chem. Res. 1991, 24, 145–152; Breslow et al., Tetrahedron, 1991, 47, 2365–2376; Anslyn et al., Angew. Chem. Int. Ed. Engl., 1997, 36, 432–450; and references therein, all of which are expressly incorporated by reference. Reactive phosphate centers are also of interest in developing scissile linkages, see Hendry et al., Prog. Inorg. Chem .: Bioinorganic Chem. 1990, 31, 201–258 also expressly incorporated by reference.

Current approaches to site-directed RNA hydrolysis include the conjugation of a reactive moiety capable of cleaving phosphodiester bonds to a recognition element capable of sequence-specifically hybridizing to RNA. In most cases, a metal complex is covalently attached to a DNA strand which forms a stable heteroduplex. Upon hybridization, a Lewis acid is placed in close proximity to the RNA backbone to effect hydrolysis; see Magda et al., J. Am. Chem. Soc. 1994, 116, 7439; Hall et al., Chem. Biology 1994, 1, 185–190; Bashkin et al., J. Am. Chem. Soc. 1994, 116, 5981–5982; Hall et al., Nucleic Acids Res. 1996, 24, 3522; Magda et al., J. Am. Chem. Soc. 1997, 119, 2293; and Magda et al., J. Am. Chem. Soc. 1997, 119, 6947, all of which are expressly incorporated by reference.

In a similar fashion, DNA-polyamine conjugates have been demonstrated to induce site-directed RNA strand scission; see for example, Yoshinari et al., J. Am. Chem. Soc. 1991, 113, 5899–5901; Endo et al., J. Org. Chem. 1997, 62, 846; and Barbier et al., J. Am. Chem. Soc. 1992, 114, 3511–3515, all of which are expressly incorporated by reference.

In a preferred embodiment, the scissile linkage is not necessarily RNA. For example, chemical cleavage moieties may be used to cleave basic sites in nucleic acids; see Belmont, et al., New J. Chem. 1997, 21, 47–54; and references therein, all of which are expressly incorporated herein by reference. Similarly, photocleavable moieties, for example, using transition metals, may be used; see Moucheron, et al., Inorg. Chem. 1997, 36, 584–592, hereby expressly by reference.

Other approaches rely on chemical moieties or enzymes; see for example Keck et al., Biochemistry 1995, 34, 12029–12037; Kirk et al., Chem. Commun. 1998, in press; cleavage of G-U basepairs by metal complexes; see Biochemistry, 1992, 31, 5423–5429; diamine complexes for cleavage of RNA; Komiyama, et al., J. Org. Chem. 1997, 62, 2155–2160; and Chow et al., Chem. Rev. 1997, 97, 1489–1513, and references therein, all of which are expressly incorporated herein by reference.

The first step of the CPT method requires hybridizing a primary scissile primer (also called a primary scissile probe) obe to the target. This is preferably done at a temperature that allows both the binding of the longer primary probe and disassociation of the shorter cleaved portions of the primary probe, as will be appreciated by those in the art. As outlined herein, this may be done in solution, or either the target or one or more of the scissile probes may be attached to a solid support. For example, it is possible to utilize "anchor probes" on a solid support or the electrode which are substantially complementary to a portion of the target sequence, preferably a sequence that is not the same sequence to which a scissile probe will bind.

Similarly, as outlined herein, a preferred embodiment has one or more of the scissile probes attached to a solid support such as a bead. In this embodiment, the soluble target diffuses to allow the formation of the hybridization complex between the soluble target sequence and the support-bound scissile probe. In this embodiment, it may be desirable to include additional scissile linkages in the scissile probes to allow the release of two or more probe sequences, such that more than one probe sequence per scissile probe may be detected, as is outlined below, in the interests of maximizing the signal. Such embodiments are generally depicted in FIGS. 34 and 35.

In this embodiment (and in other amplification techniques herein), preferred methods utilize cutting or shearing techniques to cut the nucleic acid sample containing the target sequence into a size that will allow sufficient diffusion of the target sequence to the surface of a bead. This may be accomplished by shearing the nucleic acid through mechanical forces (e.g. sonication) or by cleaving the nucleic acid using restriction endonucleases. Alternatively, a fragment containing the target may be generated using polymerase, primers and the sample as a template, as in polymerase chain reaction (PCR). In addition, amplification of the target using PCR or LCR or related methods may also be done; this may be particularly useful when the target sequence is present in the sample at extremely low copy numbers. Similarly, numerous techniques are known in the art to increase the rate of mixing and hybridization including agitation, heating, techniques that increase the overall concentration such as precipitation, drying, dialysis, centrifugation, electrophoresis, magnetic bead concentration, etc.

In general, the scissile probes are introduced in a molar excess to their targets (including both the target sequence or other scissile probes, for example when secondary or tertiary scissile probes are used), with ratios of scissile probe:target of at least about 100:1 being preferred, at least about 1000:1 being particularly preferred, and at least about 10,000:1 being especially preferred. In some embodiments the excess of probe:target will be much greater. In addition, ratios such as these may be used for all the amplification techniques outlined herein.

Once the hybridization complex between the primary scissile probe and the target has been formed, the complex is subjected to cleavage conditions. As will be appreciated, this depends on the composition of the scissile probe; if it is RNA, RNAseH is introduced. It should be noted that under certain circumstances, such as is generally outlined in WO 95/00666 and WO 95/00667, hereby incorporated by reference, the use of a double-stranded binding agent such as RNAseH may allow the reaction to proceed even at temperatures above the Tm of the primary probe:target hybridization complex. Accordingly, the addition of scissile probe to the target can be done either first, and then the cleavage agent or cleavage conditions introduced, or the probes may be added in the presence of the cleavage agent or conditions.

The cleavage conditions result in the separation of the two (or more) probe sequences of the primary scissile probe. As a result, the shorter probe sequences will no longer remain hybridized to the target sequence, and thus the hybridization complex will disassociate, leaving the target sequence intact. The optimal temperature for carrying out the CPT reactions is generally from about 5° C. to about 25° C. below the melting temperatures of the probe:target hybridization complex. This provides for a rapid rate of hybridization and high degree of specificity for the target sequence. The Tm of any particular hybridization complex depends on salt concentration, G-C content, and length of the complex, as is known in the art.

During the reaction, as for the other amplification techniques herein, it may be necessary to suppress cleavage of the probe, as well as the target sequence, by nonspecific nucleases. Such nucleases are generally removed from the sample during the isolation of the DNA by heating or extraction procedures. A number of inhibitors of single-stranded nucleases such as vanadate, inhibitors it-ACE and RNAsin, a placental protein, do not affect the activity of RNAseH. This may not be necessary depending on the purity of the RNAseH and/or the target sample.

These steps are repeated by allowing the reaction to proceed for a period of time. The reaction is usually carried out for about 15 minutes to about 1 hour. Generally, each molecule of the target sequence will turnover between 100 and 1000 times in this period, depending on the length and sequence of the probe, the specific reaction conditions, and the cleavage method. For example, for each copy of the target sequence present in the test sample 100 to 1000 molecules will be cleaved by RNAseH. Higher levels of amplification can be obtained by allowing the reaction to proceed longer, or using secondary, tertiary, or quaternary probes, as is outlined herein.

Upon completion of the reaction, generally determined by time or amount of cleavage, the uncleaved scissile probes must be removed or neutralized prior to detection, such that the uncleaved probe does not bind to a detection probe, causing false positive signals. This may be done in a variety of ways, as is generally described below.

In a preferred embodiment, the separation is facilitated by the use of beads containing the primary probe. Thus, when the scissile probes are attached to beads, removal of the beads by filtration, centrifugation, the application of a magnetic field, electrostatic interactions for charged beads, adhesion, etc., results in the removal of the uncleaved probes.

In a preferred embodiment, the separation is based on gel electrophoresis of the reaction products to separate the longer uncleaved probe from the shorter cleaved probe sequences as is known in the art.

In a preferred embodiment, the separation is based on strong acid precipitation. This is useful to separate long (generally greater than 50 nucleotides) from smaller fragments (generally about 10 nucleotides). The introduction of a strong acid such as trichloroacetic acid into the solution causes the longer probe to precipitate, while the smaller cleaved fragments remain in solution. The solution can be centrifuged or filtered to remove the precipitate, and the cleaved probe sequences can be quantitated.

In a preferred embodiment, the scissile probe contains both an ETM and an affinity binding ligand or moiety, such that an affinity support is used to carry out the separation. In this embodiment, it is important that the ETM used for detection is not on the same probe sequence that contains the affinity moiety, such that removal of the uncleaved probe, and the cleaved probe containing the affinity moiety, does not remove all the detectable ETMs. Alternatively, the scissile probe may not contain a covalently attached ETM, but just an affinity label. Suitable affinity moieties include, but are not limited to, biotin, avidin, streptavidin, lectins, haptens, antibodies, etc. The binding partner of the affinity moiety is attached to a solid support such as glass beads, latex beads, dextrans, etc. and used to pull out the uncleaved probes, as is known in the art. The cleaved probe sequences, which do not contain the affinity moiety, remain in solution and then can be detected as outlined below.

In a preferred embodiment, similar to the above embodiment, a separation sequence of nucleic acid is included in the scissile probe, which is not cleaved during the reaction. A nucleic acid complementary to the separation sequence is attached to a solid support such as a bead and serves as a catcher sequence. Preferably, the separation sequence is added to the scissile probes, and is not recognized by the target sequence, such that a generalized catcher sequence may be utilized in a variety of assays.

In a preferred embodiment, the uncleaved probe is neutralized by the addition of a substantially complementary neutralization nucleic acid, as is generally depicted in FIG. 32. This is particularly useful in embodiments utilizing capture sequences, separation sequences, and one-step systems, as the complement to a probe containing capture sequences forms hybridization complexes that are more stable due to its length than the cleaved probe sequence:detection probe complex. As will be appreciated by those in the art, complete removal of the uncleaved probe is not required, since detection is based on electron transfer through nucleic acid; rather, what is important is that the uncleaved probe is not available for binding to a detection electrode probe specific for cleaved sequences. Thus, in one embodiment, the neutralization nucleic acid is a detection probe on the surface of the electrode, at a separate "address", such that the signal from the neutralization hybridization complex does not contribute to the signal of the cleaved fragments. Alternatively, the neutralization nucleic acid may be attached to a bead; the neutralization beads are added to quench the reaction, and then removed prior to detection.

After removal or neutralization of the uncleaved probe, detection proceeds via the addition of the cleaved probe sequences to the detection compositions, as outlined below, which can utilize either "mechanism-1" or "mechanism-2" systems. A mechanism-1 system can be described as follows; the cleaved probe sequences hybridize to a first detection single-stranded probe covalently attached via a conductive oligomer to an electrode, that thus forms a second hybridization complex. The second hybridization complex, comprising detection probe:probe sequence, contains at least a first ETM. As outlined herein, this ETM may be covalently attached to either the probe (primer) sequence or the detection probe, or it may be added non-covalently as a hybridization indicator, or both. As outlined above, preferred embodiments utilize more than one ETM per hybridization complex for detection.

In a preferred embodiment, no higher order probes are used, and detection is based on the probe sequence(s) of the primary primer. Thus, in a preferred embodiment, the electrode comprises at least a first detection probe which is substantially complementary to all or part of a cleaved portion of the primary scissile probe. In one embodiment, only one type of detection probe is utilized, which can be substantially complementary to all or part of any probe sequence of the primary probe. In a preferred embodiment, more than one type of detection probe is utilized, with each detection probe being substantially complementary to all or part of each probe sequence of the primary probe. Thus, when the primary probe comprises two probe sequences, two detection probes are used; three probe sequences utilizes three detection probes. This may require the use of additional scissile linkages when the probes are bound to beads, as is described herein. The detection probes and the primary probe sequences then form hybridization complexes, which either contain covalently bound ETMs or ETMs in the form of hybridization indicators are added to the system (or both), which are then detected as is outlined herein. In a preferred embodiment, when hybridization indicators are used, they are only added to the system after the reaction is complete, to avoid the association of hybridization indicators to the probe:target complexes, although in some embodiments it may be possible to have the hybridization indicators present during the reaction.

In a preferred embodiment, the detection probes are mixed on the surface of the electrode, such that the signal from each is combined. This may be particularly preferred when the target sequence is present in low copy number. Alternatively, the detection probes may each be at a different "address" on the surface. While this reduces the possible signal from the system, it serves as an internal control in that the signal from each should be equal, all other parameters being equal. In addition, different addresses can have different densities of probes creating addresses with various sensitivities to target sequences. Systems utilizing two detection probes, each to a probe sequence of the primary probe, that is bound to a bead, are generally depicted in FIG. 30, utilizing bound ETMs.

In a preferred embodiment, at least one, and preferably more, secondary probes (also referred to herein as secondary primers) are used. The secondary scissile probes may be added to the reaction in several ways. It is important that the secondary scissile probes be prevented from hybridizing to the uncleaved primary probes, as this results in the generation of false positive signal. These methods may be described in several ways, depending on whether bead-bound probes are used.

In a preferred embodiment, the primary and secondary probes are bound to solid supports. In a preferred embodiment, the primary and secondary probes are added together, since generally the support-bound secondary probes will be unable to bind to the uncleaved primary probes on the surface of a bead. It is only upon hybridization of the primary probes with the target, resulting in cleavage and release of primary probe sequences from the bead, that the now diffusible primary probe sequences may bind to the secondary probes. In turn, the primary probe sequences serve as targets for the secondary scissile probes, resulting in cleavage and release of secondary probe sequences.

In an alternate embodiment, the beads containing the primary probes are added, the reaction is allowed to proceed for some period of time, and then the beads containing the secondary probes are added, either with removal of the primary beads or not. Alternatively, the beads containing the primary probes are removed and soluble secondary scissile probes are added.

In an alternate embodiment, the complete reaction is done in solution. In this embodiment, the primary probes are added, the reaction is allowed to proceed for some period of time, and the uncleaved primary scissile probes are removed, as outlined above. The secondary probes are then added, and the reaction proceeds. The secondary uncleaved probes are then removed, and the cleaved sequences are detected as is generally outlined herein.

As above, it is generally preferred to detect as many secondary probe sequences as possible, and the primary probe sequences may be additionally detected as well. Thus, preferred embodiments utilize detection probes that are substantially complementary to all or part of each probe sequence of a scissile probe. Alternatively, only detection probes for "higher order" probe sequences are used. Furthermore, in some embodiments, detection probes for only one of the probe sequences of any scissile probe may be used. Furthermore, as outlined above, in these embodiments, as for the others, the detection probes may be separated by sequence, or mixed, depending on the desired results.

In a preferred embodiment, at least one, and preferably more, tertiary probes are used. The tertiary scissile probes may be added to the reaction in several ways. It is important that the tertiary scissile probes be prevented from hybridizing to the uncleaved secondary probes, as this results in the generation of false positive signal. These methods may be described in several ways, depending on whether bead-bound probes are used.

In a preferred embodiment, the primary, secondary and tertiary probes are bound to solid supports. In a preferred embodiment, the primary, secondary and tertiary probes are added together, since generally the support-bound secondary probes will be unable to bind to the uncleaved primary probes on the surface of a bead and the support-bound tertiary probes will be unable to bind to the uncleaved secondary probes on the surface of a bead. It is only upon hybridization of the scissile probe with its target (i.e. either the target sequences of the sample for the primary probes, or probe sequences for each of the secondary and tertiary probes), that results in cleavage and release of probe sequences from the bead, that the now diffusable probe sequences may bind to the higher order probes.

In alternate embodiments, combinations of beads and solution probes are used, with any combination being possible: primary probe beads, soluble secondary probes, tertiary beads; soluble primary probes, soluble secondary probes, tertiary beads; primary probe beads, secondary probe beads, soluble tertiary probes; etc. What is important is that if soluble probes are used, they must be removed prior to the addition of the next higher order probe.

In an alternate embodiment, the complete reaction is done in solution. In this embodiment, the primary probes are added, the reaction is allowed to proceed for some period of time, and the uncleaved primary scissile probes are removed, as outlined above. The secondary probes are then added, and the reaction proceeds. The secondary uncleaved probes are then removed, and the tertiary probes are added, and the reaction proceeds. The uncleaved tertiary probes are then removed and the cleaved sequences are detected as is generally outlined herein.

As above, it is generally preferred to detect as many tertiary probe sequences as possible, and the secondary and primary probe sequences may be additionally detected as well. Thus, preferred embodiments utilize detection probes that are substantially complementary to all or part of each probe sequence of a scissile probe. Again, the detection sequences may be separated on the electrode, or mixed, to allow the greatest signal amplification.

In a preferred embodiment, at least one, and preferably more, quaternary probes are used. This proceeds as outlined above for tertiary probes.

Thus, CPT requires, again in no particular order, a first CPT primer comprising a first probe sequence, a scissile linkage and a second probe sequence; and a cleavage agent.

In this manner, CPT results in the generation of a large amount of cleaved primers, which then can be detected as outlined below.

In a preferred embodiment, Invader™ technology is used. Invader™ technology is based on structure-specific polymerases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail". This can then be detected. The Invader™ technology is described in U.S. Pat. Nos. 5,846,717; 5,614,402; 5,719,028; 5,541,311; and 5,843,669, all of which are hereby incorporated by reference.

Accordingly, the invention provides a first primer, sometimes referred to herein as an "invader primer", that hybridizes to a first domain of a target sequence, and a second primer, sometimes referred to herein as the signalling primer, that hybridizes to a second domain of the target sequence. The first and second target domains are adjacent. The signalling primer further comprises an overlap sequence, comprising at least one nucleotide, that is perfectly complementary to at least one nucleotide of the first target domain, and a non-complementary "tail" region. The cleavage enzyme recognizes the overlap structure and the noncomplementary tail, and cleaves the tail from the second primer. Suitable cleavage enzymes are described in the Patents outlined above, and include, but are not limited to, 5' thermostable nucleases from Thermus species, including *Thermus aquaticus, Thermus flavus* and *Thermus thermophilus*. The entire reaction is done isothermally at a temperature such that upon cleavage, the invader probe and the cleaved signalling probe come off the target stand, and new primers can bind. In this way large amounts of cleaved signalling probe (i.e. "tails") are made. The uncleaved signalling probes are removed (for example by binding to a solid support such as a bead, either on the basis of the sequence or through the use of a binding ligand attached to the portion of the signalling probe that hybridizes to the target). The cleaved signalling probes are then detected by forming an assay complex on an electrode comprising the cleaved probe ("tail") as the target, a capture probe and at least one ETM. The ETM may be covalently attached to the tail, or to a label probe which hybridizes either directly or indirectly (e.g. through the use of an amplifier probe) to the assay complex.

In a preferred embodiment, the signal amplification technique is a "sandwich" assay, as is generally described in U.S. S. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays are used when the target sequence comprises little or no ETM labels; that is, when a secondary probe, comprising the ETM labels, is used to generate the signal.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay.

Generally, sandwich signal amplification techniques may be described as follows. In preferred embodiments, although it is not required, the target sequences are immobilized on the electrode surface. This is preferably done using capture probes and optionally one or more capture extender probes; see FIG. 15. When only capture probes are utilized, it is necessary to have unique capture probes for each target sequence; that is, the surface must be customized to contain unique capture probes. Alternatively, capture extender probes may be used, that allow a "universal" surface, i.e. a surface containing a single type of capture probe that can be used to detect any target sequence. "Capture extender" probes are generally depicted in FIG. 15, and other figures, and have a first portion that will hybridize to all or part of the capture probe, and a second portion that will hybridize to a first portion of the target sequence. This then allows the generation of customized soluble probes, which as will be appreciated by those in the art is generally simpler and less costly. As shown herein, two capture extender probes may be used. This has generally been done to stabilize assay complexes (for example when the target sequence is large, or when large amplifier probes (particularly branched or dendrimer amplifier probes) are used.

In a preferred embodiment, the nucleic acids are added after the formation of the SAM, discussed below. This may be done in a variety of ways, as will be appreciated by those in the art. In one embodiment, conductive oligomers with terminal functional groups are made, with preferred embodiments utilizing activated carboxylates and isothiocyanates, that will react with primary amines that are put onto the nucleic acid, as is generally depicted in FIG. 6 using an activated carboxylate. These two reagents have the advantage of being stable in aqueous solution, yet react with primary alkylamines. However, the primary aromatic amines and secondary and tertiary amines of the bases should not react, thus allowing site specific addition of nucleic acids to the surface. This allows the spotting of probes (either capture or detection probes, or both) using known methods (ink jet, spotting, etc.) onto the surface.

In addition, there are a number of non-nucleic acid methods that can be used to immobilize a nucleic acid on a surface. For example, binding partner pairs can be utilized; i.e. one binding partner is attached to the terminus of an attachment linker, described below, and the other to the end of the nucleic acid. This may also be done without using a nucleic acid capture probe; that is, one binding partner serves as the capture probe and the other is attached to either the target sequence or a capture extender probe. That is, either the target sequence comprises the binding partner, or a capture extender probe that will hybridize to the target sequence comprises the binding partner.

Suitable binding partner pairs include, but are not limited to, hapten pairs such as biotin/streptavidin; antigens/antibodies; NTA/histidine tags; etc. In general, smaller binding partners are preferred, such that the electrons can pass from the nucleic acid into the conductive oligomer to allow detection.

In a preferred embodiment, when the target sequence itself is modified to contain a binding partner, the binding partner is attached via a modified nucleotide that can be enzymatically attached to the target sequence, for example during a PCR target amplification step. Alternatively, the binding partner should be easily attached to the target sequence.

Alternatively, a capture extender probe may be utilized that has a nucleic acid portion for hybridization to the target as well as a binding partner (for example, the capture extender probe may comprise a non-nucleic acid portion such as an alkyl linker that is used to attach a binding partner). In this embodiment, it may be desirable to cross-link the double-stranded nucleic acid of the target and capture extender probe for stability, for example using psoralen as is known in the art.

In one embodiment, the target is not bound to the electrode surface using capture probes. In this embodiment, what is important, as for all the assays herein, is that excess label probes be removed prior to detection and that the assay complex be in proximity to the surface. As will be appreciated by those in the art, this may be accomplished in other ways. For example, the assay complex comprising the ETMs may be present on beads that are added to the electrode comprising the monolayer, and then the beads brought into proximity of the electrode surface using techniques well known in the art, including gravity settling of the beads on the surface, electrostatic or magnetic interactions between bead components and the surface, using binding partner attachment as outlined above. Alternatively, after the removal of excess reagents such as excess label probes, the assay complex may be driven down to the surface, for example by pulsing the system with a voltage sufficient to drive the assay complex to the surface.

However, preferred embodiments utilize assay complexes attached via nucleic acid capture probes.

Once the target sequence has preferably been anchored to the electrode, an amplifier probe is hybridized to the target sequence, either directly, or through the use of one or more label extender probes, which serves to allow "generic" amplifier probes to be made. Preferably, the amplifier probe contains a multiplicity of amplification sequences, although in some embodiments, as described below, the amplifier probe may contain only a single amplification sequence, or at least two amplification sequences. The amplifier probe may take on a number of different forms; either a branched conformation, a dendrimer conformation, or a linear "string" of amplification sequences. Label probes comprising ETMs then hybridize to the amplification sequences (or in some cases the label probes hybridize directly to the target sequence), and the ETMs are detected using the electrode, as is more fully outlined below.

As will be appreciated by those in the art, the systems of the invention may take on a large number of different configurations, as is generally depicted in FIGS. 15, 16, 27, etc. In general, there are three types of systems that can be used: (1) "non-sandwich" systems (also referred to herein as "direct" detection) in which the target sequence itself is labeled with ETMs (again, either because the primers comprise ETMs or due to the incorporation of ETMs into the newly synthesized strand); (2) systems in which label probes directly bind to the target analytes; and (3) systems in which label probes are indirectly bound to the target sequences, for example through the use of amplifier probes.

Accordingly, the present invention provides compositions comprising an amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence, or it has a first probe sequence that is substantially complementary to a portion of an additional probe, in this case called a label extender probe, that has a first portion that is substantially complementary to the target sequence. In a preferred embodiment, the first probe sequence of the amplifier probe is substantially complementary to the target sequence.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, as is depicted in FIG. 18, the amplifier probes, or any of the other probes of the invention, may form hairpin stem-loop structures in the absence of their target. The length of the stem double-stranded sequence will be selected such that the hairpin structure is not favored in the presence of target. The use of these type of probes, in the systems of the invention or in any nucleic acid detection systems, can result in a significant decrease in non-specific binding and thus an increase in the signal to noise ratio.

Generally, these hairpin structures comprise four components. The first component is a target binding sequence, i.e. a region complementary to the target (which may be the sample target sequence or another probe sequence to which binding is desired), that is about 10 nucleosides long, with about 15 being preferred. The second component is a loop sequence, that can facilitate the formation of nucleic acid loops. Particularly preferred in this regard are repeats of GTC, which has been identified in Fragile X Syndrome as forming turns. (When PNA analogs are used, turns comprising proline residues may be preferred). Generally, from three to five repeats are used, with four to five being preferred. The third component is a self-complementary region, which has a first portion that is complementary to a portion of the target sequence region and a second portion that comprises a first portion of the label probe binding sequence. The fourth component is substantially complementary to a label probe (or other probe, as the case may be). The fourth component further comprises a "sticky end", that is, a portion that does not hybridize to any other portion of the probe, and preferably contains most, if not all, of the ETMs. The general structure is depicted in FIG. 18. As will be appreciated by those in the art, the any or all of the probes described herein may be configured to form hairpins in the absence of their targets, including the amplifier, capture, capture extender, label and label extender probes.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used, that is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below (although in some cases the amplification sequence may bind to a detection probe; see FIG. 27C). Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to whcih at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In addition, as outlined herein, linear amplification probes may form hairpin stem-loop structures, as is depicted in FIG. 18.

In one embodiment, the linear amplifier probe has a single amplification sequence. This may be useful when cycles of hybridization/disassociation occurs, forming a pool of amplifier probe that was hybridized to the target and then removed to allow more probes to bind, or when large numbers of ETMs are used for each label probe. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more ETMs are ultimately bound to the detection probes. Preamplifier molecules may be either linear or branched, and typically contain in the range of about 30–3000 nucleotides.

Thus, label probes are either substantially complementary to an amplification sequence or to a portion of the target sequence. Accordingly, the label probes can be configured in a variety of ways, as is generally described herein, depending on whether a "mechanism-1" or "mechanism-2" detection system is utilized, as described below.

Detection of the amplification reactions of the invention, including the direct detection of amplification products and indirect detection utilizing label probes (i.e. sandwich assays), is done by detecting assay complexes comprising ETMs, which can be attached to the assay complex in a variety of ways, as is more fully described below. In general, there are two basic detection mechanisms. In a preferred embodiment, detection of an ETM is based on electron transfer through the stacked π-orbitals of double stranded nucleic acid. This basic mechanism is described in U.S. Pat. Nos. 5,591,578, 5,770,369, 5,705,348, 5,824,473 and 5,780,234 and WO 98/20162, all of which are expressly incorporated by reference, and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected. This general idea is depicted in FIG. 27.

Alternatively, the ETM can be detected, not necessarily via electron transfer through nucleic acid, but rather can be directly detected on the surface of the electrode. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs.

It should be noted that these defects are to be distinguished from "holes" that allow direct contact of sample components with the detection electrode. As is more fully outlined below, the electroconduits can be generated in several general ways, including but not limited to the use of rough electrode surfaces, such as gold electrodes formulated on PC circuit boards; or the inclusion of at least two different species in the monolayer, i.e. using a "mixed monolayer", at least one of which is a electroconduit-forming species (EFS). Thus, upon binding of a target analyte, a soluble binding ligand comprising an ETM is brought to the surface, and detection of the ETM can proceed, putatively through the "electroconduits" to the electrode. Essentially, the role of the SAM comprising the defects is to allow contact of the ETM with the electronic surface of the electrode, while still providing the benefits of shielding the electrode from solution components and reducing the amount of non-specific binding to the electrodes. Viewed differently, the role of the binding ligand is to provide specificity for a recruitment of ETMs to the surface, where they can be directly detected.

Thus, the present invention is directed to the formation of assay complexes on electrodes, generally comprising SAMs. Once the assay complexes are formed, the presence or absence of the ETMs are detected as is described below and in U.S. Pat. Nos. 5,591,578; 5,824,473; 5,770,369; 5,705,348 and 5,780,234; U.S. Ser. Nos. 08/911,589; 09/135,183; 09/306,653; 09/134,058; 09/295,691; 09/238,351; 09/245,105 and 09/338,726; and PCT applications WO098/20162; PCT US99/01705; PCT US99/01703; PCT US99/10104, all of which are expressly incorporated herein by reference in their entirety.

Thus, in either embodiment, an assay complex is formed that contains an ETM, which is then detected using the detection electrode. The invention thus provides assay complexes that minimally comprise a target sequence. "Assay complex" herein is meant the collection of hybridization complexes comprising nucleic acids, including probes and targets, that contains at least one ETM and thus allows detection. The composition of the assay complex depends on the use of the different probe components outlined herein. Thus, in FIGS. 16A and 16B, the assay complex comprises the capture probe and the target sequence. The assay complexes may also include label probes, capture extender probes, label extender probes, and amplifier probes, as outlined herein, depending on the configuration used.

The assay complexes comprise at least one ETM, which can either be covalently attached to a component of the assay complex as described herein or a "hybridization indicator", described below.

The terms "electron donor moiety", "electron acceptor moiety", and "ETMs" (ETMS) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

The transition metals are complexed with a variety of ligands, to form suitable transition metal complexes, as is well known in the art. L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position.

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol [3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5, 8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp73–98), 21.1 (pp. 813–898) and 21.3 (pp 915–957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982–1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (–1) ion, that yield a class of bis(cyclopentadieyl) metal compounds, (i.e. the metallocenes); see for example Robins et al., J. Am. Chem. Soc. 104:1882–1893 (1982); and Gassman et al., J. Am. Chem. Soc. 108:4228–4229 (1986), incorporated by reference. Of these, ferrocene $[(C_5H_5)_2Fe]$ and its derivatives are prototypical examples which have been used in a wide variety of chemical (Connelly et al., Chem. Rev. 96:877–910 (1996), incorporated by reference) and electrochemical (Geiger et al., Advances in Organometallic Chemistry 23:1–93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to the nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(–1) ion, or butadiene yield potentially suitable organometallic compounds, and all such ligands, in conjuction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) one ligand is a metallocene ligand and another is a nitrogen donating ligand, with the other ligands, if needed, are either nitrogen donating ligands or metallocene ligands, or a mixture.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2, 1,9-def:6,5,10-d'e'f')diisoquinoline dichloride ($ADIQ^{2+}$); porphyrins ([meso-tetrakis(N-methyl-x-pyridinium) porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5, 5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. Preferred ETMs are metallocenes, with ferrocene being particularly preferred.

Without being bound by theory, it appears that in "mechanism-2" systems, electron transfer is facilitated when the ETM is able to penetrate ("snuggle") into the monolayer to some degree. That is, in general, it appears that hydrophobic ETMs used with hydrophobic SAMs give rise to better (greater) signals than ETMs that are charged or more hydrophilic. Thus, for example, ferrocene in solution can penetrate the monolayers of the examples and give a signal when electroconduits are present, while ferrocyanide in solution gives little or no signal. Thus, in general, hydrophobic ETMs are preferred in mechanism-2 systems; however, transition metal complexes, although charged, with one or more hydrophobic ligands, such as Ru and Os complexes, also give rise to good signals. Similarly, electron transfer between the ETM and the electrode is facilitated by the use of linkers or spacers that allow the ETM some flexibility to penetrate into the monolayer; thus the N6 compositions of the invention have a four carbon linker attaching the ETM to the nucleic acid.

In a preferred embodiment, a plurality of ETMs are used. The use of multiple ETMs provides signal amplification and thus allows more sensitive detection limits. While the use of multiple ETMs on nucleic acids that hybridize to complementary strands (i.e. mechanism-1 systems) can cause decreases in $T_m$s of the hybridization complexes depending on the number, site of attachment and spacing between the multiple ETMs, this is not a factor when the ETMs are on the recruitment linker, since this does not hybridize to a complementary sequence. Accordingly, pluralities of ETMs are preferred, with at least about 2 ETMs per assay complex being preferred, and at least about 10 being particularly preferred, and at least about 20 to 50 being especially preferred. In some instances, very large numbers of ETMs (100 to 10000 or greater) can be used.

Attachment of the ETM to the assay complex can be done in a wide variety of ways, and depends on the mechanism of detection and whether direct or indirect detection is done. In general, methods and compositions outlined in WO98/20162, expressly incorporated by reference in its entirety, can be used.

In a preferred embodiment, it is a label probe that comprises the ETMs. In a preferred embodiment, the label probe is used in a mechanism-2 detection system. Thus, as will be appreciated by those in the art, the portion of the label probe (or target, in some embodiments) that comprises the ETMs (termed herein a "recruitment linker" or "signal carrier") can be nucleic acid, or it can be a non-nucleic acid linker that links the first hybridizable portion of the label probe to the ETMs. That is, since this portion of the label probe is not required for hybridization if a mechanism-2 system is used, it need not be nucleic acid, although this may be done for ease of synthesis. In some embodiments, as is more fully outlined below, the recruitment linker may comprise double-stranded portions.

Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the linker is non-nucleic acid, and can be either a metallocene polymer or an alkyl-type polymer (including heteroalkyl, as is more fully described below) containing ETM substitution groups. These options are generally depicted in the Figures.

When a mechanism-1 detection system is used to detect the label probes, the ETMs are generally attached via either (1) or (2) above, since hybridization of the label probe to a detection probe, as outlined herein, requires the formation of a hybridization complex.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIG. 16H; this is similar to the use of an amplifier probe, except that both the primary and the secondary label probes comprise ETMs.

In a preferred embodiment, the ETM is attached to the base of a nucleoside as is generally outlined in WO 98/20162, incorporated by reference, for attachment of conductive oligomers. Attachment can be to an internal nucleoside or a terminal nucleoside.

The covalent attachment to the base will depend in part on the ETM chosen, but in general is similar to the attachment of conductive oligomers to bases, as outlined in WO 98/20162. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between $sp^2$ and sp Carbon Centers, Sonogashira, pp521–549, and pp950–953, hereby incorporated by reference). Structure 1 depicts a representative structure in the presence of the metal ion and any other necessary ligands; Structure 1 depicts uridine, although as for all the structures herein, any other base may also be used.

Structure 1

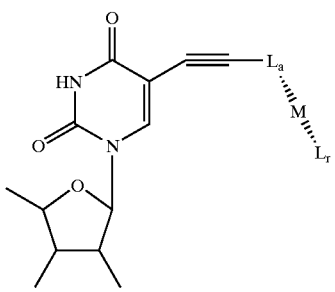

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221–7226 (1989); Telser et al., J. Am. Chem. Soc. 111:7226–7232 (1989), both of which are expressly incorporated by reference). These structures are generally depicted below in Structure 2, which again uses uridine as the base, although as above, the other bases may also be used:

Structure 2

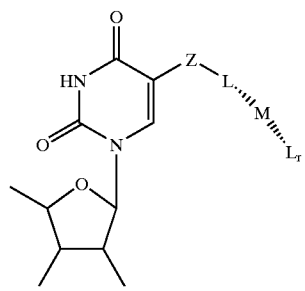

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and $L_r$ of Structure 2 are both metallocene ligands, $L_m$, as described above. Structure 3 depicts a preferred embodiment wherein the metallocene is ferrocene, and the base is uridine, although other bases may be used:

Structure 3

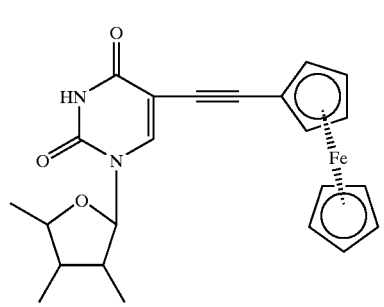

Preliminary data suggest that Structure 3 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally WO 95/15971 and WO 98/20162, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 of WO98/20162 may be replaced by ETMs; alternatively, the ETMs may be added to the free terminus of the conductive oligomer.

In a preferred embodiment, a metallocene serves as the ETM, and is attached via an amide bond as depicted below in Structure 4. The examples outline the synthesis of a preferred compound when the metallocene is ferrocene.

Structure 4

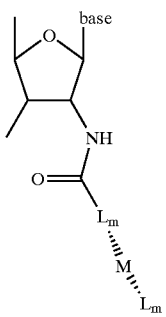

In a preferred embodiment, amine linkages are used, as is generally depicted in Structure 5.

Structure 5

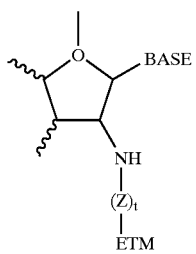

Z is a linker, as defined herein, with 1–16 atoms being preferred, and 2–4 atoms being particularly preferred, and t is either one or zero.

In a preferred embodiment, oxo linkages are used, as is generally depicted in Structure 6.

Structure 6

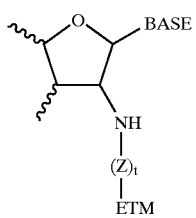

In Structure 6, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible; a variety of linkages of ETMs to nucleosides are shown in FIG. 1.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971 and WO 98/20162, incorporated by reference). Alternatively, the conductive oligomers depicted in Structures 23 and 24 of WO98/20162 may be replaced by ETMs. In a preferred embodiment, the composition has the structure shown in Structure Structure 7

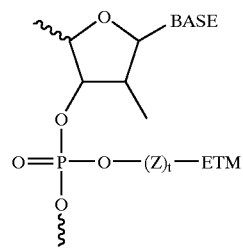

In Structure 7, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred When the ETM is attached to the base or the backbone of the nucleoside, it is possible to attach the ETMs via "dendrimer" structures, as is more fully outlined below. As is generally depicted in the Figures, alkyl-based linkers can be used to create multiple branching structures comprising one or more ETMs at the terminus of each branch. Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions.

In a preferred embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 8 (nucleic acid with a ribose-phosphate backbone) and Structure 9 (peptide nucleic acid backbone). Structures 8 and 9 depict ferrocene, although as will be appreciated by those in the art, other metallocenes may be used as well. In general, air stable metallocenes are preferred, including metallocenes utilizing ruthenium and cobalt as the metal.

Structure 8

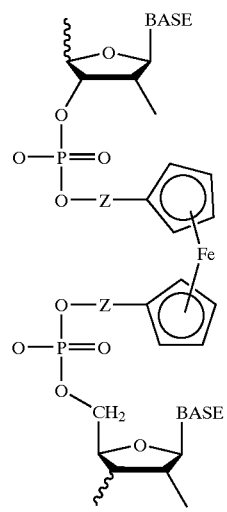

In Structure 8, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 8 depicts a ribose-phosphate backbone, although as will be appreciated by those in the art, nucleic acid analogs may also be used, including ribose analogs and phosphate bond analogs.

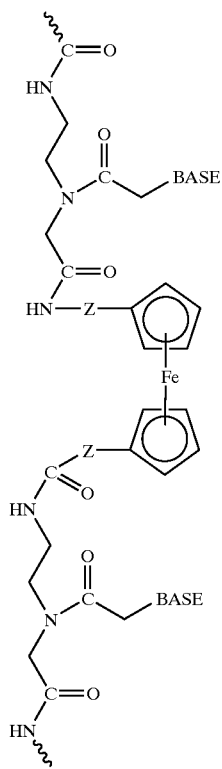

Structure 9

In Structure 9, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substituent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substitutent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 10:

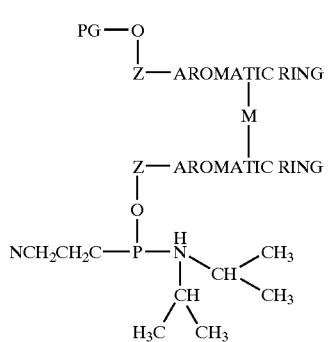

Structure 10

In Structure 10, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein. Structure 11 depicts the ferrocene derivative:

Structure 11

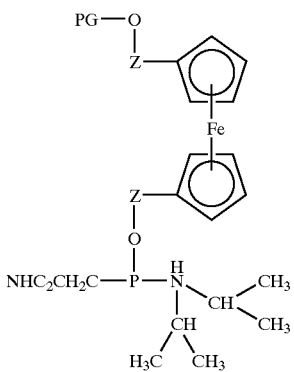

These phosphoramidite analogs can be added to standard oligonucleotide syntheses as is known in the art.

Structure 12 depicts the ferrocene peptide nucleic acid (PNA) monomer, that can be added to PNA synthesis as is known in the art and depicted within the Figures and Examples:

Structure 12

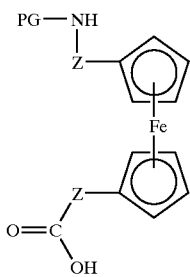

In Structure 12, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, the ETMs are attached as polymers, for example as metallocene polymers, in a "branched" configuration similar to the "branched DNA" embodiments herein and as outlined in U.S. Pat. No. 5,124, 246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 10 and 1, ETMs, such as metallocene ETMs, are added. Additional phosphoramidite ETMs such as metallocenes can be added, to form "ETM polymers", including "metallocene polymers" as depicted herein, particularly for ferrocene. In addition, in some embodiments, it is desirable to increase the solubility of the polymers by adding a "capping" group to the terminal ETM in the polymer, for example a final phosphate group to the metallocene as is generally depicted in FIG. 12. Other suitable solubility enhancing "capping" groups will be appreciated by those in the art. It should be noted that these solubility enhancing groups can be added to the polymers in other places, including to the ligand rings, for example on the metallocenes as discussed herein.

A preferred embodiment of this general idea is outlined in the Figures. In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 12, peptide nucleic acid structures containing metallocene polymers could be generated.

Thus, the present invention provides recruitment linkers of nucleic acids comprising "branches" of metallocene polymers as is generally.depicted in FIGS. 12 and 13. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo-or hetero-bifunctional inkers as are well known (see 1994 Pierce Chemical Company catalog, technical section on cross-linkers, pages 155–200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenytalanine, serine, tryptophan, and/or proline.

In a preferred embodiment, the recruitment linker comprises a metallocene polymer, as is described above.

The attachment of the recruitment linkers to the first portion of the label probe will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, the ETM is attached to the target sequence, either by incorporation into a primer, or by incorporation into the newly synthesized portion of the target sequence. Target sequences comprising covalently attached ETMs can be directly detected using either a mechanism-1 or mechanism-2 system, as is shown in the figures.

In this embodiment, it is the target sequence itself that carries the ETMs, rather than the recruitment linker of a label probe. As discussed herein, this may be done using target sequences that have ETMs incorporated at any number of positions, including either within a primer or within the newly synthesized strand, and can be attached to the nucleic acid in a variety of positions, as outlined herein. In this embodiment, as for the others of the system, the 3'-5' orientation of the probes and targets is chosen to get the ETM-containing structures (i.e. label probes, recruitment linkers or target sequences) as close to the surface of the monolayer as possible, and in the correct orientation. This may be done using attachment via insulators or conductive oligomers as is generally shown in the Figures, and may depend on which mechanism is used. In addition, as will be appreciated by those in the art, multiple capture probes can be utilized, either in a configuration wherein the 5'-3' orientation of the capture probes is different, or where "loops" of target form when multiples of capture probes are used.

Labelling of the target sequence with ETMs can also occur during synthesis of the new target strand. For example, as is described herein, it is possible to enzymatically add triphosphate nucleotides comprising the ETMs of the invention to a growing nucleic acid, for example during the previously described amplification techniques. As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Alternatively, it is possible to enzymatically add nucleotides comprising ETMs to the terminus of a nucleic acid, for example a target nucleic acid, as is more fully outlined below. In this embodiment, an effective "recruitment linker" is added to the terminus of the target sequence, that can then be used for detection. Thus the invention provides compositions utilizing electrodes comprising monolayers of conductive oligomers and capture probes, and target sequences that comprises a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, i.e. sequences designed to hybridize to complementary sequences. Thus, ETMs may be added to non-recruitment linkers as well. For example, there may be ETMs added to sections of label probes that do hybridize to components of the assay complex, for example the first portion, or to the target sequence as outlined above. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIG. 16A, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In one embodiment, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317–2323 (1993); Millan et al., Anal. Chem. 662943–2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers. Hybridization indicators include intercalators and minor and/or major groove binding moieties. In a preferred embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., Bioconj. Chem. 8:906 (1997), hereby expressly incorporated by reference. In this embodiment, changes in the redox state of certain molecules as a result of the presence of DNA (i.e. guanine oxidation by ruthenium complexes) can be detected using the SAMs comprising conductive oligomers as well.

Again, the configuration of the system will depend on the mechanism used for detection. A variety of mechanism-1 systems are depicted in FIG. 27, which shows direct detection (i.e. target sequence comprising the ETM), and indirect detection (using label probes).

A variety of mechanism-2 systems are depicted in FIG. 16, again showing direct detection (i.e. target sequence comprising the ETM), and indirect detection (using label probes).

In a preferred embodiment, the label probes directly hybridize to the target sequences, as is generally depicted in the figures. In these embodiments, the target sequence is preferably, but not required to be, immobilized on the surface using capture probes, including capture extender probes. Label probes are then used to bring the ETMs into proximity of the surface of the monolayer comprising conductive oligomers. In a preferred embodiment, multiple label probes are used; that is, label probes are designed such that the portion that hybridizes to the target sequence can be different for a number of different label probes, such that amplification of the signal occurs, since multiple label probes can bind for every target sequence. Thus, as depicted in the figures, n is an integer of at least one. Depending on the sensitivity desired, the length of the target sequence, the number of ETMs per label probe, etc., preferred ranges of n are from 1 to 50, with from about 1 to about 20 being particularly preferred, and from about 2 to about 5 being especially preferred. In addition, if "generic" label probes are desired, label extender probes can be used as generally described below for use with amplifier probes.

As above, generally in this embodiment the configuration of the system and the label probes are designed to recruit the ETMs as close as possible to the monolayer surface.

In a preferred embodiment, the label probes are hybridized to the target sequence indirectly. That is, the present invention finds use in novel combinations of signal amplification technologies and electron transfer detection on electrodes, which may be particularly useful in sandwich hybridization assays, as generally depicted in the Figures. In these embodiments, the amplifier probes of the invention are bound to the target sequence in a sample either directly or indirectly. Since the amplifier probes preferably contain a relatively large number of amplification sequences that are available for binding of label probes, the detectable signal is significantly increased, and allows the detection limits of the target to be significantly improved. These label and amplifier probes, and the detection methods described herein, may be used in essentially any known nucleic acid hybridization formats, such as those in which the target is bound directly to a solid phase or in sandwich hybridization assays in which the target is bound to one or more nucleic acids that are in turn bound to the solid phase.

The assay complexes of the invention are detected using electrodes.

By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode is an ETM as described herein. Preferred electodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, platinum, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. Electrode coils may be preferred in some embodiments as well. This allows a maximum of surface area containing the nucleic acids to be exposed to a small volume of sample.

In a preferred embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as will be appreciated by those in the art, with printed circuit board (PCB) materials being particularly preferred. Thus, in general, the suitable substrates include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), GETEK (a blend of polypropylene oxide and fiberglass), etc.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In some embodiments, glass may not be preferred as a substrate.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

The substrates can be part of a larger device comprising a detection chamber that exposes a given volume of sample to the detection electrode. Generally, the detection chamber ranges from about 1 nL to 1 ml, with about 10 $\mu$L to 500 $\mu$L being preferred. As will be appreciated by those in the art, depending on the experimental conditions and assay, smaller or larger volumes may be used.

In some embodiments, the detection chamber and electrode are part of a cartridge that can be placed into a device comprising electronic components (an AC/DC voltage source, an ammeter, a processor, a read-out display, temperature controller, light source, etc.). In this embodiment, the interconnections from each electrode are positioned such that upon insertion of the cartridge into the device, connections between the electrodes and the electronic components are established.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, preferred embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Preferred brighteners are mixtures of organic and inorganic species, with cobalt and nickel being preferred.

In general, the adhesion layer is from about 100 Å thick to about 25 microns (1000 microinches). The If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

The methods continue with the addition of SAMs as are described below. In a preferred embodiment, drop deposition techniques are used to add the required chemistry, i.e. the monolayer forming species, one of which is preferably a capture ligand comprising species. Drop deposition techniques are well known for making "spot" arrays. This is done to add a different composition to each electrode, i.e. to make an array comprising different capture ligands. Alternatively, the SAM species may be identical for each electrode, and this may be accomplished using a drop deposition technique or the immersion of the entire substrate or a surface of the substrate into the solution.

Thus, in a preferred embodiment, the electrode comprises a monolayer, comprising electroconduit forming species (EFS). As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

The detection electrode comprises a self-assembled monolayer (SAM) comprising conductive oligomers. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise conductive oligomers alone, or a mixture of conductive oligomers and insulators. As outlined herein, the efficiency of oligonucleotide hybridization may increase when the analyte is at a distance from the electrode. Similarly, non-specific binding of biomolecules, including the target analytes, to an electrode is generally reduced when a monolayer is present. Thus, a monolayer facilitates the maintenance of the nucleic acid away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accesibility to the electrode.

In general, the SAMs of the invention can be generated in a number of ways and comprise a number of different components, depending on the electrode surface and the system used. For "mechanism-1" embodiments, preferred embodiments utilize two monolayer forming species: a monolayer forming species (including insulators or conductive oligomers) and a conductive oligomer species comprising the capture binding ligand, although as will be appreciated by those in the art, additional monolayer forming species can be included as well. For "mechanism-2" systems, the composition of the SAM depends on the detection electrode surface. In general, two basic "mechanism-2" systems are described; detection electrodes comprising "smooth" surfaces, such as gold ball electrodes, and those comprising "rough" surfaces, such as those that are made using commercial processes on PC circuit boards. In general, without being bound by theory, it appears that monolayers made on imperfect surfaces, i.e. "rough" surfaces, spontaneously form monolayers containing enough electroconduits even in the absence of EFS, probably due to the fact that the formation of a uniform monolayer on a rough surface is difficult. "Smoother" surfaces, however, may require the inclusion of sufficient numbers of EFS to generate the electroconduits, as the uniform surfaces allow a more uniform monolayer to form. Again, without being bound by theory, the inclusion of species that disturb the uniformity of the monolayer, for example by including a rigid molecule in a background of more flexible ones, causes electroconduits. Thus "smooth" surfaces comprise monolayers comprising three components: an insulator species, a EFS, and a species comprising the capture ligand, although in some circumstances, for example when the capture ligand species is included at high density, the capture ligand species can serve as the EFS. "Smoothness" in this context is not measured physically but rather as a function of an increase in the measured signal when EFS are included. That is, the signal from a detection electrode coated with monolayer forming species is compared to a signal from a detection electrode coated with monolayer forming species including a EFS. An increase indicates that the surface is relatively smooth, since the inclusion of a EFS served to facilitate the access of the ETM to the electrode.

It should also be noted that while the discussion herein is mainly directed to gold electrodes and thiol-containing monolayer forming species, other types of electrodes and monolayer-forming species can be used.

It should be noted that the "electroconduits" of mechanism-2 systems do not result in direct contact of sample components with the electrode surface; that is, the electroconduits are not large pores or holes that allow physical access to the electrode. Rather, without being bound by theory, it appears that the electroconduits allow certain types of ETMs, particularly hydrophobic ETMs, to penetrate sufficiently into the monolayer to allow detection. However, other types of redox active species, including some hydrophilic species, do not penetrate into the monolayer, even with electroconduits present. Thus, in general, redox active species that may be present in the sample do not give substantial signals as a result of the electroconduits. While the exact system will vary with the composition of the SAM and the choice of the ETM, in general, the test for a suitable SAM to reduce non-specific binding that also has sufficient electroconduits for ETM detection is to add either ferrocene or ferrocyanide to the SAM; the former should give a signal and the latter should not.

Accordingly, in mechanism-1 systems, the monolayer comprises a first species comprising a conductive oligomer comprising the capture binding ligand, as is more fully outlined below, and a second species comprising a monolayer forming species, including either or both insulators or conductive oligomers.

In a preferred embodiment, the monolayer comprises electroconduit-forming species. By "electroconduit-forming species" or "EFS" herein is meant a molecule that is capable of generating sufficient electroconduits in a monolayer, generally of insulators such as alkyl groups, to allow detection of ETMs at the surface. In general, EFS have one or more of the following qualities: they may be relatively rigid molecules, for example as compared to an alkyl chain; they may attach to the electrode surface with a geometry different from the other monolayer forming species (for example, alkyl chains attached to gold surfaces with thiol groups are thought to attach at roughly 45° angles, and phenyl-acetylene chains attached to gold via thiols are thought to go down at 90° angles); they may have a structure that sterically interferes or interrupts the formation of a tightly packed monolayer, for example through the inclusion of branching groups such as alkyl groups, or the inclusion of highly flexible species, such as polyethylene glycol units; or they may be capable of being activated to form electroconduits; for example, photoactivatible species that can be selectively removed from the surface upon photoactivation, leaving electroconduits.

Preferred EFS include conductive oligomers, as defined below, and phenyl-acetylene-polyethylene glycol species. However, in some embodiments, the EFS is not a conductive oligomer.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transfering electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^{4}$ $\Omega^{-1}\text{cm}^{-1}$, with from about $10^{-5}$ to about $10^{3}$ $\Omega^{-1}\text{cm}^{-1}$ being preferred, with these S values being calculated for molecules ranging from about 20 Å to about 200 Å. As described below, insulators have a conductivity S of about $10^{-7}$ $\Omega^{-1}\text{cm}^{-1}$ or lower, with less than about $10^{-8}$ $\Omega^{-1}\text{cm}^{-1}$ being preferred. See generally Gardner et al., Sensors and Actuators A 51 (1995) 57–66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during binding ligand synthesis (i.e. nucleic acid synthesis, such that nucleosides containing the conductive oligomers may be added to a nucleic acid synthesizer during the synthesis of the compositions of the invention, ii) during the attachment of the conductive oligomer to an electrode, or iii) during binding assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 13:

Structure 13

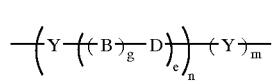

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to binding ligands such as nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a binding ligand, the right "Y", if present, is attached to the binding ligand such as a nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B—D is a bond able to conjugate with neighboring bonds (herein referred to as a Aconjugated bond@), preferably selected from acetylene, alkene, substituted alkene, amide, azo, —C=N—(including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and—NR, wherein R is as defined herein; substituted sulfur; sulfonyl (—SO$_2$—) sulfoxide (—SO—); phosphine oxide (—PO— and —RPO—; and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—(CH$_2$)$_2$CH$_3$ and —O—(CH$_2$)$_4$CH$_3$ being preferred.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, methyl, ethyl, propyl, alkoxy groups such as —O—(CH$_2$)$_2$CH$_3$ and —O—(CH$_2$)$_4$CH$_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B—D is a bond linking two atoms or chemical moieties. In a preferred embodiment, B—D is a conjugated bond, containing overlapping or conjugated π-orbitals.

Preferred B—D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—) and other conjugated bonds such as (—CH=N—, —CR=N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly preferred B—D bonds are acetylene, alkene, amide, and substituted derivatives of these three, and azo. Especially preferred B—D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B—D bonds (or D moieties, when g=0) may be all the same, or at least one may be different. For example, when m is zero, the terminal B—D bond may be an amide bond, and the rest of the B—D bonds may be acetylene bonds. Generally, when amide bonds are present, as few amide bonds as possible are preferable, but in some embodiments all the B—D bonds are amide bonds. Thus, as outlined above for the Y rings, one type of B—D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B—D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26–35 (1996); Tour, Chem. Rev. 96:537–553 (1996); Hsung et a Organometallics 14:4808–4815 (1995; and references cited therein, all of which are expressly incorporated by reference.

Particularly preferred conductive oligomers of this embodiment are depicted below:

Structure 14

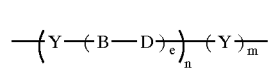

Structure 14 is Structure 13 when g is 1. Preferred embodiments of Structure 14 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B—D is acetylene and Y is phenyl or substituted phenyl (see Structure 16 below). A preferred embodiment of Structure 14 is also when e is one, depicted as Structure 15 below:

Structure 15

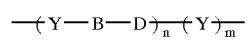

Preferred embodiments of Structure 15 are: Y is phenyl or substituted phenyl and B—D is azo; Y is phenyl or substituted phenyl and B—D is acetylene; Y is phenyl or substituted phenyl and B—D is alkene; Y is pyridine or substituted pyridine and B—D is acetylene; Y is thiophene or substi- tuted thiophene and B—D is acetylene; Y is furan or substituted furan and B—D is acetylene; Y is thiophene or furan (or substituted thiophene or furan) and B—D are alternating alkene and acetylene bonds.

Most of the structures depicted herein utilize a Structure 15 conductive oligomer. However, any Structure 15 oligomers may be substituted with any of the other structures depicted herein, i.e. Structure 13 or 20 oligomer, or other conducting oligomer, and the use of such Structure 15 depiction is not meant to limit the scope of the invention.

Particularly preferred embodiments of Structure 15 include Structures 16, 17, 18 and 19, depicted below:

Structure 16

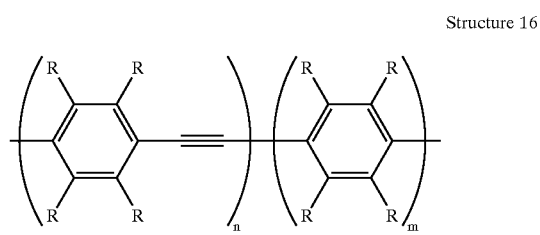

Particularly preferred embodiments of Structure 16 include: n is two, m is one, and R is hydrogen; n is three, m is zero, and R is hydrogen; and the use of R groups to increase solubility.

Structure 17

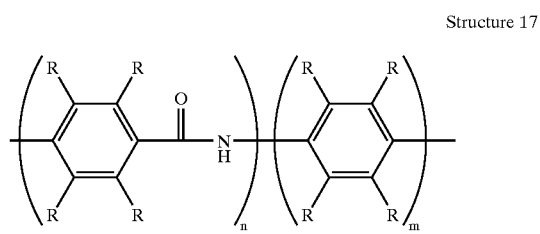

When the B—D bond is an amide bond, as in Structure 17, the conductive oligomers are pseudopeptide oligomers. Although the amide bond in Structure 17 is depicted with the carbonyl to the left, i.e. —CONH—, the reverse may also be used, i.e. —NHCO—. Particularly preferred embodiments of Structure 17 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

Structure 18

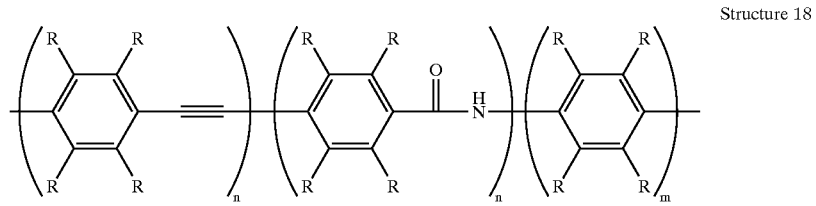

Preferred embodiments of Structure 18 include the first n is two, second n is one, m is zero, and all R groups are hydrogen, or the use of R groups to increase solubility.

Structure 19

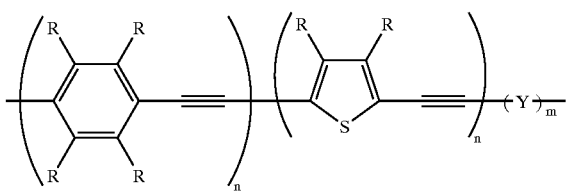

Preferred embodiments of Structure 19 include: the first n is three, the second n is from 1–3, with m being either 0 or 1, and the use of R groups to increase solubility.

In a preferred embodiment, the conductive oligomer has the structure depicted in Structure 20:

Structure 20

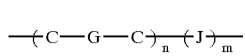

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C—G—C group is an alkene (—CH═CH—), substituted alkene (—CR═CR—) or mixtures thereof (—CH═CR— or —CR═CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 20 is zero. In a particularly preferred embodiment, m is zero and G is an alkene bond, as is depicted in Structure 21:

Structure 21

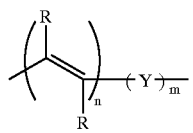

The alkene oligomer of structure 21, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 13 and 20.

In addition, particularly for use with mechanism-2 systems, the monolayer comprises conductive oligomers, and the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in the structures; for example, a B—D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, when the target analyte is a nucleic acid, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when capture binding ligands such as nucleic acids are covalently attached to the electrode using conductive oligomers, it is possible to have one type of conductive oligomer used to attach the nucleic acid, and another type functioning to detect the ETM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferrably slower than the rate through the conductive oligomers described herein.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

The length of the species making up the monolayer will vary as needed. As outlined above, it appears that binding of target analytes (for example, hybridization of nucleic acids) is more efficient at a distance from the surface. The species to which capture binding ligands are attached (as outlined below, these can be either insulators or conductive oligomers) may be basically the same length as the monolayer forming species or longer than them, resulting in the capture binding ligands being more accessible to the solvent for hybridization. In some embodiments, the conductive oligomers to which the capture binding ligands are attached may be shorter than the monolayer.

As will be appreciated by those in the art, the actual combinations and ratios of the different species making up the monolayer can vary widely, and will depend on whether mechanism-1 or -2 is used. Generally, three component systems are preferred for mechanism-2 systems, with the first species comprising a capture binding ligand containing species (termed a capture probe when the target analyte is a nucleic acid), attached to the electrode via either an insulator or a conductive oligomer. The second species are the conductive oligomers, and the third species are insulators. In this embodiment, the first species can comprise from about 90% to about 1%, with from about 20% to about 40% being preferred. When the target analytes are nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. Preferred ratios of first:second:third species are 2:2:1 for short targets, 1:3:1 for longer targets, with total thiol concentration (when used to attach these species, as is more fully outlined below) in the 500 µM to 1 mM range, and 833 µM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 systems, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

The covalent attachment of the conductive oligomers and insulators to the electrode may be accomplished in a variety of ways, depending on the electrode and the composition of the insulators and conductive oligomers used. The attachment linkers (which can comprise insulators and conductive oligomers), which are used to covalently attach nucleic acid species (capture and detection probes) to the electrode, are attached in a similar manner. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 23–25. Generally, some type of linker is used, as depicted below as "A" in Structure 22, where "X" is the conductive oligomer, "I" is an insulator and the hatched surface is the electrode:

Structure 22

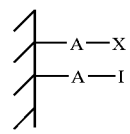

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332–3337 (1994); Lenhard et al., J. Electroanal. Chem. 78:195–201 (1977), both of which are expressly incorporated by reference). When carbon based electrodes are used, A may be an amino moiety (preferably a primary amine; see for example Deinhammer et al., Langmuir 10:1306–1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 23, 24 and 25. As will be appreciated by those in the art, other such structures can be made. In Structures 23, 24 and 25, the A moiety is just a sulfur atom, but substituted sulfur moieties may also be used.

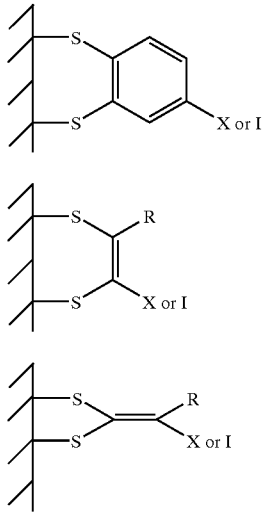

Structure 23

Structure 24

Structure 25

It should also be noted that similar to Structure 25, it may be possible to have a a conductive oligomer terminating in a single carbon atom with three sulfur moities attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 26, using the Structure 15 conductive oligomer, although as for all the structures depicted herein, any of the conductive oligomers, or combinations of conductive oligomers, may be used. Similarly, any of the conductive oligomers or insulators may also comprise terminal groups as described herein. Structure 26 depicts the "A" linker as comprising just a sulfur atom, although additional atoms may be present (i.e. linkers from the sulfur to the conductive oligomer or substitution groups). In addition, Structure 26 shows the sulfur atom attached to the Y aromatic group, but as will be appreciated by those in the art, it may be attached to the B—D group (i.e. an acetylene) as well.

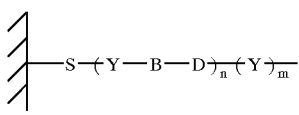

Structure 26

In general, thiol linkages are preferred when either two sets of electrodes are used (i.e. the detection electrodes comprising the SAMs are not used at high electrophoretic voltages (i.e. greater than 800 or 900 mV), that can cause oxidation of the thiol linkage and thus loss of the SAM), or, if one set of electrodes is used, lower electrophoretic voltages are used as is generally described below.

In a preferred embodiment, the electrode is a carbon electrode, i.e. a glassy carbon electrode, and attachment is via a nitrogen of an amine group. A representative structure is depicted in Structure 27. Again, additional atoms may be present, i.e. Z type linkers and/or terminal groups.

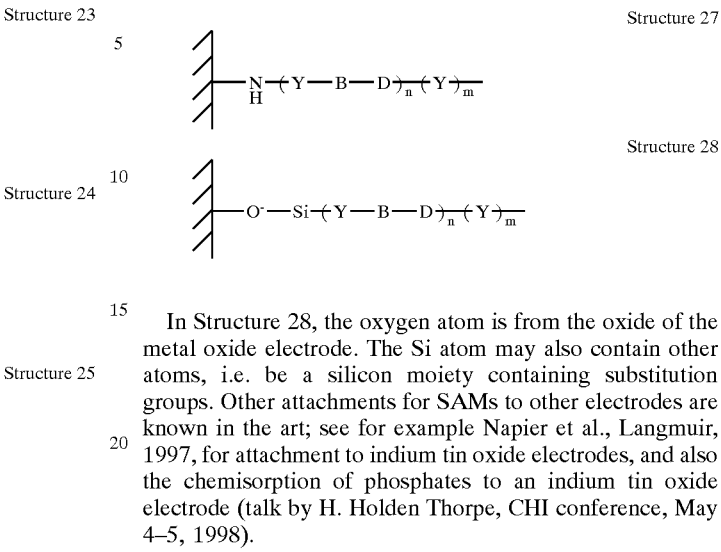

Structure 27

Structure 28

In Structure 28, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4–5, 1998).

In a preferred embodiment, the electrode comprises either capture probes to anchor the assay complexes to the electrode (used in either mechanism-1 or mechanism-2 systems), or detection probes (for mechanism-1 systems). Since the capture probes are not used for detection, the capture probes may be attached using attachment linkers, which may include either conductive oligomers or insulators, as described below. Detection probes used in mechanism-1 systems are attached using conductive oligomers.

The capture probe nucleic acid is covalently attached to the electrode, via an "attachment linker", that can be either a conductive oligomer (required for mechanism-1 systems) or an insulator. By "covalently attached" herein is meant that two moieties are attached by at least one bond, including sigma bonds, pi bonds and coordination bonds.

Thus, one end of the attachment linker is attached to a nucleic acid (or other binding ligand), and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 29:

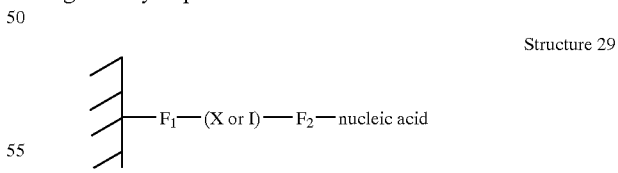

Structure 29

In Structure 29, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogeneous to both, for example, as defined herein for "Z".

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one preferred embodiment, indium-tin-oxide (ITO) is used as the electrode.

In a preferred embodiment, a gold surface is first cleaned. A variety of cleaning procedures may be employed, including, but not limited to, chemical cleaning or etchants (including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. A preferred embodiment utilizes a deposition solution comprising a mixture of various SAM species in solution, generally thiol-containing species. Mixed monolayers that contain nucleic acids are usually prepared using a two step procedure. The thiolated nucleic acid is deposited during the first deposition step (generally in the presence of at least one other monolayer-forming species) and the mixed monolayer formation is completed during the second step in which a second thiol solution minus nucleic acid is added. The second step frequently involves mild heating to promote monolayer reorganization.

In a preferred embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 $\mu$M to 10 mM, with from about 400 uM to about 1.0 mM being especially preferred. In a preferred embodiment, the deposition solution contains thiol modified DNA (i.e. nucleic acid attached to an attachment linker) and thiol diluent molecules (either conductive oligomers or insulators, with the latter being preferred). The ratio of nucleic acid to diluent (if present) is usually between 1000:1 to 1:1000, with from about 10:1 to about 1:10 being preferred and 1:1 being especially preferred. The preferred solvents are tetrahydrofuran (THF), acetonitrile, dimethylforamide (DMF), ethanol, or mixtures thereof; generally any solvent of sufficient polarity to dissolve the capture ligand can be used, as long as the solvent is devoid of functional groups that will react with the surface. Sufficient nucleic acid deposition solution is added to the vial so as to completely cover the electrode surface. The gold substrate is allowed to incubate at ambient temperature or slightly above ambient temperature for a period of time ranging from seconds to hours, with 5–30 minutes being preferred. After the initial incubation, the deposition solution is removed and a solution of diluent molecule only (from about 1 $\mu$M to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In a preferred embodiment, an aqueous deposition solution is used. As above, a clean gold surface is placed into a clean vial. A nucleic acid deposition solution in water is prepared in which the total thiol concentration is between about 1 uM and 10 mM, with from about 1 $\mu$M to about 200 uM being preferred. The aqueous solution frequently has salt present (up to saturation, with approximately 1M being preferred), however pure water can be used. The deposition solution contains thiol modified nucleic acid and often a thiol diluent molecule. The ratio of nucleic acid to diluent is usually between between 1000:1 to 1:1000, with from about 10:1 to about 1:10 being preferred and 1:1 being especially preferred. The nucleic acid deposition solution is added to the vial in such a volume so as to completely cover the electrode surface. The gold substrate is allowed to incubate at ambient temperature or slightly above ambient temperature for 1–30 minutes with 5 minutes usually being sufficient. After the initial incubation, the deposition solution is removed and a solution of diluent molecule only (10 uM–1.0 mM) in either water or organic solvent is added. The gold substrate is allowed to incubate at room temperature or above room temperature until a complete monolayer is formed (10 minutes–24 hours). The gold sample is removed from the solution, rinsed in clean solvent and used.

In a preferred embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 $\mu$M size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then preferably treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen.

In a preferred embodiment, the electrode comprising the monolayer including conductive oligomers further comprises a nucleic acid capture probe. The capture probe nucleic acid is covalently attached to the electrode. This attachment can be via a conductive oligomer or via an insulator. By "capture probe" or "anchor probe" herein is meant a component of an assay complex as defined herein that allows the attachment of a target sequence to the electrode, for the purposes of detection. As is more fully outlined below, attachment of the target sequence to the capture probe may be direct (i.e. the target sequence hybridizes to the capture probe) or indirect (one or more capture extender probes are used). By "covalently attached" herein is meant that two moieties are attached by at least one bond, including sigma bonds, pi bonds and coordination bonds. In addition, as is more fully outlined below, the capture probes may have both nucleic and non-nucleic acid portions. Thus, for example, flexible linkers such as alkyl groups, including polyethylene glycol linkers, may be used to get the nucleic acid portion of the capture probe off the electrode surface. This may be particularly useful when the target sequences are large, for example when genomic DNA or rRNA is the target.

In a preferred embodiment, the capture probe nucleic acid is covalently attached to the electrode via a conductive oligomer. The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occuring nucleic acids, although as will be appreciated by those in the art, similar techniques may be used with nucleic acid analogs, and in some cases with other binding ligands.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization (i.e. mechanism-1 systems), it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 30 is an example of this linkage, using a Structure 15 conductive oligomer and uridine as the base, although other bases and conductive oligomers can be used as will be appreciated by those in the art:

Structure 30

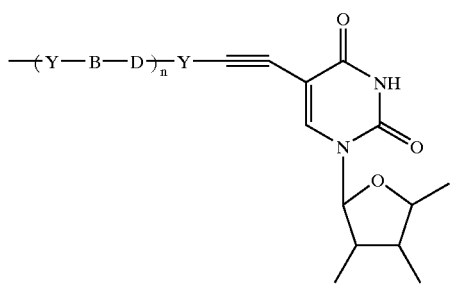

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected.

In an alternative embodiment, the attachment is any number of different Z linkers, including amide and amine linkages, as is generally depicted in Structure 31 using uridine as the base and a Structure 15 oligomer:

Structure 31

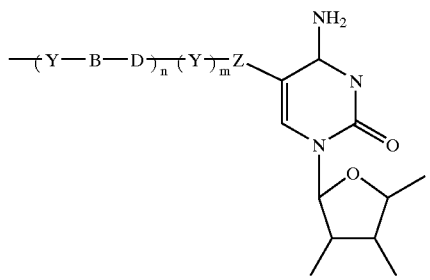

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo-or hetero-bifunctional linkers as are well known (see 1994 Pierce Chemical Company catalog, technical section on cross-linkers, pages 155–200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781–785 (1996); Mikhailopulo et al., Liebigs. Ann. Chem. 513–519 (1993); McGee et al., Nucleosides & Nucleotides 14(6): 1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 13–15 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 32 (using the Structure 13 conductive oligomer):

Structure 32

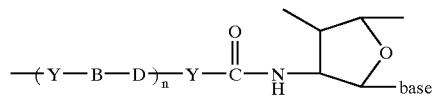

As will be appreciated by those in the art, Structure 32 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 33 and 34 depict nucleosides with the Structures 13 and 21 conductive oligomers, respectively, using the nitrogen as the heteroatom, athough other heteroatoms can be used:

Structure 33

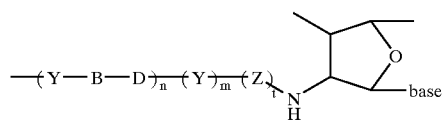

In Structure 33, preferably both m and t are not zero. A preferred Z here is a methylene group, or other aliphatic alkyl linkers. One, two or three carbons in this position are particularly useful for synthetic reasons.

Structure 34

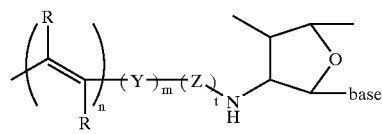

In Structure 34, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 35 depicts a direct linkage, and Structure 36 depicts linkage via an amide bond (both utilize the Structure 13 conductive oligomer, although Structure 20 conductive oligomers are also possible). Structures 35 and 36 depict the conductive oligomer in the 3' position, although the 5' position is also possible. Furthermore, both Structures 35 and 36 depict naturally occurring phosphodiester bonds, although as those in the art will appreciate, non-standard analogs of phosphodiester bonds may also be used.

Structure 35

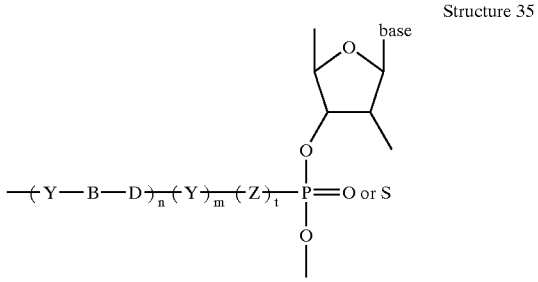

In Structure 35, if the terminal Y is present (i.e. m=1), then preferably Z is not present (i.e. t=0). If the terminal Y is not present, then Z is preferably present.

Structure 36 depicts a preferred embodiment, wherein the terminal B—D bond is an amide bond, the terminal Y is not present, and Z is a linker, as defined herein.

Structure 36

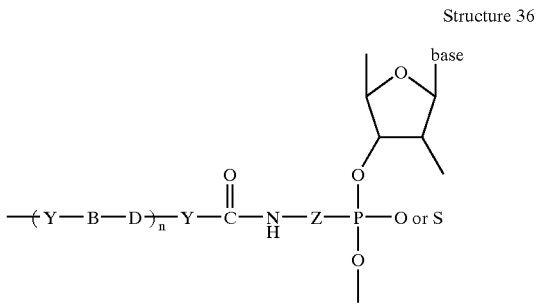

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 37. Alternatively, the conductive oligomer is attached to one ligand, and the nucleic acid is attached to another ligand, as is generally depicted below in Structure 38. Thus, in the presence of the transition metal, the conductive oligomer is covalently attached to the nucleic acid. Both of these structures depict Structure 13 conductive oligomers, although other oligomers may be utilized. Structures 37 and 38 depict two representative structures:

Structure 37

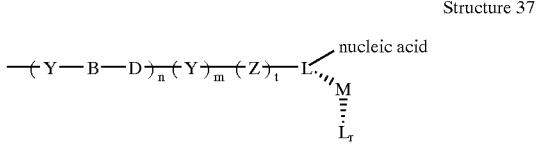

Structure 38

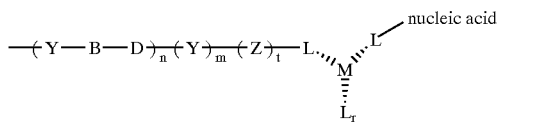

The use of metal ions to connect the nucleic acids can serve as an internal control or calibration of the system, to evaluate the number of available nucleic acids on the surface. However, as will be appreciated by those in the art, if metal ions are used to connect the nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target sequence. This may be useful for identification, calibration and/or quantification. Thus, the amount of capture probe on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture probe nucleic acids are covalently attached to the electrode via an insulator. The attachment of nucleic acids to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface. In some embodiments, there may be one type of capture probe, or one type of capture probe extender, as is more fully described below. Alternatively, different capture probes, or one capture probes with a multiplicity of different capture extender probes can be used. Similarly, it may be desirable (particular in the case of nucleic acid analytes and binding ligands in mechanism-2 systems) to use auxiliary capture probes that comprise relatively short probe sequences, that can be used to "tack down" components of the system, for example the recruitment linkers, to increase the concentration of ETMs at the surface.

Thus the present invention provides substrates comprising at least one detection electrode comprising monolayers and capture and/or detection probes, useful in target analyte detection systems.

The compositions of the invention are generally synthesized as outlined below, generally utilizing techniques well known in the art. As will be appreciated by those in the art, many of the techniques outlined below are directed to nucleic acids containing a ribose-phosphate backbone. However, as outlined above, many alternate nucleic acid analogs may be utilized, some of which may not contain either ribose or phosphate in the backbone. In these embodiments, for attachment at positions other than the base, attachment is done as will be appreciated by those in the art, depending on the backbone. Thus, for example, attachment can be made at the carbon atoms of the PNA backbone, as is described below, or at either terminus of the PNA.

The compositions may be made in several ways. A preferred method first synthesizes a conductive oligomer attached to a nucleoside, with addition of additional nucleosides to form the capture probe followed by attachment to the electrode. Alternatively, the whole capture probe may be made and then the completed conductive oligomer added, followed by attachment to the electrode. Alternatively, a monolayer of conductive oligomer (some of which have functional groups for attachment of capture probes) is attached to the electrode first, followed by attachment of the capture probe. The latter two methods may be preferred when conductive oligomers are used which are not stable in the solvents and under the conditions used in traditional nucleic acid synthesis.

In a preferred embodiment, the compositions of the invention are made by first forming the conductive oligomer covalently attached to the nucleoside, followed by the addition of additional nucleosides to form a capture probe nucleic acid, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode. A number of representative syntheses are shown in the Figures of WO98/20162, expressly incorporated herein by reference.

The conductive oligomer is then attached to a nucleoside that may contain one (or more) of the oligomer units, attached as depicted herein.

In a preferred embodiment, attachment is to a ribose of the ribose-phosphate backbone. Thus, attachment via amide and amine linkages are possible (see FIGS. 1 and 2 of WO98/20162). In a preferred embodiment, there is at least a methylene group or other short aliphatic alkyl groups (as a Z group) between the nitrogen attached to the ribose and the aromatic ring of the conductive oligomer. A representative synthesis is shown in FIG. 16 of WO98/20162.

Alternatively, attachment is via a phosphate of the ribose-phosphate backbone. Examples of two synthetic schemes are shown in FIG. 4 and FIG. 5 of WO98/20162. Although both Figures show attachment at the 3' position of the ribose, attachment can also be made via the 2' position. In FIG. 5, Z is an ethylene linker, although other linkers may be used as well, as will be appreciated by those in the art.

In a preferred embodiment, attachment is via the base. A general scheme is depicted in FIG. 3 of WO98/20162, using uridine as the nucleoside and a phenylene-acetylene conductive oligomer. As will be appreciated in the art, amide linkages are also possible, using techniques well known in the art. In a preferred embodiment, protecting groups may be added to the base prior to addition of the conductive oligomers, as is generally outlined in FIGS. 10 and 11 of WO98/20162. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways.

In one embodiment, one or more modified nucleosides are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105–118. Academic Press, San Diego, Calif. 1981). Thus, the present invention provides deoxyribonucleoside triphosphates comprising a covalently attached ETM. Preferred embodiments utilize ETM attachment to the base or the backbone, such as the ribose (preferably in the 2' position), as is generally depicted below in Structures 40 and 41:

Structure 40

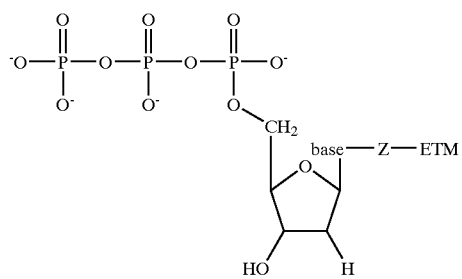

Structure 41

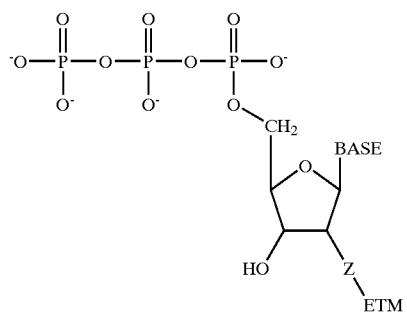

Thus, in some embodiments, it may be possible to generate the nucleic acids comprising ETMs in situ. For example, a target sequence can hybridize to a capture probe (for example on the surface) in such a way that the terminus of the target sequence is exposed, i.e. unhybridized. The addition of enzyme and triphosphate nucleotides labelled with ETMs allows the in situ creation of the label. Similarly, using labeled nucleotides recognized by polymerases can allow simultaneous amplification and detection; that is, the target sequences are generated in situ.

In a preferred embodiment, the modified nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Gait, supra; Caruthers, Science 230:281 (1985), both of which are expressly incorporated herein by reference.

For attachment of a group to the 3' terminus, a preferred method utilizes the attachment of the modified nucleoside (or the nucleoside replacement) to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers or insulators covalently attached to nucleosides attached to solid oligomeric supports such as CPG, and phosphoramidite derivatives of the nucleosides of the invention.

The invention further provides methods of making label probes with recruitment linkers comprising ETMs. These synthetic reactions will depend on the character of the recruitment linker and the method of attachment of the ETM, as will be appreciated by those in the art. For nucleic acid recruitment linkers, the label probes are generally made as outlined herein with the incorporation of ETMs at one or more positions. When a transition metal complex is used as the ETM, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, ETMs are attached to a ribose of the ribose-phosphate backbone. This is generally done as is outlined herein for conductive oligomers, as described herein, and in PCT publication WO 95/15971, using amino-modified or oxo-modified nucleosides, at either the 2' or 3' position of the ribose. The amino group may then be used either as a ligand, for example as a transition metal ligand for attachment of the metal ion, or as a chemically functional group that can be used for attachment of other ligands or organic ETMs, for example via amide linkages, as will be appreciated by those in the art. For example, the examples describe the synthesis of nucleosides with a variety of ETMs attached via the ribose.

In a preferred embodiment, ETMs are attached to a phosphate of the ribose-phosphate backbone. As outlined herein, this may be done using phosphodiester analogs such as phosphoramidite bonds, see generally PCT publication WO 95/15971, or can be done in a similar manner to that depicted in FIGS. 4 and 5 of PCT US97/20014, where the conductive oligomer is replaced by a transition metal ligand or complex or an organic ETM, as well as is outlined in the Examples.

Attachment to alternate backbones, for example peptide nucleic acids or alternate phosphate linkages will be done as will be appreciated by those in the art.

In a preferred embodiment, ETMs are attached to a base of the nucleoside. This may be done in a variety of ways. In one embodiment, amino groups of the base, either naturally occurring or added as is described herein (see the fiigures, for example), are used either as ligands for transition metal complexes or as a chemically functional group that can be used to add other ligands, for example via an amide linkage, or organic ETMs. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017–6020 (1995); Tzalis et al., Tetrahedron Lett. 36(2):3489–3490 (1995); and Tzalis et al., Chem. Communications (in press) 1996, all of which are hereby expressly incorporated by reference. See also the figures and the examples, which describes the synthesis of metallocenes (in this case, ferrocene) attached via acetylene linkages to the bases.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Once the nucleic acids of the invention are made, with a covalently attached attachment linker (i.e. either an insulator or a conductive oligomer), the attachment linker is attached to the electrode. The method will vary depending on the type of electrode used. As is described herein, the attachment linkers are generally made with a terminal "A" linker to facilitate attachment to the electrode. For the purposes of this application, a sulfur-gold attachment is considered a covalent attachment.

In a preferred embodiment, conductive oligomers, insulators, and attachment linkers are covalently attached via sulfur linkages to the electrode. However, surprisingly, traditional protecting groups for use of attaching molecules to gold electrodes are generally not ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures. However, as will be appreciated by those in the art, when the conductive oligomers do not contain nucleic acids, traditional protecting groups such as acetyl groups and others may be used. See Greene et al., supra.

This may be done in several ways. In a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 13 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides, as is described in the Examples.

The above method may also be used to attach insulator molecules to a gold electrode.

In a preferred embodiment, a monolayer comprising conductive oligomers (and optionally insulators) is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids may be made in at least one of five ways: (1) addition of the monolayer, followed by subsequent addition of the attachment linker-nucleic acid complex; (2) addition of the attachment linker-nucleic acid complex followed by addition of the monolayer; (3) simultaneous addition of the monolayer and attachment linker-nucleic acid complex; (4) formation of a monolayer (using any of 1, 2 or 3) which includes attachment linkers which terminate in a functional moiety suitable for attachment of a completed nucleic acid; or (5) formation of a monolayer which includes attachment linkers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

In a preferred embodiment, the nucleic acid is a peptide nucleic acid or analog. In this embodiment, the invention provides peptide nucleic acids with at least one covalently attached ETM or attachment linker. In a preferred embodiment, these moieties are covalently attached to an monomeric subunit of the PNA. By "monomeric subunit of PNA" herein is meant the $-NH-CH_2CH_2-N(COCH_2-$Base$)-CH_2-CO-$monomer, or derivatives (herein included within the definition of "nucleoside") of PNA. For example, the number of carbon atoms in the PNA backbone may be altered; see generally Nielsen et al., Chem. Soc. Rev. 1997 page 73, which discloses a number of PNA derivatives, herein expressly incorporated by reference. Similarly, the amide bond linking the base to the backbone may be altered; phosphoramide and sulfuramide bonds may be used. Alternatively, the moieties are attached to an internal monomeric subunit. By "internal" herein is meant that the monomeric subunit is not either the N-terminal monomeric subunit or the C-terminal monomeric subunit. In this embodiment, the moieties can be attached either to a base or to the backbone of the monomeric subunit. Attachment to the base is done as outlined herein or known in the literature. In general, the moieties are added to a base which is then incorporated into a PNA as outlined herein. The base may be either protected, as required for incorporation into the PNA synthetic reaction, or derivatized, to allow incorporation, either prior to the addition of the chemical substituent or afterwards. Protection and derivatization of the bases is shown in FIGS. 24–27 of WO98/20162. The bases can then be incorporated into monomeric subunits as shown in FIG. 28 of WO98/20162. FIGS. 29 and 30 of WO98/20162 depict two different chemical substituents, an ETM and a conductive oligomer, attached at a base. FIG. 29 depicts a representative synthesis of a PNA monomeric subunit with a ferrocene attached to a uracil base. FIG. 30 depicts the synthesis of a three unit conductive oligomer attached to a uracil base.

In a preferred embodiment, the moieties are covalently attached to the backbone of the PNA monomer. The attachment is generally to one of the unsubstituted carbon atoms of the monomeric subunit, preferably the α-carbon of the backbone, although attachment at either of the carbon 1 or 2 positions, or the α-carbon of the amide bond linking the base to the backbone may be done. In the case of PNA analogs, other carbons or atoms may be substituted as well. In a preferred embodiment, moieties are added at the α-carbon atoms, either to a terminal monomeric subunit or an internal one.

In this embodiment, a modified monomeric subunit is synthesized with an ETM or an attachment linker, or a functional group for its attachment, and then the base is added and the modified monomer can be incorporated into a growing PNA chain. FIG. 31 of WO98/20162 depicts the synthesis of a conductive oligomer covalently attached to the backbone of a PNA monomeric subunit, and FIG. 32 of WO98/20162 depicts the synthesis of a ferrocene attached to the backbone of a monomeric subunit.

Once generated, the monomeric subunits with covalently attached moieties are incorporated into a PNA using the techniques outlined in Will et al., Tetrahedron 51(44): 12069–12082 (1995), and Vanderlaan et al., Tett. Let. 38:2249–2252 (1997), both of which are hereby expressly incorporated in their entirety. These procedures allow the addition of chemical substituents to peptide nucleic acids without destroying the chemical substituents.

As will be appreciated by those in the art, electrodes may be made that have any combination of nucleic acids, conductive oligomers and insulators.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

When mechanism-1 systems are used, detection probes are covalently attached to the electrode, as above for capture probes. The detection probes are either substantially complementary to a portion of the target sequence (direct detection), or to a portion of a label probe (sandwich assay), as is depicted in the Figures.

As for all of the methods outlined herein, it may be necessary to either remove unreacted primers or configure the detection systems such that unreacted primers are not detected, depending on the method used. For example, for all of the systems, the removal of unreacted primers based on size differences can be done, or in some cases, by binding to a solid support such as a bead, using a separation tag. In addition, for PCR, SDA and NASBA, detection specificity will utilize portions of the non-primer newly synthesized strands, such that unextended primers will not be bound by capture probes on an electrode, for example. Alternatively, for example, in CPT, the first probe sequence may comprise a separation tag (e.g. biotin) or sequence (e.g. a unique sequence), that allow the binding of the unreacted primers and the cleaved first probe sequences; the use of labels in the second probe sequence (for direct detection) or the use of the second probe sequence for the basis of the capture onto an electrode or binding to a detection probe ensures that unreacted probes are not detected. Similarly, in LCR, the use of one primer for capture and the other for either label incorporation (direct detection) or detection specificity allows that detection will only proceed for the modified primers.

Once made, the compositions find use in a number of applications, as described herein. In particular, the compositions of the invention find use in hybridization assays. As will be appreciated by those in the art, electrodes can be made that have a single species of nucleic acid, i.e. a single nucleic acid sequence, or multiple nucleic acid species.

In addition, as outlined herein, the use of a solid support such as an electrode enables the use of these gene probes in an array form. The use of oligonucleotide arrays are well known in the art. In addition, techniques are known for "addressing" locations within an electrode and for the surface modification of electrodes. Thus, in a preferred embodiment, arrays of different nucleic acids are laid down on the electrode, each of which are covalently attached to the electrode via a conductive linker. In this embodiment, the number of different probe species of oligonucleotides may vary widely, from one to thousands, with from about 4 to about 100,000 being preferred, and from about 10 to about 10,000 being particularly preferred.

Once the assay complexes of the invention are made, that minimally comprise a target sequence and an ETM, detection proceeds with electronic initiation. Without being limited by the mechanism or theory, detection is based on the transfer of electrons from the ETM to the electrode.

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem 100:17050 (1996); all of which are incorporated by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200–720 mV, the ferrocene is oxided, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminiscent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp197–202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and Ru(bpy)$_2$im as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with Ru(4,7-biphenyl$_2$-phenanthroline)$_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85–277, 1988). Preferred examples display efficient fluorescence (reasonably high quantum yields) as well as low reorganization energies. These include Ru(4,7-biphenyl$_2$-phenanthroline)$_3^2$, Ru(4,4'-diphenyl-2,2'-bipyridine)$_3^{2+}$ and platinum complexes (see Cummings et al., J.Am. Chem. Soc. 118:1949–1960 (1996), incorporated by reference). Alternatively, a reduction in fluorescence associated with hybridization can be measured using these systems.

In a further embodiment, electrochemiluminescence is used as the basis of the electron transfer detection. With some ETMs such as Ru$^{2+}$(bpy)$_3$, direct luminescence accompanies excited state decay. Changes in this property are associated with nucleic acid hybridization and can be monitored with a simple photomultiplier tube arrangement (see Blackburn, G. F. *Clin. Chem.* 37: 1534–1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capicitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (I) is not accurately described by Laviron's equation. This may be due in part to the fact that this theory assumes an unlimited source and sink of electrons, which is not true in the present systems.

The AC voltametry theory that models these systems well is outlined in O'Connor et al., J. Electroanal. Chem. 466(2):

197–202 (1999), hereby expressly incorporated by reference. The equation that predicts these systems is shown below as Equation 1:

$$i_{avg} = 2nfFN_{total} \cdot \frac{\sinh\left[\frac{nF}{RT} \cdot E_{AC}\right]}{\cosh\left[\frac{nF}{RT} \cdot E_{AC}\right] + \cosh\left[\frac{nF}{RT}(E_{DC} - E_o)\right]}$$

Equation 1

In Equation 1, n is the number of electrons oxidized or reduced per redox molecule, f is the applied frequency, F is Faraday's constant, $N_{total}$ is the total number of redox molecules, $E_O$ is the formal potential of the redox molecule, R is the gas constant, T is the temperature in degrees Kelvin, and $E_{DC}$ is the electrode potential. The model fits the experimental data very well. In some cases the current is smaller than predicted, however this has been shown to be caused by ferrocene degradation which may be remedied in a number of ways.

In addition, the faradaic current can also be expressed as a function of time, as shown in Equation 2:

$$I_f(t) = \frac{q_e N_{total} nF}{2RT\left(\cosh\left[\frac{nF}{RT}(V(t) - E_0)\right] + 1\right)} \cdot \frac{dV(t)}{dt}$$

Equation 2

$I_F$ is the Faradaic current and $q_e$ is the elementary charge.

However, Equation 1 does not incorporate the effect of electron transfer rate nor of instrument factors. Electron transfer rate is important when the rate is close to or lower than the applied frequency. Thus, the true $i_{AC}$ should be a function of all three, as depicted in Equation 3.

$$i_{AC} = f(\text{Nernst factors}) f(k_{ET}) f(\text{instrument factors})$$

Equation 3

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and the ETM is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid.

Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at at least two separate frequencies, with measurements at a plurality of frequencies being preferred. A plurality of frequencies includes a scan. For example, measuring the output signal, e.g., the AC current, at a low input frequency such as 1–20 Hz, and comparing the response to the output signal at high frequency such as 10–100 kHz will show a frequency response difference between the presence and absence of the ETM. In a preferred embodiment, the frequency response is determined at at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is signficantly different depending on whether the label probes containing the ETMs are specifically or non-specifically bound to the electrode.

Accordingly, the present invention further provides apparatus for the detection of nucleic acids using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected, for example using ribosomal RNA (rRNA) as the target sequences.

In a preferred embodiment, the nucleic acids of the invention find use as probes for toxic bacteria in the screening of water and food samples. For example, samples may be treated to lyse the bacteria to release its nucleic acid (particularly rRNA), and then probes designed to recognize bacterial strains, including, but not limited to, such pathogenic strains as, Salmonella, Campylobacter, *Vibrio cholerae*, Leishmania, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 7 (SEQ ID NOS: 1–7). By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10–10^3$ being especially preferred, and less than about $10–10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

While the limits of detection are currently being evaluated, based on the published electron transfer rate through DNA, which is roughly $1–10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100–10^3$ electrons/sec, resulting in potential femptoamp sensitivity for very few molecules.

In addition to the methods outlined herein, the invention further provides compositions, generally kits, useful in the practice of the invention. The kits include the compositions including the primers and enzymes, along with any number of reagents or buffers, including additional enzymes and primers, dNTPs and/or NTPs (including substituted nucleotides), buffers, salts, inhibitors, etc. The kits can optionally include instructions for the use of the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Synthesis of Nucleoside Modified with Ferrocene at the 2' Position

The preparation of N6 is described.
Compound N1

Ferrocene (20 g, 108 mmol) and 4-bromobutyl chloride (20 g, 108 mmol) were dissolved in 450 mL dichloromethane followed by the addition of $AlCl_3$ anhydrous (14.7 g, 11 mmol). The reaction mixture was stirred at room temperature for 1 hour and 40 minutes, then was quenched by addition of 600 mL ice. The organic layer was separated and was washed with water until the aqueous layer was close to neutral (pH=5). The organic layer was dried with $Na_2SO_4$ and concentrated. The crude product was purified by flash chromatography eluting with 50/50 hexane/dichloromethane and later 30/70 hexane/dichloromethane on 300 g silica gel to afford 26.4 gm (73%) of the title product.
Compound N2

Compound N1 (6 g, 18 mmol) was dissolved in 120 mL toluene in a round bottom flask. zinc (35.9 g, 55 mmol), mercuric chloride (3.3 g, 12 mmol) and water (100 mL) were added successively. Then HCl solution (12 M, 80 mL) was added dropwise. The reaction mixture was stirred at room temperature for 16 hours. The organic layer was separated, and washed with water (2×100 mL) and concentrated. Further purification by flash chromatography (hexane) on 270 gm of silica gel provided the desired product as a brown solid (3.3 g, 58%).
Compound N3

A mixture of 13.6 gm (51 mmol) of adenosine in 400 mL dry DMF was cooled in a ice-water bath for 10 minutes before the addition of 3.0 gm (76 mmol) of NaH (60%). The reaction mixture was stirred at 0° C. for one hour before addition of Compound N2 (16.4 g, 51 mmol). Then the temperature was slowly raised to 30° C., and the reaction mixture was kept at this temperature for 4 hours before being quenched by 100 mL ice. The solvents were removed in vacuo. The resultant gum was dissolved in 300 mL water and 300 mL ethyl acetate. The aqueous layer was extracted thoroughly (3×300 mL ethyl acetate). The combined organic extracts were concentrated, and the crude product was purified by flash chromatography on 270 g silica gel. The column was eluted with 20% ethyl acetate/dichloromethane, 50% ethyl acetate/dichloromethane, 70% ethyl acetate/ dichloromethane, ethyl acetate, 1% methanol/ethyl acetate, 3% methanol/ethyl acetate, and 5% methanol/ethyl acetate. The concentration of the desired fractions provide the final product (6.5 g, 25%).
Compound N4

Compound N3 (6.5 g, 12.8 mmol) was dissolved in 150 mL dry pyridine, followed by adding TMSCl (5.6 g, 51.2 mmol). The reaction mixture was stirred at room temperature for 1.5 hours. Then phenoxyacetyl chloride (3.3 g, 19.2 mmol) was added at 0° C. The reaction was then stirred at room temperature for 4 hours and was quenched by the addition of 100 mL water at 0° C. The solvents were removed under reduced pressure, and the crude gum was further purified by flash chromatography on 90 g of silica gel (1% methanol/dichloromethane) (2.3 g, 28%).
Compound N5

Compound N4 (2.2 g, 3.4 mmol) and DMAP (200 mg, 1.6 mmol) were dissolved in 150 mL dry pyridine, followed by the addition of DMTCI (1.4 g, 4.1 mmol). The reaction was stirred under argon at room temperature overnight. The solvent was removed under reduced pressure, and the residue was dissolved in 250 mL dichloromethane. The organic solution was washed by 5% $NaHCO_3$ solution (3×250 mL), dried over $Na_2SO_4$, and concentrated. Further purification by flash chromatography on 55 g of silica gel (1% TEA/50% hexane/dichloromethane ) provided the desired product (1.3 g, 41%).
Compound N6

To a solution of N5 (3.30 gm, 3.50 mmol) in 150 mL dichloromethane. Diisopropylethylamine (4.87 mL, 8.0 eq.) and catalytic amount of DMAP (200 mg) were added. The mixture was kept at 0° C., and N,N-diisopropylamino cyanoethyl phosphonamidic chloride (2.34 mL, 10.48 mmol) was added. The reaction mixture was warmed up and stirred at room temperature overnight. After dilution by adding 150 mL of dichloromethane and 250 mL of 5% $NaHCO_3$ aqueous solution, the organic layer was separated, washed with 5% NaHCO3 (250 mL), dried over $Na_2SO_4$, and concentrated. The crude product was purified on a flash column of 66 g of silica gel packed with 1% TEA in hexane. The eluting solvents were 1% TEA in hexane (500 mL), 1% TEA and 10% dichloromethane in hexane (500 mL), 1% TEA and 20% dichloromethane in hexane (500 mL). 1% TEA and 50% dichloromethane in hexane (500 mL). Fractions containing the desired products were collected and concentrated to afford the final product (3 gm, 75%).

Example 2

Synthesis of "Branched" Nucleoside

The synthesis of N17 is described, as depicted in FIG. 11A.
Synthesis of N14

To a solution of Tert-butyldimethylsily chloride (33.38 g, 0.22 mol) in 300 mL of dichloromethane was added imidazole (37.69 g, 0.55 mol). Immediately, large amount of precipitate was formed. 2-Bromoethanol (27.68 g, 0.22 mol,.) was added slowly at room temperature. The reaction mixture was stirred at this temperature for 3 hours. The organic layer was washed with water (200 mL), 5% $NaHCO_3$ (2×250 mL), and water (200 mL). The removal of solvent afforded 52.52 g of the title product (99%).
Synthesis of N15

To a suspension of adenosine (40 g, 0.15 mol) in 1.0 L of DMF at 0° C., was added NaH (8.98 gm of 60% in mineral oil, 0.22 mol). The mixture was stirred at 0° C. for 1 hour, and N14 (35.79 gm, 0.15mol) was added. The reaction was stirred at 30° C. overnight. It was quenched by 100 mL ice-water. The solvents were removed under high vaccum. The resultant foam was dissolved in a mixture of 800 mL of ethyl acetate and 700 mL of water. The aqueous layer was further extracted by ethyl acetate (3–200 mL). The combined organic layer was dried over $Na_2SO_4$ and concentrated. The crude product was further purified on a flash column of 300 g of silica gel packed with 1% TEA in dichloromethane. The eluting solvents were dichloromethane (500 mL), 3% MeOH in dichloromethane (500 mL), 5% MeOH in dichloromethane (500 mL), and 8% MeOH in dichloromethane (2000 mL). The desired fractions were collected and concentrated to afford 11.70 g of the title product (19%).

Synthesis of N16

To a solution of N15 (11.50 gm, 27.17 mmol) in 300 mL dry pyridine cooled at 0° C., was added trimethylsily chloride (13.71 mL, 0.11 mol, 4.0). The mixture was stirred at 0° C. for min. Phenoxyacetyl chloride (9.38 mL, 67.93 mmol) was added. The reaction was stirred at 0° C. for 2.5 h. The mixture was then transferred to a mixture of 700 mL of dichloromethane and 500 mL water. The mixture was shaken well and organic layer was separated. After washing twice with 5% $NaHCO_3$ (2×300 mL), dichloromethane was removed on a rotovapor. Into the residue was added 200 mL of water, the resulting pyridine mixture was stirred at room temperature for 2 hours. The solvents were then removed under high vacuum. The gum product was co-evaporated with 100 mL of pyridine. The residue was dissolved in 250 mL of dry pyridine at 0° C., and 4,4'-dimethoxytrityl chloride (11.02 gm, 32.60 mmol) was added. The reaction was stirred at room temperature overnight. The solution was transferred to a mixture of 700 mL of dichloromethane and 500 mL of 5% $NaHCO_3$. After shaking well, the organic layer was separated, further washed with 5% $NaHCO_3$ (2–200 mL), and then concentrated. The crude product was purified on a flash column of 270 gm of silica gel packed with 1% TEA/30% $CH_2Cl_2$/Hexane. The eluting solvents were 1% TEA/50% $CH_2Cl_2$/Hexane (1000 mL), and 1% TEA /$CH_2Cl_2$ (2000 mL). The fractions containing the desired product were collected and concentrated to afford 10.0 g of the title product (43%).

Synthesis of N17

To a solution of N16 (10.0 gm, 11.60 mmol) in 300 mL dichloromethane. Diisopropylethylamine (16.2 mL) and catalytic amount of N,N-dimethylaminopyridine(200 mg) were added. The mixture was cooled in an ice-water bath, and N,N-diisopropylamino cyanoethyl phosphonamidic chloride (7.78 mL, 34.82 mmol) was added. The reaction was stirred at room temperature overnight. The reaction mixture was diluted by adding 250 mL of dichloromethane and 250 mL of 5% $NaHCO_3$. After shaking well, the organic layer was separated and washed once more with the same amount of 5% $NaHCO_3$ aqueous solution, dried over $Na_2SO_4$, and concentrated. The crude product was purified on a flash column of 120 gm of silica gel packed with 1% TEA and 10% dichloromethane in hexane. The eluting solvents were 1% TEA and 10% dichloromethane in hexane (500 mL), 1% TEA and 20% dichloromethane in hexane (500 mL), and 1% TEA and 40% dichloromethane in hexane (1500 mL). The right fractions were collected and concentrated to afford the final product (7.37 gm, 60%).

The syntheses for two other nucleotides used for branching are shown in FIGS. 11B and 11C, with the Lev protecting group. These branching nucleotides branch from the phosphate, rather than the ribose (N17), and appear to give somewhat better results.

Example 3

Synthesis of Triphosphate Nucleotide Containing an ETM

The synthesis of AFTP is described.

N3 (1.00 g, 1.97 mmol) was dissolved in 15 mL of triethyl phosphate, followed by adding diisopropylethylamine (0.69 mL, 3.9 mmol). While the mixture was kept at 0° C., and phospherous oxychloride (0.45 g, 2.93 mmol) was added. The reaction mixture was stirred at 0° C. for 4 hours, then at 4° C. overnight. Bis(tributyl)ammonium phosphate (3.24 g, 5.91 mmol.) was added, and the reaction mixture was stirred at 0° C. for six hours, and at 4° C. overnight. The white precipitate produced in the reaction was removed by filtration. The filtrate was treated with water (20 mL), and yellow precipitate was formed. The precipitate was filtrated and was dried under high vacuum to afford 0.63 g of the title product as yellow solid.

Example 4

Synthesis of Nucleoside with Ferrocene Attached Via a Phosphate

The synthesis of Y63 is described.

Synthesis of C102

A reaction mixture consisting of 10.5 gm (32.7 mmol) of N2, 16 gm of potassium acetate and 350 ml of DMF was stirred at 100° C. for 2.5 hrs. The reaction mixture was allowed to cool to room temperature and then poured into a mixture of 400 ml of ether and 800 ml of water. The mixture was shaken and the organic layer was separated. The aqueous layer was extracted twice with ether. The combined ether extracts were dried over sodium sulfate and then concentrated for column chromatography. Silica gel (160 gm) was packed with 1% TEA/Hexane. The crude was loaded and the column was eluted with 1% TEA/0–100% $CH_2Cl_2$/Hexane. Fractions containing desired product were collected and concentrated to afford 5.8 g (59.1%) of C102.

Synthesis of Y61

To a flask containing 5.1 gm (17.0 mmol) of C102 was added 30 ml of Dioxane. To this solution, small aliquots of 1 M NaOH was added over a period of 2.5 hours or until hydrolysis was complete. After hydrolysis the product was extracted using hexane. The combined extracts were dried over sodium sulfate and concentrated for chromatography. Silica gel (100 gm) was packed in 10% EtOAc/Hexane. The crude product solution was loaded and the column was eluted with 10% to 50% EtOAc in hexane. The fractions containing desired product were pooled and concentrated to afford 4.20 gm (96.1%) of Y61.

Synthesis of Y62

To a flask containing 4.10 gm (15.9 mmol) of Y61 was added 200 ml of dichloromethane and 7.72 ml of DIPEA and 4.24 gm (15.9 mmol) of bis(diisopropylamino) chlorophosphine. This reaction mixture was stirred under the presence of argon overnight. After the reaction mixture was concentrated to ⅓ of its original volume, 200 ml of hexane was added and then the reaction mixture was again concentrated to ⅓ is original volume. This procedure was repeated once more. The precipitated salts were filtered off and the solution was concentrated to afford 8.24 gm of crude Y62. Without further purification, the product was used for next step.

Synthesis of Y63

A reaction mixture of 1.0 gm (1.45 mmol) of N-PAC deoxy-adenosine, 1.77 g of the crude Y62, and 125 mg of N,N-diisopropylammonium tetrazolide, and 100 ml of dichloromethane. The reaction mixture was stirred at room temperature overnight. The reaction mixture was then diluted by adding 100 ml of $CH_2Cl_2$ and 100 mL of 5% $NaHCO_3$ solution. The organic phase was separated and dried over sodium sulfate. The solution was then concentrated for column chromatography. Silica gel (35 gm) was packed with 1% TEA/Hexane. The crude material was eluted with 1% TEA/10–40% $CH_2Cl_2$/Hexane. The fractions containing product were pooled and concentrated to afford 0.25 gm of the title product.

Example 5

Synthesis of Ethylene Glycol Terminated Wire W71
Synthesis of W55

To a flask was added 7.5 gm (27.3 mmol) of tert-butyldiphenylchlorosilane, 25.0 gm (166.5 mmol) of tri(ethylene glycol) and 50 ml of dry DMF under argon. The mixture was stirred and cooled in an ice-water bath. To the flask was added dropwise a clear solution of 5.1 gm (30.0 mmol) of $AgNO_3$ in 80 mL of DMF through an additional funnel. After the completeness of addition, the mixture was allowed to warm up to room temperature and was stirred for additional 30 min. Brown AgCl precipitate was filtered out and washed with DMF(3×10 mL). The removal of solvent under reduced pressure resulted in formation of thick syrup-like liquid product that was dissolved in about 80 ml of $CH_2Cl_2$. The solution was washed with water (6×100 mL) in order to remove unreacted starting material, ie, tris (ethylene glycol), then dried over $Na_2SO_4$. Removal of $CH_2Cl_2$ afforded ~10.5 g crude product, which was purified on a column containing 104 g of silica gel packed with 50% $CH_2Cl_2$/hexane. The column was eluted with 3–5% MeOH/$CH_2Cl_2$. The fractions containing the desired product were pooled and concentrated to afford 8.01 gm (75.5%) of the pure title product.

Synthesis of W68

To a flask containing 8.01 gm (20.6.0 mmol) of W55 was added 8.56 gm (25.8 mmol) of $CBr_4$ and 60 ml of $CH_2Cl_2$. The mixture was stirred in an ice-water bath. To the solution was slowly added 8.11 gm (31.0 mmol) of $PPh_3$ in 15 ml $CH_2Cl_2$. The mixture was stirred for about 35 min at 0° C., and allowed to warm to room temperature. The volume of the mixture was reduced to about 10.0 ml and 75 ml of ether was added. The precipitate was filtered out and washed with 2×75 ml of ether. Removal of ether gave about 15 gm of crude product that was used for purification. Silica gel (105 gm) was packed with hexane. Upon loading the sample solution, the column was eluted with 50% $CH_2Cl_2$/hexane and then $CH_2Cl_2$. The desired fractions were pooled and concentrated to give 8.56 gm (72.0%) of pure title product.

Synthesis of W69

A solution of 5.2 gm (23.6 mmol)of 4-iodophenol in 50 ml of dry DMF was cooled in an ice-water bath under Ar. To the mixture was added 1.0 gm of NaH (60% in mineral oil, 25.0 mmol) portion by portion. The mixture was stirred at the same temperature for about 35 min. and at room temperature for 30 min. A solution of 8.68 gm (19.2 mmol) of W68 in 20 ml of DMF was added to the flask under argon. The mixture was stirred at 50° C. for 12 hr with the flask covered with aluminum foil. DMF was removed under reduced pressure. The residue was dissolved in 300 ml of ethyl acetate, and the solution was washed with $H_2O$ (6×50 mL). Ethyl acetate was removed under reduced pressure and the residue was loaded into a 100 g silica gel column packed with 30% $CH_2Cl_2$/hexane for the purification. The column was eluted with 30–100% $CH_2Cl_2$/hexane. The fractions containing the desired product were pooled and concentrated to afford 9.5 gm (84.0%) of the title product.

Synthesis of W70

To a 100 ml round bottom flask containing 6.89 gm (11.6 mmol) of W69 was added 30 ml of 1 M TBAF THF solution. The solution was stirred at room temperature for 5 h. THF was removed and the residue was dissolved 150 ml of $CH_2Cl_2$. The solution was washed with $H_2O$ (4×25 mL). Removal of solvent gave 10.5 gm of semi-solid. Silica gel (65 gm) was packed with 50% $CH_2Cl_2$/hexane, upon loading the sample solution, the column was eluted with 0–3% $CH_3OH/CH_2Cl_2$. The fractions were identified by TLC ($CH_3OH:CH_2Cl_2$=5:95). The fractions containing the desired product were collected and concentrated to afford 4.10 gm (99.0% ) of the title product.

Synthesis of W71

To a flask was added 1.12 gm (3.18 mmol) of W70, 0.23 g (0.88 mmol) of $PPh_3$, 110 mg (0.19 mmol) of Pd(dba)$_2$, 110 mg (0.57 mmol) of CuI and 0.75 g (3.2 mmol) of Y4 (one unit wire). The flask was flushed with argon and then 65 ml of dry DMF was introduced, followed by 25 ml of diisopropylamine. The mixture was stirred at 55° C. for 2.5 h. All tsolvents were removed under reduced pressure. The residue was dissolved in 100 ml of $CH_2Cl_2$, and the solution was thoroughly washed with the saturated EDTA solution (2×100 mL). The Removal of $CH_2Cl_2$ gave 2.3 g of crude product. Silica gel (30 gm) was packed with 50% $CH_2Cl_2$/hexane, upon loading the sample solution, the column was eluted with 10% ethyl acetate/$CH_2Cl_2$. The concentration of the fractions containing the desired product gavel 1.35 gm (2.94 mmol) of the title product, which was further purified by recrystallization from hot hexane solution as colorless crystals.

Example 6

Synthesis of Nucleoside Attached to an Insulator

Synthesis of C108

To a flask was added 2.0 gm (3.67 mmol) of 2'-amino-5'-O-DMT uridine, 1.63 gm (3.81 mmol) of C44, 5 ml of TEA and 100 ml of dichloromethane. This reaction mixture was stirred at room temperature over for 72 hrs. The solvent was removed and dissolved in a small volume of $CH_2Cl_2$ Silica gel (35 gm) was packed with 2% $CH_3OH$/1% TEA/$CH_2Cl_2$, upon loading the sample solution, the column was eluted with the same solvent system. The fractions containing the desired product were pooled and concentrated to afford 2.5 gm (80.4%) of the title product.

Synthesis of C109

To a flask was added 2.4 gm (2.80 mmol) of C108, 4 ml of diisopropylethylamine and 80 ml of $CH_2Cl_2$ under presence of argon. The reaction mixture was cooled in an ice-water bath. Once cooled, 2.10 gm (8.83 mmol) of 2-cyanoethyl diisopropylchloro-phosphoramidite was added. The mixture was then stirred overnight. The reaction mixture was diluted by adding 10 ml of methanol and 150 ml of $CH_2Cl_2$. This mixture was washed with a 5% $NaHCO_3$ solution, dried over sodium sulfate and then concentrated for column chromatography. A 65 gm-silica gel column was packed in 1% TEA and Hexane. The crude product was loaded and the column was eluted with 1% TEA/0–20% $CH_2Cl_2$)Hexane. The fractions containing the desired product were pooled and concentrated to afford 2.69 gm (90.9%) of the title product.

Example 7

Comparison of Different ETM Attachments

A variety of different ETM attachments as depicted in FIG. 1 were compared. As shown in Table 1, a detection probe was attached to the electrode surface (the sequence containing the wire in the table). Positive (i.e. probes complementary to the detection probe) and negative (i.e. probes not complementary to the detection probe) control label probes were added.

Electrodes containing the different compositions of the invention were made and used in AC detection methods. The experiments were run as follows. A DC offset voltage between the working (sample) electrode and the reference electrode was swept through the electrochemical potential of the ferrocene, typically from 0 to 500 mV. On top of the DC offset, an AC signal of variable amplitude and frequency was applied. The AC current at the excitation frequency was plotted versus the DC offset.

The results are shown in Table 2, with the Y63, VI and IV compounds showing the best results.

| Metal Complexes | Redox Potential (mV) | 10 Hz | 100 Hz | 1,000 Hz | 10,000 Hz |
|---|---|---|---|---|---|
| I | 400 | Not clear | Not clear | Not clear | Not clear |
| II | 350 | 0.15 μA | 0.01 μA | 0.005 μA | ND |
| III (+ control) | 360 | 0.025 μA | 0.085 μA | 0.034 μA | ND |
| III (− control) | 360 | 0.022 μA | 0.080 μA | 0.090 μA | ND |
| IV | 140 | 0.34 μA | 3.0 μA | 13.0 μA | 35 μA |
| V | 400 | 0.02 μA | ND | 0.15 μA | ND |
| VI(1) | 140 | 0.22 μA | 1.4 μA | 4.4 μA | 8.8 μA |
| VI(2) | 140 | 0.22 μA | 0.78 μA | 5.1 μA | 44 μA |
| VII | 320 | 0.04 μA | ND | 0.45 μA | No Peak |
| VIII (not purified) | 360 | 0.047 μA | ND | ND | No Peak |
| Y63 | 160 | .25 μA | ND | 36 μA | 130 μA |

Not clear: There is no difference between positive control and negative control.
ND: Not determined allowed to cool to room temperature for an hour. The mixtures were then added to the electrodes, and AC detection was done.

Use of a Capture Probe, a Capture Extender Probe, an Unlabeled Target Sequence and a Label Probe A capture probe D112, comprising a 25 base sequence, was mixed with the Y5 conductive oligomer and the M44 insulator at a ratio of 2:2:1 using the methods of Example 16. A capture extender probe D179, comprising a 24 base sequence perfectly complementary to the D112 capture probe, and a 24 base sequence perfectly complementary to the 2tar target, separated by a single base, was added, with the 2tar target. The D179 molecule carries a ferrocene (using a C15 linkage to the base) at the end that is closest to the electrode. When the attachment linkers are conductive oligomers, the use of an ETM at or near this position allows verification that the D179 molecule is present. A ferrocene at this position has a different redox potential than the ETMs used for detection. A label probe D309 (dendrimer) was added, comprising a 18 base sequence perfectly complementary to a portion of the target sequence, a 13 base sequence linker and four ferrocenes attached using a branching configuration. A representative scan is shown in FIG. 20A. When the 2tar target was not added, a representative scan is shown in FIG. 20B.

Use of a Capture Probe and a Labeled Target Sequence

Example A

A capture probe D94 was added with the Y5 and M44 conductive oligomer at a 2:2:1 ratio with the total thiol Table of the Oligonucleotides Containing Different Metal Complexes

| Metal Complexes | Positive Control Sequence Containing Metal Complexes and Numbering | Negative Control Sequence Containing Metal Complexes and Numbering | Sequence Containing Wire On G Surface and Numbering |
|---|---|---|---|
| I | 5'-A(I)C (I)GA GTC CAT GGT-3' #D199_1 (SEQ ID NO: 39) | 5'-A(I)G (I)CC TAG CTG GTG-3' #D200_1 (SEQ ID NO: 40) | 5'-ACC ATG GAC TCT GT($U_w$)-3' #D201_1,2 (SEQ ID NO: 57) |
| II | 5'-A(II)C (II)GA GTC CAT GGT-3' #D211_1,2 (SEQ ID NO: 41) | 5'-A(II)G (II)CC TAG CTG GTG-3' #D212_1 (SEQ ID NO: 42) | 5'-ACC ATG GAC TCT GT($U_w$)-3' #D201_1,2 (SEQ ID NO: 57) |
| III | 5'-AAC AGA GTC CAT GGT-3' #D214_1 (SEQ ID NO: 43) | 5'-ATG TCC TAG CTG GTG-3' #D57_1 (SEQ ID NO: 44) | 5'-ACC ATG GAC TCT GT($U_w$)-3' #D201_1,2 (SEQ ID NO: 57) |
| IV | 5'-A(IV)C (IV)GA GTC CAT GGT-3' #D215_1 (SEQ ID NO: 45) | 5'-A(IV)G (IV)CC TAG CTG GTG-3' #D216_1 (SEQ ID NO: 46) | 5'-ACC ATG GAC TCT GT-$U_w$-3' #D201_1,2 (SEQ ID NO: 57) |
| V | 5'-A(V)C (V)GA GTC CAT GGT-3' #D203_1 (SEQ ID NO: 47) | 5'-A(V)G (V)CC TAG CTG GTG-3' #D204_1 (SEQ ID NO: 48) | 5'-ACC ATG GAC TCA GA($U_w$)-3' #D83_17,18 (SEQ ID NO: 58) |
| VI | 5'-A(VI)C AGA GTC CAT GGT-3' #D205_1 (SEQ ID NO: 49) | 5'-A(VI)G TCC TAG CTG GTG-3' #D206_1 (SEQ ID NO: 50) | 5'-ACC ATG GAC TCT GT($U_w$)-3' #D201_1,2 (SEQ ID NO: 57) |
| VI | 5'-A(VI)* AGA GTC CAT GGT-3' #D207_1 (SEQ ID NO: 51) | 5'-A(VI)* TCC TAG CTG GTG-3' #D208_1 (SEQ ID NO: 52) | 5'-ACC ATG GAC TCT GT($U_w$)-3' #D201_1,2 (SEQ ID NO: 57) |
| VII | 5'-A(VII)C (VII)GA GTC CAT GGT-3' #D158_3 (SEQ ID NO: 53) | 5'-A(VII)G (VII)CC TAG CTG GTG-3' #D101_2 (SEQ ID NO: 54) | 5'-ACC ATG GAC TCA GA($U_w$)-3' #D83_17,18 (SEQ ID NO: 58) |
| VIII | 5'-A(VIII)C (VIII)GA GTC CAT GGT-3' #D217_1,2,3 (SEQ ID NO: 55) | 5'-A(VIII)G (VIII)CC TAG CTG GTG-3' #D218_1 (SEQ ID NO: 56) | 5'-ACC ATG GAC TCA GA($U_w$)-3' #D83_17,18 (SEQ ID NO: 58) |

Example 8

Preferred Embodiments of the Invention

A variety of systems have been run and shown to work well, as outlined below. All compounds are referenced in FIG. 19. Generally, the systems were run as follows. The surfaces were made, comprising the electrode, the capture probe attached via an attachment linker, the conductive oligomers, and the insulators, as outlined above. The other components of the system, including the target sequences, the capture extender probes, and the label probes, were mixed and generally annealed at 90° C. for 5 minutes, and concentration being 833 μM on the electrode surface, as outlined above. A target sequence (D336) comprising a 15 base sequence perfectly complementary to the D94 capture probe, a 14 base linker sequence, and 6 ferrocenes linked via the N6 compound was used. A representative scan is shown in FIG. 20C. The use of a different capture probe, D109, that does not have homology with the target sequence, served as the negative control; a representative scan is shown in FIG. 20D.

Example B

A capture probe D94 was added with the Y5 and M44 conductive oligomer at a 2:2:1 ratio with the total thiol concentration being 833 μM on the electrode surface, as outlined above. A target sequence (D429) comprising a 15 base sequence perfectly complementary to the D94 capture probe, a C131 ethylene glycol linker hooked to 6 ferrocenes linked via the N6 compound was used. A representative scan is shown in FIG. 20E. The use of a different capture probe, D109, that does not have homology with the target sequence, served as the negative control; a representative scan is shown in FIG. 20F.

Use of a Capture Probe, a Capture Extender Probe, an Unlabeled Target Sequence and Two Label Probes with Long Linkers between the Target Binding Sequence and the ETMs The capture probe D112, Y5 conductive oligomer, the M44 insulator, and capture extender probe D179 were as outlined above. Two label probes were added: D295 comprising an 18 base sequence perfectly complementary to a portion of the target sequence, a 15 base sequence linker and six ferrocenes attached using the N6 linkage depicted in FIG. 23. D297 is the same, except that it's 18 base sequence hybridizes to a different portion of the target sequence. A representative scan is shown in FIG. 20G. When the 2tar target was not added, a representative scan is shown in FIG. 20H.

Use of a Capture Probe, a capture Extender Probe, an Unlabeled Target Sequence and Two Label Probes with Short Linkers Between the Target Binding Sequence and the ETMs The capture probe D112, Y5 conductive oligomer, the M44 insulator, and capture extender probe D179 were as outlined above. Two label probes were added: D296 comprising an 18 base sequence perfectly complementary to a portion of the target sequence, a 5 base sequence linker and six ferrocenes attached using the N6 linkage depicted in FIG. 23. D298 is the same, except that it's 18 base sequence hybridizes to a different portion of the target sequence. A representative scan is shown in FIG. 20I. When the 2tar target was not added, a representative scan is shown in FIG. 20J.

Use of Two Capture Probes, Two Capture Capture Extender Probes, an Unlabeled Large Target Sequence and Two Label Probes with Long Linkers Between the Target Binding Sequence and the ETMs This test was directed to the detection of rRNA. The Y5 conductive oligomer, the M44 insulator, and one surface probe D350 that was complementary to 2 capture sequences D417 and EU1 were used as outlined herein. The D350, Y5 and M44 was added at a 0.5:4.5:1 ratio. Two capture extender probes were used; D417 that has 16 bases complementary to the D350 capture probe and 21 bases complementary to the target sequence, and EU1 that has 16 bases complementary to the D350 capture probe and 23 bases complementary to a different portion of the target sequence. Two label probes were added: D468 comprising a 30 base sequence perfectly complementary to a portion of the target sequence, a linker comprising three glen linkers as shown in FIG. 19 (comprising polyethylene glycol) and six ferrocenes attached using N6. D449 is the same, except that it's 28 base sequence hybridizes to a different portion of the target sequence, and the polyethylene glycol linker used (C131) is shorter. A representative scan is shown in FIG. 20K.

Use of a Capture Probe, an Unlabeled Target, and a Label Probe

Example A

A capture probe D112, Y5 conductive oligomer and the M44 insulator were put on the electrode at 2:2:1 ratio with the total thiol concentration being 833 μM. A target sequence MT1 was added, that comprises a sequence complementary to D112 and a 20 base sequence complementary to the label probe D358 were combined; in this case, the label probe D358 was added to the target sequence prior to the introduction to the electrode. The label probe contains six ferrocenes attached using the N6 linkages depicted in FIG. 23. A representative scan is shown in FIG. 20L. The replacment of MT1 with NC112 which is not complementary to the capture probe resulted in no signal; similarly, the removal of MT1 resulted in no signal.

Example B

A capture probe D334, Y5 conductive oligomer and the M44 insulator were put on the electrode at 2:2:1 ratio with the total thiol concentration being 833 μM. A target sequence LP280 was added, that comprises a sequence complementary to the capture probe and a 20 base sequence complementary to the label probe D335 were combined; in this case, the label probe D335 was added to the target prior to introduction to the electrode. The label probe contains six ferrocenes attached using the N6 linkages depicted in FIG. 23. A representative scan is shown in FIG. 20M. Replacing LP280 with the LN280 probe (which is complementary to the label probe but not the capture probe) resulted in no signal.

Example 9

Monitoring of PCR Reactions Using the Invention

Monitoring of PCR reactions was done using an HIV sequence as the target sequence. Multiple reactions were run and stopped at 0 to 30 or 50 cycles. In this case, the sense primer contained the ETMs (using the N6 linkage described herein), although as will be appreciated by those in the art, triphosphate nucleotides containing ETMs could be used to label non-primer sequences. The surface probe was designed to hybridize to 16 nucleotides of non-primer sequences, immediately adjacent to the primer sequence; that is, the labeled primer sequence will not bind to the surface probe. Thus, only if amplification has occured, such that the amplified sequence will bind to the surface probe, will the detection of the adjacent ETMs proceed.

The target sequence in this case was the plasmid pBKBH10S (NIH AIDS Research and Reference Reagent program—McKesson Bioservices, Rockville Md.) which contains an 8.9 kb SstI fragment of pBH10-R3 dervied from the HXB2 clone which contains the entire HIV-1 genome and has the Genbank accession code K03455 or M38432) inserted into the SstI site on pBluescript II-KS(+). The insert is oriented such that transcription from the T7 promoter produces sense RNA.

The "sense" primer, D353, was as follows: 5'-(N6)A(N6) AGGGCTGTTGGAAATGTGG-3' (SEQ ID NO: 59). The "antisense" primer, D351, was as follows: 5'-TGTTGGCTCTGGTCTGCTCTGA-3' (SEQ ID NO: 60). The following is the expected PCR product of the reaction, comprising 140 bp:

```
5'-(N6)A(N6)AGGGCTGTTGGAAATGTGGAAAGGAAGGAC
   ACCAAATGAAGATTGTACTGAGAGACAGGCT

3'-TTTTTCCCGACAACCTTTACACCTTTC-
   CTTCCTGTGGTTTACTTTCTAACATGACTCTCTGTCCGA

AATTTTTTAGGGAAGATCTGGCCTTC-
   CTACAAGGGAAGGCCAGGGAATTTTCT-
   TCAGAGCAGACCAGAGC

TTAAAAAATCCCTTCTAGACCGGAAG-
```

GATGTTCCCTTCCGGTCCCTTAAAA-
GAAGTCTCGTCTGGTCTCG

CAACA-3' (SEQ ID NO: 61)

GTTTG-5' (SEQ ID NO: 62)

The surface capture probe (without any overlap to the sense primer) D459 was as follows: (SEQ ID NO: 63) 5'-TTGGTGTCCTTCCTTU-4 unit wire (C11)-3'.

PCR reaction conditions were standard: TAQ polymerase at TAQ 10×buffer. 1 μM of the primers was added to either 6×10$^3$, 6×10$^6$ or 6×10$^7$ molecules of template. The reaction conditions were 90° C. sec, 57° C. for 30 sec, and 70° C. for 1 minute.

The electrodes were prepared by melting 0.127 mm diamter pure gold wire on one end to form a ball. The electrodes were dipped in aqua regia for 20 seconds and tehn rinse with water. The SAM was deposited by dipping the electrode into a deposition solution of 1.3:4.0:7 D459:H6:M44 in 37:39:24 THF:ACN:water at 1 mM total thiol which was heated at 50° C. for five minutes prior to the introduction of the electrodes. The electrodes were added and then removed immediately to room temperature to sit for 15 minutes. Electrodes were then transferred to M44 (in 37:39:24 THF:ACN:water at 400 μM total thiol concentration). The electrodes sat in M44 at room tem for 5 minutes, then the following heat cycling was applied: 70° C. for 1 minute, followed by 55° C. for 30 sec, repeating this cycle 2 more times followed by a 0.3° C. ramp down to RT with soaking at RT for 10 minutes. The electrodes were taken out of M44 solution, rinsed in 2×SSC, and hybridized as follows. The PCR products were adjusted to 6×SSC (no FCS). The control was also adjusted to 6×SSC. Hybridization was carried out at RT after rinsing twice in 6×SSC for at least 1.5 hours. ACV conditions were as follows: Ag/AgCl reference electrode and Pt auxiliary electrodes were used, and NaICO$_4$ was used as the electrolyte solution. ACV measurements were carried out as follows: v=10 Hz, ε=25 mV, scan range −100 mV to 500 mV. The data is shown in FIG. 26.

Example 10

Ligation on an Electrode Surface

The design of the experiment is shown in FIG. 21 (SEQ ID NOS: 35–38), for the detection of an HIV sequence. Basically, a surface probe D368 (5'-(H2) CCTTCCTTTCCACAU-4 unit wire(C11)-3') (SEQ ID NO: 36) was attached to an electrode comprising M44 and H6 (H6 is a two unit wire terminating in an acetylene bond) at a ratio of D368:H6:M44 of 1:4:1 with a total thiol concentration of 833 uM. A ligation probe HIVLIG (5'-CCACCAGATCTTCCCTAA AAAATTAGCCTGTCT CTCAGTACAATCTTTCATTTGGTGT-3') (SEQ ID NO: 38) and the target sequence HIVCOMP (5'-ATGTGGAAAGAAAGGACACCAATTGAAA-GATTGTACTGAGAGAC AGGCTAATTTTTTAGGGAAGATCTGG-3') (SEQ ID NO: 37) was added, with ligase and the reaction allowed to proceed. The reaction conditions were as follows: 10 μM of HIVLIG annealed to HIVCOMP were hybridized to the electrode surface (in 6×SSC) for 80 min. The surface was rinsed in ligase buffer. The ligase (T4) and buffer were added and incubated for 2 hours at RT. Triton X at 10$^{-4}$ M was added at 70° C. to allow the denaturation of the newly formed hybridization complex, resulting in the newly formed long surface probe (comprising D368 ligated to the HIVLIG probe). The addition of the D456 signalling probe (5'-(N6)G(N6)CT (N60C(N60G(N6)C(N6) TTCTGCACCGTAAGCCA TCAAAGATTGTACTGAG-3') (SEQ ID NO: 35) allowed detection (results not shown). The D456 probe was designed such that it hybridizes to the HIVLIG probe; that is, the surface probe that was not ligated would not allow detection.

Example 11

Use of Capture Probes Comprising Ethylene Glycol Linkers

The capture probe for a rRNA assay containing 0,4 and 8 ethylene glycol units was tested on four separate eletrode surfaces. Surface 1 contained 2:1 ratio of H6:M44, with a total thiol concentration of 500 μM. Surface 2 contained a 2:2:1 ratio of D5681/H6/M44 with a total thiol concentration of 833 μM. Surface 3 contained a 2:2:1 ratio of D570/H6/M44 with a total thiol concentration of 833 μM. D568 was a capture probe comprising GTC AAT GAG CAA AGG TAT TAA (P282)-3' (SEQ ID NO: 64). P282 was a thiol. D569 was a capture probe comprising 4 ethylene glycol units: 5'-GTC AAT GAG CAA AGG TAT TAA (C131) (P282)-3' (SEQ ID NO: 64). D570 was a capture probe comprising 8 ethylene glycol units: 5'-GTC AAT GAG CAA AGG TAT TAA (C131) (C131) (P282)-3' (SEQ ID NO: 64). The H6 (in the protected form) was as follows: (CH$_3$)$_3$Si—(CH$_2$)$_2$—S—(C$_6$H$_5$)—C≡C—(C$_6$H$_5$)—C≡CH. M44 is the same as M43 and was as follows: HS—(CH$_2$)$_{11}$—(OCH$_2$CH$_3$)$_3$—OH. The D483 label probe hybridizes to a second portion of the rRNA target, and was as follows: 5'-(N6)C(N6) G(N6C (N6)GG CCT (N6)C(N6) G(N6)C (N6)(C131)(C131) (C131)(C131)T TAA TAC CTT TGC TC-3'(SEQ ID NO: 65. The D495 is at negative control and was as follows: 5'-GAC CAG CTA GGG ATC GTC GCC TAG GTGAG (C131) (C131)(C131)(C131) (N6)G(N6) CT(N6) C(N6)G (N6)C(N6)-3' (SEQ ID NO: 66). The results were as follows:

| | | |
|---|---|---|
| Surface 1: | D483 | ~0 (no capture probe present) |
| | D495 | 0 |
| Surface 2: | D483 | 126 nA |
| | D495 | 1.29 nA |
| Surface 3: | D483 | 19.39 nA |
| | D495 | 1.51 nA |
| Surface 4: | D483 | 84 nA |
| | D495 | 1.97 nA |

As is shown, the system is working well.

Example 12

Detection of rRNA and a Comparison of Different Amounts of ETMs

The most sensitive rRNA detection to date used D350/H6/M44 surfaces mixed in a ration of 1:3.5:1.5 deposited at a 833 μM total thiol concentration. D350 is a 4 unit wire with a 15mer DNA; H6 is a 2 unit wire; and M44 is an ethylene glycol terminated alkane chain. Better detection limites are seen when the target molecule is tethered to the sensor surface at more than one place. To date, two tether points have been used A D417 tether sequence (42mer) and a EU1 capture sequence (62mer) bound the 16S rRNA to the D350 on the surface. A series of 9 label probes (D449, D469, D489, D490, D491, D476, D475 and D477) pre-annealed to the rRNA gave the electrochemical signal. These label probes (signalling molecules) have 6 or 8 N6 or Y63 type ferrocenes. The label probes that flank the tack-down regions were replaced (one end at a time) with label probes containing either 20 or 40 ferrocenes. Additionally, a label probe that binds to a region in the middle of the tack-down regions was replaced with label probes containing either 20 or 40 ferrocenes. When 2 6-ferrocene containing label probes were replaced by 2 40-ferrocene containing label probes, there was a 12-fold increase in the positive signal. The non-specific signal went up as well, exhibiting a 1.5 increase in the signal to noise ratio. Currently the best system utilizes tacking down the rRNA in two places and used a 40-ferrocene label probe to flank the 3' tack down point and bind the remaining face of the rRNA molecule with 6-ferrocene containing label probes. Additional tack down points, and a plurality of label probes, is contemplated.

A typical experimental protocol is as follows:

Surface derivatization: 20 µL of deposition solution (1:3.5:1.5 of D350:H6:M44 at total thiol concentration of 833 µM in 43.2% THF, 45.9% ACN, 10.9% H20) was heated in a closed half milliliter eppendorf tube at 50° C. for 5 minutes. A melted gold ball electrode was inserted into the solution and then moved immediately to room temperature to incubate for 15 minutes. The electrode was then transferred into ~200 µL of 400 µM M44 in 37% TH, 39% ACN, 24% H2O, where it incubated for 5 minutes at room temperature, 2 minutes at 40° C., 2 minutes at 30° C., and then an additional 15 minutes at room temperature. The electrode was then briefly dipped in 2×SSC (aqueous buffered salt solution) and hybridized as below.

Hybridization solutions were annealed by heating at 70° C. for 30 seconds and then cooling to 22° C. over ~38 seconds. The molecules were all in 4×SSC at twice the targeted concentrations, with the rRNA at 35 U.S.C. § µM, the capture sequence at 1.0 µM, and the label probes at 3 µM. After annealing, the solution was diluted 1:1 with fetal calf serum, halving the concentrations and changing the solvent to 2×SSC with 50% FCS. It should be noted that a recent experiment with model compounds suggest that a dilution by 1.2 with bovine serum albumin may be desirable: the reduction in non-specific binding was the same, but the sample concentration is not diluted and the positive signal was enhanced by a factor of 1.5. This was not done using the rRNA target, however. Solutions were aliquotted into 20 µL volumes for hybridization.

Hybridization was done as follows: After the 2×SSC dip described above, the derivatized electrode was placed into an eppendorf tube with 20 µL hybridization solution. It was allowed to hybridize at room temperature for 10 minutes.

Immediately before measurement, the electrode was briefly dipped in room temperature 2×SSC. It was then transferred into the 1 M NaHCO$_4$ electrolyte and an alternating current voltammogram was taken with an applied alternating current of 10 Hz frequency and a 25 mV center-to-peak amplitude.

10 basic experiments were run (system components in parentheses):

System 1. rRNA is tacked down at only one point (D449+D417(EU2)+D468
System 2. rRNA is tacked down at two points
System 3. two point tack down plus two label probes comprising 20 ferrocenes each directed to a flanking region of the second tack down point
System 4. two point tack down plus two label probes comprising 40 ferrocenes each directed to a flanking region of the second tack down point
System 5. two point tack down plus two label probes comprising 20 ferrocenes each directed to a flanking region of the first tack down point
System 6. two point tack down plus two label probes comprising 40 ferrocenes each directed to a flanking region of the first tack down point
System 7. two point tack down plus a label probe comprising 25 bases that binds to the middle region (i.e. the region between the two tack down points) containing 20 ferrocenes.
System 8. two point tack down plus a label probe comprising 25 bases that binds to the middle region (i.e. the region between the two tack down points) containing 40 ferrocenes.
System 9. two point tack down plus a label probe comprising 40 bases that binds to the middle region (i.e. the region between the two tack down points) containing 20 ferrocenes.
System 10. two point tack down plus a label probe comprising 40 bases that binds to the middle region (i.e. the region between the two tack down points) containing 40 ferrocenes.

The results are shown in FIG. 22. It is clear from the results that multipoint tethering of large targets is better than single point tethering. More ETMs give larger signals, but require more binding energy; 35 bases of recognition to the target.

Example 13

Direct Comparison of Different Configurations of Ferrocenes

A comparison of different configurations of ferrocene was done, as is generally depicted in FIG. 23. FIGS. 23A, 23B, 23C and 23D schematically depict the orientation of several label probes. D94 was as follows 5'-ACC ATG CAC ACA GA(C11)-3' (SEQ ID NO: 15). D109 was as follows: 5'-CTG CGG TTA TTA AC(C11)-3' (SEQ ID NO: 67). The "+" surface was a 2:2:1 ratio of D94:H6:M44, with a total thiol concentration of 833 µM. The "−" surface was a 2:2:1 ratio of D109:H6:M44, with a total thiol concentration of 833 µM. The D548 structure was as follows: 5'-(N38)(N38)(N38) (N38)(N38)(N38) (N38)(N38)(N38) ATC TGT GTC CAT GGT-3' (SEQ ID NO: 68). On each N38 was a 5'-(H2)(C23)-3'. The D549 structure was as follows: 5'-(N38) (N38)(N38) (N38)(N38)(N38) (N38)(N38)(N38) ATC TGT GTC CAT GGT-3' (SEQ ID NO: 69). On each N38 was a 5'(H2)(C23)(C23)-3'.

The D550 structure was as follows: 5'-(N38)(N38)(N38) (N38) AT CTG TGT CCA TGG T-3' (SEQ ID NO: 70). On each N38 was a 5'-(H2)(C23)(C23)-3'. The D551 structure was as follows: 5'-(n38)(N38)(N38)(N38)ATCTG TGT CAA TGG T-3' (SEQ ID NO: 71). On each N38 was a 5'-(H2)(C23)(C23)(C23)(C23)-3'. A 5' N38 has two sites for secondary modification. A representative schematic is shown in FIG. 23E.

The results, shown in the figures, show that the D551 label probes gave the highest signals, with excellent signal-to-noise ratios.

Example 17

Ferrocene Polymers as Both Recruitment Linker and ETM

This system is shown in FIG. 25 (SEQ ID NOS: 27–29, 14, 25–26). D405 has the structure: 5'-(C23)(C23)(C23

(C23)(C23)(C23) (C23)(C23)(C23) (C23)AT CTG TGT CCA TGG T-3' (SEQ ID NO: 70). The system was run with two surfaces: the "+" surface was a 2:2:1 ratio of D94:H6:M44, with a total thiol concentration of 833 μM. The "−" surface was a 2:2:1 ratio of D109:H6:M44, with a total thiol concentration of 833 μM. The results, shown in FIG. 25B (SEQ ID NOS: 14, 25–26), show that the system gave a good signal in the presence of a complementary capture probe.

Example 18

Detection of rRNA

The objective was to develop methods for the detection of rRNA from a bacterial pathogen. Initially, purified RNA was used to optimize the strategy. Subsequently, crude lysates were analyzed. *E. coli* served as a non-infectious model bacterium target in this study.

Introduction

The high abundance of rRNA in a cell make it an appealing target for electronic detection. However, rRNA is characterized by highly defined secondary and tertiary structure that makes capturing a specific sequence within the structure difficult. The 16S rRNA transcript of *E. Coli* is 1542 bases in length, and is present at $2 \times 10^4$ copies/cell. Helper sequences have been characterized that act to specifically unfold portions of the rRNA and facilitate hybridization of probes to adjacent regions. We designed three surface capture probes and two signaling probes. Two of the capture probes were designed access sequences exposed by helper probes while a third was targeted to the 5' and of the mature transcript.

Materials and Methods

Surface probe Sequences:

D1218 5'-ATG ATC AAA CTC TTC AAT TTA
A(P282)-3' (SPA)            (SEQ ID NO: 72)

D1219 5'-CAA CCC GAA GGC CTT CTT CAT A(P282)-3'
(SPB)            (SEQ ID NO: 73)

D1220 5'-GGC TGC TGG CAC GGA GTT AGC C(P282)-3'
(SPC)            (SPB) (SEQ ID NO: 74)

Signaling Oligos:

D1216 5'-(N6)C(N6) G(N6)C (N6)GC TTA (N6)C(N6) G(N6)C
(N6)G(C131) CAC GCG GCA TGG CTG AAT CAG G-3'
(SB) (SPB)            (SEQ ID NO: 75)

D1217 5'-(N6)C(N6) G(N6)C (N6)GC TTA (N6)C(N6) G(N6)C
(N6)G(C131) GGT GCT TCT TCT GCG GGT AAC GTC
AAT GAG-3' (SC) (SPB)            (SEQ ID NO: 76)

Helper Sequences:

D1221 5'-CGA CTT GCA TGT GTT AGG CCT GCC GCC AGC
GTT CAA TCT GAG CC-3'(HA) (SPB)    (SEQ ID NO: 77)

D1222 5'-CCT CCC CGC TGA AAG TAC
TTT A-3' (HB) (SPB)            (SEQ ID NO: 78)

Total RNA was isolated and purified from a 50 mL overnight culture of *E. coli* using the Qiagen RNeasy midikit. The concentration of 16S rRNA in these samples was estimated in two ways. The optical density of the total RNA sample at 260 nanometer was determined and a fraction of that was attributed to 16S RNA. Second, the sample was analyzed by formaldehyde gel electrophoresis and subsequent staining with ethidium bromide alongside standards of known composition and mass. The abundance of the 16S rRNA was estimated from its staining intensity relative to the standard. The two estimates were in general agreement. 50 nM and 10 nM rRNA solutions were heated to 70° C. in the presence of helper sequences A and B (2.5 uM), and signaling probes B and C (125 nM), in 1M NaClO$_4$ and lysed blood for 3 minutes. After cooling, the solution was added to small cartridge chips and hybridized for 4 hours. The chips were deposited with capture probe/H6/M44 (2:2:1) in 0.9%TEA/6×SSC in the following pattern.

Capture probe A acts as an additional tack down point only, there is no signaling molecule directly adjacent to its position as there is associated with capture probes B and C. The following graph displays the peak heights of signals generated from the 50 nM and 10 nM rRNA solutions after 4 hours with both signaling B and C added at 125 nM. Purified rRNA was clearly detected at both 50 nM and 10 nM, while control surfaces, containing a randomer capture probe (R), yielded no detectable signals. Electrodes bearing triple capture probes (A, B, and C) gave rise to the largest signals, and on average, pads bearing double capture probes gave larger signals than the pads with only a single capture probe. Although there is no signaling molecule adjacent to capture probe A, the extra tack-down point in close proximity to signaling moieties B and C allows, in some cases, increased signaling (compare C alone to AC).

In an attempt to demonstrate the specificity of the system for detecting 16S rRNA, a solution of 50 nM total human heart RNA in 1M NaClO$_4$/Lysed blood with signaling probes B and C (125 nM) and helper probes A and B (2.5 uM) was placed in cartridges over the electrodes. The following overlay of voltammograms presents the output from each electrode from the array challenged with human RNA. There is no signal from any pad.

An attempt was made to directly detect *E. Coli* rRNA in cell lysates without the extra steps of RNA purification. The cell lysate was made according to Qiagen RNeasy protocol. A 50 mL overnight culture was centrifuged and the pellet was resuspended in 500 uL of 1 mg/ml lysozyme in a Tris-EDTA buffer and incubated at room temperature for 5 minutes. 1.9 mL of the guanadium isothiocynate based lysis buffer, buffer RLT, with 0.145M Beta mercaptoethanol (B-Me, to inactivate RNase ) was added. For each chip, 6% of the original 50 mL culture (141 uL of cell lysate) was added to 1 59uL of whole blood (89%)/Proteanase K solution (11%), and heated at 70 C. for 10 minutes. The lysed blood/*E. Coli* solution above was then added to 2M NaClO4 with 50 nM signaling probes B and C and 1 uM helper sequences A and B. The solution was then heated to 70° C. for 3 minutes to aid in the disruption of secondary and tertiary structure and facilitate hybridization of helper and signaling sequences. Samples prepared in the manner above were compared to another hybridization solution using guandinium hydrochloride in place of guandinium isothiocynate also with 0.145 B-Me added. After cooling, the samples were added to the arrays and hybridized overnight. Chips hybridized with either type of hybridization solutions, guandinium isothiocynate or guanadinium hydrochloride, yielded immeasurable signals and voltammograms indicative of pad or monolayer disintegration.

Since we have used guanadinium hydrochloride based solutions routinely in the past, we suspected that B-Me was detrimental to electronic detection on the CMS sensor. To test this theory, the standard NaClO4/Lysed blood hybridization buffer was used, incorporating either lysis buffer RBT(guanadinium isothiocynate) or lysis buffer AL (guanadinium hydrochloride) to make the lysed blood with and without the addition of B-Me. The standard protocol was followed, with the addition of 5 nM purified *E. coli* RNA. Arrays were hybridized overnight. All arrays containing B-Me or containing guanadinium isothiocynate lysis buffer (buffer RBT) gave immeasurable signals, while the arrays hybridized in guanadinium hydrochloride lysis buffer (buffer AL), without B-Me gave rise to standard size peaks.

Above is a scan from an array hybridized in a buffer containing lysis buffer AL (guanadinium hydrochloride) without B-Me. Peaks are seen on pads containing E. Coli rRNA capture probes, while no peaks are seen on negative control pads containing random capture probe. There is no sign of pad degradation as was seen in the scans from arrays hybridized in buffers containing B-Me or buffer RLT (guanadinium isothiocynate).

Next, we tested the possibility that there is a concentration dependence to B-Me inhibition of electronic detection. We used the HIV model oligo target and the DEMO materials to test for B-Me inhibition. 50 nM target and 125 nM signaling probe were hybridized over a DEMO array. B-Me was titrated into hybridization buffer and the electrochemical signal was measured after 1 hour and then again after 4 hours of hybridization.

Both a concentration and a time dependence were observed. At 34mM, the concentration found in the Qiagen lysis buffer, specific binding could not be detected. At 17 mM, a weak positive signal was detected after one hour that was lost by four hours. The consequence of extended incubation in B-Me is more evident in the 8.5 $\mu$M solution. A half-maximal signal is observed after 1 hour that is 1/10 maximal after four hours. However, the 4.25 mM solution gave a strong signal after 1 hour that increased slightly by four hours. The latter observation suggests that 1 mM B-Me may be tolerated by the sensor. Efforts to test that hypothesis with low target concentration and extended hybridization times are underway.

In order to test the detection limit of rRNA in E. coli crude lysates, arrays were hybridized in the presence of bacterial lysate such that the lysate comprised from 6% down to 0.1875% of the final solution. A 50 mL overnight E. coli culture, lysed in buffer AL without the addition of B-Me (guanidinium hydrochloride) was prepared in the manner described above. Another set of arrays were hybridized in a NaClO4/lysed blood solution containing purified RNA in amounts that correspond to that found in the range of lysates tested, 6% to 0.1875%. Peaks were detectable on arrays with 6% crude lysate and with 6% purified RNA after 2 hours hybridization without a significant size difference between crude and purified. Peaks were also detectable on 0.75% and 0.375% of a 50 mL culture after overnight hybridization, and barely detectable with 0.1875% of a 50 mL culture.

In the arrays hybridized with purified RNA, the inconsistency of 0.75% of the culture giving rise to larger signals than 6% of the culture may be explained by the variability from chip to chip. Each bar graph represents only two chips in this experiment. With a finite number of replicates, an outlier pad, or a chip with extremely high or low performance can drastically change a trend. The two designated columns above each had one extremely large outlier removed to decrease standard deviation which brought the peak sizes from 0.75% solution much closer to 6% solution than they were when all data was included in the graph. The representation above is a repeat experiment preformed because the first attempt yielded signal sizes from 1.5% solution that were more than one-third larger than the signals from 3.0% solution, also the result of large outliers.

The E. coli cell concentration in the culture used to prepare purified RNA and crude lysates was determined to be $4.7 \times 10^8$ /mL by a plating dilution series. Therefore 0.1875% of a 50 mL culture corresponds to $4 \times 10^7$ E. Coli cells. Assuming $1 \times 10^4$ 16S rRNA molecules per cell, we detected $4.4 \times 10^{11}$ 16S rRNA molecules. That corresponds to a 200 pM concentration in our large cartridges. Thus, our detection limit for 16S rRNA from pure RNA or crude lysates is close to our current detection limit for well-studied oligos and isolated RNA (e.g. HIV 840).

Conclusions

Throughout this experimental investigation, the largest peaks with rRNA target were seen consistently on the surfaces with the triple capture probes. The signal on pads with triple capture probes A, B, and C is much higher than on the pads with the double capture probes, B and C, even though there is no signaling molecule associated with capture probe A, (only with B and C). The additional tack-down point at the position adjacent to capture probe A may increase the signal size by holding signaling oligos in a favorable position. Alternatively, the three capture probes might increase the rate at which target molecules are captured on the electrode surface. At low target concentration, the pads baring the triple capture probe, A, B, and C were the only pads to give measurable signals, while double and single capture probes on the surface gave signals equivalent to the negative pads (too small to measure). Thus, the incorporation of multiple capture and signaling sequences on a long target, such as rRNA, increases signal size and lowers the detection limit.

Following standard protocols, Beta mercaptoethanol was added to both lysis buffers to inactivate RNase and thereby protect RNA from degradation after cell lysis. The concentration recommended by this protocol, 34 mM, resulted in complete inhibition of electrochemical signaling. Beta mercaptoethanol added at concentrations as low as 8.5 mM yielded signal size degradation over time. However, when B-Me is omitted, lysis buffer alone provides adequate protection from RNase in cell lysate to allow detection of RNA. The tolerable amount of B-Me will be established and used when assaying crude lysates.

Guanadinium isothiocynate in buffer RLT also causes inhibition of electrochemical signaling on the CMS sensor. Buffer RLT is recommended by Qiagen for use in the RNeasy Kit because guanadinium isothiocynate is a harsh denaturant and effectively inactivates RNase. This buffer is incompatible with our current system as it causes pad or signal disintegration. Whole blood lysis buffer AL, currently used as the hybridization buffer standard, uses guanadinium hydrochloride to lyse cells. It is not as stringent as guanadinium isothiocynate, but it is still effective enough in inactivating RNase as to allow detection of 93.75 uL of a 50 mL overnight culture of E. coli. It is possible that detection limits could be increased by more effectively inactivating RNase present in cell lysate.

The problems associated with large variability within and between experiments prevents both quantitative and qualitative analysis of data. Arrays that give rise to peaks that are significantly larger than the average of the same condition, as well as arrays that give rise to peaks that are significantly smaller than the average of the same condition (array to array variation) are fairly common. Some pads also occasionally give extremely large or small peaks compared to the replicates on the same array (pad to pad variation). These problems associated with variability prevent accurate analysis of results.

We claim:

1. A method for detecting a target sequence in a sample comprising:
   a) providing a rolling circle probe (RCP) comprising:
      i) a first ligation sequence substantially complementary to a first domain of said target sequence;
      ii) a second ligation sequence substantially complementary to a second domain of said target sequence; and
      iii) a priming sequence;
   b) hybridizing said first ligation sequence to said first domain and said second ligation sequence to said second domain to form a first hybridization complex;
   c) ligating said first and second ligation sequences together;
   d) adding to said first hybridization complex:
      i) a primer substantially complementary to said priming sequence;
      ii) a polymerase;
      iii) dNTPs; and
      iv) an electron transfer moiety (ETM);
      to form a rolling circle concatamer comprising at least one covalently attached ETM; and
   e) detecting said ETM as an indicator of the presence of said target sequence.

2. A method according to claim 1 wherein said RCP further comprises a third domain comprising a capture sequence, and said method further comprises hybridizing said concatamer to a capture probe covalently attached to an electrode.

3. A method according to claim 1 wherein said RCP further comprises a third domain comprising a capture probe sequence and wherein said method further comprises:
   a) cleaving said concatamer to form RCP amplicons, each of which comprises a covalently attached ETM and a capture sequence; and
   b) hybridizing said capture sequence to a capture probe covalently attached to an electrode.

4. A method according to claim 1 wherein said ETM is covalently attached to at least one of said dNTPs.

5. A method according to claim 2 wherein said electrode further comprises a self-assembled monolayer.

6. A method according to claim 5 wherein said self-assembled monolayer comprises insulators.

7. A method according to claim 1 wherein said first and second target domains are directly adjacent.

8. A method according to claim 1 wherein said first and second target domains are separated by one or more nucleotides.

9. A method according to claim 1 wherein said RCP comprises at least one nucleotide analog.

10. A method according to claim 1 wherein said primer hybridizes both to said target sequence and to said priming sequence.

11. A method according to claim 1 wherein said cleavage site comprises uracil.

12. A method for detecting a first target nucleic acid sequence comprising:
    a) hybridizing at least a first primer nucleic acid to said first target sequence to form a first hybridization complex;
    b) contacting said first hybridization complex with a first enzyme to form a modified first primer nucleic acid;
    c) disassociating said first hybridization complex;
    d) forming a first assay complex comprising at least one electron transfer moiety (ETM) and said modified first primer nucleic acid, wherein said first assay complex is covalently attached to an electrode;
    wherein said electrode is on a supporting substrate, and said substrate comprises a plurality of electrodes; and
    e) detecting electron transfer between said ETM and said electrode as an indication of the presence of said target sequence.

13. A method according to claim 12 wherein steps a) through c) are repeated prior to step d).

14. A method according to claim 12 further comprising:
    a) hybridizing at least a second primer nucleic acid to a second target sequence that is substantially complementary to said first target sequence to form a second hybridization complex;
    b) contacting said second hybridization complex with said first enzyme to form a modified second primer nucleic acid;
    c) disassociating said second hybridization complex; and
    d) forming a second assay complex comprising at least one ETM and said modified second primer nucleic acid wherein said second assay complex is covalently attached to a second electrode.

15. A method according to claim 12 wherein steps a) through c) are repeated prior to step d).

16. A method according to claim 13 wherein said first enzyme comprises a DNA polymerase and said modification is an extension of said primer such that the polymerase chain reaction (PCR) occurs.

17. A method according to claim 13 wherein said first enzyme comprises a ligase and said modification comprises a ligation of said first primer which hybridizes to a first domain of said first target sequence to a second primer which hybridizes to a second adjacent domain of said first target sequence, such that the ligase chain reaction (LCR) occurs.

18. A method according to claim 14 wherein said first enzyme comprises a ligase and said modification is a ligation of said second primer which hybridizes to a first domain of said second target sequence to a fourth primer which hybridizes to a second adjacent domain of said second target sequence, such that the ligase chain reaction (LCR) occurs.

19. A method according to claim 13 wherein said first primer comprises a first probe sequence, a first scissile linkage and a second probe sequence, wherein said first enzyme will cleave said first scissile linkage resulting in the separation of said first and said second probe sequences and the disassociation of said first hybridization complex, leaving said first target sequence intact, such that the cycling probe technology (CPT) reaction occurs.

20. A method according to claim 15 wherein said second primer comprises a third probe sequence, a second scissile linkage and a fourth probe sequence, wherein said first enzyme will cleave said second scissile linkage resulting in the separation of said third and said fourth probe sequences and the disassociation of said second hybridization complex, leaving said second target sequence intact, such that the cycling probe technology (CPT) reaction occurs.

21. A method according to claim 13 wherein said first enzyme is a polymerase that extends said first primer and said modified first primer comprises a first newly synthesized strand, and said method further comprises:
   a) the addition of a second enzyme comprising a nicking enzyme that nicks said extended first primer leaving said first target sequence intact; and
   b) extending from said nick using said polymerase, thereby displacing said first newly synthesized strand and generating a second newly synthesized strand; such that strand displacement amplification (SDA) occurs.

22. A method according to claim 15 wherein said first enzyme is a polymerase that extends a second primer and said modified first primer comprises a third newly synthesized strand, and said method further comprises:
   a) the addition of a second enzyme comprising a nicking enzyme that nicks said extended second primer leaving said second target sequence intact; and
   b) extending from said nick using said polymerase, thereby displacing said third newly synthesized strand and generating a fourth newly synthesized strand; such that strand displacement amplification (SDA) occurs.

23. A method according to claim 12 wherein said first primer is an invader primer, said method further comprises hybridizing a signaling primer to said target sequence, said enzyme comprises a structure-specific cleaving enzyme and said modification comprises a cleavage of said signaling primer, such that the Invader™ reaction occurs.

* * * * *

SEQUENCE LISTING

<160> NUMBER OF SEQ ID NOS: 78

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: synthetic.

<400> SEQUENCE: 1
gctcgaggct                                                              10

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 2
ggaattcaag gatccgaatg cc                                                22

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: synthetic.

<400> SEQUENCE: 3
cgagctccga ccttaagttc ctaggcttac ggc                                    33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: synthetic.

<400> SEQUENCE: 4
gctcgaggct ggaattcaag gatccgaatg cc                                     32

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: synthetic.

<400> SEQUENCE: 5
gctcgaggct gg                                                           12

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: synthetic.

<400> SEQUENCE: 6
cgagctccga ccttaa                                                       16

<210> SEQ ID NO 7
<211> LENGTH: 32

```
<212> TYPE: DNA
<213> ORGANISM: Artificial Sequence
<220> FEATURE:
<223> OTHER INFORMATION: Description of Artificial Sequence: synthetic.

<400> SEQUENCE: 7
cgagctccga ccttaagttc ctaggcttac gg                                        32

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: synthetic.

<400> SEQUENCE: 8
acctggtctt gacatccacg gaaggcgtgg aaatacgtat tcgtgccta                      49

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: synthetic.

<400> SEQUENCE: 9
catggttaac gtcaattgct gcggttatta a                                         31

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: synthetic.

<400> SEQUENCE: 10
gctcgcccca tggttagact gaattgctgc ggttattaa                                 39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: synthetic.

<400> SEQUENCE: 11
gctcgctatg ctcttgatgg tgctgtggaa atctactgg                                 39

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: synthetic.

<400> SEQUENCE: 12
gctcgcatgg tgctgtggaa atctactgg                                            29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: synthetic.

<400> SEQUENCE: 13
```

```
gctcgctgac tgaattgctg cggttattaa                                      30

<210> SEQ ID NO 14
<211> LENGTH: 25
<212> TYPE: DNA
<213> ORGANISM: Artificial Sequence
<220> FEATURE:
<223> OTHER INFORMATION: Description of Combined DNA/RNA
      Molecule:synthetic.
<223> OTHER INFORMATION: Description of Artificial Sequence: synthetic.

<400> SEQUENCE: 14
cttccgtgga tgtcaagacc aggau                                           25

<210> SEQ ID NO 15
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 15
accatggaca cagau                                                      15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 16
ctgcggttat taacu                                                      15

<210> SEQ ID NO 17
<211> LENGTH: 86
<212> TYPE: DNA
<213> ORGANISM: Artificial Sequence
<220> FEATURE:
<223> OTHER INFORMATION: Description of Artificial Sequence: synthetic.

<400> SEQUENCE: 17
taggcacgaa tacgtatttc cacgataaat ataattaata accgcagcaa ttgacgtata     60
aagctatccc agtagatttc cacagc                                          86

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: synthetic.

<400> SEQUENCE: 18
acgtgtccat ggtagtagct tatcgtggaa atacgtattc gtgccta                   47

<210> SEQ ID NO 19
<211> LENGTH: 39
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 19
```

```
gctcgcccca tggttagact gaattgctgc ggttattaa                    39

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: synthetic.

<400> SEQUENCE: 20
gctcgcccca tggttagact ggctgtggaa atctactgg                    39

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: synthetic.

<400> SEQUENCE: 21
gctcgccttt actccttcc tccccgctga aagtac                        36

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: synthetic.

<400> SEQUENCE: 22
cggagttagc cggtgcttct tctgcggggc tgt                          33

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: synthetic.

<400> SEQUENCE: 23
ctttactccc ttcctccccg ctgaaagtac tttacaaccc                   40

<210> SEQ ID NO 24
<211> LENGTH: 62
<212> TYPE: DNA
<213> ORGANISM: Artificial Sequence
<220> FEATURE:
<223> OTHER INFORMATION: Description of Artificial Sequence: synthetic.

<400> SEQUENCE: 24
atcctggtct tgacatccac ggaagatctc cctacagtct ccatcaggca gtttcccaga    60
ca                                                                   62

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: synthetic.

<400> SEQUENCE: 25
tctacatgcc gtacatacgg aacgtacgga gcatcctggt cttgacatcc acggaag       57

<210> SEQ ID NO 26
```

```
<211> LENGTH: 26
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 26
gctcgcccgt atgtacggca tgtaga                                          26

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: synthetic.

<400> SEQUENCE: 27
gctactacca tggacacaga u                                               21

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: synthetic.

<400> SEQUENCE: 28
acagacatca gagtaatcgc cgtctggt                                        28

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: synthetic.

<400> SEQUENCE: 29
gattactctg atgtctgtcc atctgtgtcc atggtagtag c                         41

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: synthetic.

<400> SEQUENCE: 30
gattactctg atgtctgtcc tagtacgagt cagtctctcc a                         41

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: synthetic.

<400> SEQUENCE: 31
tctacatgcc gtacatacgg aacgtacgga gcgattcgac tgacagtcgt aacctca        57

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: synthetic.
```

<400> SEQUENCE: 32
gctcgcgcga caactgtacc atctgtgtcc atggt                              35

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 33
atctgtgtcc atggt                                                    15

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: synthetic.

<400> SEQUENCE: 34
gctcgcatct gtgtccatgg tagtagc                                       27

<210> SEQ ID NO 35
<211> LENGTH: 39
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 35
gctcgcttct gcaccgtagc catgaaagat tgtactgag                          39

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 36
ccttcctttc cacau                                                    15

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: synthetic.

<400> SEQUENCE: 37
atgtggaaag gaaggacacc aaatgaaaga ttgtactgag agacaggcta atttttagg    60 gaagatctgg                                                          70

<210> SEQ ID NO 38
<211> LENGTH: 55
<212> TYPE: DNA
<213> ORGANISM: Artificial Sequence
<220> FEATURE:
<223> OTHER INFORMATION: Description of Artificial Sequence: synthetic.

<400> SEQUENCE: 38
ccagatcttc cctaaaaaat tagcctgtct ctcagtacaa tctttcattt ggtgt    55

<210> SEQ ID NO 39
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 39
acgagtccat ggt    13

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 40
agcctagctg gtg    13

<210> SEQ ID NO 41
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 41
acgagtccat ggt    13

<210> SEQ ID NO 42
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 42
agcctagctg gtg    13

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 43
aacagagtcc atggt    15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 44
atgtcctagc tggtg    15

<210> SEQ ID NO 45
<211> LENGTH: 13
<212> TYPE: DNA
<213> ORGANISM: Artificial Sequence

```
<220> FEATURE:
<223> OTHER INFORMATION: Description of Artificial Sequence: synthetic.

<400> SEQUENCE: 45
acgagtccat ggt                                                          13

<210> SEQ ID NO 46
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 46
agcctagctg gtg                                                          13

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 47
acgagtccat ggt                                                          13

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 48
agcctagctg gtg                                                          13

<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: synthetic.

<400> SEQUENCE: 49
acagagtcca tggt                                                         14

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: synthetic.

<400> SEQUENCE: 50
agtcctagct ggtg                                                         14

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 51
aagagtccat ggt                                                          13
```

```
<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 52
atcctagctg gtg                                                              13

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 53
acgagtccat ggt                                                              13

<210> SEQ ID NO 54
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 54
agcctagctg gtg                                                              13

<210> SEQ ID NO 55
<211> LENGTH: 13
<212> TYPE: DNA
<213> ORGANISM: Artificial Sequence
<220> FEATURE:
<223> OTHER INFORMATION: Description of Artificial Sequence: synthetic.

<400> SEQUENCE: 55
acgagtccat ggt                                                              13

<210> SEQ ID NO 56
<211> LENGTH: 13
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 56
agcctagctg gtg                                                              13

<210> SEQ ID NO 57
<211> LENGTH: 15
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 57
accatggact ctgtu                                                            15

<210> SEQ ID NO 58
<211> LENGTH: 15
```

```
<212> TYPE: DNA
<213> ORGANISM: Artificial Sequence
<220> FEATURE:
<223> OTHER INFORMATION: Description of Artificial Sequence: synthetic.

<400> SEQUENCE: 58
accatggact ctgtu                                                          15

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: synthetic.

<400> SEQUENCE: 59
aagggctgtt ggaaatgtgg                                                     20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 60
tgttggctct ggtctgctct ga                                                  22

<210> SEQ ID NO 61
<211> LENGTH: 137
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 61
aagggctgtt ggaaatgtgg aaaggaagga caccaaatga agattgtact gagagacagg         60 ctaattttt agggaagatc tggccttcct acaagggaag gccagggaat tttcttcaga         120
gcagaccaga gccaaca                                                       137

<210> SEQ ID NO 62
<211> LENGTH: 141
<212> TYPE: DNA
<213> ORGANISM: Artificial Sequence
<220> FEATURE:
<223> OTHER INFORMATION: Description of Artificial Sequence: synthetic.

<400> SEQUENCE: 62
gtttggctct ggtctgctct gaagaaaatt ccctggcctt cccttgtagg aaggccagat         60
cttccctaaa aaattagcct gtctctcagt acaatctttc atttggtgtc cttcctttcc        120
acatttccaa cagccctttt t                                                  141

<210> SEQ ID NO 63
<211> LENGTH: 16
<212> TYPE: DNA
<213> ORGANISM: Artificial Sequence
<220> FEATURE:
<223> OTHER INFORMATION: Description of Combined DNA/RNA Molecule:
      synthetic.
<223> OTHER INFORMATION: Description of Artificial Sequence: synthetic.

<400> SEQUENCE: 63
```
ttggtgtcct tccttu                                                16

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: synthetic.

<400> SEQUENCE: 64
gtcaatgagc aaaggtatta a                                          21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: synthetic.

<400> SEQUENCE: 65
cgcggcctcg cttaatacct ttgctc                                     26

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: synthetic.

<400> SEQUENCE: 66
gaccagctag ggatcgtcgc ctaggtgagg ctcgc                           35

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence: synthetic.

<400> SEQUENCE: 67
ctgcggttat taac                                                  14

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 68
atctgtgtcc atggt                                                 15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 69
atctgtgtcc atggt                                                 15

<210> SEQ ID NO 70
<211> LENGTH: 15
<212> TYPE: DNA
<213> ORGANISM: Artificial Sequence

```
<220> FEATURE:
<223> OTHER INFORMATION: Description of Artificial Sequence: synthetic.

<400> SEQUENCE: 70
atctgtgtcc atggt                                                        15

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: synthetic.

<400> SEQUENCE: 71
atctgtgtca atggt                                                        15

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 72
atgatcaaac tcttcaattt aa                                                22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 73
caacccgaag gccttcttca ta                                                22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 74
ggctgctggc acggagttag cc                                                22

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: synthetic.

<400> SEQUENCE: 75
cgcgcttacg cgcacgcggc atggctgaat cagg                                   34

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence: synthetic.

<400> SEQUENCE: 76
cgcgcttacg cgggtgcttc ttctgcgggt aacgtcaatg ag                          42
```

```
<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: synthetic.

<400> SEQUENCE: 77
cgacttgcat gtgttaggcc tgccgccagc gttcaatctg agcc                44

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: synthetic.

<400> SEQUENCE: 78
cctccccgct gaaagtactt ta                                        22
```